(12) United States Patent
Tang et al.

(10) Patent No.: US 6,689,806 B1
(45) Date of Patent: Feb. 10, 2004

(54) INDOLINONE COMPOUNDS AS KINASE INHIBITORS

(75) Inventors: Peng Cho Tang, Moraga, CA (US); Li Sun, Foster City, CA (US); Gerald McMahon, San Francisco, CA (US); Todd Anthony Miller, Bend, OR (US); Shahrzad Shirazian, Corte Madera, CA (US); Chung Chen Wei, Foster City, CA (US); G. Davis Harris, Jr., San Francisco, CA (US); Xiaoyuan Li, Los Altos, CA (US); Congxin Liang, Sunnyvale, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 09/534,405

(22) Filed: Mar. 22, 2000

Related U.S. Application Data

(60) Provisional application No. 60/125,945, filed on Mar. 24, 1999, provisional application No. 60/127,863, filed on Apr. 5, 1999, provisional application No. 60/131,192, filed on Apr. 26, 1999, and provisional application No. 60/132,243, filed on May 3, 1999.

(51) Int. Cl.⁷ .................. A61K 31/404; C07D 209/34
(52) U.S. Cl. .................. 514/418; 514/414; 514/415; 548/468; 548/465; 548/466; 548/486
(58) Field of Search .................. 548/468, 465, 548/466, 486; 514/414, 415, 418

(56) References Cited

U.S. PATENT DOCUMENTS

| | | | |
|---|---|---|---|
| 3,308,134 A | 3/1967 | Plostnieks | |
| 4,002,749 A | 1/1977 | Rovnyak et al. | 424/246 |
| 4,053,613 A | 10/1977 | Rovnyak et al. | 424/246 |
| 4,966,849 A | 10/1990 | Vallee et al. | 435/199 |
| 5,206,261 A * | 4/1993 | Kawaguchi et al. | 514/418 |
| 5,217,999 A | 6/1993 | Levitzki et al. | 514/613 |
| 5,302,606 A | 4/1994 | Spada et al. | 514/357 |
| 5,322,950 A * | 6/1994 | Sircar et al. | 548/253 |
| 5,330,992 A | 7/1994 | Elssenstat et al. | 514/312 |
| 5,786,488 A | 7/1998 | Tang et al. | 548/455 |
| 5,792,783 A * | 8/1998 | Tang et al. | 514/397 |
| 5,840,745 A | 11/1998 | Buzzetti et al. | 514/414 |
| 5,880,141 A | 3/1999 | Tang et al. | 514/339 |
| 5,883,113 A | 3/1999 | Tang et al. | 514/418 |
| 5,883,116 A | 3/1999 | Tang et al. | 514/418 |
| 5,886,020 A | 3/1999 | Tang et al. | 514/418 |
| RE36,256 E | 7/1999 | Spada et al. | 514/249 |

FOREIGN PATENT DOCUMENTS

| | | |
|---|---|---|
| EP | 0 252 731 A2 | 1/1988 |
| EP | 0 304 493 B1 | 3/1989 |
| EP | 0 586 226 A1 | 10/1993 |
| FR | 1 599 772 A | 7/1970 |
| GB | 1290686 * | 9/1972 |
| WO | 91-13055 | 9/1991 |
| WO | 91-15495 | 10/1991 |
| WO | 92-07830 | 5/1992 |
| WO | 92-20642 | 11/1992 |
| WO | 92-21660 | 12/1992 |
| WO | WO 93/01182 A | 1/1993 |
| WO | 93-23040 | 11/1993 |
| WO | 94-03427 | 2/1994 |
| WO | 94-10202 | 5/1994 |
| WO | 94-14808 | 7/1994 |
| WO | WO 95/01349 A | 1/1995 |
| WO | 95-14667 | 6/1995 |
| WO | 95-24190 | 9/1995 |
| WO | 96-00226 | 1/1996 |
| WO | 96-16964 | 6/1996 |
| WO | WO 96/22976 A | 8/1996 |
| WO | 96-22976 | 8/1996 |
| WO | WO 96/32380 A | 10/1996 |
| WO | 96-40116 | 12/1996 |
| WO | 98-07695 | 2/1998 |
| WO | 98-07835 | 2/1998 |
| WO | WO 98/24432 A | 6/1998 |
| WO | 98-45708 | 10/1998 |
| WO | 98-50356 | 11/1998 |
| WO | 98-56376 | 12/1998 |
| WO | 99/10325 | 3/1999 |
| WO | 99/19325 | 4/1999 |
| WO | WO 9961422 * | 12/1999 |

OTHER PUBLICATIONS

B.Franco et al,"Cinnamamide analogues as inhib.or PTK", Farmaco, 48/5,615–36(1993).*

Tao et al,"Electrochem. & peroxid. O2 mediated";J. Electroanal. Chem. 432/1–2,7–18(1997).*

A.Aldo et al,"Synth. & Cardiotonic Activity of indolinone", Eur.J.Med.Chem.,25/2,187–90(1990).*

E.Ali et al,"Regiosel.Pd–(II)–Cataly. Synthe.";J.Am.Chem. Soc. 118/18,4264–70(1996).*

Akbasak and Sunar–Akbasak., "Oncogenes: cause or consequence in the development of glial tumors," *J. Neurol. Sci.* 111:119–133 (1992).

Andreani et al., "Synthesis and potential coanthracyclinic activity of substituted 3–(5–imidazo[2,1–b] thiazolylmethylene)–2–indolinones," *Eur. J. Med. Chem.* 32:919–924 (1997).

Arteaga et al., "Blockade of the Type I Somatomedin Receptor Inhibits Growth of Human Breast Cancer Cells in Athymic Mice," *J. Clin. Invest.* 84:1418–1423 (1989).

(List continued on next page.)

*Primary Examiner*—Mukund J. Shah
*Assistant Examiner*—Sudhaker B. Patel
(74) *Attorney, Agent, or Firm*—Beth A. Burrous; Foley & Lardner

(57) ABSTRACT

The invention relates to certain indolinone compounds, their method of synthesis, and a combinatorial library consisting of the indolinone compounds of the invention. The invention also relates to methods of modulating the function of protein kinases using indolinone compounds of the invention and methods of treating diseases by modulating the function of protein kinases and related signal transduction pathways.

19 Claims, No Drawings

OTHER PUBLICATIONS

Arvidsson et al., "Try–716 in the Platelet–Derived–Growth–Factor β–Receptor Kinase Insert is Involved in GRB2 Binding and Ras Activation," *Molecular and Cellular Biology* 14(10):6715–6726 (1994).

Baserga, "Oncogenes and the Strategy of Growth Factors," *Cell* 79:927–93 (1994).

Baserga, "The Insulin–like Growth Factor I Receptor: A Key to Tumor?" *Cancer Research* 55:249–252 (1995).

Bolen et al., "The Src family of tyrosine protein kinases in hemopoietic signal transduction," *FASEB J.* 6:3403–3409 (1992).

Bolen, "Nonreceptor tyrosine protein kinases," *Oncogene* 8:2025–2031 (1993).

Cance et al., "Novel Protein Kinases Expressed in Human Breast Cancer," *Int. J. Cancer* 54:571–577 (1993).

Carpenedo et al., "Identification and Measurement of Oxindole (2–Indolinone) in the Mammalian Brain and Other Rat Organs" *Analytical Biochemistry* 244:74–79 (1997).

Chen et al., "Effects of 3,3–Dipyridylmethyl–1–Phenyl–2–Indolinone on γ–Aminobutyric Acid Elicited Chloride Current of Snail Central Neuron" *Chinese Journal of Physiology* 40(3):149–156 (1997).

Claesson–Welsh, "Signal Transduction by the PDGF Receptor," *Progress in Growth Factor Research* 5:37–54 (1994).

Coppola et al., "A Functional Insulin–Like Growth Factor I Receptor is Required for the Mitogenic and Transforming Activities of the Epidermal Growth Factor Receptor," *Molecular and Cellular Biology* 14:4588–4595 (1994).

Damiani et al., "Inhibition of Copper–Mediated Low Density Lipoprotein Peroxidation by Quinoline and Indolinone Nitroxide Radicals," *Biochemical Pharmacology* 48(6):1155–1161 (1994).

Davis et al., "Synthesis and microbiological properties of 3–Amino–1–Hydroxy–2–Indolinone and Related Compounds," *Journal of Medicinal Chemistry* 16(9):1043–1045 (1973).

De Vries et al., "The fms–Like Tyrosine Kinase, a Receptor for Vascular Endothelial Growth Factor," *Science* 255:989–991.

Decker and Lohmann–Matthes, "A quick and simple method for the quantitation of lactate dehydrogenase release in measurements of cellular cytotoxicity and tumor necrosis factor (TNF) activity," *J. Immunol. Methods* 15:61–69 (1988).

Dickson et al., "Tyrosine kinase receptor—nuclear protooncogene interactions in breast cancer," *Cancer Treatment Res.* 61:249–273 (1992).

Fantl et al., "Distinct Phosphotyrosines on a Growth Factor Receptor Bind to Specific Molecules that Mediate Different Signaling Pathways," *Cell* 69:413–423 (1992).

Fendly et al., "Characterization of Murine Monoclonal Antibodies Reactive to Either the Human Epidermal Growth Factor Receptor or HER2–neu Gene product," *Cancer Research* 50:1550–1558 (1990) (mistakenly referred to as Fendley).

Ferrara and Henzel, "Pituitary Fillicular Cells Secrete a Novel Heparin–Binding Growth Factor Specific for Vascular Endothelial Cells," *Biochemical and Biophysical Research Communications* 161:851–858 (1989).

Fingl and Woodbury, "Chapter 1—General Principles," in *The Pharmacological Basis of Therapeutics* $5^{th}$ edition, Goodman and Gilman editors, MacMillan Publishing Co., Inc., New York, pp. 1–46 (1975).

Floege et al., "Heparin suppresses mesangial cell proliferation and matrix expansion in experimental mesangioproliferative glomerulonephritis," *Kidney International* 43:369–380 (1993).

Folkman and Shing, "Angiogenesis," *J. Bio. Chem.* 267:10931–10934 (1992).

Folkman, "Ch. 24. Angiogenesis," *Congress of Thrombosis and Haemostasis* (Verstraete et al., eds.) Leuven University Press, Leuven pp. 583–596 (1987).

Folkman, "Tumor Angiogenesis, Therapeutic Implications," *New England J. Medicine* 285:1182–1186 (1971).

Folkman, "What Is Evidence that Tumors Are Angiogenesis Dependent?" *Journal of National Cancer Institute* 82:4–6 (1990).

Gazit et al., "Tyrphostins. 2. Heterocyclic and alpha–substituted benzylidenmalononitrile tyrphostins as potent inhibitors if EGF receptor and ErbB2–neu tyrosine kinases," *J. Med. Chem.* 34(6):1896–1907 (1991).

Gennaro (editor), *Remington's Pharmaceutical Sciences* (1990) (Table of Contents Only).

Goldring and Goldring, "Cytokines and Cell Growth Control," *Critical Reviews in Eukaryotic Gene Expression* 1:301–326 (1991).

Graziani et al., "Hepatocyte Growth Factor/Scatter Factor Stimulates the Ras–Guanine Nucleotide Exchanger," *The Journal of Biological Chemistry* 268(13):9165–9168 (1993).

Honegger et al., "Point Mutation at the ATP Binding Site of EGF Receptor Abolishes Protein–Tyrosine Kinase Activity and Alters Cellular Routing," *Cell* 51:199–209 (1987).

Houck et al. "Dual Regulation of Vascular Endothelial Growth Factor Bioavailability by Genetic and Proteolytic Mechanisms," *J. Bio. Chem.* 267:26031–26037 (1992).

Hu et al., "Interaction of Phosphatidylinositol 3–Kinase–Associated p85 with Epidermal Growth Factor and Platelet–Derived Growth Factor Receptors," *Molecular and Cellular Biology* 12(3):981–990 (1992).

Jellinek et al., "Inhibitor of Receptor Binding by High–Affinity RNA Ligands to Vascular Endothelial Growth Factor," *Biochemistry* 33:10450–10456 (1994).

Kashishian and Cooper, Phosphorylation Sites at the C–terminus of the Platelet–Derived Growth Factor Receptor Bind Phospholipase Cγ1, *Molecular Biology of the Cell* 4:49–57 (1993).

Kashishian et al., "Phosphorylation Sites in the PDGF receptor with Different Specificities for Binding GAP and P13 Kinase in vivo," The EMBO Journal 11(4):1373–1382 (1992).

Kato et al., "Simultaneous Determination of Amfenac Sodium and its Metabolite (7–Benzoyl–2–Oxindole) in Human Plasma by High–Performance Liquid Chromatography," *Journal of Chromatography* 616:67–71 (1993).

Kazlauskas et al., "The 64–kDa Protein That Associates with the Platelet–Derived Growth Factor Receptor β Subunit via Tyr–1009 Is The SH2–Containing Phosphotyrosine Phosphatase Syp," *Proc. Natl. Acad. Sci. USA* 90:6939–6942 (1993).

Kendall and Thomas, "Inhibition of vascular endothelial cell growth factor activity by an endogenously encoded soluble receptor," *Proc. Natl. Acad. Sci. USA* 90:10705–10709 (1993).

Kim et al., "Inhibition of vascular endothelial growth factor–induced angiogenesis suppressed tumor growth in vivo," *Nature* 362–841–844 (1993).

Kinsella et al., "Protein Kinase C Regulates Endothelial Cell Tube Formation on Basement Membrane Matrix, Matrigel," *Exp. Cell Research* 199:56–62 (1992).

Klagsburn and Soker, "VEGF–VPF: The Angiogenesis Factor Found?" *Current Biology* 3:699–702 (1993).

Koch et al., "SH2 and SH3 Domains: Elements That Control Interactions of Cytoplasmic Signaling Proteins," *Science* 252:668–674 (1991).

Komada and Kitamura, "The cell dissociation and motility triggered by scatter factor–hepatocyte growth factor are mediated through the cytoplasmic domain of the c–Met receptor," *oncogene* 8:2381–2390 (1993).

Korc et al., "Overexpression of the Epidermal Growth Factor Receptor in Human Pancreatic Cancer is Associated with Concomitant increases in the Levels of Epidermal Growth Factor and Transforming Growth Factor Alpha," *J. Clin. Invest.* 90:1352–1360 (1992).

Korzeniewski and Callewaert, "An Enzyme–Release Assay for Natural Cytotoxicity," *J. Immunol. Methods* 64:313–320 (1983).

Kumabe et al., "Amplification of $\alpha$–platelet–derived growth factor receptor gene lacking an exon coding for a portion of the extracellular region in a primary brain tumor of glial origin," *Oncogene* 7:627–633 (1992).

Lee and Donoghue, "Intracellular retention of membrane–anchored v–sis protein abrogates autocrine signal transduction," *Journal of Cell Biology* 118:1057–1070 (1992).

Levitzki et al., "Tyrosine kinase inhibition: An approach to drug development," *Science* 267:1782–1788 (1995).

Maass et al., "Viral resistance to the thiazolo–iso–indolinoes, a new class of nonnucleoside inhibitors of human immunodeficiency virus type 1 reverse transcriptase," *Antimocrobial Agents and Chemotherapy* 37(12)2612–2617 (1993).

Macauley et al., "Autocrine function for insulin–like growth factor I in human small cell lung cancer cell lines and fresh tumor cells," *Cancer Research* 50:2511–2517 (1990).

Mariani et al., "Inhibition of angiogenesis by PCE 26806, a potent tyrosine kinase inhibitor," *Experimental Therapeutics—Proceedings of the American Association for Cancer Research* 35:381 at abstract No. 2268 (Mar. 1994).

Millauer et al., "High Affinity VEGF Binding and Developmental Expression Suggest Flk–1 as a Major Regulator of Vasculogenesis and Angiogenesis," *Cell* 72:835–846.

Mohammadi et al., "Structures of the tyrosine kinase domain of fibroblast growth factor receptor in complex with inhibitors," *Science* 276(5314):955–960 (1979).

Moreto et al. "3,3–bis–(4–hydroxyphenyl)–7–methyl–2–indolinone (BHMI), the active metabolite of the laxative sulisatin" *Arzneimittel–Forschung Drug Research* 29(II):1561–1564 (1979).

Moreto et al., "Study of the laxative properties of the disodium salt of the sulfiuric diester of bis–(4–hydroxyphenyl)–7–methyl–2indolinone(Dan–603) in the rat," *European Journal of Pharmacology* 36:221–226 (1976).

Morrison et al., "Signal Transduction from Membrane to Cytoplasm: Growth Factors and Membrane–Bound Oncogene Products Increases Raf–1 Phosphorylation and Associated Protein Kinase Activity," *Proc. Natl. Acad. Sci. USA* 85; 8855–8859 (1988).

Mosmann, "Rapid Colorimetric Assay for Cellular Growth and Survival: Application to Proliferation and Cytotoxicity Assays," *J. Immunol. Methods* 65:55–63 (1983).

Nishimura et al., "Two Signaling Molecules Share a phosphotyrosine–Containing Binding Site in the Platelet–Derived Growth Factor Receptor," *Molecular and Cellular Biology* 13:6889–6896 (1993).

Plowman et al., "Receptor Tyrosine Kinases as Targets for Drug Intervention," *DN&P* 7(6):334–339 (1994).

Quinn et al., "Fetal Liver Kinase 1 as a Receptor for Vascular Endothelial Growth Factor and is Selectively Expressed in Vascular Endothelium," *Proc. Natl. Acad. Sci. USA* 90:7533–7537 (1993).

Rozakis–Adcock et al., "Association of the Shc and Grb2–Sem5 SH2–containing proteins is implicted in activation of the Ras pathway by tyrosine kinases." *Nature* 360:689–692 (1992).

Rygaard and Povlsen, "Heterotransplantation of a Human Malignant Tumor to 'Nude' Mice," *Acta path. microbiol. scand.* 77:758–760 (1969).

Sandberg–Nordqvist et al., "Characterization of Insulin–Like Growth Factor 1 in Human Primary Brain Tumors," *Cancer Research* 53:2475–2478 (1993).

Schlessinger and Ullrich, "Growth Factor Signalling by Receptor Tyrosine Kinases," *Neuron* 9:383–391 (1992).

Shibuya et al., "Nucleotide Sequence and Expression of a Novel Human Receptor–Type Tyrosine Kinase Gene (flt) closely related to the fms family", *Oncogene* 5:519–524 (1990).

Singh et al., "Indolinone derivatives as potential antimicrobial agents," *Zentralbl. Mikrobiol.* 144:105–109 (1989).

Singh et al., "Synthesis and Anticonvulsant Activity of New 1–Substituted 1'–Methyl–3–Chloro–2–Oxosprio (Azetidin–3', 4–Indol–2' Ones)," *Bollettino Chimico Farmaceutico* 133:76–79 (1994).

Slamon et al., "Studies of the HER–2–neu Proto–oncogene in Human Breast and Ovarian Cancer," *Science* 244:707–712 (1989).

Songyang et al., "SH2 Domains Recognize Specific Phosphopeptide Sequences," *Cell* 72:767–778 (1993).

Songyang et al., "Specific Motifs Recognized by the SH2 Domains of Csk, 3BP2, fps–fes, GRB–2, HCP, SHC, Syk and Vav," *Molecular and Cellular Biology* 14:2777–2785 (1994).

Spada et al., "Small molecule inhibitors of tyrosine kinase activity," *Expert Opinion on Therapeutic Patents* 5(8):805–817 (1995).

Sun et al., "Synthesis and biological evaluations of 3–substituted indolin–2–ones: A novel class of tyrosine kinase inhibitors that exhibit selectivity toward particular receptor tyrosine kinases," *J. Med. Chem.* 41(14):2588–2603 (1998).

Superti–Furga et al., "A functional screen in yeast for regulators and antagonizers of heterologous protein tyrosine kinases," *Nature Biotech* 14:600–605 (1996).

Superti–Furga et al., "Csk inhibition of c–Src activity requires both the SH2 and SH3 domains of Src," *EMBO J.* 12:2625–2634 (1993).

Takano et al., "Inhibition of antiogenesis by a novel diaminoanthraquinone that inhibits protein kinase C," *Mol. Bio. Cell* 4:358A at abstract No. 2076 (1993).

Torp et al., "Expression of the Epidermal Growth Factor Receptor Gene in Human Brain Metastases," *AMPIS* 100:713–719 (1992).

Tsai et al., "The effect of 3,3–Di–Pyridyl–Methyl–1–Phenyl–2–indoline on the nerve Terminal Currents of Mouse Skeletal Muscles," *Neuropharmacology* 31(9):943–947 (1992).

Tuzi et al., "Expression of growth factor receptors in human brain tumours," *Br. J. Cancer* 63:227–233 (1990).

Twamley–Stein et al., "The Src Family Tyrosine Kinases are Required for Platelet–Derived Growth Factor–Mediated Signal Transduction in NIH 3T3 Cells," *Proc. Natl. Acad. Sci.*, 90:7696–7700 (1993).

Vaisman et al., "Characterization of the Receptors for Vascular Endothelial Growth Factor," *J. Biol. Chem.* 265:19461–19466 (1990).

Varma and Gupta, "Nucleophilic Reactions of 2–Methyl–3–(4'–carbomethoxyphenyl)–4–quinazolinones with 2–Indolinones," *J. Indian Chem. Soc.* 66:804–805 (1989).

Voller et al., "Ch. 45—Enzyme–Linked Immunosorbent Assay," in *Manual of Clinical Immunology*, $2^{nd}$ edition, Rose and Friedman editors, American Society of Microbiology, Washington, D.C., pp. 359–371 (1980).

Walker, "The Reduction of Insoindogenides, Nitro Compounds, and Pyridines in a Series of 2–Indolinones," *J. Med. Chem.* 8(5):626–637 (1965).

Weidner et al. "Tumor Angiogenesis and Metastasis–Correlation in Invasive Breast Carcinoma," *New England Journal of Medicine* 324(1):1–8 (1991).

Wright et al., "Inhibition of Angiogenesis in Vitro and In Ovo With an Inhibitor of Cellular Protein Kinases, MDL 27032," *J. Cellular Physiology* 152:448–457 (1992).

Zaman et al., "Tyrosine Kinase Activity of Purified Recombinant Cytoplasmic Domain of Platelet–Derived Growth Factor β–Receptor (β–PDGFR) and Discovery of a Novel Inhibitor of Receptor Tyrosine Kinases," *Biochemical Pharmacology* 57(1):57–64 (1999).

Zhang et al., "Microtubule Effects of Welvistatin, a Cyanobacterial Indolinone that Circumvents Multiple Drug Resistance," *Molecular Pharmacology* 49:228–294 (1996).

Andreani et al., "Synthesis and potential coanthracyclinic activity of substituted 3–(5–imidazo[2,1–b] thiazolylmethylene)–2–indolinones," *Eur. J. Med. Chem.* 32:919–924 (1997).

Elliot et al, "Reduction of some oxindole derv. to 3–subst. oxindoles by Sod. Borohydride", J.Org.Chem. 29/8, 2438–40(1964);CAPLUS 61:69029.*

* cited by examiner

INDOLINONE COMPOUNDS AS KINASE INHIBITORS

This application claims priority to U.S. Provisional Application No. 60/125,945, filed on Mar. 24, 1999, entitled "3-Arylidenyl-6-Heterocyclyl-2-indolinones as Modulators of Protein Kinase Activity," U.S. Provisional Application No. 60/127,863, filed on Apr. 5, 1999, entitled "3-Aralkyl-2-Indolinone Derivatives as Modulators of Protein Kinase Activity," U.S. Provisional Application No. 60/131,192, filed on Apr. 26, 1999, entitled "Diaryl Indolinone Compounds as Kinase Inhibitors," and U.S. Provisional No. 60/132,243, filed on May 3, 1999.

BACKGROUND OF THE INVENTION

The following description of the background of the invention is provided to aid in understanding the invention, but is not admitted to describe or constitute prior art to the invention.

Protein kinases ("PKs") are enzymes that catalyze the phosphorylation of hydroxy groups on tyrosine, serine and threonine residues of proteins. The consequences of this seemingly simple activity are staggering. Cell growth, differentiation and proliferation, i.e., virtually all aspects of cell life, in one way or another depend on PK activity. Furthermore, abnormal PK activity has been related to a host of disorders, ranging from relatively non-life-threatening diseases such as psoriasis to extremely virulent diseases such as glioblastoma (brain cancer).

The PKs can conveniently be broken down into two classes, the protein tyrosine kinases (PTKs) and the serine-threonine kinases (STKs).

One of the prime aspects of PK activity is involvement with growth factor receptors. Growth factor receptors are cell-surface proteins. When bound by a growth factor ligand, growth factor receptors are converted to an active form that can interact with proteins on the inner surface of a cell membrane. This interaction leads to phosphorylation on tyrosine residues of the receptor as well as other amino acids and to the formation inside the cell of complexes with a variety of cytoplasmic signaling molecules. In turn, these complexes affect numerous cellular responses such as cell division (proliferation), cell differentiation, cell growth, expression of metabolic effects on the extracellular microenvironment, etc. For a more complete discussion, see Schlessinger and Ullrich, *Neuron*, 1992, 9:303–391 which is incorporated by reference, including any drawings, as if fully set forth herein.

Receptor tyrosine kinases (RTKs) are growth factor receptors with PK activity. They comprise a large family of transmembrane receptors with diverse biological activity. At present, at least nineteen (19) distinct subfamilies of RTKs have been identified. An example of these is the subfamily designated the "HER" RTKs, which includes EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer composed of two entirely extracellular glycosylated α subunits and two β subunits which contain the tyrosine kinase domain.

A third RTK subfamily is referred to as the platelet derived growth factor receptor ("PDGFR") group, which includes PDGFRα, PDGFRβ, CSFIR, c-kit and c-fms. These receptors consist of a glycosylated extracellular domain composed of variable numbers of immunoglobin-like loops, a transmembrane domain and an intracellular domain having a tyrosine kinase domain interrupted by unrelated amino acid sequences.

Another group which, because of its similarity to the PDGFR subfamily, is sometimes subsumed in the latter group, is the fetus liver kinase ("flk") receptor subfamily. This group is believed to be composed of kinase insert domain-receptor fetal liver kinase-1 (KDR/FLK-1), flk-1R, flk-4 and fms-like tyrosine kinase 1 (flt-1).

One further member of the tyrosine kinase growth factor receptor family is the fibroblast growth factor ("FGF") receptor group. This group consists of four receptors, FGFR1–4, and seven ligands, FGF1–7. While not yet well characterized, it appears that the receptors also consist of a glycosylated extracellular domain containing a variable number of immunoglobin-like loops, a transmembrane domain and an intracellular domain in which the tyrosine kinase domain is interrupted by regions of unrelated amino acid sequences.

A more complete listing of the known RTK subfamilies is described in Plowman et al., *DN&P*, 1994, 7(6):334–339 which is incorporated by reference, including any drawings, as if fully set forth herein.

In addition to the RTKs, there also exists a family of entirely intracellular PTKs called "non-receptor tyrosine kinases" or "cellular tyrosine kinases" ("CTK"). CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appears so far to be the largest group of CTKs and includes Src, Yes, Fyn, Lyn, Lck, Blk, Hck, Fgr and Yrk. For a more detailed discussion of CTKs, see Bolen, *Oncogene*, 1993, 8:2025–2031, which is incorporated by reference, including any drawings, as if fully set forth herein.

The serine-threonine kinases or STKs, like the CTKs, are predominantly intracellular although there are a few STK receptor kinases. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, atherosclerosis, angiogenesis, restenosis, ocular diseases, rheumatoid arthritis and other inflammatory disorders, immunological disorders such as autoimmune disease, cardiovascular diseases such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth is the result of a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and a number of human disorders, it is no surprise that a great deal of effort is being spent to identify ways to modulate PK activity. Some of these efforts have been directed at biomimetic approaches using large molecules patterned on those involved in the actual cellular processes (e.g., mutant ligands (U.S. Pat. No. 4,966,849); soluble receptors and antibodies (App. No. WO 94/10202, Kendall and Thomas, *Proc. Nat'l Acad. Sci.*, 1994, 90:10705–09, Kim, et al., *Nature*, 1993, 362:841–844); RNA ligands (Jelinek, et al., *Biochemistry*, 33:10450–56); Takano, et al., *Mol. Bio. Cell*, 1993, 4:358A; Kinsella, et al., *Exp. Cell Res.*, 1992, 199:56–62; Wright, et al., *J. Cellular Phys.*, 152:448–57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.*, 1994, 35:2268).

More recently, attempts have been made to identify small molecules that act as PK inhibitors. For example, bis-monocylic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as PTK inhibitors. Styryl compounds (U.S. Pat. No. 5,217,999), styryl-substituted pyridyl compounds (U.S. Pat. No. 5,302,606), quinazoline derivatives (EP App. No. 0 566 266 A1), sel-enaindoles and selenides (PCT WO 94/03427), tricyclic polyhydroxylic compounds (PCT WO 92/21660) and ben-zylphosphonic acid compounds (PCT WO 91/15495) have all been described as PTK inhibitors useful in the treatment of cancer.

SUMMARY OF THE INVENTION

The present invention is directed in part towards indolinone compounds and methods of modulating the function of protein kinases with these compounds. The methods incorporate cells that express a protein kinase. In addition, the invention describes methods of preventing and treating protein kinases-related abnormal conditions in organisms with a compound identified by the methods described herein. Furthermore, the invention pertains to pharmaceutical compositions comprising compounds identified by methods of the invention.

The present invention features indolinone compounds that potently inhibit protein kinases and related products and methods. Inhibitors of protein kinases can be obtained by adding chemical substituents to an indolinone compound. The compounds of the invention represent a new generation of therapeutics for diseases associated with one or more functional or non-functional protein kinases. Neuro-degenerative diseases and certain types of cancer fall into this class of diseases. Other diseases or disorders include dermatologic, ophthalmic, nurologic, cardiovascular, and immune disorders as well as disorders associated with abnormal angiogenesis and/or vasculogenesis. The compounds can be modified such that they are specific to their target or targets and will subsequently cause few side effects and thus represent a new generation of potential cancer therapeutics. These properties are significant improvements over the currently utilized cancer therapeutics that cause multiple side effects and deleteriously weaken patients.

It is believed the compounds of the invention will minimize or obliterate solid tumors by inhibiting the activity of the protein kinases, or will at least modulate or inhibit tumor growth and/or metastases. Protein kinases regulate proliferation of blood vessels during angiogenesis, among other functions. Increased rates of angiogenesis accompany cancer tumor growth in cells as cancer tumors must be nourished by oxygenated blood during growth. Therefore, inhibition of the protein kinase and the corresponding decreases in angiogenesis will starve tumors of nutrients and most likely obliterate them.

While a precise understanding of the mechanism by which compounds inhibit PTKs (e.g., the fibroblast growth factor receptor 1 [FGFR 1]) is not required in order to practice the present invention, the compounds are believed to interact with the amino acids of the PTKs' catalytic region. PTKs typically possess a bi-lobate structure, and ATP appears to bind in the cleft between the two lobes in a region where the amino acids are conserved among PTKs; inhibitors of PTKs are believed to bind to the PTKs through non-covalent interactions such as hydrogen bonding, Van der Waals interactions, and ionic bonding, in the same general region that ATP binds to the PTKs. More specifically, it is thought that the oxindole component of the compounds of the present invention binds in the same general space occupied by the adenine ring of ATP. Specificity of a PTK inhibitor for a particular PTK may be conferred by interactions between the constituents around the oxindole core with amino acid domains specific to individual PKs. Thus, different substitutents may contribute to preferential binding to particular PKs. The ability to select those compounds active at different ATP binding sites makes them useful in targeting any protein with such a site, including not only protein tyrosine kinases, but also serine/threonine kinases. Thus, such compounds have utility for in vitro assays on such proteins and for in vivo therapeutic effect through such proteins.

Usually, indolinone compounds that are synthesized by the condensation of an oxindole compound and a ketone compound display a mixture of the possible E and Z isomers, making the isolation of the isomer of choice difficult. The compounds of the present invention feature an intermolecular hydrogen bond between the carbonyl of the oxindole compound and the hydrogen of the 1 position of the pyrrole moiety of the ketone compounds. Said hydrogen bond eliminates the problem of having a mixture of isomers by locking the intermediates in the synthesis of the indolinone compounds in the preferred conformation.

I. DEFINITIONS

The term "compound" refers to the compound or a pharmaceutically acceptable salt, ester, amide, prodrug, isomer, or metabolite, thereof.

The term "pharmaceutically acceptable salt" refers to a formulation of a compound that does not abrogate the biological activity and properties of the compound. Pharmaceutical salts can be obtained by reacting a compound of the invention with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water solubility is beneficial. A fruther example of a prodrug might be a short peptide (polyaminoacid) bonded to an acid group wherein the peptide is metabolized to reveal the active moiety.

The term "indolinone" is used as that term is commonly understood in the art and includes a large subclass of substituted or unsubstituted compounds that are capable of being synthesized from an aldehyde moiety and an oxindole moiety.

The term "oxindole" refers to an oxindole compound substituted with chemical substituents. Oxindole compounds are of the general structure:

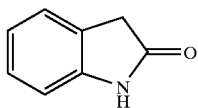

As used herein a "fused pyrrolo" group refers to the structure in brackets:

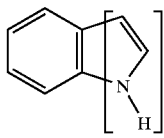

The term "substituted", in reference to the invention, refers to an oxindole compound that is derivatized with any number of chemical substituents.

As used herein, the term "alkyl" refers to an aliphatic hydrocarbon group. The alkyl moiety may be a "saturated alkyl" group, which means that it does not contain any alkene or alkyne moieties. The alkyl moiety may also an be "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a groupconsisting of at least two carbon atoms and at least one carbon-carbon triple bond. The alkyl moiety, whether saturated or unsaturated, may be branched, non-branched, or cyclic.

Preferably, the alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is(are) preferably one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl and amino, including mono- and di-substituted amino groups.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "aliphatic ring" refers to a compound which contains one or more covalently closed ring structures, and that at least one of the atoms forming the backbone is a saturated carbon atom (e.g., cyclohexane). The term "heteroaliphatic ring" refers to a ring system in which at least one of the atoms forming the backbone is a heteroatom (e.g., tetrahydropyran).

The term "amine" refers to a chemical moiety of formula —$NR_1R_2$ where $R_1$ and $R_2$ are independently selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester moieties.

The term "imine" refers to a chemical moiety of formula —N=$R_1$ where $R_1$ is selected from the group consisting of hydrogen, saturated or unsaturated alkyl, and aryl or heteroaryl ring moieties (monocyclic or bicyclic), where the ring is optionally substituted with one or more substituents independently selected from the group consisting of alkyl, halogen, trihalomethyl, carboxylate, nitro, and ester moieties.

The term "halogen" or "halo" refers to an atom selected from the group consisting of fluorine, chlorine, bromine, and iodine. The term "trihalomethyl" refers to the —$CX_3$ group, where X is a halogen.

The term "carboxylic acid" refers to a chemical moiety with formula —$(R)_n$—COOH, where R is selected from the group consisting of of alkyl, cycloalkyl, aryl, heteroaryl (bonded through a ring carbon) and heteroalicyclic (bonded through a ring carbon), as those terms are defined herein, and where n is 0 or 1.

The term "ester" refers to a chemical moiety with formula —$(R)_n$—COOR', where R and R' are independently selected from the group consisting of alkyl, cycloalkyl, aryl, heteroaryl (bonded through a ring carbon) and heteroalicyclic (bonded through a ring carbon), as those terms are defined herein, and where n is 0 or 1. As used herein, the term "carboxyalkyl" also falls within this definition.

The term "aldehyde" refers to a chemical moiety with formula —$(R)_n$—CHO, where R is as defined herein and where n is 0 or 1.

The term "sulfone" refers to a chemical moiety with formula —$SO_2$—R, where R is as defined herein.

The term "acyl" refers to chemical moieties of the general formula —C(O)R. When R is hydrogen the molecule containing the acyl group is an aldehyde. When R is selected from the group consisting of alkyl, cycloalkyl, aryl, heteroaryl (bonded through a ring carbon) and heteroalicyclic (bonded through a ring carbon), as those terms are defined herein, then the molecule containing the acyl group is a ketone.

A "thiocarbonyl" group refers to a —C(=S)—R group, where R is as defined herein.

An "O-carboxy" group refers to a RC(=O)O— group, where R is as defined herein.

A "C-carboxy" group refers to a —C(=O)OR groups where R is as defined herein.

An "acetyl" group refers to a —C(=O)CH$_3$ group.

A "trihalomethanesulfonyl" group refers to a X$_3$CS(=O)$_2$— group where X is a halogen.

A "cyano" group refers to a —C≡N group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR$_2$ group, with R as defined herein.

A "N-sulfonamido" group refers to a RS(=O)$_2$NH— group with R as defined herein.

A "trihalomethanesulfonamido" group refers to a X$_3$CS(=O)$_2$NR— group with X and R as defined herein.

An "O-carbamyl" group refers to a —OC(=O)—NR$_2$ group with R as defined herein.

An "N-carbamyl" group refers to a ROC(=O)NH— group, with R as defined herein.

An "O-thiocarbamyl" group refers to a —OC(=S)—NR$_2$ group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

By "combined," when referring to two adjacent "R" groups herein is meant that the two "R" groups are covalently bonded to each other so as to form a ring system. The ring system may be cycloalkyl, aryl, heteroaryl or heteroalicyclic.

A "combinatorial library" refers to all the compounds formed by the reaction of each compound of one dimension with a compound in each of the other dimensions in a multi-dimensional array of compounds. In the context of the present invention, the array is two dimensional and one dimension represents all the oxindoles of the invention and the second dimension represents all the aldehydes of the invention. Each oxindole may be reacted with each and every aldehyde in order to form an indolinone compound. All indolinone compounds formed in this way are within the scope of the present invention. Also within the scope of the present invention are smaller combinatorial libraries formed by the reaction of some of the oxindoles with all of the aldehydes, all of the oxindoles with some of the aldehydes, or some of the oxindoles with some of the aldehydes.

The term "pharmaceutical composition" refers to a mixture of a compound of the invention with other chemical components, such as diluents, excipients, or carriers. The pharmaceutical composition facilitates administration of the compound to an organism. Multiple techniques of administering a compound exist in the art including, but not limited to, oral, aerosol, parenteral, and topical administration. Pharmaceutical compositions can also be obtained by reacting compounds with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "physiologically acceptable" defines a carrier or diluent that does not abrogate the biological activity and properties of the compound.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "pharmaceutical composition" refers to a mixture of a compound of the invention with other chemical components, such as diluents, excipients, or carriers. The pharmaceutical composition facilitates administration of the compound to an organism. Multiple techniques of administering a compound exist in the art including, but not limited to, oral, aerosol, parenteral, and topical administration. Pharmaceutical compositions can also be obtained by reacting compounds with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "physiologically acceptable" defines a carrier or diluent that does not abrogate the biological activity and properties of the compound.

The term "function" refers to the cellular role of a protein kinase. The protein kinase family includes members that regulate many steps in signaling cascades, including cascades controlling cell growth, migration, differentiation, gene expression, muscle contraction, glucose metabolism, cellular protein synthesis, and regulation of the cell cycle.

The term "catalytic activity", in the context of the invention, defines the rate at which a protein kinase phosphorylates a substrate. Catalytic activity can be measured, for example, by determining the amount of a substrate converted to a product as a function of time. Phosphorylation of a substrate occurs at the active-site of a protein kinase. The active-site is normally a cavity in which the substrate binds to the protein kinase and is phosphorylated.

The term "substrate" as used herein refers to a molecule phosphorylated by a protein kinase. The substrate is preferably a peptide and more preferably a protein.

The term "activates" refers to increasing the cellular function of a protein kinase. The protein kinase function is preferably the interaction with a natural binding partner and most preferably catalytic activity.

The term "inhibit" refers to decreasing the cellular function of a protein kinase. The protein kinase function is preferably the interaction with a natural binding partner and most preferably catalytic activity.

The term "modulates" refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "complex" refers to an assembly of at least two molecules bound to one another. Signal transduction complexes often contain at least two protein molecules bound to one another.

The term "natural binding partner" refers to polypeptides that bind to a protein kinase in cells. Natural binding partners can play a role in propagating a signal in a protein kinase signal transduction process. A change in the interaction between a protein kinase and a natural binding partner can manifest itself as an increased or decreased probability that the interaction forms, or an increased or decreased concentration of the protein kinase/natural binding partner complex.

The term "contacting" as used herein refers to mixing a solution comprising a compound of the invention with a liquid medium bathing the cells of the methods. The solution comprising the compound may also comprise another component, such as dimethylsulfoxide (DMSO), which facilitates the uptake of the compound or compounds into the cells of the methods. The solution comprising the compound of the invention may be added to the medium bathing the cells by utilizing a delivery apparatus, such as a pipet-based device or syringe-based device.

The term "monitoring" refers to observing the effect of adding the compound to the cells of the method. The effect can be manifested in a change in cell phenotype, cell proliferation, protein kinase catalytic activity, or in the interaction between a protein kinase and a natural binding partner.

The term "effect" describes a change or an absence of a change in cell phenotype or cell proliferation. "Effect" can also describe a change or an absence of a change in the catalytic activity of the protein kinase. "Effect" can also describe a change or an absence of a change in an interaction between the protein kinase and a natural binding partner.

The term "cell phenotype" refers to the outward appearance of a cell or tissue or the function of the cell or tissue. Examples of cell phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Changes or the absence of changes in cell phenotype are readily measured by techniques known in the art.

The term "antibody" refers to an antibody (e.g., a monoclonal or polyclonal antibody), or antibody fragment, having specific binding affinity to protein kinase or its fragment.

By "specific binding affinity" is meant that the antibody binds to target (protein kinase) polypeptides with greater affinity than it binds to other polypeptides under specified conditions. Antibodies having specific binding affinity to a protein kinase may be used in methods for detecting the presence and/or amount of a protein kinase in a sample by contacting the sample with the antibody under conditions such that an immunocomplex forms and detecting the presence and/or amount of the antibody conjugated to the protein kinase. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., Nature 256:495–497 (1975), and U.S. Pat. No. 4,376, 110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

The term "aberration", in conjunction with a signal transduction process, refers to a protein kinase that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "promoting or disrupting the abnormal interaction" refers to a method that can be accomplished by administering a compound of the invention to cells or tissues in an organism. A compound can promote an interaction between a protein kinase and natural binding partners by forming favorable interactions with multiple atoms at the complex interface. Alternatively, a compound can inhibit an interaction between a protein kinase and natural binding partners by compromising favorable interactions formed between atoms at the complex interface.

"In vitro" refers to procedures performed in an artificial environment, such as, without limitation, in a test tube, in a cell, or culture medium. As used herein, "in vivo" refers to procedures performed within a living organism such as, without limitation, a mouse, rat, or rabbit.

II. COMPOUNDS OF THE INVENTION

A. 3-Arylidenyl-6-heterocyclyl-2-indolinone Derivatives

In one aspect, the present invention relates to 3-arylidenyl-6-heterocyclyl-2-indolinone derivatives having the chemical structure set forth in formula I:

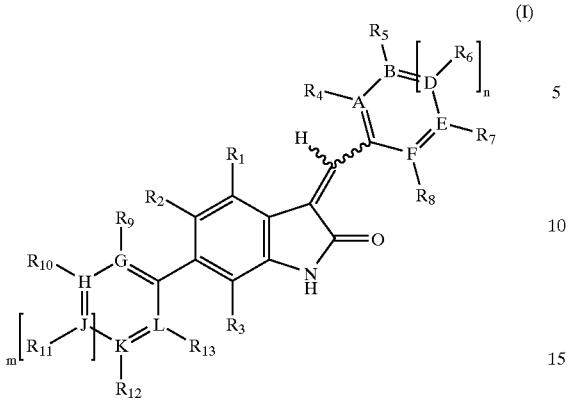

(I)

or a salt or prodrug thereof where n and m are independently 0 or 1.

When n is 1, then A, B, D, E and F are independently selected from the group consisting of carbon and nitrogen; however, no more than three of A, B, D, E and F are nitrogen at the same time and, when A, B, D, E, or F is nitrogen, then $R_4$, $R_5$, $R_6$, $R_7$ or $R_8$, respectively, does not exist.

When m is 1, then G, H, J, K and L are independently selected from the group consisting of carbon and nitrogen; however, at least one and no more than three of G, H, J, K and L are nitrogen at the same time and, when G, H, J, K or L is nitrogen, then $R_9$, $R_{10}$, $R_{11}$, $R_{12}$ or $R_{13}$, respectively, does not exist.

When n is 0, then A is selected from the group consisting of carbon and nitrogen, B and F are selected from the group consisting of carbon, nitrogen, NH, oxygen and sulfur, provided that when B or F is NH, the other cannot be NH, and E is selected from the group consisting of carbon, nitrogen, oxygen and sulfur, further provided that no more than one of B, E or F is oxygen or sulfur and provided also that at least one of A, B, E or F is a heteroatom (i.e., not carbon).

When m is 0, then G is selected from the group consisting of carbon and nitrogen, H, K and L are selected from the group consisting of carbon, nitrogen, NH, oxygen and sulfur, provided that when H or L is NH, the other cannot be NH, and K is selected from the group consisting of carbon, nitrogen, oxygen and sulfur, further provided that no more than one of H, K or L is oxygen or sulfur and provided also that at least one of G, H, K or L is a heteroatom (i.e., not carbon).

$R_1$, $R_2$, $R_3$, $R_4$, $R_5$, $R_6$, $R_7$, $R_8$, $R_9$, $R_{10}$, $R_{11}$, $R_{12}$ and $R_{13}$ are independently selected from the group consisting of hydrogen, alkyl, trihaloalkyl, cycloalkyl, alkenyl, alkynyl, aryl, heteroaryl, heteroalicyclic, hydroxy, alkoxy, mercapto, alkylthio, aryloxy, arylthio, sulfinyl, sulfonyl, S-sulfonamido, N-sulfonamido, carbonyl, C-carboxy, O-carboxy, carboxyalkyl, cyano, nitro, halo, O-carbamyl, N-carbamyl, C-amido, N-amido and —$NR_{14}R_{15}$.

$R_4$ and $R_5$ or $R_5$ and $R_6$ or $R_6$ and $R_7$ or $R_7$ and $R_8$ may combine to form a five-member or a six-member aryl or heteroaryl ring.

$R_{14}$ and $R_{15}$ are independently selected from the group consisting of hydrogen, alkyl, cycloalkyl, alkenyl, alkynyl, aryl, heteroaryl, carbonyl, sulfonyl, and, combined, a five-member or a six-member heteroalicyclic ring.

A presently preferred embodiment of this invention is a compound of formula I wherein, $R_1$, $R_2$ and $R_3$ are independently selected from the group consisting of (i) hydrogen, (ii) lower alkyl optionally substituted with one or more halo groups, (iii) lower alkoxy optionally substituted with one or more halo groups, (iv) (lower alkyl)-S-sulfonamido, (v) aryl-S-sulfonamido, (vi) halo, and (vii) —$NR_{14}R_{15}$; and, $R_4$, $R_5$, $R_6$, $R_7$, $R_8$, $R_9$, $R_{10}$, $R_{11}$, $R_{12}$, and $R_{13}$ are independently selected from the group consisting of (i) hydrogen; (ii) lower alkyl, optionally substituted with one or more groups selected from the group consisting of aryl, heteroaryl, heteroalicyclic, halo, hydroxy, lower alkoxy, mercapto, lower alkylthio, C-carboxy and —$NR_{14}R_{15}$; (iii) cycloalkyl; (iv) hydroxy; (v) lower alkoxy, optionally substituted with one or more groups selected from the group consisting of one or more halo groups, aryl, heteroaryl and heteroalicyclic; (vi) halo; (vii) carboxyalkyl; (viii) aryl, optionally substituted with one or more groups selected from the group consisting of lower alkyl optionally substituted one or more halo groups, halo, hydroxy, lower alkoxy optionally substituted with one or more halo groups, aryloxy and —$NR_{14}R_{15}$; (ix) aryloxy, optionally substituted with one or more groups selected from the group consisitng of lower alkyl optionally substituted with one or more halo groups, halo, hydroxy, lower alkoxy optionally substituted with one or more halo groups, aryloxy and —$NR_{14}R_{15}$; (x) heteroaryl, optionally substituted with one or more groups selected from the group consisting of lower alkyl optionally substituted with one or more halo groups, halo, hydroxy,. lower alkoxy optionally substituted with one or more halo groups and —$NR_{14}R_{15}$; (xi) heteroalicyclic; (xii) (lower alkyl)-C-carboxy; (xiii) (lower alkyl)carbonyl; (xiv) aryl carbonyl; (xv) (lower alkyl)-S-sulfonamido; (xvi) aryl-S-sulfonamido; (xvii) (lower alkyl)-N-sulfonamido; (xviii) aryl-N-sulfonamido; (xix) (lower alkyl)-N-carbamoyl; (xx) (lower alkyl)-C-amido; (xxi) (lower alkyl)-N-amido; (xxii) (cycloalkyl)-N-amido; and, (xxiii) —$NR_{14}R_{15}$; and $R_{14}$ and $R_{15}$ are independently selected from the group consisting of hydrogen and lower alkyl.

Another presently preferred embodiment of this invention is a compound of formula I in which n is 1; A, B, D, E and F are carbon, m is 1 and one of G, H, J, K and L is nitrogen.

It is also a presently preferred embodiment of this invention that, in a compound of formula I, n is 1; A, B, D, E and F are carbon, m is 0, G, H and K are carbon, and L is NH, oxygen or sulfur.

A still further preferred embodiment of this invention is a compound of formula I in which n is 0; A, B and E are carbon; F is NH; $R_4$ and $R_7$ are independently selected from the group consisting of hydrogen and lower alkyl; $R_5$ is selected from the group consisting of (i) lower alkyl optionally substituted with one or more groups selected from the group consisting of, hydroxy, heteroaromatic containing an NH group in the ring, heteroalicyclic containing at least one NH group in the ring, C-carboxy, and, —$NR_{14}R_{15}$; (ii) carboxyalkyl; (iii) C-carboxy; and, (iv) —$NR_{14}R_{15}$, wherein $R_{14}$ and $R_{15}$ are independently selected from the group consisting of hydrogen, lower alkyl and carbonyl; m is 1; and, one of G, H, I, J, K or L is nitrogen.

It is likewise a presently preferred embodiment of this invention that, in a compound of formula I, n is 0; A, B and E are carbon; F is NH; $R_4$ and $R_7$ are independently selected from the group consisting of hydrogen and lower alkyl; $R^5$ is selected from the group consisting of (i) lower alkyl optionally substituted with one or more groups selected from the group consisting of, hydroxy, heteroaromatic containing an NH in the ring, heteroalicyclic containing at least one NH group in the ring, C-carboxy, and, —NR$_{14}$R$_{15}$; (ii) carboxyalkyl; (iii) C-carboxy; and, (iv) —NR$_{14}$R$_{15}$, wherein R$_{14}$ and R$_{15}$ are independently selected from the group consisting of hydrogen, lower alkyl and carbonyl; m is 0; G, H and K are carbon; and, L is NH, oxygen or sulfur.

B. 3-Aralkyl-2-indolinone Derivatives

In another aspect, the present invention relates to 3-aralkyl-2-indolinone derivatives having the chemical structure set forth in formula II:

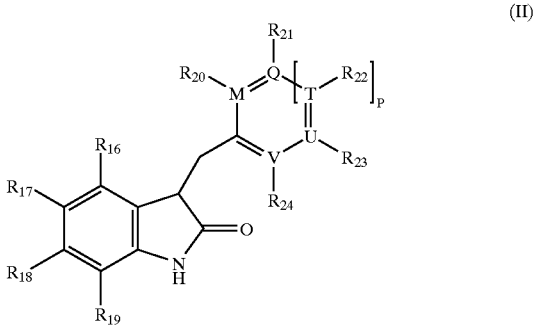

or a physiologically acceptable salt or prodrug thereof where P is 0 or 1.

When p is 1, then M, Q, T, U and V are independently selected from the group consisting of carbon and nitrogen, it being understood that, when M, Q, T, U, or V is nitrogen, R$_{20}$, R$_{21}$, R$_{22}$, R$_{23}$, or R$_{24}$, respectively, do not exist.

When p is 0, then M, Q, U, and V are independently selected from the group consisting of carbon, nitrogen, oxygen and sulfur, it being understood that, when M, Q, U, or V is oxygen or sulfur or nitrogen (wherein said nitrogen is participating in a double bond), R$_{20}$, R$_{21}$, R$_{22}$, R$_{23}$, or R$_{24}$, respectively, do not exist.

R$_{16}$, R$_{17}$, R$_{18}$, R$_{19}$, R$_{20}$, R$_{21}$, R$_{22}$, R$_{23}$, or R$_{24}$ are independently selected from the group consisting of hydrogen, alkyl, trihaloalkyl, cycloalkyl, alkenyl, alkynyl, aryl, heteroaryl, heteroalicyclic, hydroxy, alkoxy, mercapto, alkylthio, aryloxy, sulfinyl, sulfonyl, S-sulfonamido, N-sulfonamido, carbonyl, C-carboxy, O-carboxy, carboxyalkyl, cyano, nitro, halo, O-carbamyl, N-carbamyl, C-amido, N-amido and —NR$_{25}$R$_{26}$.

R$_{20}$ and R$_{21}$ or R$_{21}$ and R$_{22}$ or R$_{23}$ and R$_{23}$ or R$_{23}$ and R$_{24}$ may combine to form a five-member or a six-member aryl or heteroaryl ring.

R$_{25}$ and R$_{26}$ are independently selected from the group consisting of hydrogen, alkyl, cycloalkyl, alkenyl, alkynyl, aryl, heteroaryl, carbonyl, sulfonyl, and, combined, a five-member or a six-member heteroalicyclic ring.

A presently preferred embodiment of this invention is a compound wherein R$_{16}$, R$_{17}$, R$_{18}$, R$_{19}$, R$_{20}$, R$_{21}$, R$_{22}$, R$_{23}$, and R$_{24}$ are independently selected from the group consisting of (i) hydrogen; (ii) lower alkyl, optionally substituted with one or more groups selected from the group consisting of cycloalkyl, aryl, heteroaryl, heteroalicyclic, halo, hydroxy, C-carboxy and —NR$_{25}$R$_{26}$; (iii) cycloalkyl; (iv) hydroxy; (v) lower alkoxy,optionally substituted with one or more groups selected from the group consisting of one or more halo groups, aryl, heteroaryl and heteroalicyclic; (vi) trihalomethyl; (vii) trihalomethoxy; (viii) halo; (ix) carboxyalkyl; (x) aryl,optionally substituted with one or more groups selected from the group consisting of lower alkyl, lower alkyl substituted with one or more halo groups, trihalomethyl, trihalomethoxy, halo, hydroxy, lower alkoxy, aryloxy and —NR$_{25}$R$_{26}$; (xi) aryloxy; heteroaryl, optionally substituted with one or more groups selected from the group consisting of lower alkyl, trihalomethyl, halo, hydroxy, (lower alkyl)alkoxy, amino and —NR$_{25}$R$_{26}$; (xii) heteroalicyclic; (xiii) (lower alkyl)carboxy; (xiv) (lower alkyl) carbonyl; (xv) aryl carbonyl; (xvi) (lower alkyl)-S-sulfonamido; (xvii) aryl-S-sulfonamido; (xviii) (lower alkyl)-N-sulfonamido; (xix) aryl-N-sulfonamido; (xx) (lower alkyl)-N-carbamoyl; (xxi) (lower alkyl)-C-amido; (xxii) (lower alkyl)-N-amido; (xxiii) (cycloalkyl)-N-amido; and, (xxiv) —NR$_{25}$R$_{26}$.

Another presently preferred embodiment of this invention is a compound wherein p is 1 and M, Q, T, U, and V are carbon.

It is a further presently preferred embodiment of this invention that, when p is 1 and M, Q, T, U, and V are carbon; R$_{16}$, R$_{17}$, R$_{18}$, and R$_{19}$ are independently selected from the group consisting of (i) hydrogen; (ii) halo; (iii) hydroxy; (iv) —NR$_{25}$R$_{26}$; (v) S-sulfonamido optionally substituted with one or more groups selected from the group consisting of hydrogen, lower alkyl and aryl; (vi) lower alkyl optionally substituted with a group selected from the group consisting of hydroxy, one or more halo groups, C-carboxy, C-amido, heteroalicyclic, and —NR$_{25}$R$_{26}$; (vii) lower alkoxy optionally substituted with one or more halo groups; (viii) aryl optionally substituted with one or more groups selected from the group consisting of lower alkyl, lower alkoxy, halo, hydroxy and —NR$_{25}$R$_{26}$; (ix) N-amido optionally substituted with one or more groups selected from the group consisting of hydrogen, lower alkyl, cycloalkyl and aryl; and R$_{20}$, R$_{21}$, R$_{22}$, R$_{23}$, and R$_{24}$ are independently selected from the group consisting of (i) hydrogen; (ii) halo; (iii) hydroxy; (iv) —NR$_{25}$R$_{26}$; (v) lower alkyl optionally substituted with one or more groups selected from the group consisting of hydroxy, one or more halo groups, C-carboxy, C-amido, heteroalicyclic, and —NR$_{25}$R$_{26}$; (vi) cycloalkyl; (vii) lower alkoxy optionally substituted with one or more groups selected from the group consisting of one or more halo groups, aryl, —NR$_{25}$R$_{26}$, and heteroaryl, (viii) aryl optionally substituted with one or more groups selected from the group consisting of halo, hydroxy, lower alkoxy, —NR$_{25}$R$_{26}$, and C-carboxy.

It is yet another presently preferred embodiment of this invention that p is 1 and one or two of M, Q, T, U, or V are nitrogen.

It is likewise presently preferred that, when p is 1 and one or two of, Q, T, U, and V are nitrogen, R$_{16}$, R$_{17}$, R$_{18}$, and R$_{19}$ are independently selected from the group consisting of (i) hydrogen; (ii) halo; (iii) hydroxy; (iv) —NR$_{25}$R$_{26}$; (v) S-sulfonamido optionally substituted with one or more groups selected from the group consisting of hydrogen, lower alkyl and aryl; (vi) lower alkyl optionally substituted with a group selected from the group consisting of hydroxy, one or more halo groups, C-carboxy, C-amido, heteroalicyclic, and —NR$_{25}$R$_{26}$; (vii) lower alkoxy optionally substituted with one or more halo groups; (viii) aryl optionally substituted with one or more groups selected from the group consisting of lower alkyl, lower alkoxy, halo, hydroxy and —NR$_{25}$R$_{26}$; (ix) N-amido optionally substituted with one or more groups selected from the group consisting of hydrogen, lower alkyl, cycloalkyl and aryl; and, R$_{20}$, R$_{21}$, R$_{22}$, R$_{23}$, and R$_{24}$, whichever of these are not nitrogen, are independently selected from the group consisting of (i) hydrogen; (ii) halo; (iii) hydroxy; (iv) —NR$_{25}$R$_{26}$; (v) lower alkyl optionally substituted with one or more groups selected from the group consisting of hydroxy, one or more halo groups, C-carboxy, C-amido, heteroalicyclic, and —NR$_{25}$R$_{26}$; (vi) cycloalkyl; (vii) lower alkoxy optionally substituted with one or more groups selected from the group consisting of one or more halo groups, aryl, —NR$_{25}$R$_{26}$, and heteroaryl; and (viii) aryl optionally substituted with one or more groups selected from the group consisting of halo, hydroxy, lower alkoxy, —NR$_{25}$R$_{26}$, and C-carboxy.

It is a presently preferred embodiment of this invention that p is 1 and R$_{21}$, and R$_{22}$ combine to form a fused pyrrolo group.

In further preferred embodiments of the invention, R$_{16}$, R$_{17}$, R$_{18}$, and R$_{19}$ are independently selected from the group consisting of (i) hydrogen; (ii) halo; (iii) hydroxy; (iv) —NR$_{25}$R$_{26}$; (v) S-sulfonamido optionally substituted with one or more groups selected from the group consisting of hydrogen, lower alkyl and aryl; (vi) lower alkyl optionally substituted with a group selected from the group consisting of hydroxy, one or more halo groups, C-carboxy, C-amido, heteroalicyclic and, —NR$_{25}$R$_{26}$; (vii) lower alkoxy optionally substituted with one or more halo groups; (viii) aryl optionally substituted with one or more groups selected from the group consisting of lower alkyl, lower alkoxy, halo, hydroxy and —NR$_{25}$R$_{26}$; (ix) N-amido optionally substituted with one or more groups selected from the group consisting of hydrogen, lower alkyl, cycloalkyl and aryl.

Similarly it is preferred that R$_{20}$, R$_{23}$, and R$_{24}$ are independently selected from the group consisting of (i) hydrogen; (ii) halo; (iii) hydroxy; (iv) —NR$_{25}$R$_{26}$; (v) lower alkyl optionally substituted with one or more groups selected from the group consisting of hydroxy, one or more halo groups, C-carboxy, C-amido, heteroalicyclic and, —NR$_{25}$R$_{26}$; (vi) cycloalkyl; (vii) lower alkoxy optionally substituted with one or more groups selected from the group consisting of one or more halo groups, aryl, —NR$_{25}$R$_{26}$ and, heteroaryl; (viii) aryl optionally substituted with one or more groups selected from the group consisting of halo, hydroxy, lower alkoxy, —NR$_{25}$R$_{26}$ and, C-carboxy.

In another preferred embodiment, p is 0, M or Q is —NH, oxygen or sulfur; and, M or Q, whichever is not —NH, oxygen or sulfur, and U and V are carbon.

Other preferred embodiments include compounds in which R$_{16}$, R$_{17}$, R$_{18}$, and R$_{19}$ are independently selected from the group consisting of (i) hydrogen; (ii) halo; (iii) hydroxy; (iv) —NR$_{25}$R$_{26}$; (v) S-sulfonamido optionally substituted with one or more groups selected from the group consisting of hydrogen, lower alkyl and aryl; (vi) lower alkyl optionally substituted with a group selected from the group consisting of hydroxy, one or more halo groups, C-carboxy, C-amido, heteroalicyclic and, —NR$_{25}$R$_{26}$; (vii) lower alkoxy optionally substituted with one or more halo groups; (viii) aryl optionally substituted with one or more groups selected from the group consisting of lower alkyl, lower alkoxy, halo, hydroxy and —NR$_{25}$R$_{26}$; (ix) N-amido optionally substituted with one or more groups selected from hydrogen, lower alkyl, cycloalkyl and aryl.

In these preferred compounds R$_{20}$, R$_{21}$, R$_{23}$, and R$_{24}$ are independently selected from the group consisting of (i) hydrogen; (ii) halo; (iii) hydroxy; (iv) —NR$_{25}$R$_{26}$; (v) lower alkyl optionally substituted with one or more groups selected from the group consisting of hydroxy, one or more halo groups, C-carboxy, C-amido, heteroalicyclic and, —NR$_{25}$R$_{26}$; (vi) cycloalkyl; (vii) lower alkoxy optionally substituted with one or more groups selected from the group consisting of one or more halo groups, aryl, —NR$_{25}$R$_{26}$, and, heteroaryl.

In still further preferred embodiments, R$_{16}$, R$_{17}$, R$_{18}$, and R$_{19}$ are independently selected from the group consisting of (i) hydrogen; (ii) halo; (iii) hydroxy; (iv) —NR$_{25}$R$_{26}$; (v) S-sulfonamido optionally substituted with one or more groups selected from the group consisting of hydrogen, lower alkyl and aryl; (vi) lower alkyl optionally substituted with a group selected from the group consisting of hydroxy, one or more halo groups, C-carboxy, C-amido, heteroalicyclic and, —NR$_{25}$R$_{26}$; (vii) lower alkoxy optionally substituted with one or more halo groups; (viii) aryl optionally substituted with one or more groups selected from the group consisting of lower alkyl, lower alkoxy, halo, hydroxy and —NR$_{25}$R$_{26}$; (ix) N-amido optionally substituted with one or more groups selected from hydrogen, lower alkyl, cycloalkyl and aryl.

Preferably, R$_{20}$, R$_{23}$, and R$_{24}$ are independently selected from the group consisting of (i) hydrogen; (ii) halo; (iii) hydroxy; (iv) —NR$_{25}$R$_{26}$; (v) lower alkyl optionally substituted with one or more groups selected from the group consisting of hydroxy, one or more halo groups, C-carboxy, C-amido, heteroalicyclic and, —NR$_{25}$R$_{26}$; (vi) cycloalkyl; (vii) lower alkoxy optionally substituted with one or more groups selected from the group consisting of one or more halo groups, aryl, —NR$_{25}$R$_{26}$ and, heteroaryl; (viii) aryl optionally substituted with one or more groups selected from the group consisting of halo, hydroxy, lower alkoxy, —NR$_{25}$R$_{26}$ and, C-carboxy.

C. Diaryl Indolinone Compounds

In another aspect, the invention provides a compound having a structure set forth in formula III

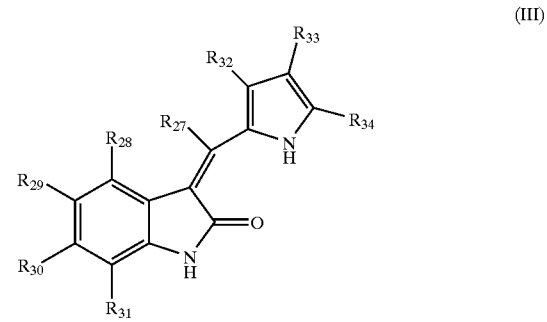

(III)

where
  (a) is selected from the group consisting of
(i) saturated or unsaturated alkyl optionally substituted with substituents selected from the group consisting of halogen, trihalomethyl, alkoxy, carboxylate, amino, nitro, ester, and a five-membered or six-membered aromatic, heteroaromatic, aliphatic, or heteroaliphatic ring moiety, where the ring moiety is optionally substituted with one, two, or three substituents independently selected from the group consisting of alkyl, halogen, trihalomethyl, carboxylate, amino, nitro, and ester moieties; and
(ii) an aromatic or heteroaromatic ring optionally substituted with one, two, or three substituents independently selected from the group consisting of alkyl, alkoxy, halogen, trihalomethyl, carboxylate, amino, nitro, and ester moieties;
(iii) an aliphatic or heteroaliphatic ring optionally substituted with one or more substituents independently selected from the group consisting of alkyl, alkoxy, halogen, trihalomethyl, carboxylate, amino, nitro, ester, and an aromatic or heteroaromatic ring optionally substituted with one or more substituents independently selected from the group consisting of alkyl, alkoxy, halogen, trihalomethyl, carboxylate, amino, nitro, and ester moieties;

(b) $R_{32}$, $R_{33}$, and $R_{34}$ are each independently selected from the group consisting of
(i) hydrogen;
(ii) saturated or unsaturated alkyl optionally substituted with one or more substituents selected from the group consisting of halogen, trihalomethyl, carboxylate, amino, nitro, ester, and a five-membered or six-membered aromatic, heteroaromatic, aliphatic, or heteroaliphatic ring moiety, where the ring moiety is optionally substituted with one or more substituents independently selected from the group consisting of alkyl, halogen, trihalomethyl, carboxylate, amino, nitro, and ester moieties;
(iii) an aromatic or heteroaromatic ring optionally substituted with one or more substituents independently selected from the group consisting of alkyl, alkoxy, halogen, trihalomethyl, carboxylate, amino, nitro, and ester moieties;
(iv) an aliphatic or heteroaliphatic ring optionally substituted with one or more substituents independently selected from the group consisting of alkyl, alkoxy, halogen, trihalomethyl, carboxylate, amino, nitro, ester, and an aromatic or heteroaromatic ring optionally substituted with one or more substituents independently selected from the group consisting of alkyl, alkoxy, halogen, trihalomethyl, carboxylate, amino, nitro, and ester moieties;
(v) an amine of formula $-(X_1)_{n1}-NX_2X_3$, where
$X_1$ is selected from the group consisting of saturated or unsaturated alkyl, and five-membered or six-membered aromatic, heteroaromatic, or aliphatic ring moieties,
n1 is 0 or 1, and
$X_2$ and $X_3$ are independently selected from the group consisting of hydrogen, saturated or unsaturated alkyl, and five-membered or six-membered aromatic, heteroaromatic, or aliphatic ring moieties;
(vi) a nitro of formula $-NO_2$;
(vii) a halogen or trihalomethyl;
(viii) a ketone of formula $-(X_4)_{n4}-CO-X_5$, where
$X_4$ and $X_5$ are independently selected from the group consisting of alkyl and five-membered or six-membered aromatic, heteroaromatic, aliphatic, or heteroaliphatic ring moieties,
the alkyl and ring moieties are optionally substituted with one, two, or three substituents independently selected from the group consisting of alkyl, halogen, trihalomethyl, carboxylate, amino, nitro, and ester moieties and where, and
n4 is 0 or 1;
(ix) a carboxylic acid of formula $-(X_6)_{n6}-COOH$ or ester of formula $-(X_7)_{n7}-COO-X_8$, where
$X_6$, $X_7$, and $X_8$ and are independently selected from the group consisting of alkyl and five-membered or six-membered aromatic, heteroaromatic, aliphatic, or heteroaliphatic ring moieties, and
n6 and n7 are independently 0 or 1;
(x) an alcohol of formula $-(X_9)_{n9}-OH$ or an alkoxyalkyl moiety of formula $-(X_{10})_{n10}-O-X_{11}$, where
$X_9$, $X_{10}$, and $X_{11}$ are independently selected from the group consisting of saturated or unsaturated alkyl, and five-membered or six-membered aromatic, heteroaromatic, aliphatic, or heteroaliphatic ring moieties,
the alkyl and ring moieties are optionally substituted with one or more substituents independently selected from the group consisting of alkyl, halogen, trihalomethyl, carboxylate, amino, nitro, and ester, and
n9 and n10 are independently 0 or 1;
(xi) an amide of formula $-(X_{12})_{n12}-NHCOX_{13}$, or of formula $-(X_{14})_{n14}-CONX_{15}X_{16}$, where
$X_{12}$ and $X_{14}$ are each independently selected from the group consisting of alkyl, hydroxyl, and five-membered or six-membered aromatic, heteroaromatic, aliphatic, or heteroaliphatic ring moieties,
the ring is optionally substituted with one or more substituents independently selected from the group consisting of alkyl, halogen, trihalomethyl, carboxylate, amino, nitro, and ester, and
n12 and n14 are independently 0 or 1,
$X_{13}$, $X_{15}$, and $X_{16}$ are each independently selected from the group consisting of hydrogen, alkyl, hydroxyl, and five-membered or six-membered aromatic, heteroaromatic, aliphatic, or heteroaliphatic ring moieties,
the ring is optionally substituted with one or more substituents independently selected from the group consisting of alkyl, halogen, trihalomethyl, carboxylate, amino, nitro, and ester;
(xii) a sulfonamide of formula $-(X_{17})n_{17}-SO_2NX_{18}X_{19}$, where
$X_{17}$ is selected from the group consisting of alkyl, and five-membered or six-membered aromatic, heteroaromatic, aliphatic, or heteroaliphatic ring moieties
the alkyl and ring moieties are optionally substituted with one or more substituents independently selected from the group consisting of alkyl, halogen, trihalomethyl, carboxylate, amino, nitro, and ester,
n17 is 0, 1, or 2,
$X_{18}$, and $X_{19}$ are independently selected from the group consisting of hydrogen, alkyl, and five-membered or six-membered aromatic, heteroaromatic, aliphatic, or heteroaliphatic ring moieties the alkyl and ring moieties are optionally substituted with one or more substituents independently selected from the group consisting of alkyl, halogen, trihalomethyl, carboxylate, amino, nitro, and ester, or
where $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, amino, nitro, and ester;
(xiii) an aldehyde of formula $-(X_{20})_{n20}-CO-H$ where
$X_{20}$ is selected from the group consisting of saturated or unsaturated alkyl, and five-membered or six-membered aromatic, heteroaromatic, aliphatic, or heteroaliphatic ring moieties,
the alkyl and ring moieties are optionally substituted with one or more substituents independently selected from the group consisting of alkyl, halogen, trihalomethyl, carboxylate, amino, nitro, and ester, and
n20 is 0 or 1;
(xiv) a sulfone of formula $-(X_{21})_{n21}-SO_2-X_{22}$, where
$X_{21}$ and $X_{22}$ are independently selected from the group consisting of saturated or unsaturated alkyl, and five-membered or six-membered aromatic, heteroaromatic, aliphatic, or heteroaliphatic ring moieties,
the alkyl and ring moieties are optionally substituted with one or more substituents independently selected from the group consisting of alkyl, halogen, trihalomethyl, carboxylate, amino, nitro, and ester, and
n21 is 0 or 1; and
(xv) a thiol of formula $-(X_{23})_{n23}-SH$ or a thioether of formula $-(X_{24})_{n24}-S-X_{25}$, where
$X_{23}$, $X_{24}$, and $X_{25}$ are independently selected from the group consisting of saturated or unsaturated alkyl, and five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, and n23 and n24 are independently 0 or 1; or $R_{33}$ and $R_{34}$ taken together form a six-membered aliphatic or aromatic ring, optionally substituted with one or more substituents independently selected from the group consisting of alkyl, halogen, trihalomethyl, carboxylate, amino, nitro, and ester; and (c) $R_{28}$, $R_{29}$, $R_{30}$, and $R_{31}$ are each independently selected from the group consisting of (i) hydrogen;

(ii) saturated or unsaturated alkyl optionally substituted with one or more substituents selected from the group consisting of hydroxy, halogen, trihalomethyl, carboxylate, amino, nitro, ester, and a five-membered or six-membered aromatic, heteroaromatic, aliphatic, or heteroaliphatic ring moiety, the ring moiety is optionally substituted with one or more substituents independently selected from the group consisting of alkyl, halogen, trihalomethyl, carboxylate, amino, nitro, and ester moieties;

(iii) an aromatic or heteroaromatic ring optionally substituted with one or more substituents independently selected from the group consisting of alkyl, alkoxy, halogen, trihalomethyl, carboxylate, amino, nitro, and ester moieties;

(iv) an aliphatic or heteroaliphatic ring optionally substituted with one or more substituents independently selected from the group consisting of alkyl, alkoxy, halogen, trihalomethyl, carboxylate, amino, nitro, ester, and an aromatic or heteroaromatic ring optionally substituted with one or more substituents independently selected from the group consisting of alkyl, alkoxy, halogen, trihalomethyl, carboxylate, amino, nitro, and ester moieties;

(v) an amine of formula —$(X_1)_{n1}$—$NX_2X_3$, where $X_1$ is selected from the group consisting of saturated or unsaturated alkyl, and five-membered or six-membered aromatic, heteroaromatic, or aliphatic ring moieties, n1 is 0 or 1, and $X_2$, and $X_3$ are independently selected from the group consisting of hydrogen, saturated or unsaturated alkyl, and five-membered or six-membered aromatic, heteroaromatic, or aliphatic ring moieties;

(vi) a nitro of formula —$NO_2$;

(vii) a halogen or trihalomethyl;

(viii) a ketone of formula —$(X_4)_{n4}$—CO—$X_5$, where $X_4$ and $X_5$ are independently selected from the group consisting of alkyl and five-membered or six-membered aromatic, heteroaromatic, aliphatic, or heteroaliphatic ring moieties, the alkyl and ring moieties are optionally substituted with one, two, or three substituents independently selected from the group consisting of alkyl, halogen, trihalomethyl, carboxylate, amino, nitro, and ester moieties, and n4 is 0 or 1;

(ix) a carboxylic acid of formula —$(X_6)_{n6}$—COOH or ester of formula —$(X_7)_{n7}$—COO—$X_8$, where $X_6$, $X_7$, and $X_8$ and are independently selected from the group consisting of alkyl and five-membered or six-membered aromatic, heteroaromatic, aliphatic, or heteroaliphatic ring moieties, and n6 and n7 are independently 0 or 1;

(x) an alcohol of formula —$(X_9)_{n9}$—OH or an alkoxyalkyl moiety of formula —$(X_{10})_{n10}$—O—$X_{11}$ where $X_9$, $X_{10}$, and $X_{11}$ are independently selected from the group consisting of saturated or unsaturated alkyl, and five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, and n9 and n10 are independently 0 or 1;

(xi) an amide of formula —$(X_{12})_{n2}$—$NHCOX_{13}$, or of formula —$(X_{14})_{n14}$—$CONX_{15}X_{16}$, where $X_{12}$ and $X_{14}$ are each independently selected from the group consisting of alkyl, hydroxyl, and five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, n12 and n14 are independently 0 or 1, and $X_{13}$, $X_{15}$, and $X_{16}$ are each independently selected from the group consisting of hydrogen, alkyl, hydroxyl, and five-membered or six-membered aromatic, heteroaromatic, aliphatic, or heteroaliphatic ring moieties, and the alkyl and ring moieties are optionally substituted with one or more substituents independently selected from the group consisting of alkyl, halogen, trihalomethyl, carboxylate, amino, nitro, and ester;

(xii) a sulfonamide of formula —$(X_{17})_{n17}$—$SO_2NX_{18}X_{19}$, where $X_{17}$ is selected from the group consisting of alkyl, five-membered or six-membered aromatic, heteroaromatic, aliphatic, or heteroaliphatic ring moieties the alkyl and ring moieties are optionally substituted with one or more substituents independently selected from the group consisting of alkyl, halogen, trihalomethyl, carboxylate, amino, nitro, and ester, and n17 is 0, 1, or 2, and $X_{18}$, and $X_{19}$ are independently selected from the group consisting of hydrogen, alkyl, five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, or $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, amino, nitro, and ester;

(xiii) an aldehyde of formula —$(X_{20})_{n20}$—CO—H where $X_{20}$ is selected from the group consisting of saturated or unsaturated alkyl, and five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, and n20 is 0 or 1;

(xiv) a sulfone of formula —$(X_{21})_{n21}$—$SO_2$—$X_{22}$, where $X_{21}$ and $X_{22}$ are independently selected from the group consisting of saturated or unsaturated alkyl, and five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, and n21 is 0 or 1; and (xv) a thiol of formula —$(X_{23})_{n23}$—SH or a thioether of formula —$(X_{24})_{n24}$—S—$X_{25}$, where $X_{23}$, $X_{24}$, and $X_{25}$ are independently selected from the group consisting of saturated or unsaturated alkyl, and five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, and n23 and n24 are independently 0 or 1.

In preferred embodiments, the invention relates to a compound of formula III where (a) $R_{31}$ is hydrogen;

(b) $R_{32}$, $R_{33}$, and $R_{34}$ are each independently selected from the group consisting of (i) hydrogen;

(ii) saturated alkyl optionally substituted with a six-membered heteroaliphatic ring moiety;

(iii) an amine of formula —$(X_1)_{n1}$—$NX_2X_3$, where $X_1$ is saturated alkyl, n1 is 0 or 1, and $X_2$ and $X_3$ are independently selected from the group consisting of hydrogen and saturated alkyl;

(iv) a carboxylic acid of formula —$(X_6)_{n6}$—COOH or ester of formula —$(X_7)_{n7}$—COO—$X_8$, where $X_6$, $X_7$, and $X_8$ are alkyl, and n6 and n7 are independently 0 or 1; and (v) an amide of formula —$(X_{14})_{n14}$—$CONX_{15}X_{16}$, where $X_4$ is alkyl, n12 and n14 are independently 0 or 1, and $X_{15}$ and $X_{16}$ are each independently selected from the group consisting of hydrogen and alkyl;

or $R_7$ is as described herein and $R_8$ and $R_9$ taken together form an optionally substituted six-membered aliphatic or aromatic ring; and (c) $R_{28}$, $R_{29}$, and $R_{30}$ are each independently selected from the group consisting of (i) hydrogen;

(ii) saturated alkyl;

(iii) a halogen or trihalomethyl;

(iv) a carboxylic acid of formula —$(X_6)_{n6}$—COOH or ester of formula —$(X_7)_{n7}$—COO—$X_8$, where $X_6$, $X_7$, and $X_8$ and are alkyl, and n6 and n7 are independently 0 or 1;

(v) an alcohol of formula —$(X_9)_{n9}$—OH or an alkoxyalkyl moiety of formula —$(X_{10})_{n10}$—O—$X_{11}$, where $X_9$, $X_{10}$, and $X_{11}$ are alkyl, and n9 and n10 are independently 0 or 1;

(vi) an amide of formula —$(X_{12})_{n12}$—$NHCOX_{13}$, or of formula —$(X_{14})_{n14}$—$CONX_{15}X_{16}$, where $X_{12}$ and $X_{14}$ are alkyl, n12 and n14 are independently 0 or 1, and $X_{13}$, $X_{15}$, and $X_{16}$ are each independently selected from the group consisting of hydrogen and alkyl; and (vii) a sulfonamide of formula —$(X_{17})_{n17}$—$SO_2NX_{18}X_{19}$, where $X_{17}$ is alkyl, and n17 is 0, 1, or 2, and $X_{18}$ and $X_{19}$ are independently selected from the group consisting of hydrogen and alkyl.

More preferably, in the compounds of formula III (a) $R_{28}$ is selected from the group consisting of hydrogen, methyl, and 2-hydroxyethyl;

(b) $R_{29}$ is selected from the group consisting of hydrogen, methyl, chloro, bromo, carboxy, methoxy, —NHC(O)—$CH_3$, and —$SO_2N(CH_3)_2$;

(c) $R_{30}$ is selected from the group consisting of hydrogen, chloro, methoxy, and —NHC(O)—$CH_3$;

(d) $R_{31}$ is hydrogen;

(e) $R_{32}$ is selected from the group consisting of hydrogen, methyl, —$CH_2CH_2C(O)OH$, —$CH_2CH_2C(O)NH_2$, —$CH_2CH_2CH_2N(CH_3)_2$, and 3-morpholinopropyl; and (f) $R_{33}$ and $R_{34}$ are each independently selected from the group consisting of hydrogen, methyl, —$CH_2CH_2C(O)OH$, —$CH_2CH_2CH_2N(CH_3)_2$, and 3-morpholinopropyl, or $R_8$ and $R_9$ taken together form a six-membered aromatic or aliphatic ring.

The preferred diaryl indolinone compounds of the invention are those which are preferably formed by the reaction of a ketone compound with and oxindole compound. The ketone compound is preferably selected from the group consisting of

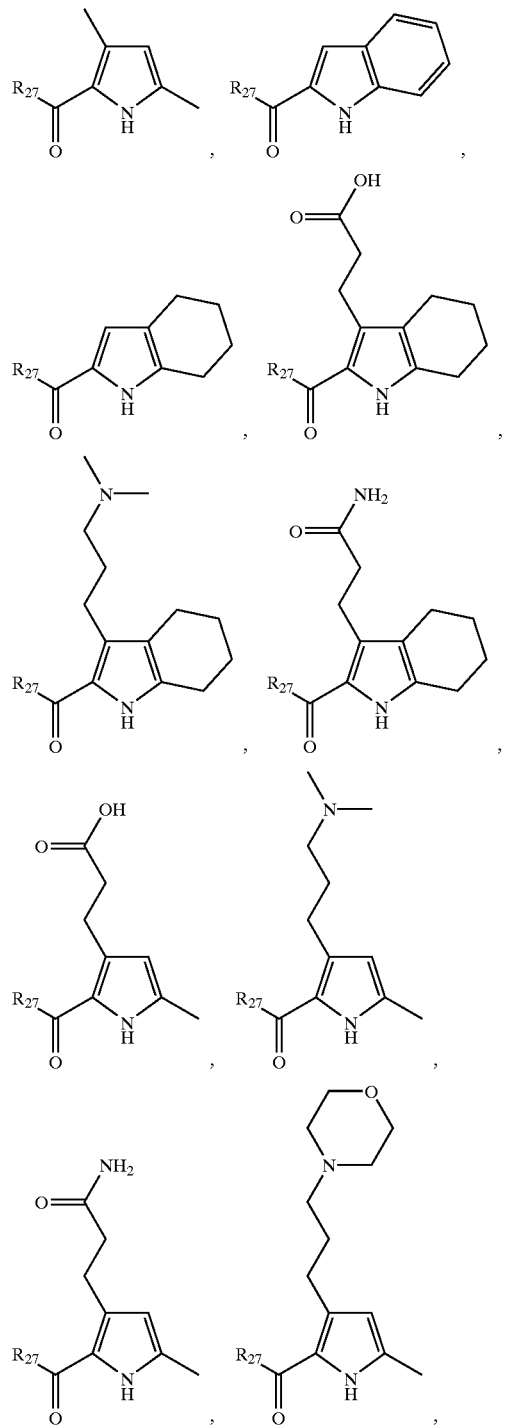

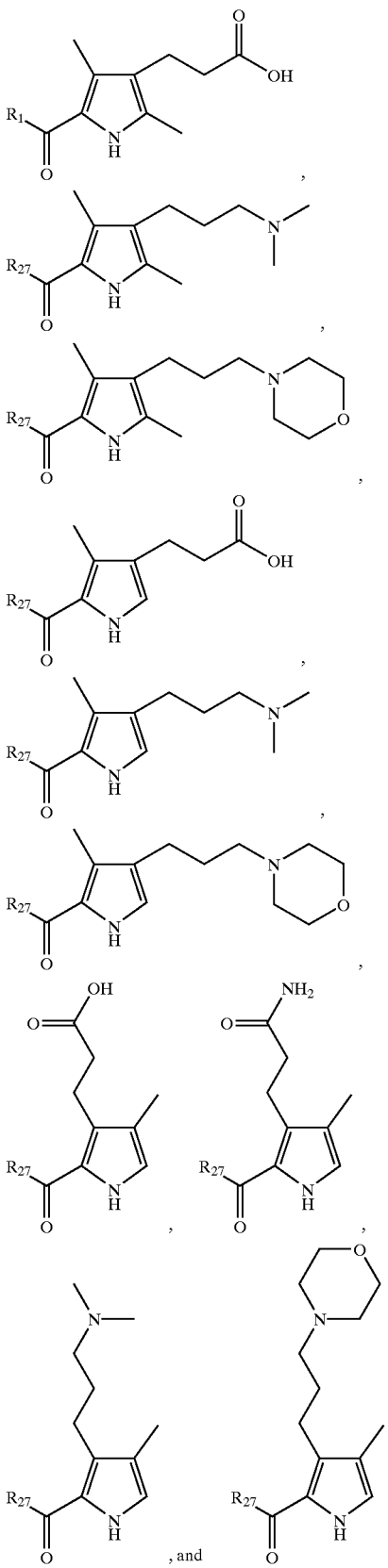

In the above structures $R_{27}$ is selected from the group consisting of (i) saturated or unsaturated alkyl optionally substituted with substituents selected from the group consisting of halogen, trihalomethyl, alkoxy, carboxylate, amino, nitro, ester, and a five-membered or six-membered aromatic, heteroaromatic, aliphatic, or heteroaliphatic ring moiety, wherein said ring moiety is optionally substituted with one, two, or three substituents independently selected from the group consisting of alkyl, halogen, trihalomethyl, carboxylate, amino, nitro, and ester moieties; and (ii) an aromatic or heteroaromatic ring optionally substituted with one, two, or three substituents independently selected from the group consisting of alkyl, alkoxy, halogen, trihalomethyl, carboxylate, amino, nitro, and ester moieties;

(iii) an aliphatic or heteroaliphatic ring optionally substituted with one or more substituents independently selected from the group consisting of alkyl, alkoxy, halogen, trihalomethyl, carboxylate, amino, nitro, ester, and an aromatic or heteroaromatic ring optionally substituted with one or more substituents independently selected from the group consisting of alkyl, alkoxy, halogen, trihalomethyl, carboxylate, amino, nitro, and ester moieties.

The oxindole compound is preferably selected from the group consisting of 1,3-dihydro-indol-2-one, 4-methyl-1,3-dihydro-indol-2-one, 4-(2-hydroxy-ethyl)-1,3-dihydro-indol-2-one, 5-chloro-1,3-dihydro-indol-2-one, 5-bromo-1,3-dihydro-indol-2-one, 5-methoxy-1,3-dihydro-indol-2-one, 2-oxo-2,3-dihydro-1H-indole-5-carboxylic acid, 2-oxo-2,3-dihydro-1H-indole-5-sulfonic acid dimethylamide, N-(2-oxo-2,3-dihydro-1H-indole-5-yl)-acetamide, 6-chloro-1,3-dihydro-indol-2-one, 6-methoxy-1,3-dihydro-indol-2-one, and N-(5-methyl-2-oxo-2,3-dihydro-1H-indole-6-yl)-acetamide.

D. 4-Substituted Indolinone Compounds

In a further aspect, the invention provides a compound having a structure set forth in formula IV or formula V:

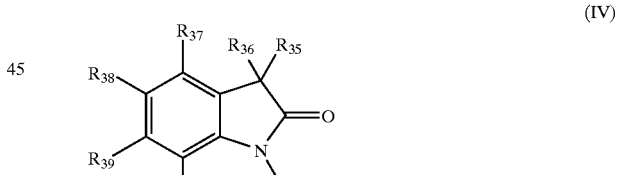

(IV)

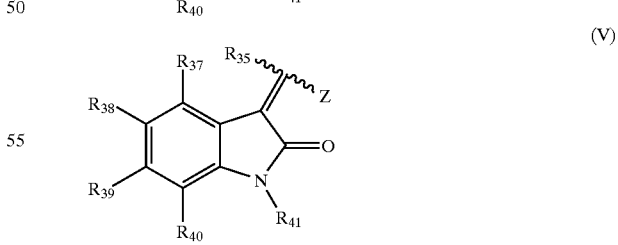

(V)

where (a) $R_{35}$, $R_{36}$, and $R_{41}$ are each independently selected from the group consisting of (i) hydrogen;

(ii) saturated or unsaturated alkyl optionally substituted with substituents selected from the group consisting of halogen, trihalomethyl, alkoxy, carboxylate, amino, nitro, ester, and a five-membered or six-membered aromatic, heteroaromatic, aliphatic, or heteroaliphatic ring moiety, where the ring moiety is optionally substituted with one, two, or three substituents independently selected from the group consisting of alkyl, halogen, trihalomethyl, carboxylate, amino, nitro, and ester moieties; and (iii) an aromatic or heteroaromatic ring optionally substituted with one, two, or three substituents independently selected from the group consisting of alkyl, alkoxy, halogen, trihalomethyl, carboxylate, amino, nitro, and ester moieties;

(b) $R_{37}$ is an ethyl-2-oxy group of formula —$CH_2CH_2$—O—R, where R is selected from the group consisting of (i) hydrogen;

(ii) saturated or unsaturated alkyl optionally substituted with substituents selected from the group consisting of halogen, trihalomethyl, carboxylate, amino, nitro, ester, and a five-membered or six-membered aromatic, heteroaromatic, aliphatic, or heteroaliphatic ring moiety, and the ring moiety is optionally substituted with one, two, or three substituents independently selected from the group consisting of alkyl, halogen, trihalomethyl, carboxylate, amino, nitro, and ester moieties;

(iii) an aromatic or heteroaromatic ring optionally substituted with one or more substituents independently selected from the group consisting of alkyl, aryl, alkoxy, halogen, trihalomethyl, carboxylate, amino, nitro, and ester moieties (iv) a substituent of formula —$C(E)NX_{15}X_{16}$, where $X_{15}$, and $X_{16}$ are each independently selected from the group consisting of hydrogen, alkyl, hydroxyl, sulfone of formula —$SO_2$—$X_{22}$, and five-membered or six-membered aromatic, heteroaromatic, aliphatic, or heteroaliphatic ring moieties, the ring is optionally substituted with one or more substituents independently selected from the group consisting of alkyl, aryl, halogen, trihalomethyl, carboxylate, amino, nitro, and ester, $X_{22}$ is selected from the group consisting of saturated or unsaturated alkyl, and five-membered or six-membered aromatic, heteroaromatic, aliphatic, or heteroaliphatic ring moieties, the ring is optionally substituted with one or more substituents independently selected from the group consisting of alkyl, halogen, trihalomethyl, carboxylate, amino, nitro, and ester, E is selected from the group consisting of oxygen and sulfur; and (c) $R_{38}$, $R_{39}$, and $R_{40}$ are each hydrogen;

(d) Z is a 5, 6, 7, 8, 9, or 10 membered, monocyclic or bicyclic, aromatic or heteroaromatic, ring moiety, optionally substituted with one or more substituents selected from the group consisting of (i) hydrogen;

(ii) saturated or unsaturated alkyl optionally substituted with one or more substituents selected from the group consisting of hydroxy, halogen, trihalomethyl, carboxylate, amino, nitro, ester, and a five-membered or six-membered aromatic, heteroaromatic, aliphatic, or heteroaliphatic ring moiety, the ring moiety is optionally substituted with one or more substituents independently selected from the group consisting of alkyl, halogen, trihalomethyl, carboxylate, amino, nitro, and ester moieties;

(iii) an aromatic or heteroaromatic ring optionally substituted with one or more substituents independently selected from the group consisting of alkyl, alkoxy, halogen, trihalomethyl, carboxylate, amino, nitro, and ester moieties;

(iv) an aliphatic or heteroaliphatic ring optionally substituted with one or more substituents independently selected from the group consisting of alkyl, alkoxy, halogen, trihalomethyl, carboxylate, amino, nitro, ester, and an aromatic or heteroaromatic ring optionally substituted with one or more substituents independently selected from the group consisting of alkyl, alkoxy, halogen, trihalomethyl, carboxylate, amino, nitro, and ester moieties;

(v) an amine of formula —$(X_1)_{n1}$—$NX_2X_3$, where $X_1$ is selected from the group consisting of saturated or unsaturated alkyl, and five-membered or six-membered aromatic, heteroaromatic, or aliphatic ring moieties, n1 is 0 or 1, and $X_2$, and $X_3$ are independently selected from the group consisting of hydrogen, saturated or unsaturated alkyl, and five-membered or six-membered aromatic, heteroaromatic, or aliphatic ring moieties;

(vi) a nitro of formula —$NO_2$;

(vii) a halogen or trihalomethyl;

(viii) a ketone of formula —$(X_4)_{n4}$—CO—$X_5$, where $X_4$ and $X_5$ are independently selected from the group consisting of alkyl and five-membered or six-membered aromatic, heteroaromatic, aliphatic, or heteroaliphatic ring moieties, the alkyl and ring moieties are optionally substituted with one, two, or three substituents independently selected from the group consisting of alkyl, halogen, trihalomethyl, carboxylate, amino, nitro, and ester moieties, and n4 is 0 or 1;

(ix) a carboxylic acid of formula —$(X_6)_{n6}$—COOH or ester of formula —$(X_7)_{n7}$—COO—$X_8$, where $X_6$, $X_7$, and $X_8$ and are independently selected from the group consisting of alkyl and five-membered or six-membered aromatic, heteroaromatic, aliphatic, or heteroaliphatic ring moieties, and n6 and n7 are independently 0 or 1;

(x) an alcohol of formula —$(X_9)_{n9}$—OH or an alkoxyalkyl moiety of formula —$(X_{10})_{n10}$—O—$X_{11}$, where $X_9$, $X_{10}$, and $X_{11}$ are independently selected from the group consisting of saturated or unsaturated alkyl, and five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, and n9 and n 10 are independently 0 or 1;

(xi) an amide of formula —$(X_{12})_{n12}$—$NHCOX_{13}$, or of formula —$(X_{14})_{n14}$—$CONX_{15}X_{16}$, where $X_{12}$ and $X_{14}$ are each independently selected from the group consisting of alkyl, hydroxyl, and five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, n12 and n14 are independently 0 or 1, and $X_{13}$, $X_{15}$, and $X_{16}$ are each independently selected from the group consisting of hydrogen, alkyl, hydroxyl, and five-membered or six-membered aromatic, heteroaromatic, aliphatic, or heteroaliphatic ring moieties, and the alkyl and ring moieties are optionally substituted with one or more substituents independently selected from the group consisting of alkyl, halogen, trihalomethyl, carboxylate, amino, nitro, and ester;

(xii) a sulfonamide of formula —$(X_{17})_{n17}$—$SO_2NX_{18}X_{19}$, where $X_{17}$ is selected from the group consisting of alkyl, five-membered or six-membered aromatic, heteroaromatic, aliphatic, or heteroaliphatic ring moieties the alkyl and ring moieties are optionally substituted with one or more substituents independently selected from the group consisting of alkyl, halogen, trihalomethyl, carboxylate, amino, nitro, or ester, and n17 is 0, 1, or 2, and $X_{18}$, and $X_{19}$ are independently selected from the group consisting of hydrogen, alkyl, five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, or ester, or $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, amino, nitro, and ester;

(xiii) an aldehyde of formula —$(X_{20})_{n20}$—CO—H where $X_{20}$ is selected from the group consisting of saturated or unsaturated alkyl, and five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, and n20 is 0 or 1;

(xiv) a sulfone of formula —$(X_{21})_{n21}$—$SO_2$—$X_{22}$, where $X_{21}$ and $X_{22}$ are independently selected from the group consisting of saturated or unsaturated alkyl, and five-membered or six-membered aromatic, heteroaromatic, aliphatic, or heteroaliphatic ring moieties, the alkyl and ring moieties are optionally substituted with one or more substituents independently selected from the group consisting of alkyl halogen, trihalomethyl, carboxylate, amino, nitro, and ester, and n21 is 0 or 1; and (xv) a thiol of formula —$(X_{23})_{n23}$—SH and a thioether of formula —$(X_{24})_{n24}$—S—$X_{25}$, where $X_{23}$, $X_{24}$, and $X_{25}$ are independently selected from the group consisting of saturated or unsaturated alkyl, and five-membered or six-membered aromatic, heteroaromatic, aliphatic, or heteroaliphatic ring moieties, the alkyl and ring moieties are optionally substituted with one or more substituents independently selected from the group consisting of alkyl, halogen, trihalomethyl, carboxylate, amino, nitro, and ester, and n23 and n24 are independently 0 or 1.

In preferred embodiments, the invention relates to a compound of formula IV or formula V, where (a) $R_{35}$, $R_{36}$, and $R_{41}$ are hydrogen;

(b) $R_{37}$ is an ethyl-2-oxy group of formula —$CH_2CH_2$—O—R, where R is selected from the group consisting of hydrogen, saturated alkyl, an aromatic ring optionally substituted with one or more substituents independently selected from the group consisting of alkyl, aryl, and alkoxy moieties, and a substituent of formula —C(E)NHX$_{15}$, where $X_{15}$ is selected from the group consisting of alkyl, sulfone of formula —$SO_2$—$X_{22}$, and six-membered aromatic or aliphatic ring moieties, the ring is optionally substituted with one or more substituents independently selected from the group consisting of alkyl and aryl, $X_{22}$ is selected from the group consisting of saturated alkyl, and optionally substituted six-membered aromatic ring moieties, and E is selected from the group consisting of oxygen and sulfur, and;

(c) Z is a 5, 6, or 9 membered, monocyclic or bicyclic, aromatic or heteroaromatic, ring moiety, optionally substituted with one or more substituents selected from the group consisting of (i) hydrogen;

(ii) saturated alkyl, (iii) an optionally substituted aromatic or heteroaromatic ring;

(iv) an amine of formula —$(X_1)_{n1}$—$NX_2X_3$, where $X_1$ is alkyl, n1 is 0 or 1, and $X_2$ and $X_3$ are independently selected from the group consisting of hydrogen and saturated alkyl;

(v) a halogen or trihalomethyl;

(vi) a carboxylic acid of formula —$(X_6)_{n6}$—COOH, where $X_6$ is alkyl, and n6 is 0 or 1; and (vii) an alcohol of formula —$(X_9)_{n9}$—OH or an alkoxyalkyl moiety of formula —$(X_{10})_{n10}$—O—$X_{11}$, where $X_9$, $X_{10}$, and $X_{11}$ are alkyl, and n9 and n10 are independently 0 or 1.

More preferably, in the compounds of formula IV or formula V, $R_{37}$ is an ethyl-2-oxy group of formula —$CH_2CH_2$—O—R, wherein R is selected from the group consisting of hydrogen, methyl, ethyl, 2-isopropylphenyl, 3-isopropylphenyl, 4-isopropylphenyl, 4-methoxyphenyl, biphen-3-yl, 5-chloropyridin-3-yl, ethylcarbamyl, tert-butylcarbamyl, cyclohexylcarbamyl, phenylcarbamyl, benzene sulfonylcarbamyl, biphen-2-yl-carbamyl, and phenylthiocarbamyl, and Z is selected from the group consisting of 4-bromophenyl, 2-pyridyl, 6-methyl-2-pyridyl, 1H-indol-5-yl, 4-methoxy-3-thiophenphenyl, 4-(3-dimethylamino)-3,5-dimethyl-1H-pyrrol-2-yl, 3-hydroxy-6-methyl-pyridin-2-yl, 4-(3-dimethylaminopropyl)-3,5-dimethyl-1H-pyrrol-2-yl, 3-carboxy-2,4-dimethyl-1H-pyrrol-2-yl, and isopropylcarbamyl.

The preferred compounds of the invention are listed in Table 1.

TABLE 1

| Compound Number | Compound Name |
|---|---|
| IN-001 | 4-[2-(3-isopropyl-phenoxy)-ethyl]-1,3-dihydro-indol-2-one |
| IN-002 | 4-[2-(2-isopropyl-phenoxy)-ethyl]-1,3-dihydro-indol-2-one |
| IN-003 | 4-[2-(biphenyl-3-yloxy)-ethyl]-1,3-dihydro-indol-2-one |
| IN-004 | 3-(4-bromo-benzylidene)-4-(2-hydroxy-ethyl)-1,3-dihydro-indol-2-one |
| IN-005 | 4-(2-hydroxy-ethyl)-3-pyridin-2-ylmethylene-1,3-dihydro-indol-2-one |
| IN-006 | 4-(2-hydroxy-ethyl)-3-(6-methyl-pyridin-2-ylmethylene)-1,3-dihydro-indol-2-one |
| IN-007 | 4-(2-hydroxy-ethyl)-3-(1H-indol-5-ylmethylene)-1,3-dihydro-indol-2-one |

TABLE 1-continued

| Compound Number | Compound Name |
|---|---|
| IN-008 | 4-(2-hydroxy-ethyl)-3-(4-methoxy-3-thiophen-2-yl-benzylidene)-1,3-dihydro-indol-2-one |
| IN-009 | 3-[4-(3-dimethylamino-propyl)-3,5-dimethyl-1H-pyrrol-2-ylmethylene]-4-(2-hydroxy-ethyl)-1,3-dihydro-indol-2-one |
| IN-010 | phenyl-thiocarbamic acid O-(2-(2-oxo-2,3-dihydro-1H-indol-4-yl)-ethyl]ester |
| IN-011 | phenyl-carbamic acid 2-(2-oxo-2,3-dihydro-1H-indol-4-yl)-ethyl ester |
| IN-012 | tert-butyl-carbamic acid 2-(2-oxo-2,3-dihydro-1H-indol-4-yl)-ethyl ester |
| IN-013 | cyclohexyl-carbamic acid 2-(2-oxo-2,3-dihydro-1H-indol-4-yl)-ethyl ester |
| IN-014 | benzene sulfonyl-carbamic acid 2-(2-oxo-2,3-dihydro-1H-indol-4-yl)-ethyl ester |
| IN-015 | biphenyl-2-yl-carbamic acid 2-(2-oxo-2,3-dihydro-1H-indol-4-yl)-ethyl ester |
| IN-016 | ethyl-carbamic acid 2-(2-oxo-2,3-dihydro-1H-indol-4-yl)-ethyl ester |
| IN-017 | 4-[2-(4-methoxy-phenoxy)-ethyl]-1,3-dihydro-indol-2-one |
| IN-018 | 4-(2-methoxy-ethyl)-1,3-dihydro-indol-2-one |
| IN-019 | 4-(2-ethoxy-ethyl)-1,3-dihydro-indol-2-one |
| IN-020 | 4-[2-(4-isopropyl-phenoxy)-ethyl]-1,3-dihydro-indol-2-one |
| IN-021 | 4-[2-(5-chloro-pyridin-3-yloxy)-ethyl]-1,3-dihydro-indol-2-one |
| IN-022 | 4-(2-hydroxy-ethyl)-3-(3-hydroxy-6-methyl-pyridin-2-ylmethylene)-1,3-dihydro-indol-2-one |
| IN-023 | 3-[4-(3-dimethylamino-propyl)-3,5-dimethyl-1H-pyrrol-2-ylmethylene]-4-[2-(3-isopropyl-phenoxy)-ethyl]-1,3-dihydro-indol-2-one |
| IN-024 | 3-(5-{4-[2-(4-isopropyl-phenoxy)-ethyl]-2-oxo-1,2-dihydro-indol-3-ylidenemethyl}-2,4-dimethyl-1H-pyrrol-3-yl)-propionic acid |
| IN-025 | Isopropyl-carbamic acid 2-(2-oxo-2,3-dihydro-1H-indol-4-yl)-ethyl ester |

Some of the above compounds have the structure of formula VI, with the R substituent as defined in Table 2.

TABLE 2

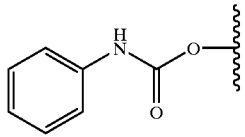

(VI)

| Compound Number | R |
|---|---|
| IN-001 | 3-isopropyl-phenoxy |
| IN-002 | 2-isopropyl-phenoxy |
| IN-003 | biphenyl-3-yloxy |
| IN-010 | 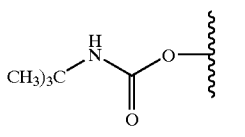 |

TABLE 2-continued

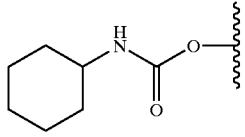

(VI)

| Compound Number | R |
|---|---|
| IN-011 | 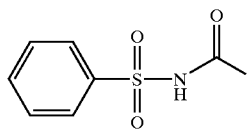 |
| IN-012 | 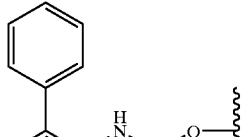 |
| IN-013 | 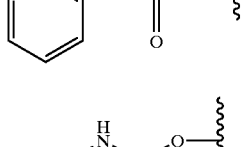 |
| IN-014 | 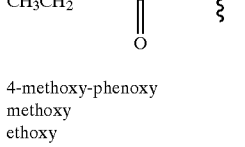 |
| IN-015 | 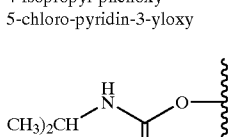 |
| IN-016 | 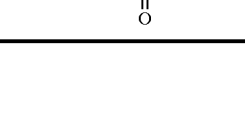 |
| IN-017 | 4-methoxy-phenoxy |
| IN-018 | methoxy |
| IN-019 | ethoxy |
| IN-020 | 4-isopropyl-phenoxy |
| IN-021 | 5-chloro-pyridin-3-yloxy |
| IN-025 |  |

Other compounds of the invention have the structure set forth in formula VII, with the substituents as defined in Table 3.

TABLE 3

(VII)

[Structure: indolin-2-one with R-CH2-CH2- substituent and =Z group, H atoms labeled on the benzene ring]

| Compound Number | R | Z |
|---|---|---|
| IN-004 | hydroxy | 4-bromophenyl |
| IN-005 | hydroxy | pyridin-2-yl |
| IN-006 | hydroxy | 6-methyl-pyridin-2-yl |
| IN-007 | hydroxy | 1H-indol-5-yl |
| IN-008 | hydroxy | 4-methoxy-3-thiophen-2-yl-phenyl |
| IN-009 | hydroxy | 4-(3-dimethylamino-propyl)-3,5-dimethyl-1H-pyrrol-2-yl |
| IN-022 | hydroxy | 3-hydroxy-6-methyl-pyridin-2-yl |
| IN-023 | 3-isopropyl-phenoxy | 4-(3-dimethylamino-propyl)-3,5-dimethyl-1H-pyrrol-2-yl |
| IN-024 | 4-isopropyl-phenoxy | 4-carboxy-3,5-dimethyl-1H-pyrrol-2-yl |

III. COMBINATORIAL LIBRARIES AND SYNTHETIC PROCEDURES

A. General Notes on Synthetic Procedures

To synthesize the compounds of the invention a base may be used. The base is preferably a nitrogen base or an inorganic base. "Nitrogen bases" are commonly used in the art and are selected from acyclic and cyclic amines. Examples of nitrogen bases include, but are not limited to, ammonia, methylamine, trimethylamine, triethylamine, aniline, 1,8-diazabicyclo[5.4.0]undec-7-ene, diisopropylethylamine, pyrrolidine, piperidine, and pyridine or substituted pyridine (e.g., 2,6-di-tertbutylpyridine). "Inorganic bases" are bases that do not contain any carbon atoms. Examples of inorganic bases include, but are not limited to, hydroxide, phosphate, bisulfate, hydrosulfide, and amide anions. Those skilled in the art know which nitrogen base or inorganic base would match the requirements of the reaction conditions. In certain embodiments of the invention, the base used may be pyrrolidine or piperidine. In other embodiments the base may be the hydroxide anion, preferably used as its sodium or potassium salt.

The synthesis of the compounds of the invention may take place in a solvent. The solvent of the reaction is preferably a protic solvent or an aprotic solevent. "Protic solvents" are those that are capable of donating a proton to a solute. Examples of protic solvents include, but are not limited to, alcohols and water. "Aprotic solvents" are those solvents that, under normal reaction conditions, do not donate a proton to a solute. Typical organic solvents, such as hexane, toluene, benzene, methylene chloride, dimethylformamide, chloroform, tetrahydrofuran, are some of the examples of aprotic solvents. Other aprotic solvents are also within the scope used by the present invention. In some preferred embodiments, the solvent of the reaction is an alcohol, which may preferably be isopropanol or most preferably ethanol. Water is another preferred protic solvent. Dimethylformamide, known in the chemistry art as DMF, is a preferred aprotic solvent.

The synthetic method of the invention calls for the reaction to take place at elevated temperatures which are temperatures that are greater than room temperature. More preferably, the elevated temperature is preferably about 30–150° C., more preferably about 80–100° C., and most preferably about 80–90° C., which is about the temperature at which ethanol boils (i.e., the boiling point of ethanol). By "about" a certain temperature it is meant that the temperature range is preferably within 10° C. of the listed temperature, more preferably within 5° C. of the listed temperature, and most preferably within 2° C. of the listed temperature. Therefore, by way of example, by "about 80° C." it is meant that the temperature range is preferably 80±10° C., more preferably 80±5° C., and most preferably 80±2° C.

The synthetic method of the invention may be accompanied by the step of screening a library for a compound of the desired activity and structure—thus, providing a method of synthesis of a compound by first screening for a compound having the desired properties and then chemically synthesizing that compound.

B. 3-Arylidenyl-6-Heterocyclyl-2-Indolinone Derivatives

An additional aspect of this invention is a combinatorial library of at least ten 3-arylidenyl-6-heterocyclyl-2-indolinone compounds that can be formed by condensing oxindoles of structure 2 with aldehydes of structure 3.

As used herein, "condensing" or "condensation" refers to a reaction by which two molecules are combined to give one molecule. In particular with regard the present invention a condensation refers to the reaction shown in Scheme I.

SCHEME I

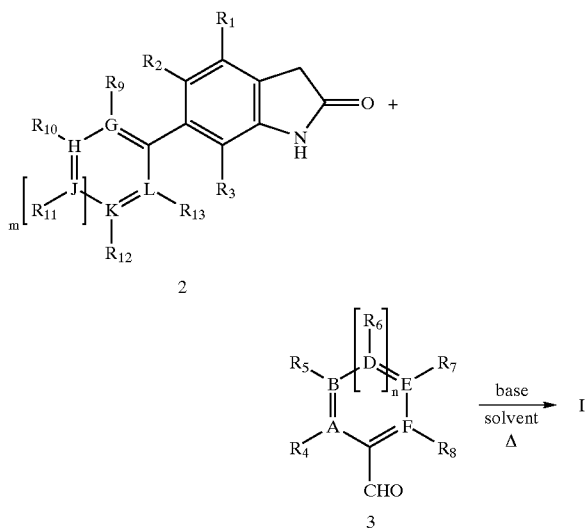

The oxindole in the above combinatorial library is preferably selected from the group consisting of 6-(pyridin-2-yl)-2-oxindole, 6-(pyridin-3-yl)-2-oxindole, 6-(pyridine-4-yl)-2-oxindole, 6-(pyrimidin-2-yl)-2-oxindole, 6-(pyrimidin-4-yl)-2-oxindole, 6-(pyrimidin-5-yl)-2-oxindole, 6-(triazinyl)-2-oxindole, 6-(pyrrol-2-yl)-2- oxindole, 6-(pyrrol-3-yl)-2-oxindole, 6-(thiophen-2-yl)-2-oxindole, 6-(thiophen-3-yl)-2-oxindole, 6-(furan-2-yl)-2-oxindole, 6-(furan-3-yl)-2-oxindole, 6-(imidazol-2-yl)-2-oxindole, 6-(imidazol-4-yl)-2-oxindole, 6-(thiazol-2-yl)-2-oxindole, 6-(thiazol-4-yl)-2-oxindole, 6-(oxazol-2-yl)-2-oxindole, 6-(oxazol-4-yl)-2-oxindole, 6-(thiadiazol-2-yl)-2-oxindole, 6-(oxadiazolyl)-2-oxindole and 6-(triazol-2-yl)-2-oxindole, 6-(3methylisoxazole-5-yl)-2-oxindole,6-(3-methylisothiazole-5-yl)-2-oxindole, 6-(3,5-dimethyl-isoxazole-4-yl)-2-oxindole, 6-(thiazole-2-yl)-2-oxindole, 6-(thiazole-4-yl)-2-oxindole, 6-(thiazole-5-yl)-2-oxindole, 6-(3-methylthiophene-2-yl)-2-oxindole, 6-(4-methylthiophene-2-yl)-2-oxindole, 6-(5-methylthiophene-2-yl)-2-oxindole, 6-(5-chlorothiophene-2-yl)-2-oxindole, 6-(4-methylfuran-2-yl)-2-oxindole The aldehyde in the above combinatorial library is preferably selected from the group consisting of, without limitation, benzaldehyde, 3-isopropyl-p-anisaldehyde, 2-methyl-5-isopropyl-p-anisaldehyde, 3,5-diisopropyl-p-anisaldehyde, 3-cyclopentyl-p-anisaldehyde, 3-cyclohexyl-p-anisaldehyde, 3-phenyl-p-anisaldehyde, 3,5-dimethyl-p-anisaldehyde, 2-hydroxy-3,5-dichlorobenzaldehyde, 2-hydroxy-5-chlorobenzaldehyde, 2-hydroxy-4-methoxy-5-(4-methoxyphenyl)benzaldehyde, 3-cyclopentyl-4-methoxybenzaldehyde, 3-cyclopentyl-4-hydroxybenzaldehyde, 3-(2-thienyl)-4-methoxybenzaldehyde, 2-hydroxybenzaldehyde, 2-hydroxy-4-methoxybenzaldehyde, 2-hydroxy-5-bromobenzaldehyde, 2-methylpyridine-6-carboxaldehyde, 3-tert-butyl-4-hydroxy-5-bromobenzaldehyde, 3-bromobenzaldehyde, 3,5-diisopropyl-4-[2-(N-morpholino)ethyl]benzaldehyde,indole-5-carboxaldchyde, 2-hydroxy-3-fluorobenzaldehyde, 3-cyclohexyl-4-[2-(N-morpholino)ethyl]benzaldehyde, 3-(3-thienyl)-4-methoxybenzaldehyde, 2-methyl-5-isopropyl-4-methoxy-benzaldehyde, 2,3-dihydrobenzofuran-5-carboxaldehyde, 2,2-dimethylchroman-6-carboxaldehyde, 3-(thiophen-3-yl)-4-methoxybenzaldehyde, 3-(3-acetylaminophenyl)-4-methoxy-benzaldehyde, 2-naphthyl-4,5-dimethoxybenzaldehyde, 2-(3-methoxyphenyl)-4,5-dimethoxybenzaldehyde, 3-(pyridin-3-yl)-p-anisaldehyde, 2-(3-ethoxyphenyl)-4,5-dimethoxybenzaldehyde, 3-isopropyl-4-[2-(N-morpholino)ethoxy]benzaldehyde, 3,5-diisopropyl-4-[2-(N-morpholino)ethoxy]benzaldehyde, 2-(2-methoxyphenyl)-4,5-dimethoxybenzaldehyde, 3-(3-ethoxyphenyl)-p-anisaldehyde, 3-(thiophen-2-yl)-4-[2-(N-morpholino)ethoxy]-benzaldehyde, 2-(thiophen-2-yl)-4,5-dimethoxybenzaldehyde, 2,4-dimethyl-3-[3-dimethylaminopropyl]-pyrrole-5-carboxaldehyde, 2,4-dimethyl-3-[3-carboxypropyl]-pyrrole-5-carboxaldehyde, 2,4-dimethyl-3-[3-(N-morpholino)prop-1-yl]-pyrrole-5-carboxaldehyde, 2,4-dimethyl-3-[2-dimethylaminoethyl]-pyrrole-5-carboxaldehyde, 2,4-dimethyl-3-[2-carboxyethyl]-pyrrole-5-carboxaldehyde and 2,4-dimethyl-3-[2-(N-morpholino)propyl]-pyrrole-5-carboxaldehyde, 3-isopropyl-4-[2-(N-morpholino)propoxy]benzaldehyde, 3,5-diisopropyl-4-[2-(N-morpholino)propoxy]benzaldehyde, 3-(thiophen-2-yl)-4-[2-N-morpholino)propoxy]benzaldehyde,.

Another aspect of this invention provides a method for the synthesis of 3-arylidenyl-6-heterocyclyl-2-indolinone of formula I comprising condensing an oxindole of formula 2 with an aldehyde of formula 3 in a solvent, preferably in the presence of a base.

Examples of the oxindoles of formula 2 that may be condensed with an aldehyde of formula 3 to give a 3-arylidenyl-6-heterocyclyl-2-indolinones of formula I are 6-(pyridin-2-yl)-2-oxindole, 6-(pyridin-3-yl)-2-oxindole, 6-(pyridine-4-yl)-2-oxindole, 6-(pyrimidin-2-yl)-2-oxindole, 6-(pyrimidin-4-yl)-2-oxindole, 6-(pyrimidin-5-yl)-2-oxindole, 6-(triazinyl)-2-oxindole, 6-(pyrrol-2-yl)-2-oxindole, 6-(pyrrol-3-yl)-2-oxindole, 6-(thiophen-2-yl)-2-oxindole, 6-(thiophen-3-yl)-2-oxindole, 6-(furan-2-yl)-2-oxindole, 6-(furan-3-yl)-2-oxindole, 6-(imidazol-2-yl)-2-oxindole, 6-(imidazol-4-yl)-2-oxindole, 6-(thiazol-2-yl)-2-oxindole, 6-(thiazol-4-yl)-2-oxindole, 6-(oxazol-2-yl)-2-oxindole, 6-(oxazol-4-yl)-2-oxindole, 6-(thiadiazol-2-yl)-2-oxindole, 6-(oxadiazol-2-yl)-2-oxindole and 6-(triazol-2-yl)-2-oxindole, 6-(3methylisoxazole-5-yl)-2-oxindole, 6-(3-methylisothiazole-5-yl)-2-oxindole, 6-(3,5-dimethyl-isoxazole-4-yl)-2-oxindole, 6-(thiazole-2-yl)-2-oxindole, 6-(thiazole-4-yl)-2-oxindole, 6-(thiazole-5-yl)-2-oxindole, 6-(3-methylthiophene-2-yl)-2-oxindole, 6-(4-methylthiophene-2-yl)-2-oxindole, 6-(5-methylthiophene-2-yl)-2-oxindole, 6-(5-chlorothiophene-2-yl)-2-oxindole, 6-(4-methylfuran-2-yl)-2-oxindole.

Examples of aldehydes of structure 3 which may be condensed with oxindoles of structure 2 to give a compound of this invention are, without limitation, benzaldehyde, 3-isopropyl-p-anisaldehyde, 2-methyl-5-isopropyl-p-anisaldehyde, 3,5-diisopropyl-p-anisaldehyde, 3-cyclopentyl-p-anisaldehyde, 3-cyclohexyl-p-anisaldehyde, 3-phenyl-p-anisaldehyde, 3,5-dimethyl-p-anisaldehyde, 2-hydroxy-3,5-dichlorobenzaldehyde, 2-hydroxy-5-chlorobenzaldehyde, 2-hydroxy-4-methoxy-5-(4-methoxyphenyl)benzaldehyde, 3-cyclopentyl-4-methoxybenzaldehyde, 3-cyclopentyl-4-hydroxybenzaldehyde, 3-(2-thienyl)-4-methoxybenzaldehyde, 2-hydroxybenzaldehyde, 2-hydroxy-4-methoxybenzaldehyde, 2-hydroxy-5-bromobenzaldehyde, 2-methylpyridine-6-carboxaldehyde, 3-tert-butyl-4-hydroxy-5-bromobenzaldehyde, 3-bromobenzaldehyde, hydroxy-3-fluorobenzaldehyde, 3-cyclohexyl-4-[2-(N-morpholino)ethyl]benzaldehyde, 3-(3-thienyl)-4-methoxybenzaldehyde, 2-methyl-5-isopropyl-4-methoxy-benzaldehyde, 2,3-dihydrobenzofuran-5-carboxaldehyde, 2,2-dimethylchroman-6-carboxaldehyde, 3-(thiophen-3-yl)-4-methoxybenzaldehyde, 3-(3-acetylaminophenyl)-4-methoxy-benzaldehyde, 2-naphthyl-4,5-dimethoxybenzaldehyde, 2-(3-methoxypheny-4,5-dimethoxybenzaldehyde, 3-(pyridin-3-yl)-p-anisaldehyde, 2-(3-ethoxyphenyl)-4,5-dimethoxybenzaldehyde, 3-isopropyl-4-[2-(N-morpholino)ethoxy]benzaldehyde, 3,5-diisopropyl -4-[2-(N-morpholino)ethoxy]benzaldehyde, 2-(2-methoxyphenyl)-4,5-dimethoxybenzaldehyde, 3-(3-ethoxyphenyl)-p-anisaldehyde, 3-(thiophen-2-yl)-4-[2-(N-morpholino)ethoxy]-benzaldehyde, 2-(thiophen-2-yl)-4,5-dimethoxybenzaldehyde, 2,4-dimethyl-3-[3-dimethylaminopropyl]-pyrrole-5-carboxaldehyde, 2,4-dimethyl-3[2-carboxypropyl]-pyrrole-5-carboxaldehyde, 2,4-dimethyl-3-[3-(N-morpholino)propyl-1-yl]-pyrrole-5-carboxaldehyde, 2,4-dimethyl-3-[2-dimethylaminoethyl]-pyrrole-5-carboxaldehyde, 2,4-dimethyl-3-[2-carboxyethyl]-pyrrole-5-carboxaldehyde and 2,4-dimethyl-3-[2-(N-morpholino)ethyl]prop-1-yl]-pyrrole-5-carboxaldehyde, 3-isopropyl-4-[2-(N-morpholino)propoxy]benzaldehyde, 3,5-di isopropyl-4-[2-(N-morpholino)propoxy]benzaldehyde, 3-(thiophen-2-yl)-4-[2-N-morpholino)propoxy]benzaldehyde.

C. 3-Aralkyl-2-Indolinone Derivatives

Another aspect of this invention is a combinatorial library of at least ten 3-aralkyl-2-indolinone compounds that can be formed by condensing oxindoles of structure 4 with aldehydes of structure 5 and then reducing the 3-position double bond of the resultant 3-arylidene-2-oxindole. In particular, the condensation refers to reaction "A" in Scheme II. Compound 4 is the "3-arylidene-2-oxindole" referred to above.

"Reducing," as used herein, refers to the addition of hydrogen across the double

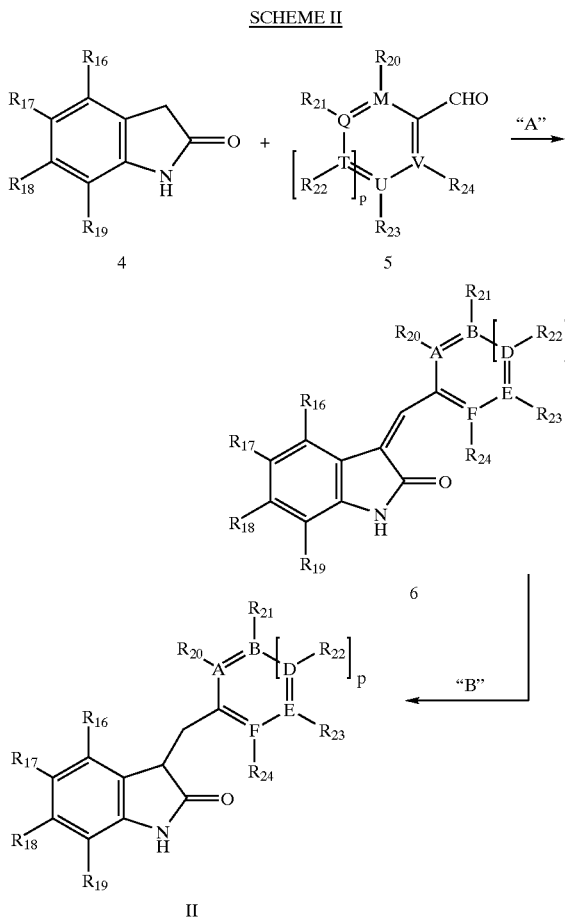

(Reaction "B") to give compound II in Scheme II.

The oxindole in the above combinatorial library is preferably selected from the group consisting of oxindole itself and substituted oxindoles such as, without limitation, 5-fluorooxindole, 6-fluorooxindole, 7-fluorooxindole, 6-trifluoromethyloxindole, 5-chlorooxindole, 6-chlorooxindole, indole-4-carboxylic acid, 5-bromooxindole, 6-(acetamido)-oxindole, 4-methyloxindole, 5-methyloxindole, 4-methyl-5-chlorooxindole, 5-ethyloxindole, 6-hydroxyoxindole, 6-(cyclopentylcarboxamido)oxindole, 5-acetyloxindole, oxindole-5-carboxylic acid, 5-methoxyoxindole, 6-methoxyoxindole, 5-aminooxindole, 6-aminooxindole, 4-[2-(N-morpholino)ethyl]-oxindole, 7-azaoxindole, oxindole-4-carabamic acid t-butyl ester, oxindole-6-carbamic acid t-butyl ester, 4-(2-carboxyethyl)oxindole, 4-n-butyloxindole, 4,5-dimethoxyoxindole, 6-(methanesulfonamido)oxindole, 6-(benzamido)oxindole, 5-ethoxyoxindole, 6-phenyloxindole, 4-(2-hydroxyeth-1-yl)oxindole, 6-(2-methoxyphen-1-yl)oxindole, 6-(3-methoxyphen-1-yl)oxindole and 6-(4-methoxyphen-1-yl)oxindole.

The aldehyde in the above combinatorial library is preferably selected from the group consisting of, without limitation, benzaldehyde itself as well as 3-isopropyl-p-anisaldehyde, 2-methyl-5-isopropyl-p-anisaldehyde, 3,5-diisopropyl-p-anisaldehyde, 3-cyclopentyl-p-anisaldehyde, 3-cyclohexyl-p-anisaldehyde, 3-phenyl-p-anisaldehyde, 3,5-dimethyl-p-anisaldehyde, 2-hydroxy-3,5-dichlorobenzaldehyde, 2-hydroxy-5-chlorobenzaldehyde, 2-hydroxy-4-methoxy-5-(4-methoxyphenyl)benzaldehyde, 3-cyclopentyl-4-methoxybenzaldehyde, 3-cyclopentyl-4-hydroxybenzaldehyde, 3-(2-thienyl)-4-methoxybenzaldehyde, 2-hydroxybenzaldehyde, 2-hydroxy-4-methoxybenzaldehyde, 2-hydroxy-5-bromobenzaldehyde, 2-methylpyridine-6-carboxaldehyde, 3-tert-butyl-4-hydroxy-5-bromobenzaldehyde, 3-bromobenzaldehyde, 3,5-diisopropyl-4-[2-(N-morpholino)ethyl]benzaldehyde, indole-5-carboxaldehyde, 2-hydroxy-3-fluorobenzaldehyde, 3-cyclohexyl-4-[2-(N-morpholino)ethyl]benzaldehyde, 3-(3-thienyl)-4-methoxybenzaldehyde, 2-methyl-5-isopropyl-4-methoxybenzaldehyde, 2,3-dihydrobenzofuran-5-carboxaldehyde, 2,2-dimethylchroman-6-carboxaldehyde, 3-(thiophen-3-yl)-4-methoxybenzaldehyde, 3-(3-acetylaminophenyl)-4-methoxy-benzaldehyde, 2-naphthyl-4,5-dimethoxybenzaldehyde, 2-(3-methoxyphenyl)-4,5-dimethoxybenzaldehyde, 3-(pyrid-3-yl)-p-anisaldehyde, 2-(3-ethoxyphenyl)-4,5-dimethoxybenzaldehyde, 3-isopropyl-4-[2-(N-morpholino)ethoxy]benzaldehyde, 3,5-diisopropyl-4-[2-(N-morpholino)ethoxy]benzaldehyde, 2-(2-methoxyphenyl)-4,5-dimethoxybenzaldehyde, 3-(3-ethoxyphenyl)-p-anisaldehyde, 3-(thiophen-2-yl)-4-[2-(N-morpholino)ethoxy]-benzaldehyde, 2-(thiophen-2-yl)-4,5-dimethoxybenzaldehyde, 2,4-dimethyl-3-[3-dimethylaminoprop-1-yl]-pyrrole-5-carboxaldehyde, 2,4-dimethyl-3-[3-carboxyprop-1-yl]-pyrrole-5-carboxaldehyde, 2,4-dimethyl-3-[3-(N-morpholino)prop-1-yl]-pyrrole-5-carboxaldehyde, 2,4-dimethyl-3-[2-dimethylaminoethyl]-pyrrole-5-carboxaldehyde, 2,4-dimethyl-3-[2-carboxyethyl]-pyrrole-5-carboxaldehyde and 2,4-dimethyl-3-[2-(N-morpholino)ethyl]prop-1-yl]-pyrrole-5-carboxaldehyde.

Another aspect of this invention provides a method for the synthesis of 3-aralkyl-2-indolinone of formula II comprising condensing an oxindole of formula 4 with an aldehyde of formula 5 in a solvent, preferably in the presence of a base, optionally isolating the resultant 3-arylidene-2-oxindole and then reducing the 3-arylidene-2-oxindole.

Examples of the oxindoles of formula 4 that may be condensed with an aldehyde of formula 5 and the product reduced to give the 3-aralkyl-2-indolinones of formula II are oxindole itself and substituted oxindoles such as, without limitation, 5-fluorooxindole, 6-fluorooxindole, 7-fluorooxindole, 6-trifluoromethyloxindole, 5-chlorooxindole, 6-chlorooxindole, indole-4-carboxylic acid, 5-bromooxindole, 6-(acetamido)-oxindole, 4-methyloxindole, 5-methyloxindole, 4-methyl-5-chlorooxindole, 5-ethyloxindole, 6-hydroxyoxindole, 6-(cyclopentylcarboxamido)oxindole, 5-acetyloxindole, oxindole-5-carboxylic acid, 5-methoxyoxindole, 6-methoxyoxindole, 5-aminooxindole, 6-aminooxindole, 4-[2-(N-morpholino)ethyl]-oxindole, 7-azaoxindole, oxindole-4-carabamic acid t-butyl ester, oxindole-6-carbamic acid t-butyl ester, 4-(2-carboxyethyl)oxindole, 4-n-butyloxindole, 4,5-dimethoxyoxindole, 6-(methanesulfonamido)oxindole, 6-(benzamido)oxindole, 5-ethoxyoxindole, 6-phenyloxindole, 4-(2-hydroxyeth-1-yl)oxindole, 6-(2-methoxyphen-1-yl)oxindole, 6-(3-methoxyphen-1-yl)oxindole and 6-(4-methoxyphen-1-yl)oxindole.

Examples of aldehydes of structure 3 which may be condensed with oxindoles of structure 4 and the product reduced to give a compound of this invention are, without limitation, benzaldehyde itself as well as 3-isopropyl-p-anisaldehyde, 2-methyl-5-isopropyl-p-anisaldehyde, 3,5-diisopropyl-p-anisaldehyde, 3-cyclopentyl-p-anisaldehyde, 3-cyclohexyl-p-anisaldehyde, 3-phenyl-p-anisaldehyde, 3,5-dimethyl-p-anisaldehyde, 2-hydroxy-3,5-dichlorobenzaldehyde, 2-hydroxy-5-chlorobenzaldehyde, 2-hydroxy-4-methoxy-5-(4-methoxyphenyl)benzaldehyde, 3-cyclopentyl-4-methoxybenzaldehyde, 3-cyclopentyl-4-hydroxybenzaldehyde, 3-(2-thienyl)-4-methoxybenzaldehyde, 2-hydroxybenzaldehyde, 2-hydroxy-4-methoxybenzaldehyde, 2-hydroxy-5-bromobenzaldehyde, 2-methylpyridine-6-carboxaldehyde, 3-tert-butyl-4-hydroxy-5-bromobenzaldehyde, 3-bromobenzaldehyde, 3,5-diisopropyl-4-[2-(N-morpholino)ethyl]benzaldehyde,indole-5-carboxaldehyde, 2-hydroxy-3-fluorobenzaldehyde, 3-cyclohexyl-4-[2-(N-morpholino)ethyl]benzaldehyde, 3-(3-thienyl)-4-methoxybenzaldehyde, 2-methyl-5-isopropyl-4-methoxybenzaldehyde, 2,3-dihydrobenzofuran-5-carboxaldehyde, 2,2-dimethylchroman-6-carboxaldehyde, 3-(thiophen-3-yl)-4-methoxybenzaldehyde, 3-(3-acetylaminophenyl)-4-methoxybenzaldehyde, 2-naphthyl-4,5-dimethoxybenzaldehyde, 2-(3-methoxyphenyl)-4,5-dimethoxybenzaldehyde, 3-(pyrid-3-yl)-p-anisaldehyde, 2-(3-ethoxyphenyl)-4,5-dimethoxybenzaldehyde, 3-isopropyl-4-[2-(N-morpholino)ethoxy]benzaldehyde, 3,5-diisopropyl-4-[2-(N-morpholino)ethoxy]benzaldehyde, 2-(2-methoxyphenyl)-4,5-dimethoxybenzaldehyde, 3-(3-ethoxyphenyl)-p-anisaldehyde, 3-(thiophen-2-yl)-4-[2-(N-morpholino)ethoxy]-benzaldehyde, 2-(thiophen-2-yl)-4,5-dimethoxybenzaldehyde, 2,4-dimethyl-3-[3-dimethylaminoprop-1-yl]-pyrrole-5-carboxaldehyde, 2,4-dimethyl-3-[3-carboxyprop-1-yl]-pyrrole-5-carboxaldehyde, 2,4-dimethyl-3-[3-(N-morpholino)prop-1-yl]-pyrrole-5-carboxaldehyde, 2,4-dimethyl-3-[2-dimethylaminoethyl]-pyrrole-5-carboxaldehyde, 2,4-dimethyl-3-[2-carboxyethyl]-pyrrole-5-carboxaldehyde and 2,4-dimethyl-3-[2-(N-morpholino)ethyl]prop-1-yl]-pyrrole-5-carboxaldehyde.

D. Diaryl Indolinone Compounds

In another aspect, the invention provides a combinatorial library of at least 10 indolinone compounds that can be formed by reacting an oxindole with a ketone, where the oxindole has the following structure

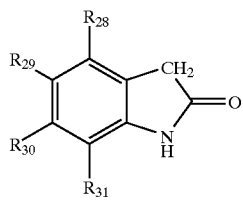

and the ketone has the following structure

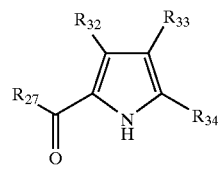

and $R_{27}$, $R_{28}$, $R_{29}$, $R_{30}$, $R_{31}$, $R_{32}$, $R_{33}$, and $R_{34}$ are as described herin.

The oxindole in the above combinatorial library is preferrably selected from the group consisting of 1,3-dihydro-indol-2-one, 4-methyl-1,3-dihydro-indol-2-one, 4-(2-hydroxy-ethyl)-1,3-dihydro-indol-2-one, 5-chloro-1,3-dihydro-indol-2-one, 5-bromo-1,3-dihydro-indol-2-one, 5-methoxy-1,3-dihydro-indol-2-one, 2-oxo-2,3-dihydro-1H-indole-5-carboxylic acid, 2-oxo-2,3-dihydro-1H-indole-5-sulfonic acid dimethylamide, N-(2-oxo-2,3-dihydro-1H-indole-5-yl)-acetamide, 6-chloro-1,3-dihydro-indol-2-one, 6-methoxy-1,3-dihydro-indol-2-one, and N-(5-methyl-2-oxo-2,3-dihydro-1H-indole-6-yl)-acetamide.

The ketone is preferably selected from the group consisting of

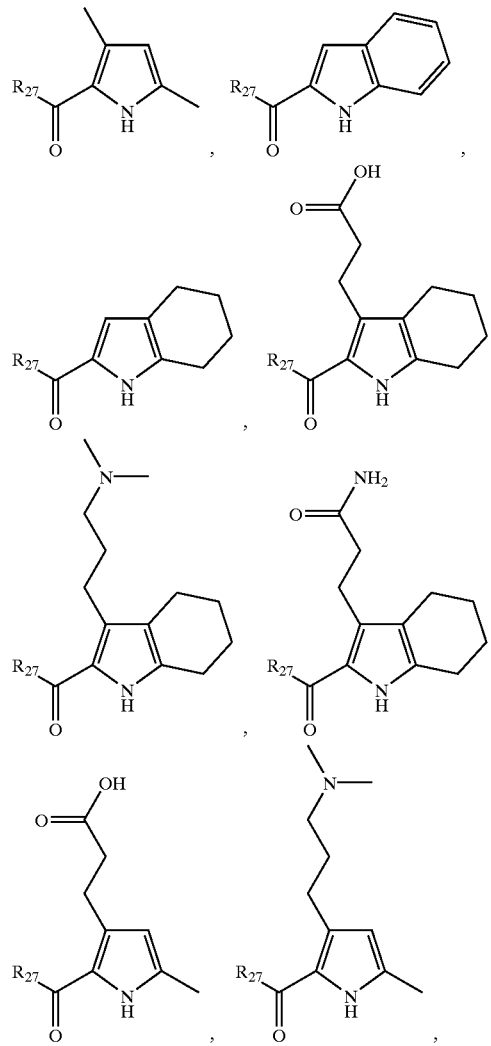

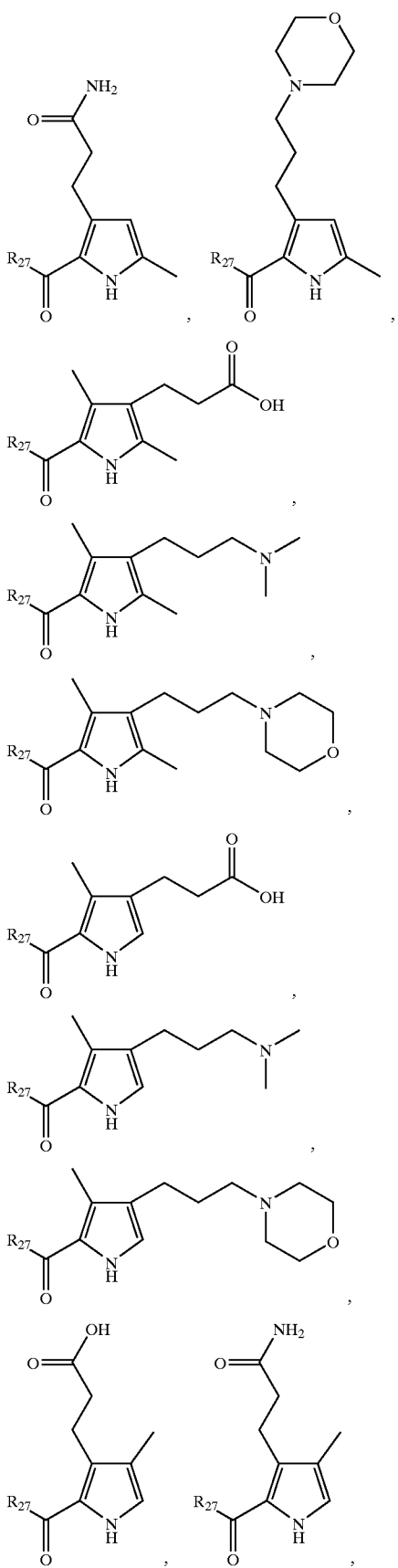

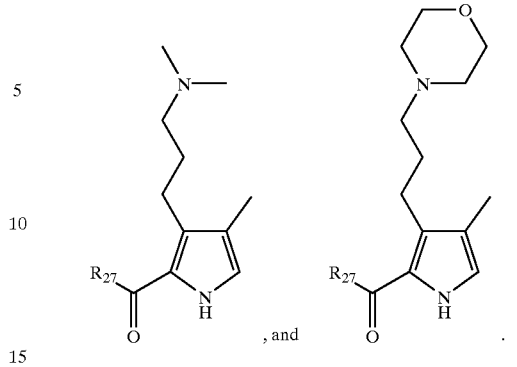

, and

Another aspect of the invention provides for a method for synthesizing a compound of formula III, as described herein, comprising the step of reacting a first reactant with a second reactant in a solvent and in the presence of a base at elevated temperatures, where the first reactant is an oxindole having the following structure

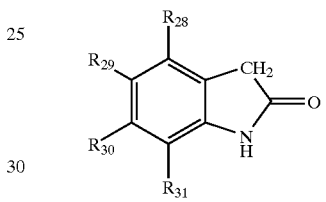

and the second reactant is a ketone having the following structure

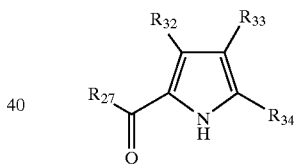

and $R_{27}$, $R_{28}$, $R_{29}$, $R_{30}$, $R_{31}$, $R_{32}$, $R_{33}$, and $R_{34}$ are as described herin.

The first reactant is preferably an oxindole selected from the group consisting of 1,3-dihydro-indol-2-one, 4-methyl-1,3-dihydro-indol-2-one, 4-(2-hydroxy-ethyl)-1,3-dihydro-indol-2-one, 5-chloro-1,3-dihydro-indol-2-one, 5-bromo-1,3-dihydro-indol-2-one, 5-methoxy-1,3-dihydro-indol-2-one, 5-carboxy-1,3-dihydro-indol-2-one, 5-dimethylsulfonamido-1,3-dihydro-indol-2-one, 5-formamido-1,3-dihydro-indol-2-one, 6-chloro-1,3-dihydro-indol-2-one, 6-methoxy-1,3-dihydro-indol-2-one, and 5-methyl-6-formamido-1,3-dihydro-indol-2-one.

The second reactant is preferably a ketone selected from the group consisting of

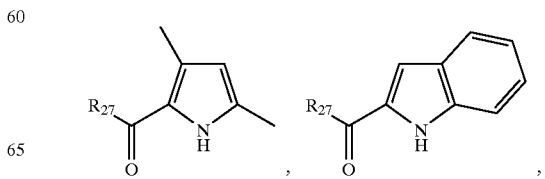

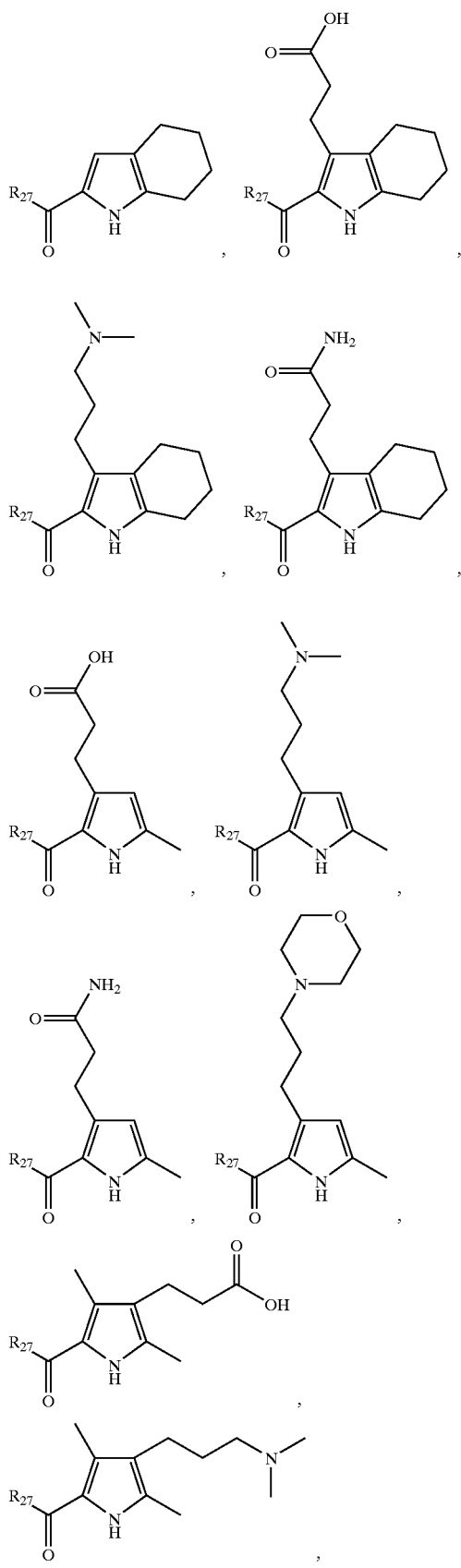

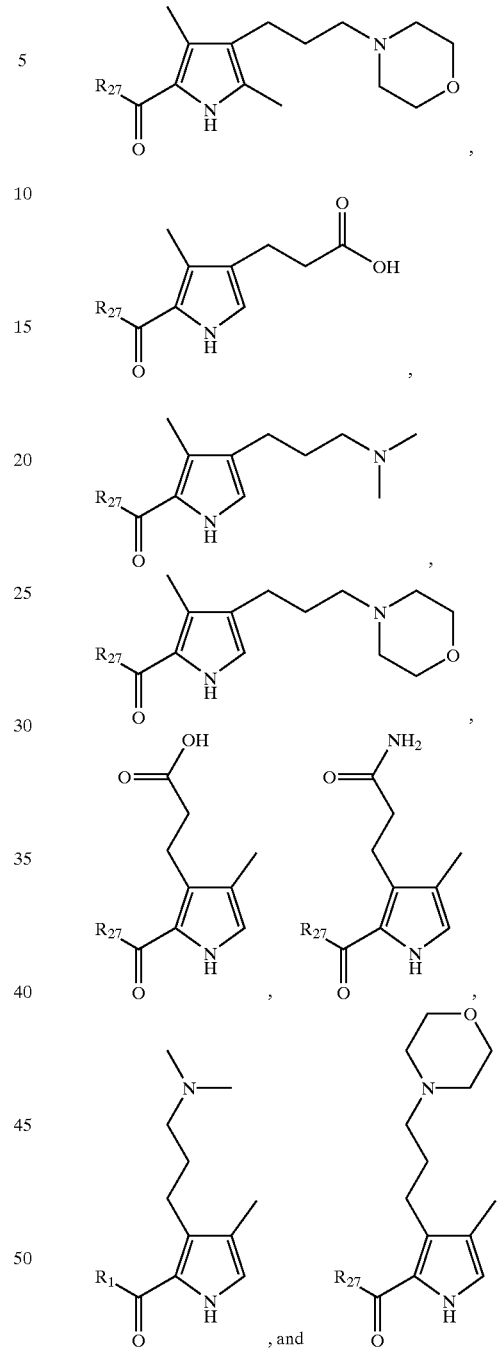

E. 4-Substituted Indolinone Compounds

In another aspect, the invention provides a combinatorial library of at least 10 indolinone compounds that can be formed by reacting an oxindole with an aldehyde, where the oxindole has a structure set forth in formula I, as defined herein, and where the aldehyde has the formula

Z—C(O)—H where Z is as defined herein.

The oxindole in the above combinatorial library is preferrably selected from the group consisting of 4-[2-(3- isopropyl-phenoxy)-ethyl]-1,3-dihydro-indol-2-one, 4-[2-(2-isopropyl-phenoxy)-ethyl]-1,3-dihydro-indol-2-one, 4-[2-(biphenyl-3-yloxy)-ethyl]-1,3-dihydro-indol-2-one, 4-(2-hydroxy-ethyl)-1,3-dihydro-indol-2-one, phenyl-thiocarbamic acid O-[2-(2-oxo-2,3-dihydro-1H-indol-4-yl)-ethyl]ester, phenyl-carbamic acid 2-(2-oxo-2,3-dihydro-1H-indol-4-yl)-ethyl ester, tert-butyl-carbamic acid 2-(2-oxo-2,3-dihydro-1H-indol-4-yl)-ethyl ester, cyclohexyl-carbamic acid 2-(2-oxo-2,3-dihydro-1H-indol-4-yl)-ethyl ester, benzene sulfonyl-carbamic acid 2-(2-oxo-2,3-dihydro-1H-indol-4-yl)-ethyl ester, biphenyl-2-yl-carbamic acid 2-(2-oxo-2,3-dihydro-1H-indol-4-yl)-ethyl ester, ethyl-carbamic acid 2-(2-oxo-2,3-dihydro-1H-indol-4-yl)-ethyl ester, 4-[2-(4-methoxy-phenoxy)-ethyl]-1,3-dihydro-indol-2-one, 4-(2-methoxy-ethyl)-1,3-dihydro-indol-2-one, 4-(2-ethoxy-ethyl)-1,3-dihydro-indol-2-one, 4-[2-(4-isopropyl-phenoxy)-ethyl]-1,3-dihydro-indol-2-one, 4-[2-(5-chloro-pyridin-3-yloxy)-ethyl]-1,3-dihydro-indol-2-one, and isopropyl-carbamic acid 2-(2-oxo-2,3-dihydro-1H-indol-4-yl)-ethyl ester.

The aldehyde is preferably selected from the group consisting of

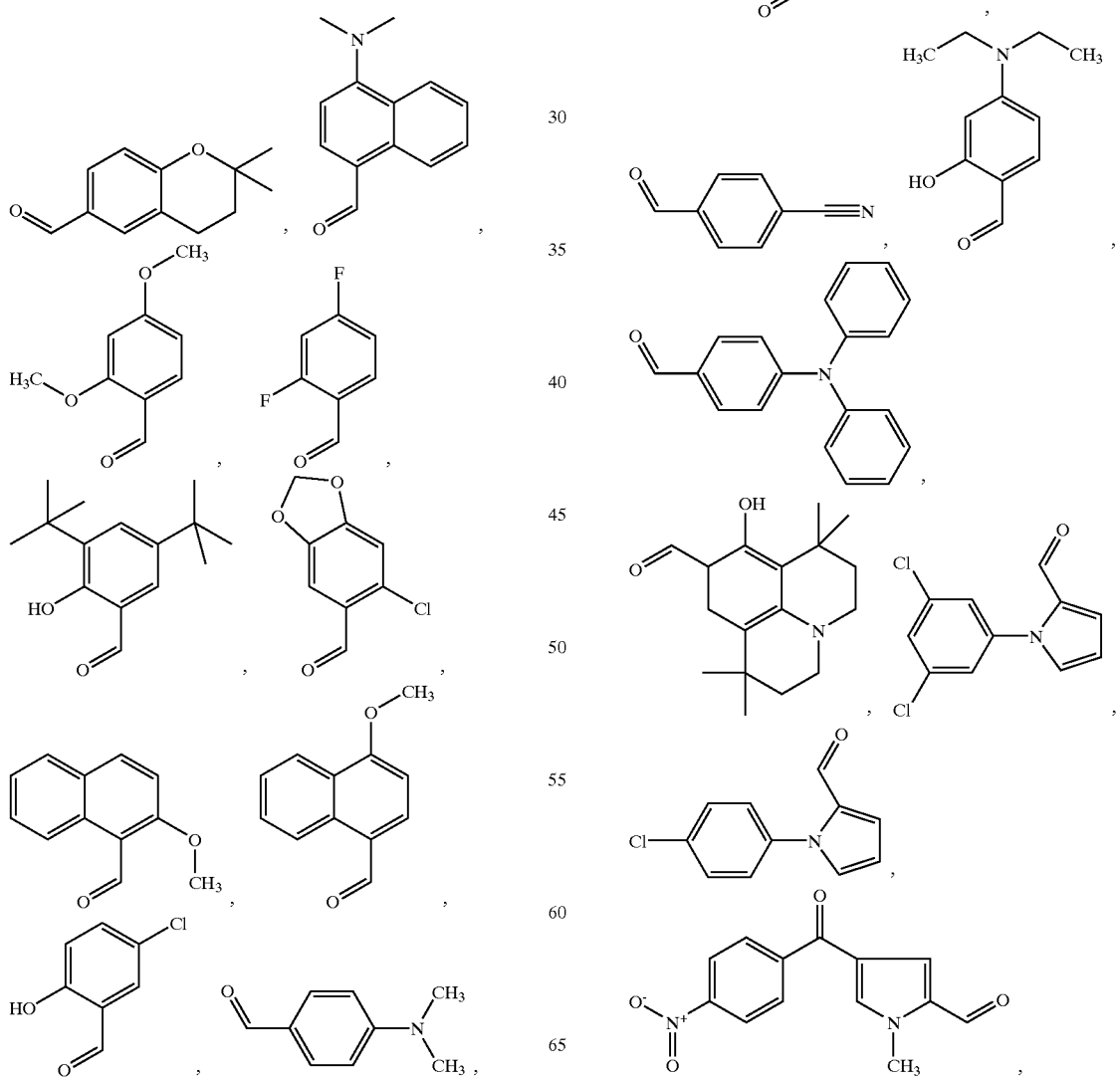
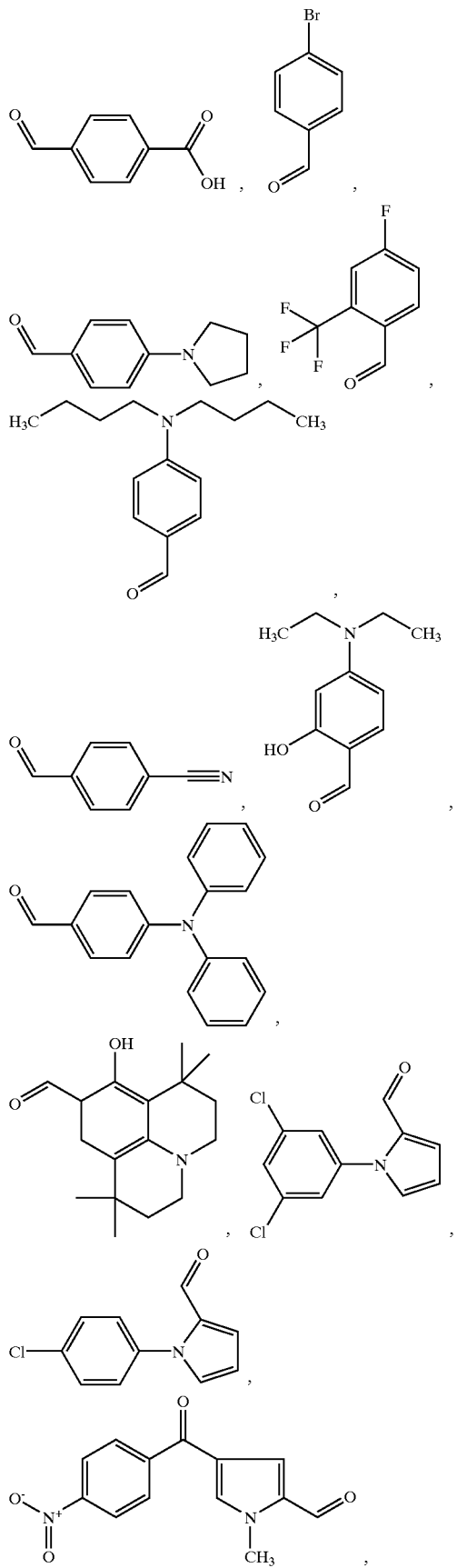

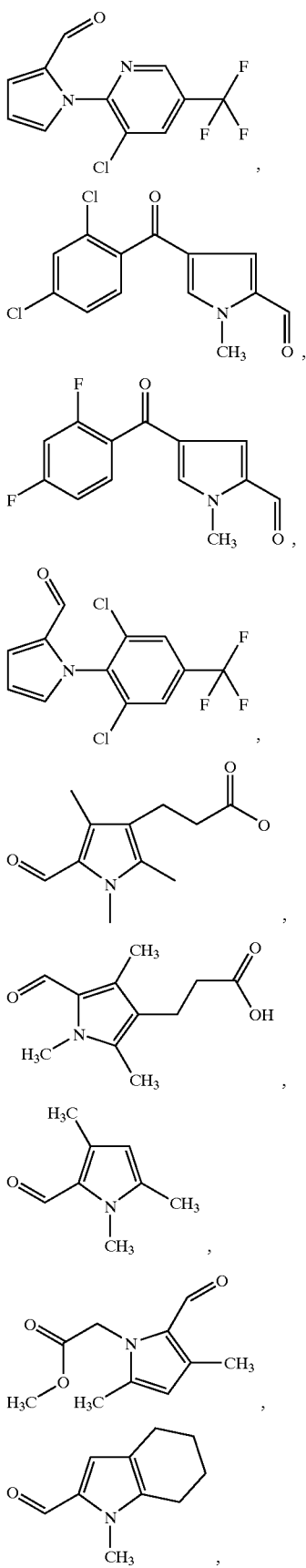
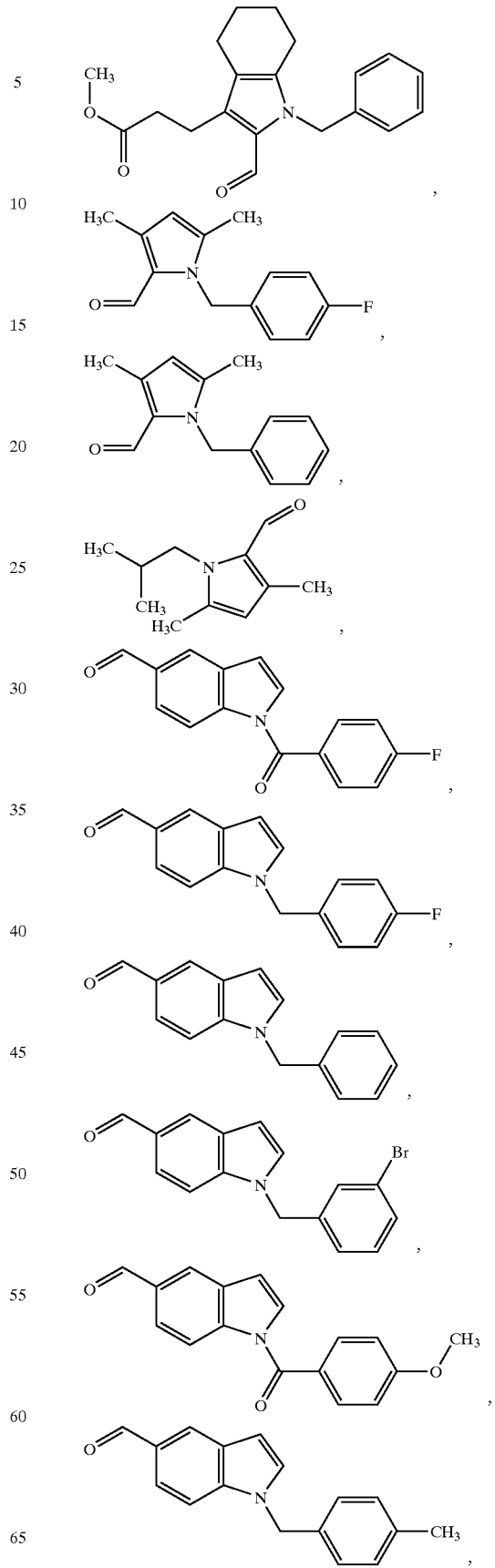

-continued
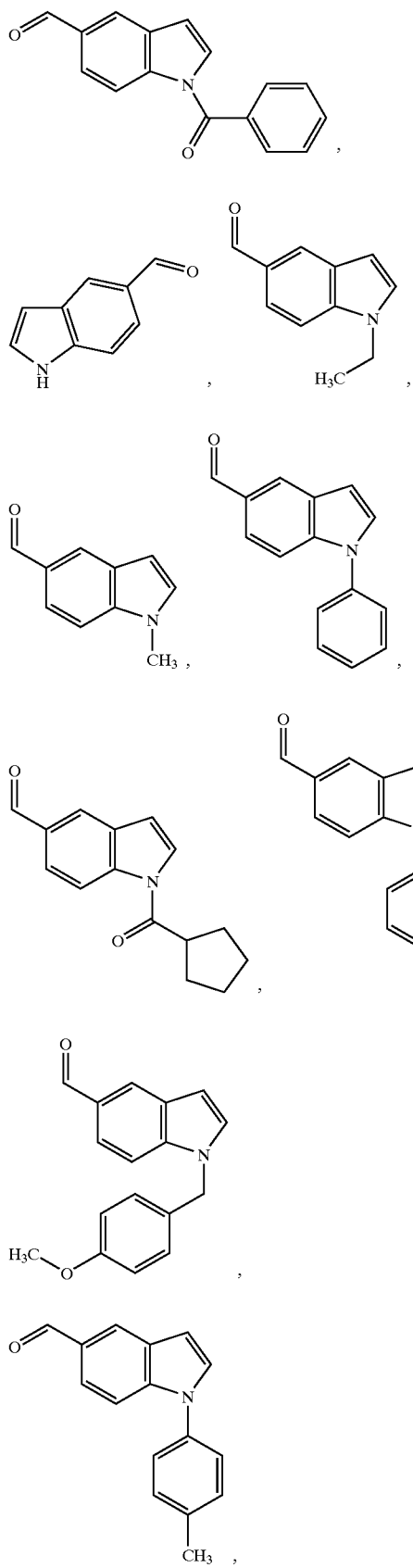
-continued
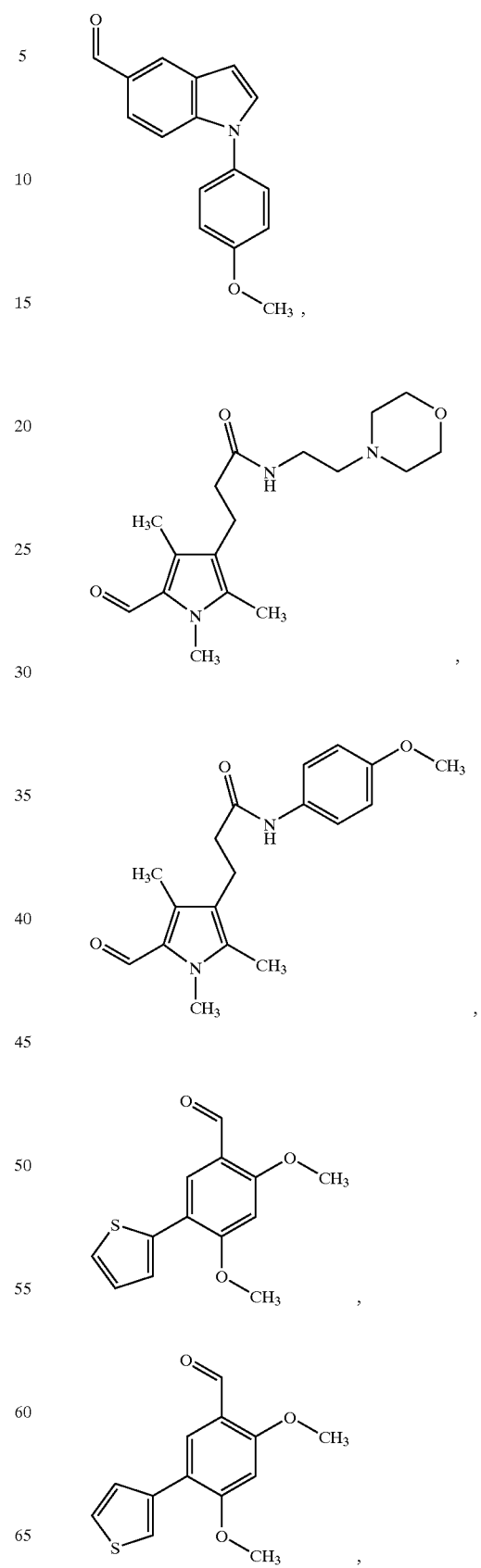

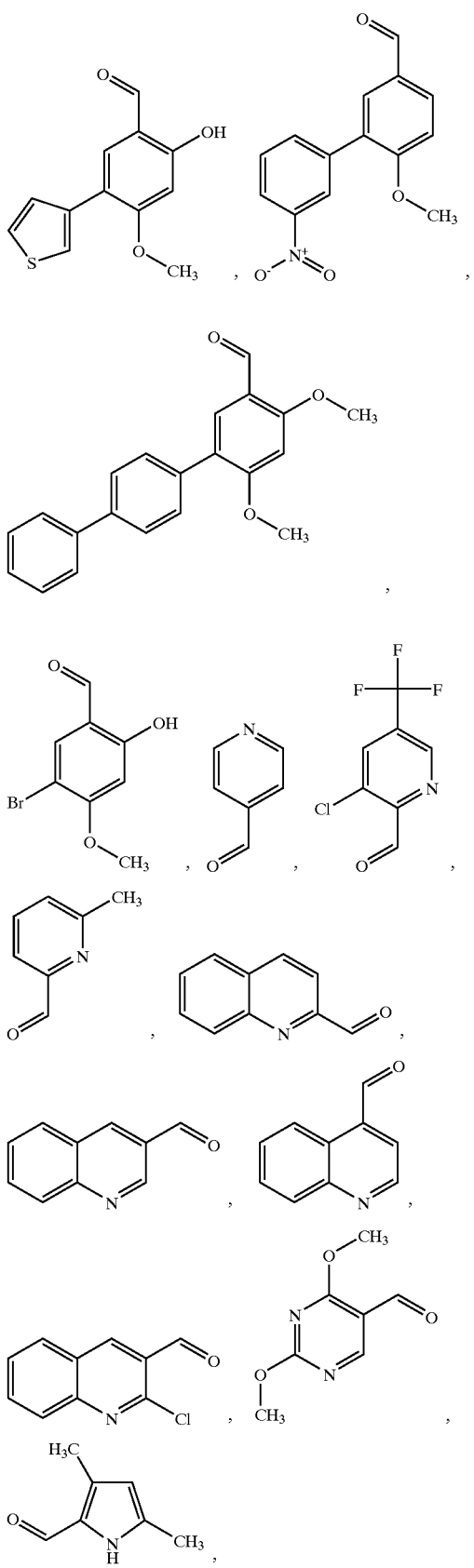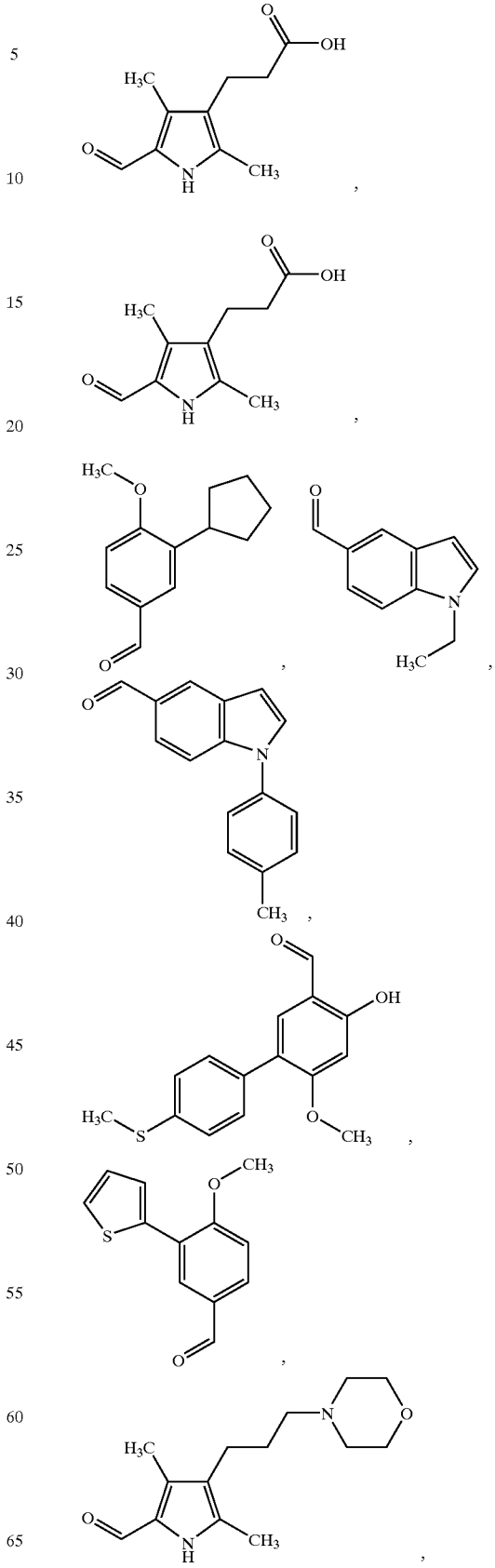

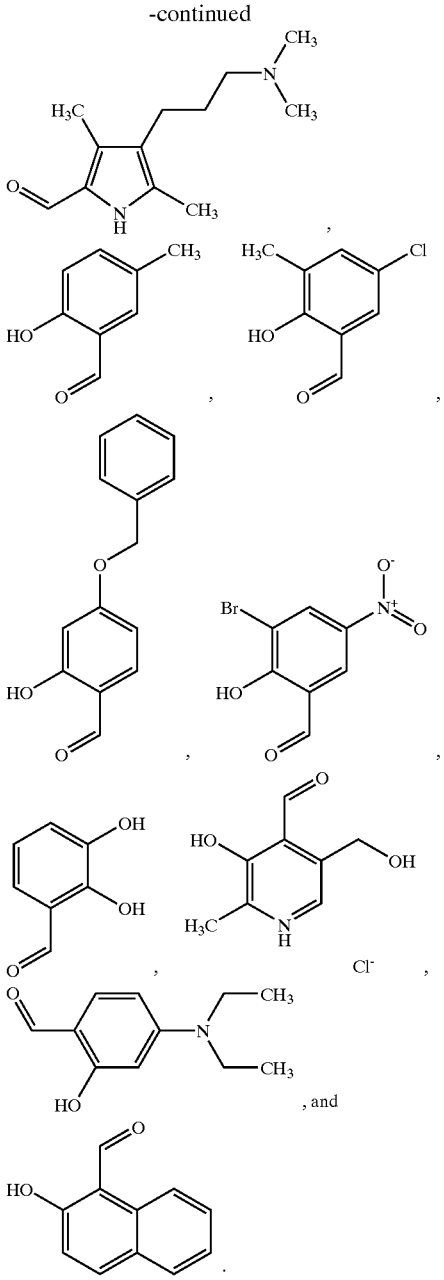

, and

Another aspect of the invention provides for a method for synthesizing a compound of formula IV or formula V, as described herein. The method of synthesizing a compound of formula IV, comprises the step of reacting a first reactant with a second reactant in a solvent and in the presence of a mixture of other reagents. The reaction may take place at ambient temperatures or at elevated temperatures.

The first reactant is preferably an oxindole, more preferably 4-(2-hydroxyethyl)-1,3-dihydro-indol-2-one. The second reactant is preferably selected from the group consisting of an alcohol, an iodoalkyl, an alkyl or aryl isocyanate, and an alkyl or aryl isothiocyanate, and more preferably is selected from the group consisting of 3-isopropylphenol, 2-isopropylphenol, 3-phenylphenol, 4-methoxyphenol, 5-chloro-3-pyridinol, methyl iodide, ethyl iodide, phenyl isocyanate, tert-butyl isocyanate, cyclohexyl isocyanate, benzenesulfonyl isocyanate, 2-biphenylyl isocyanate, ethyl isocyanate, isopropyl isocyanate, and phenyl isothiocyanate.

The "mixture of other reagents" generally refers to a mixture of synthetic reagents or solvents that would facilitate the synthesis of the compounds of the invention, and may include a mixture of diethyl azodicarboxylate with triphenylphosphine in a solvent, or silver trifluoromethanesulfonate, by itself or with a base, in a solvent, or a mixture of solvents.

The method of synthesizing a compound of formula V, comprises the step of reacting a first reactant with a second reactant in a solvent and in the presence of a base at elevated temperatures, where the first reactant is an oxindole having a structure set forth in formula I, as defined herein, and the second reactant is an aldehyde, having the formula

Z—C(O)—H where Z is as defined herein.

The first reactant is preferably an oxindole selected from the group consisting of 4-[2-(3-isopropyl-phenoxy)-ethyl]-1,3-dihydro-indol-2-one, 4-[2-(2-isopropyl-phenoxy)-ethyl]-1,3-dihydro-indol-2-one, 4-[2-(biphenyl-3-yloxy)-ethyl]-1,3-dihydro-indol-2-one, 4-(2-hydroxy-ethyl)-1,3-dihydro-indol-2-one, phenyl-thiocarbamic acid O-[2-(2-oxo-2,3-dihydro-1H-indol-4-yl)-ethyl]ester, phenyl-carbamic acid 2-(2-oxo-2,3-dihydro-1H-indol-4-yl)-ethyl ester, tert-butyl-carbamic acid 2-(2-oxo-2,3-dihydro-1H-indol-4-yl)-ethyl ester, cyclohexyl-carbamic acid 2-(2-oxo-2,3-dihydro-1H-indol-4-yl)-ethyl ester, benzene sulfonyl-carbamic acid 2-(2-oxo-2,3-dihydro-1H-indol-4-yl)-ethyl ester, biphenyl-2-yl-carbamic acid 2-(2-oxo-2,3-dihydro-1H-indol-4-yl)-ethyl ester, ethyl-carbamic acid 2-(2-oxo-2,3-dihydro-1H-indol-4-yl)-ethyl ester, 4-[2-(4-methoxy-phenoxy)-ethyl]-1,3-dihydro-indol-2-one, 4-(2-methoxy-ethyl)-1,3-dihydro-indol-2-one, 4-(2-ethoxy-ethyl)-1,3-dihydro-indol-2-one, 4-[2-(4-isopropyl-phenoxy)-ethyl]-1,3-dihydro-indol-2-one, 4-[2-(5-chloro-pyridin-3-yloxy)-ethyl]-1,3-dihydro-indol-2-one, and isopropyl-carbamic acid 2-(2-oxo-2,3-dihydro-1H-indol-4-yl)-ethyl ester.

The second reactant is preferably an aldehyde selected from the group consisting of 4-bromobenzaldehyde, 2-pyridinecarboxaldehyde, 6-methyl-2-pyridinecarbaldehyde, 1H-indole-5-carbaldehyde, 4-methoxy-3-thiophen-2-yl-benzaldehyde, 4-(3-dimethylamino-propyl)-3,5-dimethyl-1H-pyrrole-2-carbaldehyde, 3-hydroxy-6-ethyl-pyridine-2-carbaldehyde, 4-(3-dimethylamino-propyl)-3,5-dimethyl-1H-pyrrole-2-carbaldehyde, and 4-carboxyethyl-3,5-dimethyl-2-formylpyrrole.

IV. BIOLOGICAL ACTIVITY AND PHARMACEUTICAL COMPOSITIONS

In another aspect, the invention features a pharmaceutical composition comprising (i) a physiologically acceptable carrier, diluent, or excipient; and (ii) a compound as described herein.

The invention also features a method of modulating the function of a protein kinase with a compound of the invention, comprising the step of contacting cells expressing the protein kinase with the compound.

A still further aspect of this invention is that the protein kinase whose catalytic activity is being modulated by a compound of this invention is selected from the group consisting of receptor protein tyrosine kinases, cellular tyrosine kinases and serine-threonine kinases.

It is an aspect of this invention that the receptor protein kinase whose catalytic activity is modulated by a compound of this invention is selected from the group consisting of EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R. In addition, it is an aspect of this invention that the cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, Blk, Hck, Fgr and Yrk. Another aspect of this invention is that the serine-threonine protein kinase whose catalytic activity is modulated by a compound of this invention is selected from the group consisting of CDK2 and Raf.

A protein kinase natural binding partner can bind to a protein kinase's intracellular region with high affinity. High affinity represents an equilibrium binding constant on the order of $10^{-6}$ M or less. In addition, a natural binding partner can also transiently interact with a protein kinase intracellular region and chemically modify it. Protein kinase natural binding partners are chosen from a group that includes, but is not limited to, SRC homology 2 (SH2) or 3 (SH3) domains, other phosphoryl tyrosine binding (PTB) domains, guanine nucleotide exchange factors, protein phosphatases, and other protein kinases. Methods of determining changes in interactions between protein kinases and their natural binding partners are readily available in the art.

The compounds of the invention preferably modulate the activity of the protein tyrosine kinase in vitro. These compounds preferably show positive results in one or more in vitro assays for an activity corresponding to treatment of the disease or disorder in question (such as the assays described in the Examples below).

The invention also features a method of identifying compounds that modulate the function of protein kinase, comprising the following steps: (a) contacting cells expressing the protein tyrosine kinase with the compound; and (b) monitoring an effect upon the cells. The effect upon the cells is preferably a change or an absence of a change in cell phenotype, more preferably it is a change or an absence of a change in cell proliferation, even more preferably it is a change or absence of a change in the catalytic activity of the protein kinase, and most preferably it is a change or absence of a change in the interaction between the protein kinase with a natural binding partner, as described herein.

In a preferred embodiment, the invention features a method for identifying the compounds of the invention, comprising the following steps: (a) lysing the cells to render a lysate comprising protein tyrosine kinase; (b) adsorbing the protein tyrosine kinase to an antibody; (c) incubating the adsorbed protein tyrosine kinase with a substrate or substrates; and (d) adsorbing the substrate or substrates to a solid support or antibody; where the step of monitoring the effect on the cells comprises measuring the phosphate concentration of the substrate or substrates.

In yet another aspect, the invention features a method for treating a disease related to unregulated kinase signal transduction, where the method includes the step of administering to a subject in need thereof a therapeutically effective amount of a compound of the invention as described herein.

The invention also features a method of regulating kinase signal transduction comprising administering to a subject a therapeutically effective amount of a compound of the invention as described herein.

Furthermore, the invention features a method of preventing or treating an abnormal condition in an organism, where the abnormal condition is associated with an aberration in a signal transduction pathway characterized by an interaction between a protein kinase and a natural binding partner, where the method comprises the following steps: (a) administering a compound of the invention as described herein; and (b) promoting or disrupting the abnormal interaction. The organism is preferably a mammal and the abnormal condition is preferably cancer. The abnormal condition may also preferably be selected from the group consisting of hypertension, depression, generalized anxiety disorder, phobias, post-traumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's disease, endocrine disorders, vasospasm, cerebellar ataxia, and gastrointestinal tract disorders.

As used herein, "PK related disorder," "PK driven disorder," and "abnormal PK activity" all refer to a condition characterized by inappropriate; i.e., under or, more commonly, over, PK catalytic activity, where the particular PK can be an RTK, a CTK or an STK. Inappropriate catalytic activity can arise as the result of either: (1) PK expression in cells which normally do not express PKs; (2) increased PK expression leading to unwanted cell proliferation, differentiation and/or growth; or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor; (2) inhibiting (that is, slowing to some extent, preferably stopping) tumor metastasis; (3) inhibiting to some extent (that is, slowing to some extent, preferably stopping) tumor growth; and/or, (4) relieving to some extent (or, preferably, eliminating) one or more symptoms associated with the cancer.

It is an aspect of this invention that the above-referenced protein kinase related disorder is selected from the group consisting of a receptor protein tyrosine kinase related disorder, a cellular tyrosine kinase disorder and a serine-threonine kinase related disorder.

In yet another aspect of this invention, the above referenced protein kinase related disorder is selected from the group consisting of an EGFR related disorder, a PDGFR related disorder, an IGFR related disorder and a flk related disorder.

The above referenced protein kinase related disorder is a cancer selected from the group consisting of squamous cell carcinoma, astrocytoma, glioblastoma, lung cancer, bladder cancer, head and neck cancer, melanoma, ovarian cancer, prostate cancer, breast cancer, small-cell lung cancer and glioma in a further aspect of this invention.

The above referenced protein kinase related disorder is selected from the group consisting of diabetes, immunlogical disorders such as autoimmune disorder, a hyperproliferation disorder, restinosis, fibrosis, psoriasis, osteoarthritis, rheumatoid arthritis, an inflammatory disorder, angiogenesis, cardiovascular disease such as aetherosclerosis, and renal disease, in yet another aspect of this invention.

In addition to modulating PK activity, the compounds of this invention may inhibit the activity of protein phosphatases which are enzymes which remove phosphate groups from phosphorylated proteins. Thus the compounds disclosed herein may also represent a new generation of therapeutic compounds for diseases and disorders associated with abnormal phosphatase activity (such as, without limitation, diabetes, cell proliferation disorders and inflammatory disorders). The terms defined herein with respect to PKs would be understood by one skilled in the art to have the same or similar meaning with regard to phosphastases.

The summary of the invention described above is non-limiting and other features and advantages of the invention will be apparent from the following description of the preferred embodiments, and from the claims.

DETAILED DESCRIPTION OF THE INVENTION

The present invention relates to compounds capable of regulating and/or modulating cellular signal transduction and, in preferred embodiments, receptor and non-receptor tyrosine kinase signal transduction.

Receptor-kinase mediated signal transduction is initiated by extracellular interaction with a specific growth factor (ligand), followed by receptor dimerization, transient stimulation of the intrinsic protein kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects to the extracellular microenvironment). See, Schlessinger and Ullrich, 1992, *Neuron* 9:303–391.

It has been shown that tyrosine phosphorylation sites in growth factor receptors unction as high-affinity binding sites for SH2 (src homology) domains of signaling molecules. Fantl et al., 1992, *Cell* 69:413–423; Songyang et al., 1994, *Mol. Cell. Biol.* 4:2777–2785); Songyang et al., 1993, *Cell* 72:767–778; and Koch et al., 1991, *Science* 252:668–678. Several intracellular substrate proteins that associate with receptor kinases have been identified. They may be divided into two principal groups: (1) substrates which have a catalytic domain; and (2) substrates which lack such domain but serve as adapters and associate with catalytically active molecules. Songyang et al., 1993, *Cell* 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767–778. These observations suggest that the function of each receptor kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis).

This invention is therefore directed to compounds which regulate, modulate and/or inhibit kinase signal transduction by affecting the enzymatic activity of the receptor kinases (RKs) and/or the non-receptor kinases and interfering with the signal transduced by such proteins. More particularly, the present invention is directed to compounds which regulate, modulate and/or inhibit the RK and/or non-receptor kinase mediated signal transduction pathways as a therapeutic approach to cure many kinds of solid tumors, including but not limited to carcinoma, sarcoma, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

I. Target Diseases to be Treated by the Compounds of the Invention

The compounds described herein are useful for treating disorders related to unregulated kinase signal transduction, including cell proliferative disorders, fibrotic disorders-and metabolic disorders.

Cell proliferative disorders which can be treated or further studied by the present invention include cancers, blood vessel proliferative disorders and mesangial cell proliferative disorders.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness. Conversely, disorders related to the shrinkage, contraction or closing of blood vessels, such as restenosis, are also implicated.

Fibrotic disorders refer to the abnormal formation of extracellular matrix. Examples of fibrotic disorders include hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Other fibrotic disorders implicated include atherosclerosis (see, below).

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. The PDGF-R has been implicated in the maintenance of mesangial cell proliferation. Floege et al., 1993, *Kidney International* 43:47S–54S.

PKs have been associated with such cell proliferative disorders. For example, some members of the receptor tyrosine kinase family have been associated with the development of cancer. Some of these receptors, like the EGFR (Tuzi et al., 1991, *Br. J. Cancer* 63:227–233; Torp et al., 1992, *APMIS* 100:713–719) HER2/neu (Slamon et al., 1989, *Science* 244:707–712) and the PDGF-R (Kumabe et al., 1992, *Oncogene* 7:627–633) are overexpressed in many tumors and/or persistently activated by autocrine loops. In fact, in the most common and severe cancers these receptor overexpressions (Akbasak and Suner-Akbasak et al., 1992, *J. Neurol. Sci.* 111:119–133; Dickson et al., 1992, *Cancer Treatment Res.* 61:249–273; Korc et al., 1992, *J. Clin. Invest.* 90:1352–1360) and autocrine loops (Lee and Donoghue, 1992, *J. Cell. Biol.* 118:1057–1070; Korc et al., supra; Akbasak and Suner-Akbasak et al., supra) have been demonstrated. For example, the EGFR receptor has been associated with squamous cell carcinoma, astrocytoma, glioblastoma, head and neck cancer, lung cancer and bladder cancer. HER2 has been associated with breast, ovarian, gastric, lung, pancreas and bladder cancer. The PDGF-R has been associated with glioblastoma, lung, ovarian, melanoma and prostate cancer. The RK c-met has been generally associated with hepatocarcinogenesis and thus hepatocellular carcinoma. Additionally, c-met has been linked to malignant tumor formation. More specifically, the RK c-met has been associated with, among other cancers, colorectal, thyroid, pancreatic and gastric carcinoma, leukemia and lymphoma. Additionally, over-expression of the c-met gene has been detected in patients with Hodgkin's disease, Burkitt's disease, and the lymphoma cell line. Fik has likewise been associated with a broad spectrum of tumors including, without limitation, mammary, ovarian and lung tumors as well as gliomas such as glioblastoma.

The IGF-IR, in addition to being implicated in nutritional support and in type-II diabetes, has also been associated with several types of cancers. For example, IGF-I has been implicated as an autocrine growth stimulator for several tumor types, e.g., human breast cancer carcinoma cells (Arteaga et al., 1989, *J. Clin. Invest.* 84:1418–1423) and small lung tumor cells (Macauley et al., 1990, *Cancer Res.* 50:2511–2517). In addition, IGF-I, integrally involved in the normal growth and differentiation of the nervous system, appears to be an autocrine stimulator of human gliomas. Sandberg-Nordqvist et al., 1993, *Cancer Res.* 53:2475–2478. The importance of the IGF-IR and its ligands in cell proliferation is further supported by the fact that many cell types in culture (fibroblasts, epithelial cells, smooth muscle cells, T-lymphocytes, myeloid cells, chondrocytes, osteoblasts, the stem cells of the bone marrow) are stimulated to grow by IGF-I. Goldring and Goldring, 1991, *Eukaryotic Gene Expression* 1:301–326. In a series of recent publications, Baserga even suggests that IGF-I-R plays a central role in the mechanisms of transformation and, as such, could be a preferred target for therapeutic interventions for a broad spectrum of human malignancies. Baserga, 1995, *Cancer Res.* 55:249–252; Baserga, 1994, *Cell* 79:927–930; Coppola et al., 1994, *Mol. Cell. Biol.* 14:4588–4595.

Some protein kinases (PKs) have been implicated in many types of cancer including, notably, breast cancer (Cance, et al., *Int. J. Cancer*, 54:571–77 (1993)).

The association between abnormalities in RKs and disease are not restricted to cancer, however. For example, RKs have been associated with metabolic diseases like psoriasis, diabetes mellitus, wound healing, inflammation, and neurodegenerative diseases. These diseases include, but are not limited to hypertension, depression, generalized anxiety disorder, phobias, post-traumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's disease, endocrine disorders, vasospasm, cerebellar ataxia, and gastrointestinal tract disorders. For example, the EGF-R is indicated in corneal and dermal wound healing. Defects in the Insulin-R and the IGF-1R are indicated in type-II diabetes mellitus. A more complete correlation between specific RKs and their therapeutic indications is set forth in Plowman et al., 1994, *DN&P* 7:334–339.

Not only receptor type kinases, but also many cellular kinases (CKs) including src, abl, fps, yes, fyn, lyn, lck, blk, hck, fgr, yrk (reviewed by Bolen et al., 1992, *FASEB J.* 6:3403–3409) are involved in the proliferative and metabolic signal transduction pathway and thus in indications of the present invention. For example, mutated src (v-src) has been demonstrated as an oncoprotein ($pp60^{v-src}$) in chicken. Moreover, its cellular homolog, the proto-oncogene $pp60^{c-src}$ transmits oncogenic signals of many receptors. For example, overexpression of EGF-R or HER2/neu in tumors leads to the constitutive activation of $pp60^{c-src}$ which is characteristic for the malignant cell but absent from the normal cell. On the other hand, mice deficient for the expression of c-src exhibit an osteopetrotic phenotype, indicating a key participation of c-src in osteoclast function and a possible involvement in related disorders. Similarly, Zap 70 is implicated in T-cell signaling.

Furthermore, the identification of CTK modulating compounds to augment or even synergize with RK aimed blockers is an aspect of the present invention.

Additionally, both RKs and non-receptor type kinases have been connected to hyperimmune disorders.

Further, the compounds of the present invention are also effective in treating diseases that are related to the PYK-2 protein. This protein, its cellular function, and diseases related to them are set forth in detail in U.S. applications Ser. No. 08/357,642, filed Dec. 15, 1994, by Lev et al., and entitled "PYK2 RELATED PRODUCTS AND METHODS", and Ser. No. 08/460,626, filed Jun. 2, 1995, by Lev et al., and entitled "PYK2 RELATED PRODUCTS AND METHODS", both of which are hereby incorporated by reference herein in their entirety, including any drawings.

Finally, the present invention is directed towards oxindole and indolinone compounds and methods of modulating the functions of protein phosphatases, as well as methods of preventing and treating protein phosphatase related abnormal conditions in organisms with a compound of the method identified above. The compounds of the invention, as well as compounds obtained by adding chemical substituents, may potently inhibit the action of phosphatases and may represent a new generation of therapeutics for diseases associated with defects in said phosphatases. Terms defined above with respect to kinases have a similar meaning to one skilled in the art with respect to phosphatases. Both RKs and non-receptor type kinases have been connected to hyperimmune disorders.

The compounds of the present invention are also effective in treating diseases that are related to the PYK-2 protein. This protein, its cellular function, and diseases related to them are set forth in detail in U.S. Pat. No. 5,837,524, issued Nov. 17, 1998, to Lev et al., and entitled "PYK2 RELATED PRODUCTS AND METHODS," and U.S. Pat. No. 5,837,815, issued Nov. 17, 1998, to Lev et al., and entitled "PYK2 RELATED PRODUCTS AND METHODS," both of which are hereby incorporated by reference herein in their entirety, including any drawings.

II. KDR/FLK-1 a. The KDR/FLK-1 Receptor and VEGF

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman and Shing, 1992, *J. Biological Chem.* 267:10931–34. However, many diseases are driven by persistent unregulated or inappropriate angiogenesis. For example, in arthritis, new capillary blood vessels invade the joint and destroy the cartilage. In diabetes, new capillaries in the retina invade the vitreous, bleed and cause blindness. Folkman, 1987, in: *Congress of Thrombosis and Haemostasis* (Verstraete, et. al, eds.), Leuven University Press, Leuven, pp.583–596. Ocular neovascularization is the most common cause of blindness and dominates approximately twenty (20) eye diseases.

Moreover, vasculogenesis and/or angiogenesis have been associated with the growth of malignant solid tumors and metastasis. A tumor must continuously stimulate the growth of new capillary blood vessels for the tumor itself to grow. Furthermore, the new blood vessels embedded in a tumor provide a gateway for tumor cells to enter the circulation and to metastasize to distant sites in the body. Folkman, 1990, *J. Natl. Cancer Inst.* 82:4–6; Klagsbrunn and Soker, 1993, *Current Biology* 3:699–702; Folkman, 1991, *J. Natl., Cancer Inst.* 82:4–6; Weidner et al., 1991, *New Engl. J. Med.* 324:1–5.

Several polypeptides with in vitro endothelial cell growth promoting activity have been identified. Examples include acidic and basic fibroblastic growth factor (aFGF, bFGF), vascular endothelial growth factor (VEGF) and placental growth factor. Unlike aFGF and bFGF, VEGF has recently been reported to be an endothelial cell specific mitogen. Ferrara and Henzel, 1989, *Biochem. Biophys. Res. Comm.* 161:851–858; Vaisman et al., 1990, *J. Biol. Chem.* 265:19461–19566.

Thus, the identification of the specific receptors to which VEGF binds is an important advancement in the understanding of the regulation of endothelial cell proliferation. Two structurally closely related RKs have been identified to bind VEGF with high affinity: the flt-1 receptor (Shibuya et al., 1990, *Oncogene* 5:519–524; De Vries et al., 1992, *Science* 255:989–991) and the KDR/FLK-1 receptor, discussed in the U.S. patent application Ser. No. 08/193,829. Consequently, it had been surmised that these RKs may have a role in the modulation and regulation of endothelial cell proliferation.

Evidence, such as the disclosure set forth in copending U.S. application Ser. No. 08/193,829, strongly suggests that VEGF is not only responsible for endothelial cell proliferation, but also is a prime regulator of normal and pathological angiogenesis. See generally, Klagsbum and Soker, 1993, *Current Biology* 3:699–702; Houck et al, 1992, *J. Biol. Chem.* 267:26031–26037. Moreover, it has been shown that KDR/FLK-1 and flt-1 are abundantly expressed in the proliferating endothelial cells of a growing tumor, but not in the surrounding quiescent endothelial cells. Plate et al., 1992, *Nature* 359:845–848; Shweiki et al., 1992, *Nature* 359:843–845.

b. Identification Of Agonists And Antagonists To The KDR/FLK-1 Receptor

In view of the deduced importance of RKs in the control, regulation and modulation of endothelial cell proliferation and potentially vasculogenesis and/or angiogenesis, many attempts have been made to identify RK "inhibitors" using a variety of approaches. These include the use of mutant ligands (U.S. Pat. No. 4,966,849); soluble receptors and antibodies (Application No. WO 94/10202; Kendall and Thomas, 1994, *Proc. Natl. Acad. Sci. USA* 90:10705–10709; Kim et al., 1993, *Nature* 362:841–844); and RNA ligands (Jellinek et al., 1994, *Biochemistry* 33:10450–10456).

Furthermore, kinase inhibitors (WO 94/03427; WO 92/21660; WO 91/15495; WO 94/14808; U.S. Pat. No. 5,330,992; Mariani et al., 1994, *Proc. Am. Assoc. Cancer Res.* 35:2268), and inhibitors acting on receptor kinase signal transduction pathways, such as protein kinase C inhibitors have been identified (Schuchter et al., 1991, *Cancer Res.* 51:682–687); Takano et al., 1993, *Mol. Bio. Cell* 4:358A; Kinsella et al., 1992, *Exp. Cell Res.* 199:56–62; Wright et al., 1992, *J. Cellular Phys.* 152:448–57).

More recently, attempts have been made to identify small molecules which act as kinase inhibitors for use in the treatment of cancer. Consequently, there is an unmet need for the identification and generation of effective small compounds which selectively inhibit the signal transduction of the KDR/FLK-1 receptor in order to effectively and specifically suppress vasculogenesis.

Consequently, there is an unmet need for the identification and generation of effective small compounds which selectively inhibit the signal transduction of the KDR/FLK-1 receptor in order to effectively and specifically suppress vasculogenesis.

Some of the compounds of the present invention demonstrate excellent activity in biological assays and thus these compounds and related compounds are expected to be effective in treating Flk related disorders such as those driven by persistent unregulated or inappropriate angiogenesis.

III. Pharmaceutical Formulations And Routes Of Administration

The compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., latest edition.

a) Routes Of Administration

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

b) Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with one or more compound of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection maybe presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the PK modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

c) Effective Dosage.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the PK activity). Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p.1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

d) Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

IV. Biological Activity of the Compounds of the Invention

The compounds of the present invention were tested for their ability to inhibit most of protein kinase activity. The biological assays and results of these inhibition studies are reported herein. The methods used to measure modulation of protein kinase function are similar to those described in International Publication No. WO 98/07695, published Mar. 26, 1998, by Tang et al., and entitled "Indolinone Combinatorial Libraries and Related Products and Methods for the Treatment of Disease," with respect to the high throughput aspect of the method. The WO 98/07695 publication is incorporated herein by reference in its entirety, including any drawings.

V. Pharmaceutical Compositions and Administration of Compounds of the Invention

Methods of preparing pharmaceutical formulations of the compounds, methods of determining the amounts of compounds to be administered to a patient, and modes of administering compounds to an organism are disclosed in the WO 98/07695 publication, and International patent publication number WO 96/22976, by Buzzetti et al., and entitled "Hydrosoluble 3-Arylidene-2-Oxindole Derivatives as Tyrosine Kinase Inhibitors," published Aug. 1, 1996, both of which are incorporated herein by reference in their entirety, including any drawings. Those skilled in the art will appreciate that such descriptions are applicable to the present invention and can be easily adapted to it.

EXAMPLES

The examples below are non-limiting and are merely representative of various aspects and features of the present invention. The examples describe methods for synthesizing compounds of the invention and methods for measuring an effect of a compound on the function-of protein kinases.

The cells used in the methods are commercially available. The nucleic acid vectors harbored by the cells are also commercially available and the sequences of genes for the various protein kinases are readily accessible in sequence data banks. Thus, a person of ordinary skill in the art can readily recreate the cell lines in a timely manner by combining the commercially available cells, the commercially available nucleic acid vectors, and the protein kinase genes using techniques readily available to persons of ordinary skill in the art.

SYNTHETIC PROCEDURES

Example 1

Procedure for Synthesizing the Compounds of the Invention

The compounds of this invention, as well as the precursor 2-oxindoles and aldehydes, may be readily synthesized using techniques well known in the chemical arts. It will be appreciated by those skilled in the art that other synthetic pathways for forming the compounds of the invention are available and that the following is offered by way of example and not limitation. Furthermore, the compounds whose syntheses are described below are likewise not to be construed as limiting the scope of this invention in any manner whatsoever.

A. 3-Arylidenyl-6-Heterocyclyl-2-Indolinone Derivatives
Compound AHI-1: 3-(4-Methoxy-3-thiophen-2-yl-benzylidene)-6-pyridin-3-yl-1,3-dihydroindol-2-one To a warm, stirred solution of 6-bromo-2-oxindole (4 g, 26.3 mmol) in 60 mL toluene and 60 mL ethanol was added tetrakis(triphenylphosphine)palladium(0) (2.3 g, 1.9 mmol) followed by 2M aqueous sodium carbonate (50 mL, 100 mmol) and pyridine-3-boronic acid, propanediol ester (5 g, 30.7 mmol). The mixture was stirred at 100° C. in an oil bath for 12 hours. The reaction mixture was cooled, diluted with ethyl acetate (500 mL) and washed with saturated sodium bicarbonate (200 mL), water (200 mL) and brine (200 mL). The organic layer was separated, dried over anhydrous magnesium sulfate and concentrated to afford a brown solid. The solid was triturated with methylene chloride/diethyl ether to give 2.32 g (42%) of 6-pyridin-3-yl-1,3-dihydro-indol-2-one as a brown solid.

$^1$H NMR (360 MHz, DMSO-d$_6$) δ 10.51 (s, 1H, NH), 8.81 (d, J=2.5 Hz, 1H, Ar—H), 8.55 (dd, J=1.8 and 5.7 Hz, 1H, Ar—H), 8 (m, 1H, Ar—H), 7.45 (dd, J=5.7 and 9.3 Hz, 1H, Ar—H), 7.3 (m, 2H, Ar—H), 7.05 (s, 1H, Ar—H), 3.51 (s, 2H, CH$_2$CO).

MS: 210 [M]$^+$.

A mixture of 6-pyridin-3-yl-1,3-dihydro-indol-2-one (100 mg, 0.5 mmol), 4-methoxy-3-thiophen-2-yl-benzaldehyde (110 mg, 0.5 mmol) and piperidine (0.23 mL) in ethanol (4 mL) was heated to reflux and stirred overnight. The reaction mixture was then cooled and diluted with ether to afford a precipitate which removed by filtration. Thefiltrate was column chromatographed (eluant—isopropanol/dichloromethane) to give 30 mg (15%) of 3-(4-methoxy-3-thiophen-2-yl-benzylidene)-6-pyridin-3-yl-1,3-dihydroindol-2-one as a yellow solid.

$^1$H NMR (360 MHz, DMSO-d$_6$) δ 10.72 (s, 1H, NH), 8.86 (d, J=2.2 Hz, 1H), 8.57 (m, 1H), 8.12 (d, J=1.8 Hz, 1H), 8.04 (m, 1H), 7.76 (m, 2H), 7.68 (s, 1H), 7.65 (d, J=2.9 Hz, 1H), 7.58 (d, J=5 Hz, 1H), 7.46–7.49 (m, 1H), 7.32 (d, J=8.6 Hz, 1H), 7.25 (m, 1H), 7.13–7.16 (m, 2H), 4.0 (s, 3H, OCH$_3$).

MS EI: 410 [M]$^+$.

Compound AHI-2: 3-(2-Hydroxybenzylidene)-6-pyridin-3-yl-1,3-dihydroindol-2-one

A mixture of 6-pyridin-3-yl-1,3-dihydroindol-2-one (100 mg, 0.5 mmol), 2-hydroxybenzaldehyde (60 mg, 0.5 mmol) and piperidine (0.23 mL) in ethanol (4 mL) was heated to reflux and stirred overnight. The reaction mixture was concentrated and column chromatographed (eluant—isopropanol/dichloromethane) to give 100 mg (64%) of 3-(2-hydroxybenzylidene)-6-pyridin-3-yl-1,3-dihydroindol-2-one as a yellow solid.

$^1$H NMR (360 MHz, DMSO-d$_6$) δ 10.68 (s, 1H, NH), 10.19 (s, br, 1H, OH), 8.84 (d, J=2.2 Hz, 1H), 8.56 (m, 1H), 8.01–8.05 (m, 1H), 7.73 (s, 1H, H-vinyl), 7.65 (d, J=7.2 Hz, 1H), 7.60 (d, J=8.3 Hz, 1H), 7.45–7.49 (m, 1H), 7.32 (m, 1H), 7.22 (dd, J=1.8 & 7.9 Hz, 1H), 7.13 (d, J=1.4 Hz, 1H), 6.98 (d, J=7.9 Hz, 1H), 6.94 (t, J=7.9 Hz, 1H).

MS EI: 314 [M]$^+$.

Compound AHI-3: 3-(4-Methoxy-3-thiophen-2-yl-benzylidene)-6-thiophen-2-yl-1,3-dihydroindol-2-one To a warm, stirred solution of 6-bromo-2-oxindole (4 g, 26.3 mmol) dissolved in 60 mL toluene and 60 mL ethanol was added tetrakis(triphenylphosphine)palladium(0) (2.3 g, 1.9 mmol) followed by 2M aqueous sodium carbonate (50 mL, 100 mmol) and thiophene-2-boronic acid (4.38 g, 34.2 mmol) in three portions over 1.5 hours. The mixture was stirred at 100° C. in an oil bath for 12 hours. The mixture was then diluted with ethyl acetate (400 mL) and washed with saturated sodium bicarbonate (200 mL), water (200 mL) and brine (200 mL). The organic layer was separated, dried over anhydrous magnesium sulfate and concentrated to give 2.53 g (42%) of 6-thiophen-2-yl-1,3-dihydro-indol-2-one a tan solid.

$^1$H NMR (360 MHz, DMSO-d$_6$) δ 10.42 (s, 1H, NH), 7.50 (dd, J=0.83 and 4.97 Hz, 1H, Ar—H), 7.43 (dd, J=0.89 and 3.52 Hz, 1H, Ar—H), 7.21 (s, 2H, Ar—H), 7.10 (dd, J=3.31 and 4.82 Hz, 1H, Ar—H), 7.01 (s, 1H, Ar—H), 3.47 (s, 2H, CH$_2$CO).

MS EI: 215 [M]$^+$.

A mixture of 6-thiophen-2-yl-1,3-dihydroindol-2-one (100 mg, 0.5 mmol), 4-methoxy-3-thiophen-2-benzaldehyde (110 mg, 0.5 mmol) and piperidine (0.23 mL) in ethanol (4 mL) was stirred at reflux overnight. The reaction mixture was concentrated and column chromatographed (eluant—isopropanol/dichloromethane) to give 100 mg (48%) of 3-(4-methoxy-3-thiophen-2-ylbenzylidene)-6-thiophen-2-yl-1,3-dihydroindol-2-one as a yellow-brown solid.

$^1$H NMR (360 MHz, DMSO-d$_6$) δ 10.63 (s, br, 1H, NH), 8.10 (d, J=2.2 Hz, 1H), 7.51–7.74 (m, 7H), 7.31 (d, J=8.3 Hz, 1H), 7.21 (dd, J=1.8 & 7.9 Hz, 1H), 7.10–7.15 (m, 3H), 4.0 (s, 3H, OCH$_3$).

MS EI: 415 [M]$^+$.

Compound AHI-4: 3-(2-Hydroxybenzylidene)-6-thiophen-2-yl-1,3-dihydroindol-2-one

A mixture of 6-thiophen-2-yl-1,3-dihydroindol-2-one (100 mg, 0.5 mmol), 2-hydroxybenzaldehyde (60 mg, 0.5 mmol) and piperidine (0.23 mL) in ethanol (4 mL) was stirred at reflux overnight. The reaction mixture was concentrated and column chromatographed (eluant— isopropanol/dichloromethane) to give 80 mg (50%) of 3-(2-hydroxybenzylidene)-6-thiophen-2-yl-1,3-dihydroindol-2-one as a yellow-orange solid.

$^1$H NMR (360 MHz, DMSO-d$_6$) δ 10.60 (s, br, 1H, NH), 10.17 (s, br, 1H, OH), 7.68 (s, 1H), 7.64 (d, J=7.2 Hz, 1H), 7.48–7.56 (m, 3H), 7.31 (m, 1H), 7.19 (dd, J=1.8 & 7.9 Hz, 1H), 7.13 (m, 1H), 7.08 (d, J=0.7 Hz, 1H), 6.90–6.98 (m, 2H).

MS EI: 319 [M]$^+$.

Compound AHI-5: 3-(4-Methoxy-3-thiophen-2-yl-benzylidene)-6-thiophen-3-yl-1,3-dihydroindol-2-one To a warm, stirred solution of 6-bromo-2-oxindole (4 g, 26.3 mmol) dissolved in 60 mL toluene and 60 mL ethanol was added tetrakis(triphenylphosphine)palladium(0) (2.3 g, 1.9 mmol) followed by 2M aqueous sodium carbonate (50 mL, 100 mmol) and thiophene-3-boronic acid (4.3 g, 33.6 mmol). The mixture was stirred at 100° C. in an oil bath for 12 hours. The reaction mixture was cooled, diluted with ethyl acetate (500 mL), washed with IN hydrochloric acid (200 mL), water (200 mL), saturated sodium bicarbonate (200 mL) and brine (200 mL). The organic layer was separated, dried over anhydrous magnesium sulfate and concentrated to give a black solid. The solid was triturated with methylene chloride to give 2.02 g (36%) of 6-thiophen-3-yl-1,3-dihydroindol-2-one as a purple-gray solid.

$^1$H NMR (360 MHz, DMSO-d$_6$) δ 10.49 (s, 1H, NH), 7.77 (s, 1H, Ar—H), 7.59 (m, 1H, Ar—H), 7.45 (m, 1H, Ar—H), 7.24 (m, 2H, Ar—H), 7.07 (m, 1H, Ar—H), 3.46 (s, 2H, CH$_2$CO).

MS m/z: 215 [M]$^+$.

A mixture of 6-thiophen-3-yl-1,3-dihydroindol-2-one (100 mg, 0.5 mmol), 4-methoxy-3-thiophen-2-benzaldehyde (110 mg, 0.5 mmol) and piperidine (0.23 mL) in ethanol (4 mL) was stirred at reflux overnight. The precipitate was collected by vacuum filtration, washed with ethanol and dried to give 100 mg (48%) of 3-(4-methoxy-3-thiophen-2-yl-benzylidene)-6-thiophen-3-yl-1,3-dihydroindol-2-one as a yellow-brown solid.

$^1$H NMR (360 MHz, DMSO-d$_6$) δ 10.63 (s, br, 1H, NH), 9.06 (d, J=2.2 Hz, 1H), 8.37 (d, 1H), 7.86 (m, 1H), 7.82 (s, 1H, H-vinyl), 7.72 (d, J=7.9 Hz, 1H), 7.63 (m, 2H), 7.58 (m, 1H), 7.53 (m, 1H), 7.37 (m, 1H), 7.26 (d, J=7.9 Hz, 1H), 7.16 (m, 1H), 7.11 (m, 1H), 4.0 (s, 3H, OCH$_3$).

MS EI: 415 [M]$^+$.

Compound AHI-6: 3-(2-Hydroxybenzylidene)-6-thiophen-3-yl-1,3-dihydroindol-2-one

A mixture of 6-thiophen-3-yl-1,3-dihydroindol-2-one (100 mg, 0.5 mmol), 2-hyroxy-benzaldehyde (60 mg, 0.5 mmol) and piperidine (0.23 mL) in ethanol (4 mL) was stirred at reflux overnight. The precipitate was collected by vacuum filtration, washed with ethanol and dried to give 110 mg (69%) of 3-(2-hydroxybenzylidene)-6-thiophen-3-yl-1,3-dihydroindol-2-one as yellow-red crystals.

$^1$H NMR (360 MHz, DMSO-d$_6$) δ 10.60 (s, 1H, NH), 10.16 (s, br, 1H, OH), 7.85 (m, 1H), 77.62–7.67 (m, 3H), 7.49–7.54 (m, 2H), 7.29 (m, 1H), 7.22 (m, 1H), 7.13 (d, 1H), 6.90–6.98 (m, 2H).

MS EI: 319 [M]$^+$.

Compound AHI-7: 3-[4-(3-Dimethylaminopropyl)-3,5-dimethyl-1H-pyrrol-2-ylmethylene]-6-pyridin-3-yl-1,3-dihydroindol-2-one A mixture of 6-pyridin-3-yl-1,3-dihydroindol-2-one (100 mg, 0.48 mmol), 4-(3-dimethylaminopropyl)-3,5-dimethyl-1H-pyrrole-2-carboxaldehyde (100 mg, 0.48 mmol), and piperidine (1 drop) in ethanol (2 mL) was stirred at reflux overnight. The precipitate was collected by vacuum filtration, washed with ethanol and dried to give 3-[4-(3-dimethylaminopropyl)-3,5-dimethyl-1H-pyrrol-2-ylmethylene]-6-pyridin-3-yl-1,3-dihydroindol-2-one.

$^1$H NMR (360 MHz, DMSO-d$_6$) δ 13.40 (s, 1H, NH), 10.85 (s, 1H, NH), 8.85 (d, J=1.8 Hz, 1H), 8.52 (dd, J=1.8 & 5.2 Hz, 1H), 8.01–8.04 (m, 1H), 7.82 (d, J=8.2 Hz, 1H), 7.61 (s, 1H, H-vinyl), 7.43–7.47 (m, 1H), 7.32 (dd, J=1.6 & 8.2 Hz, 1H), 7.13 (d, J=1.6 Hz, 1H), 2.4 (t, J=7.3 Hz, 2H, CH$_2$CH$_2$CH$_2$N(CH$_3$)$_2$), 2.29 (s, 3H, CH$_3$), 2.26 (s, 3H, CH$_3$), 2.18 (t, J=7.3 Hz, CH$_2$CH$_2$CH$_2$N(CH$_3$)$_2$), 2.12 (s, 6H, CH$_2$CH$_2$CH$_2$N(CH$_3$)$_2$), 1.49–1.57 (m, 2H, CH$_2$CH$_2$CH$_2$N(CH$_3$)$_2$).

MS EI 400 [M]$^+$.

Compound AHI-8: 3-[4-(3-Dimethylaminopropyl)-3,5-dimethyl-1H-pyrrol-2-ylmethylene]-6-thiophen-2-yl-1,3-dihydroindol-2-one A mixture of 6-thiophen-2-yl-1,3-dihydroindol-2-one (100 mg, 0.46 mmol), 4-(3-dimethylaminopropyl)-3,5-dimethyl-1H-pyrrole-2-carboxaldehyde (100 mg, 0.48 mmol), and piperidine (1 drop) in ethanol (2 mL) was stirred at reflux overnight. The precipitate was collected by vacuum filtration, washed with ethanol and dried to give 3-[4-(3-dimethylaminopropyl)-3,5-dimethyl-1H-pyrrol-2-ylmethylene]-6-thiophen-2-yl-1,3-dihydro-indol-2-one.

$^1$H NMR (360 MHz, DMSO-d$_6$) δ 13.35 (s, 1H, NH), 10.76 (s, 1H, NH), 7.72 (d, J=7.9 Hz, 1H), 7.55 (s, 1H, H-vinyl), 7.47 (dd, J=1.1 & 5.0 Hz, 1H), 7.43 (dd, J=1.1 & 3.6 Hz, 1H), 7.27 (dd, J=1.5 & 7.9 Hz, 1H), 7.11 (dd, J=3.6 & 5.0 Hz, 1H), 7.08 (d, J=1.5 Hz, 1H), 2.4 (t, J=7.3 Hz, 2H, CH$_2$CH$_2$CH$_2$N(CH$_3$)$_2$), 2.29 (s, 3H, CH$_3$), 2.26 (s, 3H, CH$_3$), 2.17 (t, J=7.3 Hz, CH$_2$CH$_2$CH$_2$N(CH$_3$)$_2$), 2.11 (s, 6H, CH$_2$CH$_2$CH$_2$N(CH$_3$)$_2$), 1.49–1.57 (m, 2H, CH$_2$CH$_2$N(CH$_3$)$_2$).

MS EI 405 [M]$^+$.

B. 3-Aralkyl-2-Indolinone Derivatives

General Synthesis

Method A: Suzuki Coupling

A mixture of tetrakis(triphenylphosphine)palladium(0) (3% equiv.), aryl bromide (1 equiv.), 2 M aqueous sodium carbonate (2.5 equiv.) and boronic acid (1.2 equiv.) in equal amount of toluene and ethanol is refluxed for 12 hours. The reaction is poured into water and extracted with ethyl acetate. The organic layers are washed with base and brine, dried and concentrated. The residue is purified by column chromatography to give the product.

Method B: Condensation of Oxindoles and Aldehydes

One equivalent of oxindole, 1 equivalent of the aldehyde and 1–5 equivalents of piperidine (or pyrrolidine) in enough ethanol to make a solution which is 0.5–1.0 M in the oxindole are stirred at 90–100° C. for 1–18 hours. The mixture is cooled to room temperature and, if a precipitate forms, it is collected by vacuum filtration, washed with ethanol and dried to give the product. When no precipitate forms upon cooling of the reaction mixture, the mixture is concentrated and the residue purified by column chromatography.

Method C: Reduction Using Palladium on Carbon

A solution of the indolinone in methanol containing a couple of drops of acetic acid is hydrogenated over palladium on carbon overnight at room temperature. The catalyst is removed by filtration, rinsed with methanol and the filtrate concentrated to give the reduced product.

Method D: Reduction Using Sodium Borohydride

To a mixture of the indolinone (1 equiv.) in methanol and dimethylforamide is added sodium borohydride (10 equiv.). The mixture is stirred at room temperature for ½–3 hours. The reaction is then poured into water, extracted with ethyl acetate, washed with brine, dried and concentrated to give the reduced product.

Method E: Reduction Using Pearlman's Catalyst

A solution of the indolinone in methanol is hydrogenated over Pearlman's catalyst at room temperature for ½–10 hours. The catalyst is removed by filtration, rinsed with methanol and the filtrate concentrated to give the reduced product.

b. Specific Compound Syntheses

The specific syntheses of compounds of this invention which follow are presented by way of example only and are not to be construed as limiting the scope of this invention in any manner.

Compound AAI-1: 6-Methoxy-3-(4-methoxy-3-thiophen-3-ylbenzyl)-1,3-dihydroindol-2-one Tetrakis(triphenylphosphine)palladium(0) (1.35 g, 1.17 mmol) was added to a solution of 4-methoxy-3-bromobenzaldehyde (6.72 g, 31.26 mmol) dissolved in toluene (45 mL) and ethanol (45 mL). To the solution was added 2M aqueous sodium carbonate (80 mL, 78 mmol). Thiophene-3-boronic acid (5 g, 39.07 mmol) was then added to the mixture. The mixture was refluxed for 12 hours after which it was poured into water (200 mL) and extracted with ethyl acetate (2×150 mL). The organic layer was washed with saturated aqueous sodium bicarbonate (150 mL) and brine (150 mL), dried over anhydrous magnesium sulfate and concentrated. Chromatography (silica, 20% ethyl acetate/hexanes) afforded 6 g (88%) of 3-(3-thiophene)-4-methoxybenaldehyde as a yellow oil.

$^1$H NMR (360 MHz, DMSO-$d_6$) δ 9.92 (s, 1H, CHO), 8.04 (d, 1H, J=2.4 Hz, 1×Ar—H), 7.8 (m, 2H, Ar—H), 7.58 (dd, 1H, J=3.1 and 5.5 Hz, thiophene and Ar—H), 7.50 (dd, 1H, J=1.6 and 5.1 Hz, Ar—H), 7.28 (d, 1H, J=8.7 Hz, thiophene), 3.94 (s, 3H, OCH$_3$).

MS m/z: 219.2 [M+1]$^+$.

A mixture of 3(3-thiophene)-4-methoxybenzaldehyde (0.53 g, 2.45 mmol), 6-methoxy-2-oxindole (0.4 g, 2.45 mmol) and piperidine (1.2 mL, 12.25 mmol) in 5 mL of ethanol was held in a sealed tube at 100° C. for 12 hours. The reaction was cooled and added to diethyl ether (150 mL) and hexanes (150 mL). The solid which formed was removed by filtration, washed with diethyl ether and then hexanes and dried to give 0.57 g (64%) of 6-methoxy-3-(4-methoxy-3-thiophen-3-ylbenzylidene)-1,3-dihydroindol-2-one as a mustard yellow solid.

$^1$H NMR (360 MHz, DMSO-$d_6$) δ 10.45 (s, 1H, NH), 8.78 (d, J=2.3 Hz, 1H, Ar—H), 8.30 (dd, J=2.1 and 8.7 Hz, 1H, Ar—H), 7.8 (dd, 1H, J=1.5 and 2.9 Hz, Ar—H), 7.5 (m, 3H, 2×Ar—H and Ar—CH=C), 7.18 (d, J=8.9 Hz, 1H, Ar—H), 6.55 (dd, 1H, J=2.1 and 8.5 Hz, Ar—H), 6.39 (d, 1H, J=2.3 Hz, Ar—H), 3.91 (s, 3H, OCH$_3$), 3.76 (s, 3H, OCH$_3$), 2.04 (s, 3H, NHCOCH$_3$).

MS m/z: 364.1 [M+1]$^+$.

To a mixture of 6-methoxy-3-(4-methoxy-3-thiophen-3-ylbenzylidene)-1,3-dihydroindol-2-one (363 mg, 1 mmol) in methanol (10 mL) and dimethylforamide (5 mL) was added sodium borohydride (380 mg, 10 mmol) in portions. The reaction was stirred at room temperature for 3 hours. The reaction mixture was quenched with water (100 mL) and extracted into ethyl acetate (200 mL). The organic layer was washed with brine, dried over anhydrous sodium sulfate and concentrated. The residue was chromatographed on silica gel (ethyl acetate:hexane 2:3 then 1:1) to give 215 mg (59%) of the title compound as a faint orange crystalline solid.

$^1$H NMR (360 MHz, DMSO-$d_6$) δ 10.2 (s, br, 1H, NH), 7.61 (dd, J=1.4 & 2.8 Hz, 1H), 7.51 (dd, J=3.2 & 4.7 Hz, 1H), 7.31 (dd, J=1.3 & 4.9 Hz, 1H), 7.25 (d, J=2.5 Hz, 1H), 7.0 (dd, J=2.2 & 8.6 Hz, 1H), 6.85, 6.88, 6.90, 6.92 (m, 2H), 6.42 (dd, J=2.5 & 8.3 Hz, 1H), 6.28 (d, J=2.2 Hz, 1H), 3.76 (s, 3H, OCH$_3$), 3.67–3.73 (m, 1H, Ar—CHCO), 3.67 (s, 3H, OCH$_3$), 3.24 (dd, J=4.7 & 13.7 Hz, 1H, 1×ArCH$_2$), 2.91 (dd, J=7.2 & 13.7 Hz, 1H, 1×ArCH$_2$).

MS-EI m/z: 365 [M]$^+$.

Compound AAI-2: Cyclopentanecarboxylic Acid [3-(3,5-Dichloro-2-hydroxybenzyl)-2-oxo-2,3-dihydro-1H-indol-6-yl]-amide Cyclopentanecarboxylic acid (2-oxo-2,3-dihydro-1H-indol-6-yl)-amide was condensed with 3,5-dichlorosalicylaldehyde using method B to give a mixture of isomers of cyclopentanecarboxylic acid [3-(3,5-dichloro-2-hydroxy-benzylidene)-2-oxo-2,3-dihydro-1H-indol-6-yl]-amide as an orange solid which was reduced using method D to give 10 mg (40%) of cyclopentanecarboxylic acid [3-(3,5-dichloro-2-hydroxybenzyl)-2-oxo-2,3-dihydro-1H-indol-6-yl]-amide as an off-white crystalline solid.

$^1$H NMR (360 MHz, DMSO-$d_6$) δ 10.2 (s, br, 1H, NH), 10.39 (s, br, 1H, NH), 9.72 (s, br, 1H), 9.54 (s, br, 1H), 7.35 (m, 2H), 7.09 (m, 1H), 6.91 (d, J=7.2 Hz, 1H), 6.55 (d, J=7.2 Hz, 1H), 3.73 (m, 1H, 1×Ar—CHCO), 3.23 (m, 1H, 1×ArCH$_2$), 2.8 (m, 1H, 1×ArCH$_2$), 2.72 (m, 1H, CH-cpentyl), 1.8 (m, 2H, cpentyl), 1.65 (m, 4H, cpentyl), 1.53 (m, 2H, cpentyl).

MS-EI m/z: 419 [M]$^+$.

Compound AAI-3: Cyclopentanecarboxylic Acid [3-(5-Chloro-2-hydroxybenzyl)-2-oxo-2,3-dihydro-1H-indol-6-yl]-amide Cyclopentanecarboxylic acid (2-oxo-2,3-dihydro-1H-indol-6-yl)-amide was condensed with 5-chlorosalicylaldehyde using method B to give cyclopentanecarboxylic acid [3-(5-chloro-2-hydroxy-benzylidene)-2-oxo-2,3-dihydro-1H-indol-6-yl]-amide which was reducted using method D to give 34.4 mg (68%) cyclopentanecarboxylic acid [3-(5-chloro-2-hydroxybenzyl)-2-oxo-2,3-dihydro-1H-indol-6-yl]-amide as an off-white crystalline solid.

$^1$H NMR (360 MHz, DMSO-$d_6$) δ 10.33 (s, br, 1H, NH), 9.72 (s, br, 1H, NH), 9.71 (s, br, 1H, OH), 7.34 (m, 1H), 7.07 (dd, J=2.5 & 8.3 Hz, 1H), 7.03 (d, J=2.5 Hz, 1H), 6.88 (m, 1H), 6.79 (d, J=8.3 Hz, 1H), 6.43 (d, J=6.8 Hz, 1H), 3.72 (m, 1H, 1×Ar—CHCO), 3.20 (dd, J=5.4 & 13.7 Hz, 1H, 1×ArCH$_2$), 2.72 (m, 1H, CH-cpentyl), 2.62 (dd, J=9.2 & 13.7 Hz, 1H, 1×ArCH$_2$), 1.81 (m, 2H, cpentyl), 1.65 (m, 4H, cpentyl), 1.52 (m, 2H, cpentyl).

MS-EI m/z: 384 & 386 [M]$^+$.

Compound AAI-4: 3-(4-Hydroxy-6,4'-dimethoxybiphenyl-3-ylmethyl)-1,3-dihydroindol-2-one 2-Hydroxy-4-methoxybenzaldehyde (20 g, 131.4 mmol) was brominated to give 5-bromo-2-hydroxy-4-methoxybenzaldehyde as a light yellow solid, followed by coupling with 4-methoxyphenylboronic acid (750 mg, 4.94 mmol) using method A to give 800 mg (75%) of 4-hydroxy-6,4'-dimethoxybiphenyl-3-carbaldehyde as a light yellow solid.

$^1$H NMR (360 MHz, DMSO-$d_6$) δ 11.06 (s, br, 1H, OH), 10.04 (s, 1H, CHO), 7.55 (s, 1H), 7.35 (d, J=8.6 Hz, 2H), 6.94 (d, J=8.6 Hz, 2H), 6.63 (s, 1H), 3.81 (s, 3H, OCH$_3$), 3.77 (s, 3H, OCH$_3$).

MS-EI m/z: 258 [M]⁺.

2-Oxindole was condensed with 4-hydroxy-6,4'-dimethoxybiphenyl-3-carbaldehyde using method B to give a mixture of isomers of 3-(4-hydroxy-6,4'-dimethoxybiphenyl-3-ylmethylene)-1,3-dihydroindol-2-one, followed by reduction using method E to give 4.5 mg (75%) of 3-(4-hydroxy-6,4'-dimethoxybiphenyl-3-ylmethyl)-1,3-dihydroindol-2-one as a white solid.

MS-EI m/z: 375 [M]⁺.

Compound AAI-5: 3-(3-Cyclopentyl-4-methoxybenzyl)-5-fluoro-1,3-dihydroindol-2-one 5-Fluoro-2-oxindole was condensed with 3-cyclopentyl-4-methoxybenzaldehyde using method B to give 3-(3-cyclopentyl-4-methoxybenzylidene)-5-fluoro-1,3-dihydroindol-2-one as a yellow-orange solid, followed by reduction using method E to give 0.78 g (78%) of 3-(3-cyclopentyl-4-methoxybenzyl)-5-fluoro-1,3-dihydroindol-2-one as a white solid.

$^1$H NMR (360 MHz, DMSO-$d_6$) δ 10.19 (s, 1H, NH), 6.8 (m, 4H, 4×Ar—H), 6.73 (d, J=7.92 Hz, 1H, Ar—H), 6.64 (dd, J=4.32 and 8.28 Hz, 1H, Ar—H), 3.73 (m, 1H, 1×Ar—CH—CO), 3.68 (s, 3H, OCH$_3$), 3.25 (dd, J=5.4 and 14.0 Hz, 1H, 1×Ar—CH$_2$), 3.15 (m, 1H, CH-cpentyl), 2.93 (dd, J=7.2 and 14.0 Hz, 1H, 1×Ar—CH$_2$), 1.8 (br m, 2H, cpentyl), 1.6 (br m, 4H, cpentyl), 1.37 (br m, 1H, cpentyl), 1.25 (br m, 1H, cpentyl).

MS m/z: 339 [M]⁺.

Compound AAI-6: N-[3-(4-Methoxy-3-thiophen-2-ylbenzyl)-2-oxo-2,3-dihydro-1H-indol-6-yl]-acetamide 4-Methoxy-3-bromobenzaldehyde (1.5 g) was coupled with thiophene-2-boronic acid (0.98 g) using method A to give 1.3 g (87%) of 3-(2-thiophene)-4-methoxybenzaldehyde as a yellow oil.

$^1$H NMR (360 MHz, DMSO-$d_6$) δ 9.92 (s, 1H, CHO), 8.2 (d, 1H, J=3 Hz, 1×Ar—H), 7.8 (dd, 1H, J=10 and 10 Hz, SCHCHCH), 7.65 (m, 1H, Ar—H), 7.60 (dd, 1H, J=2 and 6 Hz, Ar—H), 7.32 (d, 1H, J=10 Hz, SCHCHCH), 7.13 (d, 1H, J=10 and 6 Hz, SCHCHCH), 3.99 (s, 3H, OCH$_3$).

6-Acetamido-2-oxindole was condensed with 3-(2-thiophene)-4-methoxybenzaldehyde to give N-[3-(4-methoxy-3-thiophen-2-ylbenzylidene)-2-oxo-2,3-dihydro-1H-indol-6-yl]-acetamide as a yellow solid which was reduced using method E to give 0.04 g (80%) of N-[3-(4-methoxy-3-thiophen-2-ylbenzyl)-2-oxo-2,3-dihydro-1H-indol-6-yl]-acetamide as a white solid.

$^1$H NMR (360 MHz, DMSO-d6) δ 10.19 (s, 1H, NH), 9.80 (s, 1H, NHAc), 7.59 (dd, J=1.08 and 2.88 Hz, 1H, Ar—H), 7.49 (dd, J=5.04 and 2.88 Hz, 1H, Ar—H), 7.30 (dd, J=1.08 and 5.04 Hz, 1H, Ar—H), 7.2 (m, 2H, 2×Ar—H), 6.98 (dd, J=2.16 and 8.28 Hz, 1H, Ar—H), 6.9 (m, 3H, 3×Ar—H), 3.75 (s, 3H, OCH$_3$), 3.7 (m, 1H, Ar—CH—CO), 2.93 (dd, J=7.2 and 13.7 Hz, 1H, Ar—CH), 1.98 (s, 3H, NHCOCH$_3$).

MS m/z: 392 [M]⁺.

Compound AAI-7: N-{3-[3-Cyclohexyl-4-(2-morpholin-4-ylethoxy)-benzyl]-2-oxo-2,3-dihydro-1H-indol-6-yl}-acetamide 6-Acetamido-2-oxindole was condensed with 3-cyclohexyl-4-morpholinoethoxybenzaldehyde using method B to give a mixture of isomers of N-{3-[3-cyclohexyl-4-(2-morpholin-4-ylethoxy)-benzylidene]-2-oxo-2,3-dihydro-1H-indol-6-yl}-acetamide as a mustard yellow solid which was reduced using method E to give 0.04 g (80%) of N-{3-[3-cyclohexyl-4-(2-morpholin-4-ylethoxy)-benzyl]-2-oxo-2,3-dihydro-1H-indol-6-yl}-acetamide as a white solid.

$^1$H NMR (360 MHz, DMSO-$d_6$) δ 10.14 (s, 1H, NH), 9.79 (s, 1H, NHAc), 7.22 (s, 1H, Ar—H), 6.8 (m, 5H, 5×Ar—H), 4.0 (br s, 2H), 3.6 (br m, 5H), 3.1 (m, 2H), 2.7 (m, 5H), 1.97 (s, 3H, NHCOCH$_3$), 1.7 (br m, 6H), 1.2 (br m, 6H).

MS m/z: 491.9 [M]⁺.

Compound AAI-8: 3-(4-Methoxy-3-thiophen-3-ylbenzyl)-5-(2-morpholin-4-ylethyl)-1,3-dihydroindol-2-one A solution of 5-(2-chloroethyl)-2-oxindole (2.3 g), morpholine (1.2 mL) and diisopropylethylamine (1.2 mL) in dimethylsulfoxide (10 mL) was stirred overnight at 100° C. The mixture was cooled, poured into water and extracted with ethyl acetate. The organic layer was washed with brine, dried and evaporated. The residue was chromatographed (silica gel, 5% methanol in chloroform) to give 0.9 g (31%) of 5-(2-morpholin-4-ylethyl)-2-oxindole as a white solid.

$^1$HNMR (360 MHz, DMSO-$d_6$) δ 10.21 (s, br, 1H, NH), 7.06 (s, br, 1H, H-4), 7.0 (d, J=8 Hz, 1H, H-6), 6.71 (d, J=8 Hz, 1H, H-7), 3.55–3.58 (m, 4H), 3.41 (s, 2H, H-3), 2.63–2.68 (m, 2H), 2.39–2.47 (m, 6H).

5-(2-Morpholin-4-ylethyl)-2-oxindole was condensed with 3(3-thiophene)-4-methoxybenzaldehyde using method B to give 3-(4-methoxy-3-thiophen-3-yl-benzylidene)-5-(2-morpholin-4-ylethyl)-1,3-dihydroindol-2-one as an orange-yellow solid which was reduced using method E to give 0.03 g (60%) of 3-(4-methoxy-3-thiophen-3-yl-benzyl)-5-(2-morpholin-4-ylethyl)-1,3-dihydroindol-2-one as a white solid.

$^1$H NMR (360 MHz, DMSO-$d_6$) δ 10.16 (s, 1H, NH), 7.57 (br d, J=1.8 Hz, 1H, Ar—H), 7.51 (dd, J=3.24 and 5.4 Hz, 1H, Ar—H), 7.27 (br d, J=5.4 Hz, 1H, Ar—H), 7.21 (br d, J=1.8 Hz, 1H, Ar—H), 6.9 (m, 3H, 3×Ar—H), 6.7 (m, 1H, Ar—H), 6.62 (d, J=7.9 Hz, 1H, Ar—H), 3.75 (s on m, 4H, OCH$_3$ and Ar—CH—CO), 3.67 (br m, 6H), 2.98 (m, 3H), 2.7 (m, 4H).

MS m/z: 448.9 [M]⁺.

Compound AAI-9: 3-(5-Isopropyl-4-methoxy-2-methylbenzyl)-1,3-dihydroindol-2-one

2-Oxindole was condensed with 5-isopropyl-4-methoxy-2-methylbenzaldehyde using method B to give 0.25 g of 3-(5-Isopropyl-4-methoxy-2-methylbenzylidene)-1,3-dihydroindol-2-one as a yellow-orange solid which was reduced using method E to give 2 g (100%) of 3-(5-isopropyl-4-methoxy-2-methylbenzyl)-1,3-dihydroindol-2-one as a white solid.

$^1$H NMR (360 MHz, DMSO-$d_6$) δ 10.30 (s, 1H, NH), 7.10 (m, 1H, Ar—H), 6.78 (m, 3H, Ar—H), 6.68 (m, 2H, Ar—H), 3.7 (s, 3H, OCH$_3$), (m, 1H, Ar—CH—CO), 3.62 (dd, J=4.6 and 9.3 Hz, 1H, Ar—CH—CO), 3.23 (dd, J=4.6 and 14 Hz, 1H, 1×Ar—CH), 3.1 (m, 1H, CH-isopropyl), 2.75 (dd, J=9.36 and 14 Hz, 1H, 1×Ar—CH$_2$), 2.2 (s, 3H, Ar—CH$_3$), 1.02 (d, J=6.8 Hz, 3H, isopropyl), 0.97 (d, J=7.5 Hz, 3H, isopropyl).

Compound AAI-10: 3-(3,5-Diisopropyl-4-methoxybenzyl)-1,3-dihydroindol-2-one

2-Oxindole was condensed with 3,5-diisopropyl-4-methoxybenzaldehyde using method B to give 3-(3,5-diisopropyl-4-methoxy-benzylidene)-1,3-dihydro-indol-2-one as a yellow-orange solid which was reduced using method E to give 2 g (100%) of 3-(3,5-diisopropyl-4-methoxybenzyl)-1,3-dihydroindol-2-one as a white solid.

$^1$H NMR (360 MHz, DMSO-$d_6$) δ 10.21 (s, 1H, NH), 7.07 (m, 1H, Ar—H), 6.8 (m, 4H, Ar—H), 6.69 (d, J=7.5 Hz, 1H, Ar—H), 3.7 (m, 1H, Ar—CH—CO), 3.57 (s, 3H, OCH$_3$), 3.2 (dd, J=4.6 and 13 Hz, 1H, 1×Ar—CH$_2$), 3.14 (m, 2H, CH-isopropyl), 2.86 (dd, J=7.5 and 13.6 Hz, 1H, 1×Ar—CH$_2$), 1.08 (d, J=6.8 Hz, 6H, isopropyl), 1.02 (d, J=6.8 Hz, 6H, isopropyl).

Compound AAI-11: 3-(3-Cyclopentyl-4-hydroxybenzyl)-5-fluoro-1,3-dihydroindol-2-one 3-(3-Cyclopentyl-4-hydroxybenzylidene)-5-fluoro-1,3-dihydroindol-2-one (0.045 g) was reduced using method E to give 0.025 g (56%) of 3-(3-cyclopentyl-4-hydroxybenzyl)-5-fluoro-1,3-dihydroindol-2-one as a tan foam.

$^1$H NMR (360 MHz, DMSO-$d_6$) δ 10.18 (s, 1H, NH), 8.9 (s, 1H, Ar—H), 6.89 (m, 1H, Ar—H), 6.7 (m, 3H, Ar—H), 6.56 (d, J=8.28 Hz, 1H, Ar—H), 3.68 (m, 1H), 3.16 (m, 2H), 2.84 (m, 1H), 1.8 to 1.2 (m, 8H, cpentyl).

MS m/z: 325 [M]$^+$.

Compound AAI-12: 3-Benzyl-4-(2-hydroxyethyl)-1,3-dihydroindol-2-one 4-(2-Hydroxyethyl)-1,3-dihydroindol-2-one was condensed with 4-bromobenzaldehyde using method B to give 3-(4-bromobenzylidene)-4-(2-hydroxy-ethyl)-1,3-dihydroindol-2-one as a yellow solid which was reduced using method E to give 0.2 g (91%) of 3-benzyl-4-(2-hydroxyethyl)-1,3-dihydroindol-2-one as a yellow/orange foam.

$^1$H NMR (360 MHz, DMSO-$d_6$) δ 10.09 (s, 1H, NH), 7.0 (m, 3H, Ar—H), 6.99 (m, 1H, Ar—H), 6.91 (m, 2H, Ar—H), 6.45 (d, J=7.9 Hz, 1H, Ar—H), 3.8 (m, 1H), 3.67 (m, 2H), 3.3 (m, 2H), 2.9 (m, 1H), 2.7 (m, 1H), 2.75 (dd, J=9.36 and 14 Hz, 1H, 1×Ar—CH$_2$), 2.2 (s, 3H, Ar—CH$_3$), 1.02 (d, J=6.8 Hz, 3H, isopropyl), 0.97 (d, J=7.5 Hz, 3H, isopropyl).

MS m/z: 267 [M]$^+$.

Compound AAI-13: 3-(2-Hydroxybenzyl)-6-(3-methoxyphenyl)-1,3-dihydroindol-2-one 6-(3-Methoxyphenyl)-1,3-dihydroindol-2-one was condensed with salicylaldehyde using method B to give 3-(2-hydroxybenzylidene)-6-(3-methoxyphenyl)-1,3-dihydroindol-2-one as a yellow solid which was reducted using method E to give 0.03 g (66%) of 3-(2-hydroxy-benzyl)-6-(3-methoxy-phenyl)-1,3-dihydro-indol-2-one as a white solid.

Compound AAI-14: 3-(4-Bromobenzyl)-4-(2-hydroxyethyl)-1,3-dihydroindol-2-one 3-(4-Bromobenzylidene)-4-(2-hydroxyethyl)-1,3-dihydroindol-2-one (0.18 g, 0.52 mmol) was reduced using method D to give 0.17 g (95%) of 3-(4-bromobenzyl)-4-(2-hydroxyethyl)-1,3-dihydroindol-2-one as a white solid.

MS m/z: 345/347 [M]$^+$.

Compound AAI-15: 5-Chloro-3-[3,5-diisopropyl-4-(2-morpholin-4-ylethoxy)-benzyl]-1,3-dihydroindol-2-one 5-Chloro-2-oxindole was condensed with 3,5-diisopropyl-4-(2-morpholin-4-yl-ethoxy)-benzaldehyde using method B to give 5-chloro-3-[3,5-diisopropyl-4-(2-morpholin-4-ylethoxy)-benzylidene]-1,3-dihydroindol-2-one as a brownish-orange solid which was reduced using method E to give 1.3 g (100%) of 5-chloro-3-[3,5-diisopropyl-4-(2-morpholin-4-ylethoxy)-benzyl]-1,3-dihydroindol-2-one as a yellow/orange foam.

MS m/z: 471 [M]$^+$.

Compound AAI-16: 3-(1H-Indol-5-ylmethyl)-4-methyl-1,3-dihydroindol-2-one

4-Methyl-2-oxindole was condensed with 1H-indole-5-carbaldehyde using method B to give 3-(1H-indol-5-ylmethylene)-4-methyl-1,3-dihydroindol-2-one as a white solid which was reduced using method C to give 20 mg (40%) of 3-(1H-indol-5-ylmethyl)-4-methyl-1,3-dihydroindol-2-one.

MS-EI m/z:276 [M]$^+$.

Compound AAI-17: 3-(1H-Indol-5-ylmethyl)-1,3-dihydroindol-2-one

2-Oxindole (133 mg, 1 mmol) was condensed with 1H-indole-5-carbaldehyde (145 mg, 1 mmol) using method B to give 155 mg (60%) of 3-(1H-indol-5-ylmethylene)-1,3-dihydroindol-2-one as a white solid.

$^1$H NMR (360 MHz, DMSO-$d_6$) δ 11.38 (s, 1H, NH), 10.47 (s, 1H, NH), 7.96 (s, 1H), 7.76 (m, 2H), 7.47–7.54 (m, 2H), 7.43 (t, 1H), 7.19 (t, 1H), 6.82–6.88 (m, 2H), 6.54 (m, 1H).

3-(1H-Indol-5-ylmethylene)-1,3-dihydroindol-2-one (80 mg, 0.31 mmol) was reduced using method C to give 76 mg (95%) of 3-(1H-indol-5-ylmethyl)-1,3-dihydro-indol-2-one.

MS-EI m/z: 262 [M]$^+$.

Compound AAI-18: 3-[4-(3-Dimethylaminopropyl)-3,5-dimethyl-1H-pyrrol-2-ylmethyl]-1,3-dihydroindol-2-one 2-Oxindole (133 mg, 1.0 mmol) was condensed with 4-(3-dimethylaminopropyl)-3,5-dimethyl-1H-pyrrole-2-carbaldehyde (208 mg, 1.0 mmol) using method B to give 168.3 mg (52%) of 3-[4-(3-dimethylaminopropyl)-3,5-dimethyl-1H-pyrrol-2-ylmethylene]-1,3-dihydro-indol-2-one as a yellow solid.

$^1$HNMR (360 MHz, DMSO-$d_6$) δ 13.38 (s, 1H, NH), 10.70 (s, 1H, NH), 7.68 (d, J=7.54 Hz, 1H, H-4), 7.53 (s, 1H, H-vinyl), 7.06 (t, J=7.54 Hz, 1H, H-6), 6.94 (t, J=7.54 Hz, 1H, H-5), 6.85 (d, J=7.54 Hz, 1H, H-7), 2.38 (t, J=7.25 Hz, 2H, (CH$_3$)$_2$NCH$_2$CH$_2$CH$_2$), 2.27 (s, 3H, CH$_3$), 2.23 (s, 3H, CH$_3$), 2.17 (t, J=7.25 Hz, 2H, (CH$_3$)$_2$NCH$_2$CH$_2$CH$_2$), 2.11 (s, 6H, (CH$_3$)$_2$NCH$_2$CH$_2$CH$_2$), 1.52 (quint., J=7.25 Hz, 2H, (CH$_3$)$_2$NCH$_2$CH$_2$CH$_2$).

MS m/z: 323 [M]$^+$.

3-[4-(3-Dimethylaminopropyl)-3,5-dimethyl-1H-pyrrol-2-ylmethylene]-1,3-dihydro-indol-2-one (13 mg, 0.04 mmol) was reduced using method C to give 6 mg (46%) of 3-[4-(3-dimethylaminopropyl)-3,5-dimethyl-1H-pyrrol-2-ylmethyl]-1,3-dihydro-indol-2-one.

MS-EI m/z: 325 [M]$^+$.

Compound AAI-19: 5-Bromo-3-[4-(3-dimethylaminopropyl)-3,5-dimethyl-1H-pyrrol-2-ylmethyl]-1,3-dihydroindol-2-one 5-Bromo-1,3-dihydroindol-2-one was condensed with 4-(3-dimethylamino-propyl)-3,5-dimethyl-1H-pyrrole-2-carbaldehyde (208 mg, 1.0 mmol) using method B to give 284.9 mg (71%) of 5-bromo-3-[4-(3-dimethylaminopropyl)-3,5-dimethyl-1H-pyrrol-2-ylmethylene]-1,3-dihydroindol-2-one as a red solid.

$^1$HNMR (360 MHz, DMSO-$d_6$) δ 13.42 (s, 1H, NH), 10.81 (s, 1H, NH), 7.98 (d, J=1.89 Hz, 1H), 7.66 (s, 1H, H-vinyl), 7.17 (dd, J=1.89 & 8.23 Hz, 1H), 6.79 (d, J=8.23 Hz, 1H), 2.38 (t, J=7.23 Hz, 2H, (CH$_3$)$_2$NCH$_2$CH$_2$CH$_2$), 2.27 (s, 3H, CH$_3$), 2.25 (s, 3H, CH$_3$), 2.16 (t, J=7.23 Hz, 2H, (CH$_3$)$_2$NCH$_2$CH$_2$CH$_2$), 2.10 (s, 6H, (CH$_3$)$_2$NCH$_2$CH$_2$CH$_2$), 1.51 (quint., J=7.23 Hz, 2H, (CH$_3$)$_2$NCH$_2$CH$_2$CH$_2$).

MS m/z: 401/403 [M]$^+$.

5-Bromo-3-[4-(3-dimethylaminopropyl)-3,5-dimethyl-1H-pyrrol-2-ylmethylene]-1,3-dihydroindol-2-one (50 mg, 0.12 mmol) was reduced using method D to give 5-bromo-3-[4-(3-dimethylaminopropyl)-3,5-dimethyl-1H-pyrrol-2-ylmethyl]-1,3-dihydro-indol-2-one.

MS m/z: 404 [M]$^+$.

Compound AAI-20: 3-[4-(3-Dimethylamino-propyl)-3,5-dimethyl-1H-pyrrol-2-ylmethyl]-6-(2-methoxy-phenyl)-1,3-dihydro-indol-2-one 6-(2-Methoxyphenyl)-1,3-dihydroindol-2-one (239 mg, 1.0 mmol)was condensed with 4-(3-dimethylaminopropyl)-3,5-dimethyl-1H-pyrrole-2-carbaldehyde (208 mg, 1.0 mmol) using method B to give 333 mg (83%) of 3-[4-(3-dimethylaminopropyl)-3,5-dimethyl-1H-pyrrol-2-ylmethylene]-6-(2-methoxyphenyl)-1,3-dihydro-indol-2-one as a yellow solid.

$^1$HNMR (360 MHz, DMSO-$d_6$) δ 6 13.38 (s, 1H, NH), 10.72 (s, 1H, NH), 7.70 (d, J=8.06 Hz, 1H), 7.55 (s, 1H,

H-vinyl), 7.28–7.36 (m, 2H), 7.14 (d, J=8.32 Hz, 1H), 7.04 (dd, J=1.21, 8.06 Hz, 1H), 6.99 (d, J=7.42 Hz, 1H), 6.99 (d, J=1.21 Hz, 1H) 3.76 (s, 3H, OCH$_3$), 2.39 (t, J=7.24 Hz, 2H, (CH$_3$)$_2$NCH$_2$CH$_2$CH$_2$), 2.28 (s, 3H, CH$_3$), 2.25 (s, 3H, CH$_3$), 2.18 (t, J=7.24 Hz, 2H, (CH$_3$)$_2$NCH$_2$CH$_2$CH$_2$), 2.11 (s, 6H, (CH$_3$)$_2$NCH$_2$CH$_2$CH$_2$), 1.53 (quint., J=7.24 Hz, 2H, (CH$_3$)$_2$NCH$_2$CH$_2$CH$_2$).

MS m/z: 429 [M]$^+$.

3-[4-(3-Dimethylaminopropyl)-3,5-dimethyl-1H-pyrrol-2-ylmethylene]-6-(2-methoxyphenyl)-1,3-dihydroindol-2-one (54 mg, 0.126 mmol) was reduced using method C to give 45 mg (86%) of 3-[4-(3-dimethylaminopropyl)-3,5-dimethyl-1H-pyrrol-2-ylmethyl]-6-(2-methoxyphenyl)-1,3-dihydroindol-2-one.

MS-EI m/z: 431 [M]$^+$.

Compound AAI-21: 3-[4-(3-Dimethylaminopropyl)-3,5-dimethyl-1H-pyrrol-2-ylmethyl]-6-(3-methoxyphenyl)-1,3-dihydroindol-2-one 6-(3-Methoxyphenyl)-1,3-dihydroindol-2-one (239 mg, 1.0 mmol) was condensed with 4-(3-dimethylaminopropyl)-3,5-dimethyl-1H-pyrrole-2-carbaldehyde (208 mg, 1.0 mmol) using method B to give 333 mg (83%) of 3-[4-(3-dimethylaminopropyl)-3,5-dimethyl-1H-pyrrol-2-ylmethylene]-6-(3-methoxyphenyl)-1,3-dihydroindol-2-one as a red solid.

$^1$HNMR (360 MHz, DMSO-d$_6$) δ 13.38 (s, 1H, NH), 10.80 (s, 1H, NH), 7.60 (d, J=8.06 Hz, 1H), 7.57 (s, 1H, H-vinyl), 7.35 (t, J=8.15 Hz, 1H), 7.26 (dd, J=1.39, 8.06 Hz, 1H), 7.19 (d, br, J=8.15 Hz, 1H), 7.13 (m, 1H), 7.09 (d, J=1.39 Hz, 1H), 6.90 (dd, J=2.57, 8.15 Hz, 1H), 3.81 (s, 3H, OCH$_3$), 2.39 (t, J=7.17 Hz, 2H, (CH$_3$)$_2$NCH$_2$CH$_2$CH$_2$), 2.29 (s, 3H, CH$_3$), 2.25 (s, 3H, CH$_3$), 2.17 (t, J=7.17 Hz, 2H, (CH$_3$)$_2$NCH$_2$CH$_2$CH$_2$), 2.11 (s, 6H, (CH$_3$)$_2$NCH$_2$CH$_2$CH$_2$), 1.53 (quint., J=7.17 Hz, 2H, (CH$_3$)$_2$NCH$_2$CH$_2$CH$_2$).

MS m/z: 429 [M]$^+$.

3-[4-(3-Dimethylaminopropyl)-3,5-dimethyl-1H-pyrrol-2-ylmethylene]-6-(3-methoxyphenyl)-1,3-dihydroindol-2-one (50 mg, 0.12 mmol) was reduced using method C to give 40 mg (77%) of 3-[4-(3-dimethylaminopropyl)-3,5-dimethyl-1H-pyrrol-2-ylmethyl]-6-(3-methoxyphenyl)-1,3-dihydroindol-2-one.

MS-EI m/z: 429 [M-2]$^+$.

Compound AAI-22: 3-[4-(3-Dimethylaminopropyl)-3,5-dimethyl-1H-pyrrol-2-ylmethyl]-6-(4-methoxyphenyl)-1,3-dihydroindol-2-one 6-(4-Methoxyphenyl)-1,3-dihydroindol-2-one (239 mg, 1.0 mmol) was condensed with 4-(3-dimethylaminopropyl)-3,5-dimethyl-1H-pyrrole-2-carbaldehyde (208 mg, 1.0 mmol) using method B to give 333 mg (83%) of 3-[4-(3-dimethylaminopropyl)-3,5-dimethyl-1H-pyrrol-2-ylmethylene]-6-(4-methoxyphenyl)-1,3-dihydroindol-2-one as a brown solid.

$^1$HNMR (360 MHz, DMSO-d$_6$) δ 13.35 (s, 1H, NH), 10.77 (s, 1H, NH), 7.73 (d, J=7.82 Hz, 1H), 7.56 (d, J=8.83 Hz, 2H), 7.54 (s, 1H, H-vinyl), 7.20 (dd, J=1.64, 7.82 Hz, 1H), 7.04 (d, J=1.64 Hz), 7.00 (d, J=8.83 Hz, 2H), 3.78 (s, 3H, OCH$_3$), 2.39 (t, J=7.24 Hz, 2H, (CH$_3$)$_2$NCH$_2$CH$_2$CH$_2$), 2.28 (s, 3H, CH$_3$), 2.25 (s, 3H, CH$_3$), 2.17 (t, J=7.24 Hz, 2H, (CH$_3$)$_2$NCH$_2$CH$_2$CH$_2$), 2.11 (s, 6H, (CH$_3$)$_2$NCH$_2$CH$_2$CH$_2$), 1.52 (quint., J=7.24 Hz, 2H, (CH$_3$)$_2$NCH$_2$CH$_2$CH$_2$).

MS m/z: 429 [M]$^+$.

3-[4-(3-Dimethylaminopropyl)-3,5-dimethyl-1H-pyrrol-2-ylmethylene]-6-(4-methoxyphenyl)-1,3-dihydroindol-2-one (69 mg, 0.16 mmol) was reduced using method C to give 65 mg (94%) of 3-[4-(3-dimethylaminopropyl)-3,5-dimethyl-1H-pyrrol-2-ylmethyl]-6-(4-methoxyphenyl)-1,3-dihydroindol-2-one.

MS-EI m/z: 431 [M]$^+$.

Compound AAI-23: 5-Chloro-3-[4-(3-dimethylaminopropyl)-3,5-dimethyl-1H-pyrrol-2-ylmethyl]-1,3-dihydroindol-2-one 5-Chloro-1,3-dihydroindol-2-one (167 mg, 1.0 mmol) was condensed with 4-(3-dimethylaminopropyl)-3,5-dimethyl-1H-pyrrole-2-carbaldehyde (208 mg, 1.0 mmol) using method B to give 188.7 mg (53%) of 5-chloro-3-[4-(3-dimethylaminopropyl)-3,5-dimethyl-1H-pyrrol-2-ylmethylene]-1,3-dihydroindol-2-one as a brown solid.

$^1$HNMR (360 MHz, DMSO-d$_6$) δ 13.43 (s, 1H, NH), 10.84 (s, 1H, NH), 7.87 (d, J=1.85 Hz, 1H), 7.66 (s, 1H, H-vinyl), 7.05 (dd, J=1.85, 8.15 Hz, 1H), 6.83 (d, J=8.15 Hz, 1H), 2.36–2.45 (m, 4H, (CH$_3$)$_2$NCH$_2$CH$_2$CH$_2$), 2.30 (s, 6H, (CH$_3$)$_2$NCH$_2$CH$_2$CH$_2$), 2.28 (s, 3H, CH$_3$), 2.26 (s, 3H, CH$_3$), 1.58 (quint., J=7.52 Hz, 2H, (CH$_3$)$_2$NCH$_2$CH$_2$CH$_2$).

MS m/z: 357 [M–1]$^+$.

5-Chloro-3-[4-(3-dimethylaminopropyl)-3,5-dimethyl-1H-pyrrol-2-ylmethylene]-1,3-dihydroindol-2-one (63 mg, 0.18 mmol) was reduced using method C to give 15 mg (24%) of 5-chloro-3-[4-(3-dimethylaminopropyl)-3,5-dimethyl-1H-pyrrol-2-ylmethyl]-1,3-dihydroindol-2-one.

MS-EI m/z: 325 [M–Cl]$^+$.

Compound AAI-24: 3-(3-Fluoro-2-hydroxybenzyl)-6-phenyl-1,3-dihydroindol-2-one 6-phenyl-2-oxindole (50 mg, 0.3 mmol) was condensed with 3-fluoro-2-hydroxybenzaldehyde (50 mg, 0.36 mmol) using method B to give 52 mg (53%) of 3-(3-fluoro-2-hydroxybenzylidene)-6-phenyl-1,3-dihydroindol-2-one as a yellow/orange solid.

$^1$HNMR (300 MHz, DMSO-d$_6$) δ 10.71 (s, 1H, NH), 10.32 (s, 1H, OH), 7.60–7.64 (m, 3H), 7.43–7.51 (m, 4H), 7.37 (d, J=7.2 Hz, 1H), 7.3 (m, 1H), 7.16 (m, 1H), 7.09 (d, J=1.2 Hz, 1H), 6.92–6.99 (m, 1H).

MS-EI m/z: 331 [M]$^+$.

3-(3-Fluoro-2-hydroxybenzylidene)-6-phenyl-1,3-dihydroindol-2-one (26 mg, 0.08 mmol) was reduced using method E to give 26 mg (100%) 3-(3-fluoro-2-hydroxybenzyl)-6-phenyl-1,3-dihydroindol-2-one.

MS m/z: 333 [M]$^+$.

Compound AAI-25: 3-(2-Hydroxy-4-methoxybenzyl)-6-phenyl-1,3-dihydroindol-2-one

6-Phenyl-2-oxindole (50 mg, 0.3 mmol) was condensed with 2-hydroxy-4-methoxybenzaldehyde (50 mg, 0.33 mmol) using method B to give 70 mg (68%) of 3-(2-hydroxy-4-methoxybenzylidene)-6-phenyl-1,3-dihydroindol-2-one as a yellow/orange solid.

$^1$HNMR (300 MHz, DMSO-d$_6$) δ 10.60 (s, 1H, NH), 9.80 (s, 1H, OH), 7.35–7.38 (m, 5H), 7.45 (t, J=7.5 Hz, 2H), 7.37 (d, J=7.5 Hz, 1H), 7.17 (d, J=7.5 Hz, 1H), 7.08 (s, 1H), 6.53–6.58 (m, 2H), 3.78 (s, 3H, OCH$_3$).

MS-EI m/z: 343 [M]$^+$.

3-(2-Hydroxy-4-methoxybenzylidene)-6-phenyl-1,3-dihydroindol-2-one (80 mg, 0.23 mmol) was reduced using method E to give 80 mg (100%) 3-(2-hydroxy-4-methoxybenzyl)-6-phenyl-1,3-dihydroindol-2-one.

MS m/z: 345 [M]$^+$.

Compound AAI-26: 3-(5-Bromo-2-hydroxybenzyl)-6-phenyl-1,3-dihydroindol-2-one

6-Phenyl-2-oxindole (50 mg, 0.3 mmol) was condensed with 5-bromosalicylaldehyde (50 mg, 0.25 mmol) using method B to give 80 mg (82%) of 3-(5-bromo-2-hydroxybenzylidene)-6-phenyl-1,3-dihydroindol-2-one as a yellow/orange solid.

$^1$HNMR (300 MHz, DMSO-d$_6$) δ 10.70 (s, 1H, NH), 10.52 (s, 1H, OH), 7.74 (d, J=2 Hz, 1H), 7.62–7.65 (m, 2H), 7.56 (s, 1H, H-vinyl), 7.43–7.49 (m, 4H), 7.37 (m, 1H), 7.20 (dd, J=2, 8 Hz, 1H), 7.09 (d, J=1.2 Hz, 1H), 6.95 (d, J=8 Hz, 1H).

MS-EI m/z: 391/393 [M]+.

3-(5-bromo-2-hydroxybenzylidene)-6-phenyl-1,3-dihydroindol-2-one (23 mg, 0.06 mmol) was reduced using method E to give 23 mg (100%) 3-(5-bromo-2-hydroxybenzyl)-6-phenyl-1,3-dihydroindol-2-one.

MS m/z: 393/395 [M]+.

Compound AAI-27: 4-(2-Hydroxyethyl)-3-(6-methylpyridin-2-ylmethyl)-1,3-dihydroindol-2-one 4-(2-Hydroxyethyl)-1,3-dihydroindol-2-one (89 mg, 0.5 mmol) was condensed with 6-methyl-2-pyridinecarbaldehyde (61 mg, 0.5 mmol) using method B to give 4-(2-hydroxyethyl)-3-(6-methylpyridin-2-ylmethylene)-1,3-dihydroindol-2-one as a yellow solid.

$^1$HNMR (360 MHz, DMSO-$d_6$) δ 10.53 (s, 1H, NH), 8.18 (d, J=7.5 Hz, 1H), 7.68 (t, J=7.5 Hz, 1H), 7.64 (s, 1H), 7.19 (d, J=7.5 Hz, 1H), 7.14 (t, J=7.5 Hz, 1H), 6.82 (d, J=7.5 Hz, 1H), 6.68 (m, 1H), 4.78 (t, J=5 Hz, 1H, OH), 3.68–3.74 (m, 2H, CH$_2$CH$_2$OH), 3.02 (t, J=7 Hz, 2H, CH$_2$CH$_2$OH), 2.49 (s, 3H, CH$_3$).

MS-EI m/z: 280 [M]+.

4-(2-Hydroxyethyl)-3-(6-methylpyridin-2-ylmethylene)-1,3-dihydroindol-2-one (16 mg, 0.06 mmol) was reduced using method E to give 16 mg (100%) of 4-(2-hydroxyethyl)-3-(6-methylpyridin-2-ylmethyl)-1,3-dihydroindol-2-one.

MS m/z: 282 [M]+.

Compound AAI-28: 3-(3-Bromo-5-tert-butyl-4-hydroxybenzyl)-5-chloro-1,3-dihydroindol-2-one 5-Chloro-2-oxindole (167 mg, 1 mmol) was condensed with 3-bromo-5-tert-butyl-4-hydroxybenzaldehyde (308.5 mg, 1.2 mmol) using method B to give 329 mg (81%) of 3-(3-bromo-5-tert-butyl-4-hydroxybenzylidene)-5-chloro-1,3-dihydroindol-2-one as a mixture of isomers.

MS m/z: 407 [M+1]+.

3-(3-bromo-5-tert-butyl-4-hydroxybenzylidene)-5-chloro-1,3-dihydroindol-2-one (1 g, 2.46 mmol) was reduced using method C to give 1.005 g (100%) of 3-(3-bromo-5-tert-butyl-4-hydroxybenzyl)-5-chloro-1,3-dihydroindol-2-one as a mixture of isomers.

$^1$H NMR (360 MHz, DMSO-$d_6$) δ 10.29 & 10.16 (2s, 1H, NH), 9–9.01 (s, br, 1H, OH), 7.05–7.13 (m, 1H), 6.8–6.9 (m, 1H), 6.66–6.77 (m, 3H), 6.55–6.6 (m, 1H), 3.65 (m, 1H), 3.19 (m, 1H), 2.8 (m, 1H), 1.2 & 1.21 (2s, 9H, C(CH$_3$)$_3$).

MS m/z: 408/410 [M]+.

C. Diaryl Indolinone Compounds

General Synthesis

Condensation of ketones and oxindoles:

A reaction mixture of the proper indolin-2-ones (1.0 equiv.), the appropriate ketone (1.2 equiv.), and piperidine or pyrrolidine (0.1 equiv.) in ethanol (1–2 mL/1.0 mmol oxindole) is stirred at 90° C. for 3–5 h. After cooling, the precipitate is filtered, washed with cold ethanol, and dried to yield the target compound.

4-(3,5-dimethyl-1H-pyrrol-2-yl)-4-oxo-butyric acid

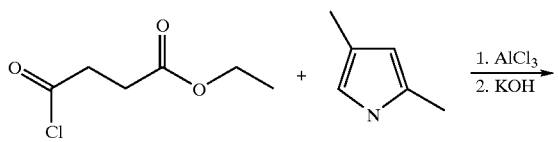

-continued

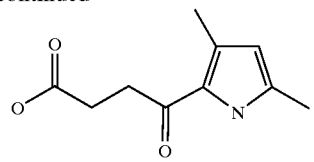

To a mixture of 13.3 g (0.1 mol) of aluminum chloride in dichloromethane (150 mL) was added 10 g (0.105 mol) of 2,4-dimethylpyrrole at room temperature. The resulting solution was stirred t room temperature for 15 minutes and added with 16.4 g (0.1 mol) of ethyl succinyl chloride. The reaction mixture was stirred at room temperature for 2 days and quenched with saturated sodium carbonate. The mixture was then diluted with water (100 mL) and dichloromethane (300 mL). The organic layer was separated and concentrated. The residue was taken into ethanol (30 mL) and 1 N potassium hydroxide (30 mL) and heated at 90° C. for 2 hours. The cooled mixture was then diluted with water and extracted with ethyl acetate. The basic aqueous layer was acidified with 6 N hydrochloric acid until pH 3. The mixture was then extracted with ethyl acetate (3×). The combined organic extracts were washed with brine, dried over sodium sulfate and concentrated. The residue was stirred with ethyl acetate (20 mL) and the solid was collected by filtration to give 820 mg of 4-(3,5-dimethyl-1H-pyrrol-2-yl)-4-oxo-butyric acid as a dark solid.

$^1$HNMR (300 MHz, DMSO-$d_6$) δ 12.01 (s, br, 1H, COOH), 11.18 (s, 1H, NH), 5.75 (d, J=2.1 Hz, 1H, H-pyrrole), 2.88 (t, J=6.6 Hz, 2H, CH$_2$CH$_2$), 2.49 (t, J=6.6 Hz, 2H, under DMSO), 2.24 (s, 3H, CH$_3$), 2.15 (s, 3H, CH$_3$). MS EI 195 [M]+.

This will then be condensed with oxindole.

3-[(3,5-Dimethyl-1H-pyrrol-2-yl)-(4-methoxyphenyl)-methylene]-1,3-dihydro-indol-2-one (DAI-I)

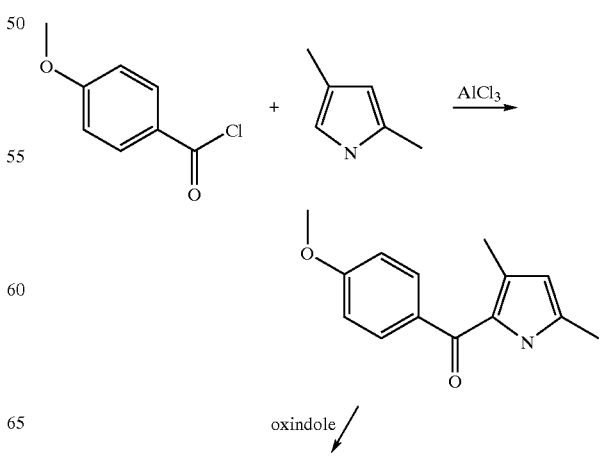

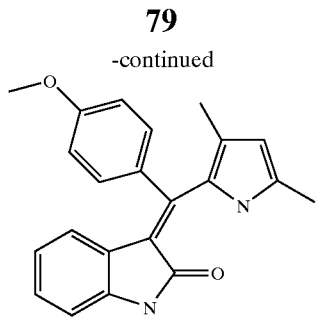

Aluminum chloride (1.3 equiv.) in dichloromethane was added to the benzoyl chloride (1 equiv.) at room temperature, followed by a solution of 2,4-dimethylpyrrole (1.6 equiv.) in dichloromethane. The mixture was then stirred at room temperature for overnight. The reaction was diluted with ethyl acetate, washed with brine, dried and concentrated. The residue was chromatographed eluting with ethyl acetate and hexane to give the ketone.

(3,5-Dimethyl-1H-pyrrol-2-yl)-(4-methoxy-phenyl)-methanone (50 mg, 0.22 mmol), oxindole (50 mg, 0.37 mmol), pyrrolidine (0.3 mL) and 1,8-diazabicyclo[5.4.0]undec-7-ene (0.1 mL) in dimethylforamide (1 mL) was heated at 150–160° C. for 1 day. Sodium hydride (12 mg) was added to the reaction mixture and the heating was continued for 3 days. The reaction was poured into water and extracted with ethyl acetate. The organic layer was washed with water, dried and concentrated. The residue was chromatographed eluting with ethyl acetate and dichloromethane to give 6 mg of 3-[(3,5-dimethyl-1H-pyrrol-2-yl)-(4-methoxy-phenyl)-methylene]-1,3-5-dihydro-indol-2-one as a yellow solid.

$^1$H NMR (300 MHz, DMSO-$d_6$) δ 14.06 (s, 1H, NH), 10.79 (s, 1H, NH), 7.18 (d, J=9 Hz, 2H), 7.10 (d, J=9 Hz, 2H), 6.89 (t, J=8 Hz, 1H), 6.75 (d, J=8 Hz, 1H), 6.45 (m, 1H), 5.87 (d, J=2.7 Hz, 1H, H-pyrrole), 5.40 (d, J=8 Hz, 1H), 3.84 (s, 3H, OCH$_3$), 2.27 (s, 3H, CH$_3$), 1.30 (s, 3H, CH$_3$).

MS EI 344 [M]$^+$.

3-[(3,4-dimethoxy-phenyl)-(3,5-dimethyl-1H-pyrrol-2-yl)-methylene]-1,3-dihydro-indol-2-one (DAI-II)

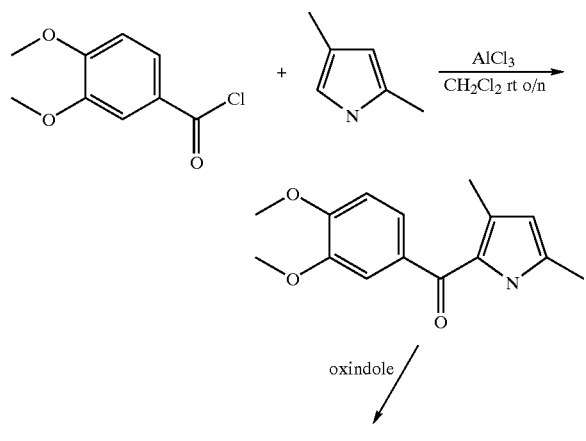

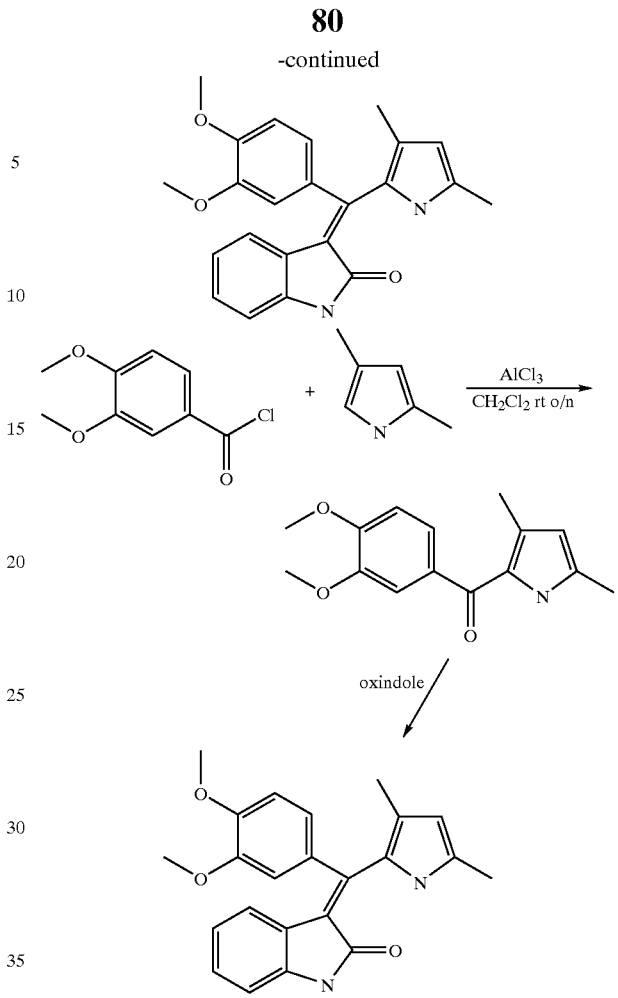

Aluminum chloride (1.7 g, 12.75 mmol) in dichloromethane (100 mL) was added to the 3,4-dimethoxybenzoyl chloride (2.0 g, 10 mmol) at room temperature, followed by a solution of 2,4-dimethylpyrrole (1.5 g, 15.8 mmol) in dichloromethane (5 mL). The mixture was then stirred at room temperature for overnight. The reaction was diluted with ethyl acetate, washed with brine, dried and concentrated. The residue was chromatographed eluting with ethyl acetate and hexane to give 1 g (39%) of (3,4-dimethoxy-phenyl)-(3,5-dimethyl-1H-pyrrol-2-yl)-methanone as a solid.

$^1$H NMR (300 MHz, DMSO-$d_6$) δ 11.15 (s, 1H, NH), 7.18 (m, 2H, Ar—H), 7.03 (d, 1H, Ar—H), 5.80 (d, 1H, H-pyrrole), 3.81 (s, 3H, OCH$_3$), 3.77 (s, 3H, OCH$_3$), 2.17 (s, 3H, CH$_3$), 1.97 (s, 3H, CH$_3$).

MS 260.2 [M+1]$^+$.

(3,4-Dimethoxy-phenyl)-(3,5-dimethyl-1H-pyrrol-2-yl)-methanone (100 mg, 0.4 mmol), oxindole (100 mg, 0.8 mmol), pyrrolidine (0.2 mL) and 1,8-diazabicyclo[5.4.0]undec-7-ene (a few drops) in dimethylforamide (1.5 mL) was heated at 160° C. for 2 hours. Sodium hydride (18 mg) was added to the reaction mixture and the heating was continued at 160° C. for 3 days. The reaction was poured into water and extracted with ethyl acetate. The organic layer was washed with water, dried and concentrated. The residue was chromatographed eluting with ethyl acetate and hexane to give 5 mg of 3-[(3,4-dimethoxy-phenyl)-(3,5-dimethyl-1H-pyrrol-2-yl)-methylene]-1,3-dihydro-indol-2-one. MS EI 374 [M]$^+$.

D. 4-Substituted Indolinone Compounds

Compound IN-001

4-[2-(3-Isopropyl-phenoxy)-ethyl]-1,3-dihydro-indol-2-one

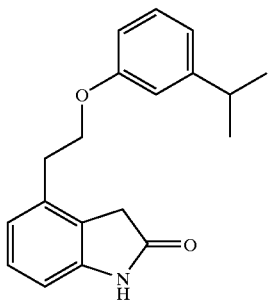

Diethyl azodicarboxylate (0.47 mL, 3 mmol) was added to a solution of triphenylphosphine (0.786 g, 3 mmol) in tetrahydrofuran (10 mL) under nitrogen atmosphere. The mixture was stirred for 15 minutes. To it was then added 4-(2-hydroxy-ethyl)-1,3-dihydro-indol-2-one (0.53 g, 3 mmol) (Hayler, J. D.; Howie, S. L. B.; Giles, R. G.; Negus, A.; Oxley, P. W.; et al; J. Heteocycl. Chem.; 32; 3; 1995; 875–882), followed by 3-isopropylphenol (0.41 mL, 3 mmol). The mixture was stirred at room temperature for one day and the solvent was evaporated. The residue was chromatographed on silica gel eluting with ethyl acetate: hexane 1:9 to give 120 mg (14%) of 4-[2-(3-isopropyl-phenoxy)-ethyl]-1,3-dihydro-indol-2-one.

$^1$HNMR (360 MHz, DMSO-d6) δ 10.31 (s, br, 1H, NH), 7.09–7.12 (m, 2H, Ar—H), 6.88 (d, J=7.6 Hz, 1H, Ar—H), 6.67–6.79 (m, 4H, Ar—H), 4.16 (t, J=6.7 Hz, 2H, OCH$_2$CH$_2$), 3.5 (s, 2H, H-3, CH$_2$), 2.93 (t, J=6.7 Hz, 2H, OCH$_2$CH$_2$), 2.82 (m, 1H, CH(CH$_3$)$_2$), 1.16 (d, J=6.8 Hz, 6H, CH(CH$_3$)$_2$). MS-EI 295 [M]$^+$.

Compound IN-002

4-[2-(2-Isopropyl-phenoxy)-ethyl]-1,3-dihydro-indol-2-one

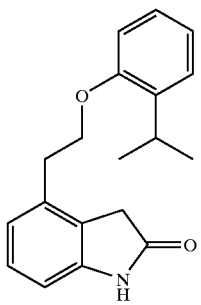

Diethyl azodicarboxylate (1.58 mL, 10 mmol) was added to a solution of triphenylphosphine (2.62 g, 10 mmol) in tetrahydrofuran (20 mL) under nitrogen atmosphere. The mixture was stirred for 15 minutes. To it was then added 4-(2-hydroxy-ethyl)-1,3-dihydro-indol-2-one (1.77 g, 10 mmol) followed by 2-isopropylphenol (1.36 mL, 10 mmol). The mixture was stirred at room temperature for 18 hours and the solvent was evaporated. The residue was chromatographed on silica gel eluting with ethyl acetate: hexane 2:8 to give 0.26 g (9%) of 4-[2-(2-isopropyl-phenoxy)-ethyl]-1,3-dihydro-indol-2-one as a light yellow solid.

$^1$HNMR (360 MHz, DMSO-d$_6$) δ 10.29 (s, br, 1H, NH), 7.08–7.14 (m, 3H, Ar—H), 6.83–6.93 (m, 3H, Ar—H), 6.67 (d, J=7.2 Hz, 1H, Ar—H), 4.18 (t, J=6.4 Hz, 2H, CH$_2$CH$_2$O), 3.47 (s, 2H, H-3, CH$_2$), 3.11 (m, 1H, CH(CH$_3$)$_2$), 2.96 (t, J=6.4 Hz, 2H, CH$_2$CH$_2$O), 1.05 (d, J=6.8 Hz, 6H, CH(CH$_3$)$_2$). MS-EI 295 [M]$^+$.

Compound IN-003

4-[2-(Biphenyl-3-yloxy)-ethyl]-1,3-dihydro-indol-2-one

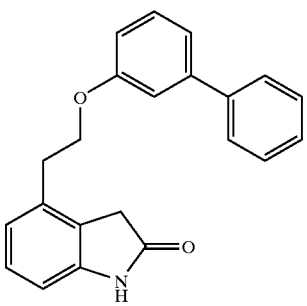

Diethyl azodicarboxylate (1.58 mL, 10 mmol) was added to a solution of triphenylphosphine (2.62 g, 10 mmol) in tetrahydrofuran (20 mL) under nitrogen atmosphere. The mixture was stirred for 15 minutes. To it was then added 4-(2-hydroxy-ethyl)-1,3-dihydro-indol-2-one (1.77 g, 10 mmol) followed by 3-phenylphenol (1.7 g, 10 mmol). The mixture was stirred at room temperature for one day and the solvent was evaporated. The residue was dissolved in ethyl acetate (150 mL) and the organic solvent was washed with 2 N hydrochloric acid (3×50 mL), saturated sodium bicarbonate solution and brine. The residue was chromatographed on silica gel eluting with ethyl acetate: hexane 2:8 to give 1.19 g (36%) of 4-[2-(biphenyl-3-yloxy)-ethyl]-1,3-dihydro-indol-2-one.

$^1$HNMR (360 MHz, DMSO-d$_6$) δ 10.30 (s, br, 1H, NH), 7.63–7.65 (m, 2H, Ar—H), 7.41–7.45 (m, 2H, Ar—H), 7.32–7.36 (m, 2H, Ar—H), 7.2 (m, 1H, Ar—H), 7.16 (m, 1H, Ar—H), 7.12 (t, J=7.9 Hz, 1H, Ar—H), 6.89–6.93 (m, 2H, Ar—H), 6.68 (d, J=7.2 Hz, 1H, Ar—H), 4.26 (t, J=6.8 Hz, 2H, CH$_2$CH$_2$O), 3.52 (s, 2H, H-3, CH$_2$), 2.98 (t, J=6.8 Hz, 2H, CH$_2$CH$_2$O).

Compound IN-004

3-(4-Bromo-benzylidene)-4-(2-hydroxy-ethyl)-1,3-dihydro-indol-2-one

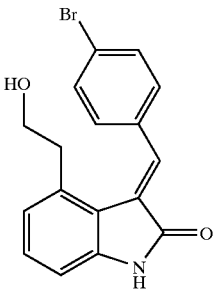

A mixture of 4-(2-hydroxy-ethyl)-1,3-dihydro-indol-2-one (3.0 g, 17 mmol), 4-bromobenzaldehyde (3.1 g, 17 mmol) and piperidine (8.4 mL, 85 mmol) in ethanol (113 mL) was heated at 90° C. for overnight. The reaction mixture was concentrated and the residue was chromatographed on a column of silica gel to give 2.4 g (41%) of 3-(4-bromo-benzylidene)-4-(2-hydroxy-ethyl)-1,3-dihydro-indol-2-one as a yellow orange solid.

$^1$HNMR (360 MHz, DMSO-$d_6$) δ 10.53 (s, 1H, NH), 7.96 (d, J=7.4 Hz, 2H), 7.69 (s, 1H, H-vinyl), 7.61 (d, J=7.4 Hz, 2H, Ar—H), 7.12 (m, 1H, Ar—H), 6.81 (d, J=7.4 Hz, 1H, Ar—H), 6.67 (d, J=7.4 Hz, 1H, Ar—H), 4.80 (m, 1H, OH), 3.69 (m, 2H, CH$_2$C$\underline{H}_2$OH), 3.04 (m, 2H, C$\underline{H}_2$CH$_2$OH).

MS-EI 343/345 [M]$^+$.

Compound IN-005

4-(2-Hydroxy-ethyl)-3-pyridin-2-ylmethylene-1,3-dihydro-indol-2-one

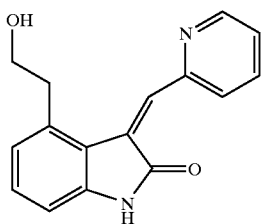

A mixture of 4-(2-hydroxy-ethyl)-1,3-dihydro-indol-2-one (80 mg, 0.45 mmol) and 2-pyridinecarboxaldehyde (60 mg, 0.56 mmol) in 1% of piperidine in ethanol (5 mL) was heated at 90° C. for 8 hours. The reaction mixture was concentrated and the residue was chromatographed on a column of silica gel. It was then triturated with ethyl acetate and hexane to give 55 mg (46%) of 4-(2-hydroxy-ethyl)-3-pyridin-2-ylmethylene-1,3-dihydro-indol-2-one.

$^1$HNMR (360 MHz, DMSO-$d_6$) δ 10.58 (s, br, 1H, NH), 8.64 (d, J=4.7 Hz, 1H, Ar—H), 8.40 (d, J=8.3 Hz, 1H), 7.81 (dt, J=1.8 & 7.7 Hz, 1H, Ar—H), 7.7 (s, 1H, H-vinyl), 7.34 (m, 1H, Ar—H), 7.16 (t, J=7.6 Hz, 1H), 6.83 (d, J=7.6 Hz, 1H, Ar—H), 6.69 (d, J=7.6 Hz, 1H, Ar—H), 4.80 (t, J=5.2 Hz, 1H, OH), 3.71 (m, 2H, —CH$_2$C$\underline{H}_2$OH), 3.03 (t, J=7.2 Hz, 2H, —C$\underline{H}_2$CH$_2$OH).

MS-EI 267 [M+1]$^+$.

Compound IN-006

4-(2-Hydroxy-ethyl)-3-(6-methyl-pyridin-2-ylmethylene-1,3-dihydro-indol-2-one

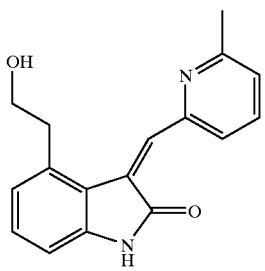

A mixture of 4-(2-hydroxy-ethyl)-1,3-dihydro-indol-2-one (89 mg, 0.5 mmol), 6-methyl-2-pyridine-carbaldehyde (61 mg, 0.5 mmol) and piperidine (0.1 mL) in 1.0 mL of ethanol was heated at 100° C. for 1 hour and cooled to room temperature. The precipitate was filtered and recrystallized from ethyl acetate and hexanes to give 4-(2-hydroxy-ethyl)-3-(6-methyl-pyridin-2-ylmethylene)-1,3-dihydro-indol-2-one as a yellow solid.

$^1$HNMR (360 MHz, DMSO-$d_6$) δ 10.53 (s, 1H, NH), 8.18 (d, J=7.5 Hz, 1H), 7.68 (t, J=7.5 Hz, 1H), 7.64 (s, 1H), 7.19 (d, J=7.5 Hz, 1H), 7.14 (t, J=7.5 Hz, 1H), 6.82 (d, J=7.5 Hz, 1H), 6.68 (m, 1H), 4.78 (t, J=5 Hz, 1H, OH), 3.68–3.74 (m, 2H, CH$_2$C$\underline{H}_2$OH), 3.02 (t, J=7 Hz, 2H, C$\underline{H}_2$CH$_2$OH), 2.49 (s, 3H, CH$_3$).

MS-EI 280 [M]$^+$.

Compound IN-007

4-(2-Hydroxy-ethyl)-3-(1H-indol-5-ylmethylene)-1,3-dihydro-indol-2-one

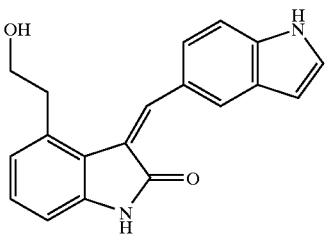

Indole-5-carboxylic acid (5.02 g, 31.3 mmol) in tetrahydrofuran (40 mL) was added slowly to the lithium aluminium hydride (1.88 g, 49.5 mmol) stirred in tetrahydrofuran (125 mL) under nitrogen with external heating so as to maintain a gently reflux. The mixture was heated at reflux for 2 hours and cooled to room temperature. 2 N sodium hydroxide (10 mL) was then added dropwise to the reaction mixture. The precipitate was removed by filtration and the filtrate was concentrated. It was dissolved in dichloromethane (80 mL), washed with 2 N sodium hydroxide (10 mL), water (20 mL) and brine (20 mL), dried over anhydrous sodium sulfate and concentrated to give about 5 g of (1H-indol-5-yl)-methanol.

A mixture of (1H-indol-5-yl)-methanol (3.8 g, 25.8 mmol) and manganese oxide (5 g, 57.5 mmol) in dichloromethane (50 mL) was stirred at room temperature for 60 hours. After the usual work-up and chromatography, 1.5 g (40%) of 1H-indole-5-carbaldehyde was obtained.

A mixture of 4-(2-hydroxy-ethyl)-1,3-dihydro-indol-2-one (39 mg, 0.22 mmol), 1H-indole-5-carbaldehyde (32 mg, 0.22 mmol) and 1 drop of piperidine in ethanol was heated at 90° C. for overnight and cooled to room temperature. The reaction mixture was concentrated and the residue was purified on silica gel column to give 48 mg (72%) of 4-(2-hydroxy-ethyl)-3-(1H-indol-5-ylmethylene)-1,3-dihydro-indol-2-one as a yellow solid.

$^1$HNMR (360 MHz, DMSO-$d_6$) 11.28 (s, br, 1H, NH), 10.48 (s, br, 1H, NH), 8.59 (s, 1H), 8.06 (d, 1H), 7.89 (s, 1H,

H-vinyl), 7.4 (m, 2H), 7.06 (t, J=7 Hz, 1H, H-6), 6.09 (d, J=7 Hz, 1H, H-5), 6.68 (d, J=7 Hz, 1H, H-7), 6.53 (s, 1H), 4.86 (t, 1H, OH), 3.75 (m, 2H, —CH$_2$CH$_2$OH), 3.11 (m, 2H, —CH$_2$CH$_2$OH). MS-EI 304 [M]$^+$.

Compound IN-008

4-(2-Hydroxy-ethyl)-3-(4-methoxy-3-thiophen-2-yl-benzylidene)-1,3-dihydro-indol-2-one

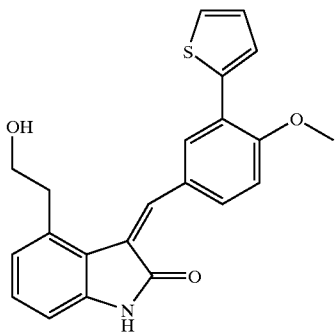

Tetrakis(triphenylphosphine)palladium(0) (0.24 g, 0.21 mmol) was added to a solution of 4-methoxy-3-bromobenzaldehyde (1.5 g, 6.98 mmol) in toluene (15 mL) and ethanol (15 mL), followed by a 2 M aqueous solution of sodium carbonate (14 mL, 28 mmol). To this mixture was added thiophene-2-boronic acid (0.98 g, 7.68 mmol), and the mixture was heated to reflux. After 3 hours, the reaction was partitioned between water (100 mL) and ethyl acetate (250 mL). The organic layer was washed with saturated aqueous sodium bicarbonate (75 mL) and brine (75 mL), dried with magnesium sulfate and concentrated. Chromatography (silica, 20% ethyl acetate/hexanes) afforded 1.3 g (87%) of 4-methoxy-3-thiophen-2-yl-benzaldehyde as a yellow oil.

$^1$H NMR (360 MHz, DMSO-d$_6$) δ 9.92 (s, 1H, CHO), 8.2 (d, 1H, J=3 Hz, 1×Ar—H), 7.8 (dd, 1H, J=10 and 10 Hz, SCHCHCH), 7.65 (m, 1H, Ar—H), 7.60 (dd, 1H, J=2 and 6 Hz, Ar—H), 7.32 (d, 1H, J=10 Hz, SCHCHCH), 7.13 (d, 1H, J=10 and 6 Hz, SCHCHCH), 3.99 (s, 3H, OCH$_3$).

A mixture of 4-(2-hydroxy-ethyl)-1,3-dihydro-indol-2-one (1.6 g, 9.2 mmol), 4-methoxy-3-thiophen-2-yl-benzaldehyde (2 g, 9.2 mmol) and piperidine (4.5 mL, 85 mmol) in ethanol (46 mL) was heated to reflux for overnight. The reaction mixture was concentrated and the residue was chromatographed on a column of silica gel to give 1.63 g (47%) of 4-(2-hydroxy-ethyl)-3-(4-methoxy-3-thiophen-2-yl-benzylidene)-1,3-dihydro-indol-2-one as a yellow orange solid. $^1$HNMR (300 MHz, DMSO-d$_6$) δ 10.53 (s, br, 1H, NH), 8.73 (d, J=2.1 Hz, 1H), 8.10 (dd, J=2.2 & 9.1 Hz, 1H), 7.74 (s, 1H, H-vinyl), 7.56–7.65 (m, 2H), 7.07–7.22 (m, 3H), 6.81 (d, J=7.5 Hz, 1H), 6.68 (dd, J=0.6, 7.5 Hz, 1H), 4.87 (t, J=4.5 Hz, 1H, OH), 3.97 (s, 3H, OCH$_3$), 3.68–3.75 (m, 2H, CH$_2$CH$_2$OH), 3.09 (t, J=4.5 Hz, 2H, CH$_2$CH$_2$OH).

MS-EI 377 [M]$^+$.

Compound IN-009

3-[4-(3-Dimethylamino-propyl)-3,5-dimethyl-1H-pyrrol-2-ylmethylene]-4-(2-hydroxy-ethyl)-1,3-dihydro-indol-2-one

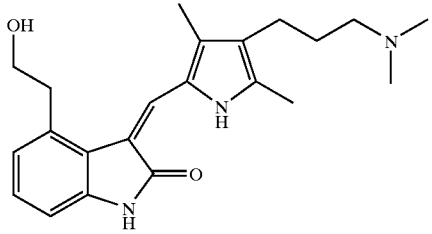

To the suspension of 3-(2,4-dimethyl-1H-pyrrol-3-yl)-propionic acid (10 g, 60.8 mmol) in 60 mL of dichloromethane was added 1,1'-carbonyldiimidazole (11.6 g, 71.8 mmol) followed by the addition of 2 M dimethylamine solution in tetrahydrofuran (30 mL) and N,N-diisopropylethylamine (Hunig's base, 10 mL, 60.8 mmol). The dark red reaction mixture was stirred at room temperature overnight and poured into ice water. The organic layer was washed with brine until pH of 6, dried over anhydrous sodium sulfate, and concentrated. The crude product was purified on a silica gel column eluting with dichloromethane-methanol (98:2) to give 9.8 g (83%) of 3-(2,4-dimethyl-1H-pyrrol-3-yl)-N,N-dimethyl-propionamide as a yellow oil.

To the suspension of lithium aluminum hydride (2.3 g, 60 mmol) in tetrahydrofuran (50 mL) was added a solution of 3-(2,4-dimethyl-1H-pyrrol-3-yl)-N,N-dimethyl-propionamide (9.81 g, 50 mmol) in THF (50 mL) dropwise. The reaction mixture was stirred at 80° C. for 1 hour and cooled with ice bath. Ice cube was added into the reaction mixture slowly until no more gas generated. A few drops of 2 N sodium hydroxide was added and the reaction mixture was stirred at room temperature for 30 minutes, extracted with ethyl acetate, dried over anhydrous sodium sulfate and concentrated to give 6.8 g (75%) of [3-(2,4-dimethyl-1H-pyrrol-3-yl)-propyl]-dimethylamine as an orange oil which was used without further purification.

To the ice-cooled solution of N,N-dimethylformamide (6.0 mL, 76 mmol) in dichloromethane (30 mL) was added phosphorus oxychloride (7.0 mL, 76 mmol) dropwise. Upon addition of phosphorus oxychloride, the reaction mixture was stirred at room temperature for 15 minutes and a solution of [3-(2,4-dimethyl-1H-pyrrol-3-yl)-propyl]-dimethyl-amine (6.8 g, 38 mmol) in dichloromethane (20 mL) was added dropwise at 0° C. The final reaction mixture was refluxed at 60° C. for 4 hours and cooled with ice bath. Ice cube was added to the reaction mixture slowly followed by addition of 2 N sodium hydroxide to adjust pH to 12. The reaction mixture was stirred at room temperature for 30 minutes and extracted with ethyl acetate. The organic-layer was washed with brine, dried over anhydrous sodium sulfate and concentrated to give crude product which was purified on a silica gel column eluting with dichloromethane-methanol-ammonium hydroxide (9:1:0.01) to give 5 g (63%) of 4-(3-dimethylamino-propyl)-3,5-dimethyl-1H-pyrrole-2-carbaldehyde as a dark red oil.

$^1$HNMR (360 MHz, DMSO-d$_6$) δ 11.33 (s, br, 1H, NH-1), 9.40 (s, 1H, CHO-2), 2.30 (t, J=7.42 Hz, 2H, (CH$_3$)$_2$NCH$_2$CH$_2$CH$_2$-4), 2.18 (s, 3H, CH$_3$-3), 2.15 (t, J=7.42 Hz, 2H, (CH$_3$)$_2$NCH$_2$CH$_2$CH$_2$-4), 2.14 (s, 3H, CH$_3$-5), 2.10 (s, 6H, (C$\underline{H}_3$)$_2$NCH$_2$CH$_2$CH$_2$-4), 1.47 (quint., J=7.42 Hz, 2H, (CH$_3$)$_2$NCH$_2$C$\underline{H}_2$CH$_2$-4);

MS 208 ([M+1]$^+$.

A mixture of 4-(2-hydroxy-ethyl)-1,3-dihydro-indol-2-one (177 mg, 1.0 mmol), 4-(3-dimethylamino-propyl)-3,5-dimethyl-1H-pyrrole-2-carbaldehyde (208 mg, 1.0 mmol) and 3 drops of pyrrolidine in 2.0 mL of ethanol was refluxed at 90° C. for 4 hours and cooled to room temperature. The precipitate was filtered, washed with cold ethanol and hexane, and dried in a vacuum oven overnight to give 360.6 mg (98%) of 3-[4-(3-dimethylamino-propyl)-3,5-dimethyl-1H-pyrrol-2-ylmethylene]-4-(2-hydroxy-ethyl)-1,3-dihydro-indol-2-one.

$^1$HNMR (300 MHz, DMSO-d$_6$) δ 13.47 (s, br, 1H, NH), 10.79 (s, br, 1H, NH), 7.56 (s, 1H, H-vinyl), 6.99 (m, 1H, Ar—H), 6.76 (m, 2H, Ar—H), 4.9 (s, br, 1H, OH), 3.7 (m, 2H, CH$_2$), 3.07 (m, 2H, CH$_2$), 2.93 (m, 2H, CH$_2$), 2.67 (s, 6H, 2×CH$_3$), 2.42 (m, 2H, CH$_2$), 2.29 (s, 3H, CH$_3$), 2.20 (s, 3H, CH$_3$), 1.73 (m, 2H, CH$_2$).

Compound IN-010

Phenyl-thiocarbamic acid O-[2-(2-oxo-2,3-dihydro-1H-indol-4-yl)-ethyl]ester

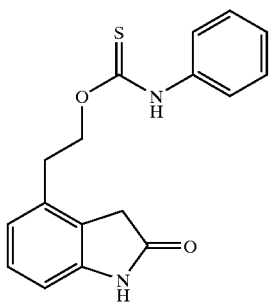

Phenyl isothiocyanate (0.45 mL, 3.75 mmol) was added dropwise to a stirred mixture of 4-(2-hydroxy-ethyl)-1,3-dihydro-indol-2-one (443 mg, 2.5 mmol) in tetrahydrofuran (5 mL). The mixture was stirred at room temperature for 20 hours and then 70° C. for 8 hours. One mL of dimethylforamide was added to the mixture to make it homogenous and the heating was continued for another 42 hours. The reaction was cooled, poured into 1 N sodium hydroxide solution (100 mL) and extracted with ethyl acetate (200 mL). The organic layer was washed with 1 N hydrochloric acid (100 mL) and brine, dried over anhydrous sodium sulfate and concentrated. The residue was recrystallized from methanol/ethyl acetate/hexane to give 452 mg (58%) of phenyl-thiocarbamic acid O-[2-(2-oxo-2,3-dihydro-1H-indol-4-yl)-ethyl]ester as a white solid.

$^1$HNMR (360 MHz, DMSO-d$_6$) δ 11.00 (s, br, 1H, NH), 10.30 (s, br, 1H, NH), 7.58 (s, br, 1H, Ar—H), 7.25 (s, br, 3H, Ar—H), 7.11 (t, J=7.9 Hz, 2H, Ar—H), 6.85 (m, 1H, Ar—H), 6.68 (d, J=7.2 Hz, 1H, Ar—H), 4.67 (m, 2H, OC$\underline{H}_2$CH$_2$), 3.27 (s, 2H, H-3), 2.95 (m, 2H, OCH$_2$C$\underline{H}_2$).

MS-EI 312 [M]$^+$.

Compound IN-011

Phenyl-carbamic acid 2-(2-oxo-2,3-dihydro-1H-indol-4-yl)-ethyl ester

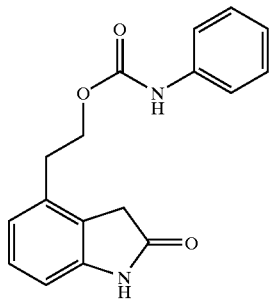

Phenyl isocyanate (0.652 mL, 6 mmol) was added dropwise to a stirred mixture of 4-(2-hydroxy-ethyl)-1,3-dihydro-indol-2-one (709 mg, 4 mmol) in tetrahydrofuran (8 mL), dimethylforamide (2 mL) and pyridine (3 drops). The mixture was heated at 70° C. for 15 hours. The reaction was cooled, poured into 1 N sodium hydroxide solution (100 mL) and extracted with ethyl acetate (200 mL). The organic layer was washed with 1 N hydrochloric acid (100 mL) and brine, dried over anhydrous sodium sulfate and concentrated. The residue was recrystallized from methanol/ethyl acetate/hexane to give 953 mg (80%) of phenyl-carbamic acid 2-(2-oxo-2,3-dihydro-1H-indol-4-yl)-ethyl ester as an off-white powder.

$^1$HNMR (360 MHz, DMSO-d$_6$) δ 10.30 (s, br, 1H, NH), 9.52 (s, br, 1H, NH), 7.42 (d, J=7.9 Hz, 2H, Ar—H), 7.24 (m, 2H, Ar—H), 7.11 (t, J=7.5 Hz, 1H, Ar—H), 6.96 (m, 1H, Ar—H), 6.84 (d, J=7.5 Hz, 1H, Ar—H), 6.69 (d, J=7.5 Hz, 1H, Ar—H), 4.28 (t, J=6.8 Hz, 2H, OC$\underline{H}_2$CH$_2$), 3.48 (s, 2H, H-3), 2.85 (t, J=6.8 Hz, 2H, OCH$_2$C$\underline{H}_2$). MS-EI 296 [M]$^+$.

Compound IN-012 tert-Butyl-carbamic acid 2-(2-oxo-2,3-dihydro-1H-indol-4-yl)-ethyl ester

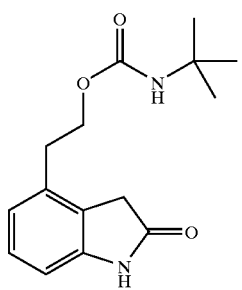

Tert-butyl isocyanate (0.685 mL, 6 mmol) was added dropwise to a stirred mixture of 4-(2-hydroxy-ethyl)-1,3-dihydro-indol-2-one (709 mg, 4 mmol) in tetrahydrofuran (8 mL), dimethylforamide (2 mL) and pyridine (3 drops). The mixture was heated at 70° C. for 15 hours and 80° C. for 39 hours. 0.457 mL of tert-butyl isocyanate was added to the reaction and continued to heat at 90° C. for 24 hours. More tert-butyl isocyanate (0.457 mL) was added and continued to heat at 90° C. for 37 hours. The reaction was cooled, poured into 1 N sodium hydroxide solution (100 mL) and extracted with ethyl acetate (200 mL). The organic layer was washed with 1 N hydrochloric acid (100 mL) and brine, dried over anhydrous sodium sulfate and concentrated. The residue was recrystallized from methanol/ethyl acetate/hexane to give 130 mg (12%) of tert-butyl-carbamic acid 2-(2-oxo-2,3-dihydro-1H-indol-4-yl)-ethyl ester.

¹HNMR (300 MHz, DMSO-d₆) δ 10.30 (s, br, 1H, NH), 7.09 (t, J=7.6 Hz, 1H, Ar—H), 6.81 (s, 1H, NHC(CH₃)₃), 6.80 (d, J=7.6 Hz, 1H, Ar—H), 6.65 (d, J=7.6 Hz, 1H, Ar—H), 4.07 (m, 2H, OCH₂CH₂), 3.45 (s, 2H, H-3), 2.73–2.74 (m, 2H, OCH₂CH₂), 1.18 (s, 3H, 3×CH₃). MS-EI 276 [M]⁺.

Compound IN-013

Cyclohexyl-carbamic acid 2-(2-oxo-2,3-dihydro-1H-indol-4-yl)-ethyl ester

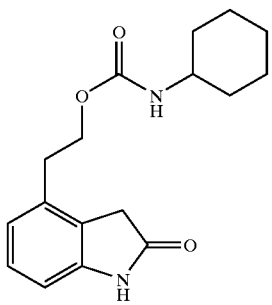

Cyclohexyl isocyanate (0.766 mL, 6 mmol) was added dropwise to a stirred mixture of 4-(2-hydroxy-ethyl)-1,3-dihydro-indol-2-one (709 mg, 4 mmol) in tetrahydrofuran (8 mL), dimethylforamide (2 mL) and pyridine (3 drops). The mixture was heated at 70° C. for 16 hours. 0.511 mL of cyclohexyl isocyanate was added to the reaction and continued to heat at 80° C. for 24 hours. More cyclohexyl isocyanate (0.255 mL) was added and continued to heat at 85° C. for 24 hours. The reaction was cooled, poured into 1 N sodium hydroxide solution (100 mL) and extracted with ethyl acetate (200 mL). The organic layer was washed with 1 N hydrochloric acid (100 mL) and brine, dried over anhydrous sodium sulfate and concentrated. The residue was recrystallized from methanol/ethyl acetate/hexane to give 317 mg of the product. A second crop of product (32 mg) was obtained from the mother liquor followed by column chromatography (1:1 ethyl acetate:hexane). A total of 349 mg (29%) of cyclohexyl-carbamic acid 2-(2-oxo-2,3-dihydro-1H-indol-4-yl)-ethyl ester as a white powder was obtained.

¹HNMR (360 MHz, DMSO-d₆) δ 10.28 (s, br, 1H, NH), 7.09 (t, J=7.6 Hz, 1H, Ar—H), 6.97 (d, br, J=6.6 Hz, 1H, CONHCH), 6.79 (d, J=7.6 Hz, 1H, Ar—H), 6.65 (d, J=7.6 Hz, 1H, Ar—H), 4.11 (t, J=6.6 Hz, 2H, OCH₂CH₂), 3.44 (s, 2H, H-3), 3.25–3.35 (m, 1H, CONHCH), 2.75 (t, J=6.6 Hz, 2H, OCH₂CH₂), 1.5–1.8 (m, c-hexyl). MS-EI 302 [M]⁺.

Compound IN-014

Benzene sulfonyl-carbamic acid 2-(2-oxo-2,3-dihydro-1H-indol-4-yl)-ethyl ester

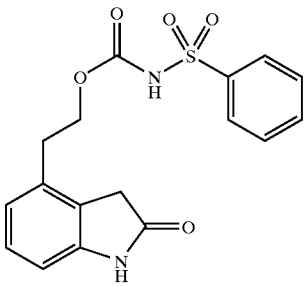

Benzene sulfonyl isocyanate (1.07 mL, 8 mmol) was added dropwise to a stirred mixture of 4-(2-hydroxy-ethyl)-1,3-dihydro-indol-2-one (709 mg, 4 mmol) in tetrahydrofuran (8 mL), dimethylforamide (2 mL) and pyridine (3 drops) under nitrogen atmosphere. The mixture was heated at 80° C. for 15 hours. The reaction was cooled, poured into 1 N sodium hydroxide solution (100 mL) and extracted with ethyl acetate (200 mL). The organic layer was discarded and the basic aqueous layer was acidified with 6 N hydrochloric acid (18 mL) followed by extraction into ethyl acetate. The organic layer was washed with brine, dried over anhydrous sodium sulfate and concentrated. The residue was recrystallized from methanol/ethyl acetate/hexane to give 390 mg (27%) of benzene sulfonyl-carbamic acid 2-(2-oxo-2,3-dihydro-1H-indol-4-yl)-ethyl ester as an off-white powder.

¹HNMR (360 MHz, DMSO-d₆) δ 12.03 (s, br, 1H, NH), 10.30 (s, br, 1H, NH), 7.83 (d, J=7.2 Hz, 2H, Ar—H), 7.68–7.72 (m, 1H, Ar—H), 7.58–7.62 (m, 2H, Ar—H), 7.05 (t, J=7.7 Hz, 1H), 6.71 (d, J=7.7 Hz, 1H), 6.64 (d, J=7.7 Hz, 1H), 4.17 (t, J=6.3 Hz, 2H, OCH₂CH₂), 3.42 (s, 2H, H-3), 2.71 (t, J=6.3 Hz, 2H, OCH₂CH₂).

MS 360 [M]⁺.

Compound IN-015

Biphenyl-2-yl-carbamic acid 2-(2-oxo-2,3-dihydro-1H-indol-4-yl)-ethyl ester

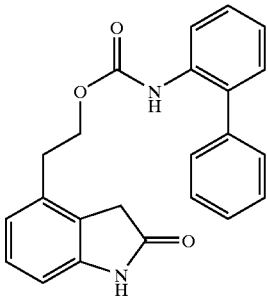

2-Biphenylyl isocyanate (1.15 mL, 6.7 mmol) was added dropwise to a stirred mixture of 4-(2-hydroxy-ethyl)-1,3-dihydro-indol-2-one (709 mg, 4 mmol) in tetrahydrofuran (8 mL), dimethylforamide (2 mL) and pyridine (3 drops) under nitrogen atmosphere. The mixture was heated at 80° C. for 15 hours. The reaction was cooled, quenched with 1 N sodium hydroxide solution (100 mL) and extracted with ethyl acetate (200 mL). The organic layer was washed with brine, dried over anhydrous sodium sulfate and concentrated. The residue was chromatographed on silica gel eluting with ethyl acetate:hexane 3:2 to give 1.188 g (80%) of biphenyl-2-yl-carbamic acid 2-(2-oxo-2,3-dihydro-1H-indol-4-yl)-ethyl ester as a white fluffy solid.

$^1$HNMR (360 MHz, DMSO-$d_6$) δ 10.28 (s, br, 1H, NH), 8.57 (s, 1H, NH), 7.25–7.41 (m, 9H, Ar—H), 7.08 (t, J=7.6 Hz, 1H, Ar—H), 6.73 (d, J=7.6 Hz, 1H, Ar—H), 6.66 (d, J=7.6 Hz, 1H, Ar—H), 4.09 (t, J=6.4 Hz, 2H, OC$\underline{H}_2$CH$_2$), 3.35 (s, 2H, CH$_2$, H-3), 2.69 (t, J=6.4 Hz, 2H, OCH$_2$C$\underline{H}_2$).

MS-EI 372 [M]$^+$.

Compound IN-016

Ethyl-carbamic acid 2-(2-oxo-2,3-dihydro-1H-indol-4-yl)-ethyl ester

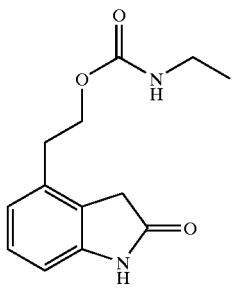

Ethyl isocyanate (0.633 mL, 8 mmol) was added dropwise to a stirred mixture of 4-(2-hydroxy-ethyl)-1,3-dihydro-indol-2-one (709 mg, 4 mmol) in tetrahydrofuran (8 mL) and dimethylforamide (2 mL) under nitrogen atmosphere. The mixture was heated at 80° C. for 48 hours. The reaction was cooled, poured into water (100 mL) and extracted with ethyl acetate (200 mL). The organic layer was washed with brine, dried over anhydrous sodium sulfate and concentrated. The residue was chromatographed on silica gel eluting with ethyl acetate/hexane to give 158 mg (16%) of ethyl-carbamic acid 2-(2-oxo-2,3-dihydro-1H-indol-4-yl)-ethyl ester as a white powder.

$^1$HNMR (360 MHz, DMSO-$d_6$) δ 10.28 (s, br, 1H, NH), 7.08 (t, J=7.7 Hz, 1H, Ar—H), 7.03 (m, br, 1H, NH), 6.78 (d, J=7.7 Hz, 1H, Ar—H), 6.64 (d, J=7.7 Hz, 1H, Ar—H), 4.10 (t, J=6.5 Hz, 2H, OC$\underline{H}_2$CH$_2$), 3.43 (s, 2H, H-3), 2.91–2.99 (m, 2H, C$\underline{H}_2$CH$_3$), 2.74 (t, J=6.5 Hz, 2H, OCH$_2$C$\underline{H}_2$), 0.96 (t, J=7.3 Hz, 3H, CH$_2$CH$_3$).

MS-EI 248 [M]$^+$.

Compound IN-017

4-[2-(4-Methoxy-phenoxy)-ethyl]-1,3-dihydro-indol-2-one

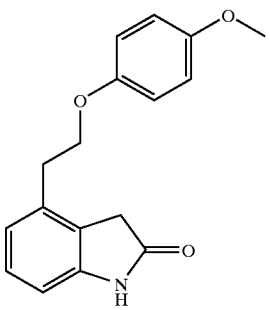

Diethyl azodicarboxylate (0.47 mL, 3 mmol) was added to a solution of triphenylphosphine (0.786 g, 3 mmol) in tetrahydrofuran (10 mL) under nitrogen atmosphere. The mixture was stirred for 15 minutes. To it was then added 4-(2-hydroxy-ethyl)-1,3-dihydro-indol-2-one (0.53 g, 3 mmol) followed by 4-methoxyphenol (0.372 g, 3 mmol). The mixture was stirred at room temperature for 18 hours and the solvent was evaporated. The residue was dissolved in ethyl acetate (150 mL) and the organic solvent was washed with 2 N hydrochloric acid (3×30 mL), saturated sodium bicarbonate solution and brine. The residue was chromatographed on silica gel eluting with ethyl acetate: hexane 2:8 to give 0.14 g (16%) 4-[2-(4-Methoxy-phenoxy)-ethyl]-1,3-dihydro-indol-2-one.

$^1$HNMR (300 MHz, DMSO-$d_6$) δ 10.33 (s, br, 1H, NH), 7.10 (t, J=7.8 Hz, 1H, Ar—H), 6.83–6,87 (m, 5H, Ar—H), 6.67 (d, J=7.5 Hz, 1H, Ar—H), 4.10 (t, J=6.9 Hz, 2H, OC$\underline{H}_2$CH$_2$), 3.67 (s, 3H, OCH$_3$), 3.49 (s, 2H, CH$_2$, H-3), 2.91 (t, J=6.9 Hz, 2H, OCH$_2$C$\underline{H}_2$).

Compound IN-018

4-(2-Methoxy-ethyl)-1,3-dihydro-indol-2-one

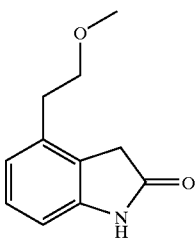

Methyl iodide (1.41 g, 10 mmol) was added to a stirred mixture of silver trifluoromethanesulfonate (2.56 g, 10 mmol) and 4-(2-hydroxy-ethyl)-1,3-dihydro-indol-2-one (0.88 g, 5 mmol) in dichloromethane (20 mL) at 0° C. The precipitate formed after 5–10 minutes changed color from yellow to gray then dark purple. The mixture was stirred at room temperature for 2 hours. The reaction mixture was diluted with dichloromethane and filtered through celite. The filtrate was concentrated and chromatographed on silica gel to give 4-(2-methoxy-ethyl)-1,3-dihydro-indol-2-one.

$^1$HNMR (360 MHz, DMSO-$d_6$) δ 10.27 (s, br, 1H, NH), 7.07 (t, J=7.6 Hz, 1H, Ar—H), 6.78 (d, J=7.6 Hz, 1H, Ar—H), 6.65 (d, J=7.6 Hz, 1H, Ar—H), 3.51 (t, J=6.7 Hz, 2H, OC$\underline{H}_2$CH$_2$), 3.42 (s, 2H, H-3, CH$_2$), 3.22 (s, 3H, OCH$_3$), 2.71 (t, J=6.7 Hz, 2H, OCH$_2$C$\underline{H}_2$). MS-EI 191 [M]$^+$.

93

Compound IN-019

4-(2-Ethoxy-ethyl)-1,3-dihydro-indol-2-one

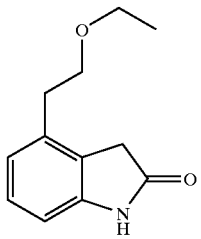

Ethyl iodide (o.47 mL, 6 mmol) was added to a stirred mixture of silver trifluoromethanesulfonate (1.35 g, 5.2 mmol) 2,6-di-tert-butylpyridine (1 g, 5.2 mmol) and 4-(2-hydroxy-ethyl)-1,3-dihydro-indol-2-one (0.53 g, 3 mmol) in dichloromethane (10 mL) at 0° C. The mixture was warmed to room temperature and stirred for 2 hours. The precipitate formed after 5–10 minutes changed color from yellow to brown. The reaction mixture was diluted with dichloromethane (100 mL) and washed with 1 N hydrochloric acid, saturated sodium bicarbonate and brine, dried and concentrated. The residue was chromatographed on silica gel to give 180 mg (29%) of 4-(2-ethoxy-ethyl)-1,3-dihydro-indol-2-one as a purple oil.

$^1$HNMR (360 MHz, DMSO-$d_6$) δ 10.27 (s, br, 1H, NH), 7.07 (t, J=7.8 Hz, 1H, Ar—H), 6.78 (d, J=7.8 Hz, 1H, Ar—H), 6.65 (d, J=7.8 Hz, 1H, Ar—H), 3.54 (t, J=6.9 Hz, 2H, OC$\underline{H}_2$CH$_2$), 3.38–3.45 (m, 2H, OC$\underline{H}_2$CH$_3$), 3.43 (s, 2H, H-3, CH$_2$), 2.71 (t, J=6.9 Hz, 2H, OCH$_2$C$\underline{H}_2$), 1.07 (t, J=7.0 Hz, 3H, OCH$_2$C$\underline{H}_3$).

MS 206.2 [M+]$^+$.

Compound IN-020

4-[2-(4-Isopropyl-phenoxy)-ethyl]-1,3-dihydro-indol-2-one

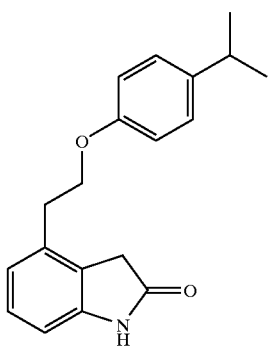

Diethyl azodicarboxylate (1.58 mL, 10 mmol) was added to a solution of triphenylphosphine (2.62 g, 10 mmol) in tetrahydrofuran (20 mL) under nitrogen atmosphere. The mixture was stirred for 15 minutes. To it was then added 4-(2-hydroxy-ethyl)-1,3-dihydro-indol-2-one (1.77 g, 10 mmol) followed by 4-isopropylphenol (1.36 g, 10 mmol). The mixture was stirred at room temperature for one day and the solvent was evaporated. The residue was chromatographed on silica gel eluting with ethyl acetate:hexane 2:8 to give 1.1 g (37%) of 4-[2-(4-isopropyl-phenoxy)-ethyl]-1,3-dihydro-indol-2-one as a light yellow solid.

94

$^1$HNMR (360 MHz, DMSO-$d_6$) δ 10.30 (s, br, 1H, NH), 7.11 (d, J=7.2 Hz, 2H), 7.1 (t, J=7.6 Hz, 1H, Ar—H), 6.87 (d, J=7.6 Hz, 1H), 6.82 (d, J=7.2 Hz, 2H, Ar—H), 6.68 (d, J=7.6 Hz, 1H, Ar—H), 4.14 (t, J=6.8 Hz, 2H, CH$_2$C$\underline{H}_2$O), 3.49 (s, 2H, H-3, CH$_2$), 2.93 (t, J=6.8 Hz, 2H, C$\underline{H}_2$CH$_2$O), 2.81 (m, 1H, C$\underline{H}$(CH$_3$)$_2$), 1.15 (d, J=6.5 Hz, 6H, CH(C$\underline{H}_3$)$_2$).

MS-EI 295 [M]$^+$.

Compound IN-021

4-[2-(5-Chloro-pyridin-3-yloxy)-ethyl]1,3-dihydro-indol-2-one

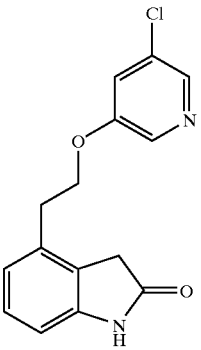

Diethyl azodicarboxylate (1.74 g, 10 mmol) was added to a solution of triphenylphosphine (2.62 g, 10 mmol) in tetrahydrofuran (20 mL) under nitrogen atmosphere. The mixture was stirred for 15 minutes. To it was then added 4-(2-hydroxy-ethyl)-1,3-dihydro-indol-2-one (1.77 g, 10 mmol) followed by 5-chloro-3-pyridinol (1.29 g, 10 mmol). The mixture was stirred at room temperature for 2 days. The precipitate was collected by vacuum filtration, washed with ethyl acetate and dried to give 1.05 g (36%) of 4-[2-(5-chloro-pyridin-3-yloxy)-ethyl]-1,3-dihydro-indol-2-one as a light brown solid.

$^1$HNMR (360 MHz, DMSO-$d_6$) δ 10.31 (s, br, 1H, NH), 8.23 (d, J=2.3 Hz, 1H, Ar—H), 8.17 (d, J=2.3 Hz, 1H, Ar—H), 7.58 (t, J=2.3 Hz, 1H, Ar—H), 7.11 (t, J=7.9 Hz, 1H, Ar—H), 6.87 (d, J=7.9 Hz, 1H, Ar—H), 6.68 (d, J=7.9 Hz, 1H, Ar—H), 4.30 (t, J=6.9 Hz, 2H, CH$_2$C$\underline{H}_2$O), 3.51 (s, 2H, CH$_2$, H-3), 2.97 (t, J=6.9 Hz, 2H, C$\underline{H}_2$CH$_2$O).

MS-EI 288 [M]$^+$.

Compound IN-022

4-(2-Hydroxy-ethyl)-3-(3-hydroxy-6-methyl-pyridin-2-ylmethylene)-1,3-dihydro-indol-2-one

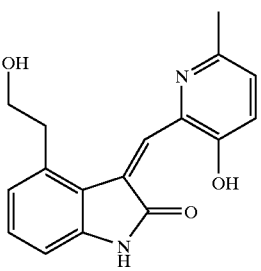

A mixture of 4-(2-hydroxy-ethyl)-1,3-dihydro-indol-2-one (51 mg, 0.3 mmol), 3-hydroxy-6-methyl-pyridine-2-carbaldehyde (45 mg, 0.33 mmol) and 1 drop of pyrrolidine in 2.0 mL of ethanol was heated at 90° C. for 4 hours and cooled to room temperature. The precipitate was filtered, washed with cold ethanol and hexane, and dried in a vacuum oven overnight to give mixture of isomers of 4-(2-hydroxy-ethyl)-3-(3-hydroxy-6-methyl-pyridin-2-ylmethylene)-1,3-dihydro-indol-2-one.

MS-EI 296 [M]+.

Compound IN-023

3-[4-3-Dimethylamino-propyl)-3,5-dimethyl-1H-pyrrol-2-ylmethylene]-4-[2-(3-isopropyl-phenoxy)-ethyl]-1,3-dihydro-indol-2-one

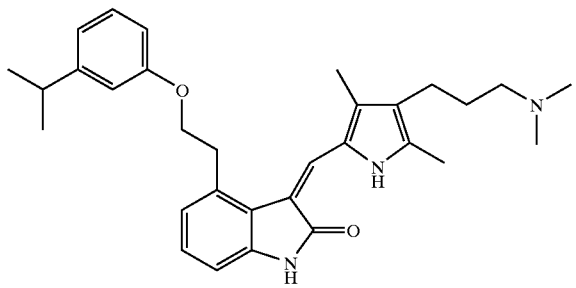

A mixture of 4-[2-(3-isopropyl-phenoxy)-ethyl]-1,3-dihydro-indol-2-one (28 mg, 0.095 mmol), 4-(3-dimethylamino-propyl)-3,5-dimethyl-1H-pyrrole-2-carbaldehyde (20 mg, 0.095 mmol) and 1 drop of pyrrolidine in 1.0 mL of ethanol was heated at 90° C. for 4 hours and cooled to room temperature. The precipitate was filtered, washed with cold ethanol and hexane, and dried in a vacuum oven overnight to give 40 mg (87%) of 3-[4-(3-dimethylamino-propyl)-3,5-dimethyl-1H-pyrrol-2-ylmethylene]-4-[2-(3-isopropyl-phenoxy)-ethyl]-1,3-dihydro-indol-2-one.

¹HNMR (360 MHz, DMSO-d₆) δ 13.44 (s, 1H, NH), 10.77 (s, 1H, CONH), 7.59 (s, 1H, H-vinyl), 7.16 (t, J=7.2 Hz, 1H), 7.04 (t, J=7.5 Hz, 1H), 6.89 (d, J=7.5 Hz, 1H, H-5), 6.79 (d, J=7.1 Hz, 1H), 6.77 (d, J=7.2 Hz, 1H), 6.75 (s, 1H), 6.72 (d, J=7.5 Hz, 1H), 4.23 (t, J=6.8 Hz, 2H), 3.39 (t, J=7.4 Hz, 2H), 2.80 (m, 1H, CH(CH₃)₂), 2.34 (t, J=7.4 Hz, 2H), 2.27 (s, 3H, CH₃-pyrrole), 2.13 (t, J=7.4 Hz, 2H), 2.08 (s, 6H, (CH₃)₂NCH₂CH₂CH₂), 2.04 (s, 3H, CH₃-pyrrole), 1.47 (quint., J=57.4 Hz, 2H, (CH₃)₂NCH₂CH₂CH₂), 1.13 (d, J=7.2 Hz, 6H, CH(CH₃)₂). MS-EI 485 [M]+.

Compound IN-024

3-(5-{4-[2-(4-Isopropyl-phenoxy)-ethyl]-2-oxo-1,2-dihydro-indol-3-ylidenemethyl}-2,4-dimethyl-1H-pyrro-3-yl)-propionic acid

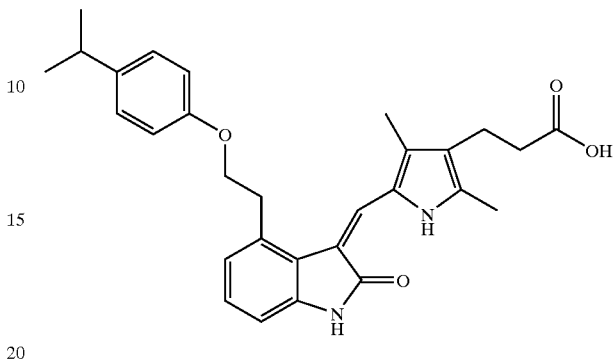

2-Benzyloxycarbonyl-3,5-dimethyl-4-(2-methoxycarbonylethyl)pyrrole (Aldrich, 2.0 g) was hydrogenated over 0.2 g of 10% palladium on carbon in 40 mL of methanol for 2 hours at room temperature. The catalyst was removed by filtration and washed with 40 mL of methanol. The filtrate was evaporated to dryness and dried overnight in a vacuum oven to give 1.3 g (92% yield) of 2-carboxy-3,5-dimethyl-4-(2-methoxycarbonylethyl)pyrrole.

2-Carboxy-3,5-dimethyl-4-(2-methoxycarbonylethyl)pyrrole (1.3 g) was ground with 0.5 g of anhydrous sodium acetate and then heated at 100° C. for 3 days. The mixture was dissolved in water, extract with ethyl acetate and chromatographed on a column of silica gel in ethyl acetate-:hexane 1:3 to give 0.4 g (38% yield) of 2,4-dimethyl-3-(2-methoxycarbonylethyl)pyrrole as a thick pale yellow oil.

2,4-Dimethyl-3-(2-methoxycarbonylethyl)pyrrole (0.35 g) and 0.5 g of the Vilsmeier reagent (Aldrich) in 10 mL of dichloroethane were stirred at room temperature under nitrogen for 2 hours. The reaction mixture was concentrated and treated with 10 mL of 6 M sodium hydroxide solution and then extracted three times with 10 mL of ethyl acetate. The ethyl acetate extracts were combined, dried over anhydrous sodium sulfate and evaporated to dryness to give 0.24 g (60% yield) of 2,4-dimethyl-5-formyl-3-(2-methoxycarbonylethyl)pyrrole as a brown oil.

2,4-Dimethyl-5-formyl-3-(2-methoxycarbonylethyl)pyrrole (0.23 g, 1.2 mmol) in 6N sodium hydroxide (10 mL) was heated at 100° C. for 2 hours. The reaction mixture was cooled to room temperature, acidified with 6 N hydrochloric acid and extracted three times with 10 mL of ethyl acetate. The combined organic layers were washed with 10 mL of water and 5 mL of brine, dried over anhydrous sodium sulfate and evaporated to dryness to give 230 mg (106% yield) of crude 4-carboxyethyl-3,5-dimethyl-2-formylpyrrole as a brown oil.

A mixture of 4-[2-(4-isopropyl-phenoxy)-ethyl]-1,3-dihydro-indol-2-one (118 mg, 0.4 mmol), 4-carboxyethyl-3,5-dimethyl-2-formylpyrrole (78 mg, 0.4 mmol) and piperidine (0.3 mL) in 1.0 mL of ethanol was heated in a sealed tube at 90° C. for 18 hours and cooled to room temperature. The reaction mixture was concentrated and the residue was dissolved in methylene chloride followed by the addition of diethyl ether. The precipitate was filtered and washed with ethyl acetate to give 110 mg (58%) of 3-(5-{4-[2-(4-isopropyl-phenoxy)-ethyl]-2-oxo-1,2-dihydro-indol-3-ylidenemethyl}-2,4-dimethyl-1H-pyrrol-3-yl)-propionic acid (piperidine salt).

$^1$HNMR (300 MHz, DMSO-d$_6$) δ 13.42 (s, 1H, NH), 10.82 (s, br, 1H, NH), 7.55 (s, 1H, H-vinyl), 7.09 (d, J=8.7 Hz, 2H), 7.02 (t, J=7.5 Hz, 1H), 6.87 (d, J=7.5 Hz, 1H), 6.83 (d, J=8.7 Hz, 2H), 6.79 (d, J=7.5 Hz, 1H), 4.21 (t, J=7.4 Hz, 2H, CH$_2$CH$_2$O), 3.37 (t, J=6.7 Hz, 2H, CH$_2$), 2.72–2.82 (m, 1H, CH̲(CH$_3$)$_2$), 2.56 (t, J=6.7 Hz, 2H, CH$_2$), 2.26 (s, 3H, CH$_3$), 2.14 (t, J=7.4 Hz, 2H, CH$_2$CH$_2$O), 2.04 (s, 3H, CH$_3$), 1.13 (d,J=7 Hz, 6H, CH(CH̲$_3$)$_2$).

MS-EI 472 [M]$^+$.

Compound IN-025

Isopropyl-carbamic acid 2-(2-oxo-2,3-dihydro-1H-indol-4-yl)-ethyl ester

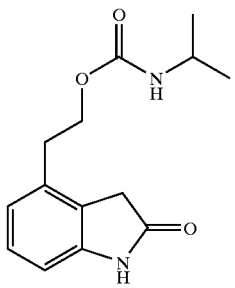

A mixture of 4-(2-hydroxy-ethyl)-1,3-dihydro-indol-2-one (3 g, 16.93 mmol) and isopropyl isocyanate (2.49 mL, 25.40 mmol) in tetrahydrofuran (16 mL) and dimethylformamide (6 mL) was heated at 80° C. for 64 hours. The reaction mixture was poured into water and extracted with ethyl acetate (400 mL), washed with brine, dried (sodium sulfate), and concentrated. The residue was recrystallized form methanol, ethyl acetate and hexanes to give 1.136 g (26%) of isopropyl-carbamic acid 2-(2-oxo-2,3-dihydro-1H-indol-4-yl)-ethyl ester as crystalline solid.

Assay Procedures

The following in vitro assays may be used to determine the level of activity and effect of the different compounds of the present invention on one or more of the PKs. Similar assays can be designed along the same lines for any PK using techniques well known in the art.

The cellular/catalytic assays described herein are performed in an ELISA format. The general procedure is a follows: a compound is introduced to cells expressing the test kinase, either naturally or recombinantly, for some period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The cellular/biologic assays described herein measure the amount of DNA made in response to activation of a test kinase, which is a general measure of a proliferative response. The general procedure for this assay is as follows: a compound is introduced to cells expressing the test kinase, either naturally or recombinantly, for some period of time after which, if the test kinase is a receptor, a ligand known to activate the receptor is added. After incubation at least overnight, a DNA labeling reagent such as Bromodeoxyuridine (BrdU) or 3H-thymidine is added. The amount of labeled DNA is detected with either an anti-BrdU antibody or by measuring radioactivity and is compared to control cells not contacted with a test compound.

Cellular/Catalytic Assays

Enzyme linked immunosorbent assays (ELISA) may be used to detect and measure the presence of PK activity. The ELISA may be conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. Of Microbiology, Washington, D.C.

The disclosed protocol may be adapted for determining activity with respect to a specific PK. For example, the preferred protocols for conducting the ELISA experiments for specific PKs is provided below. Adaptation of these protocols for determining a compound's activity for other members of the RTK family, as well as for CTKs and STKs, is well within the scope of knowledge of those skilled in the art.

Example 2

FLK-1

An ELISA assay was conducted to measure the kinase activity of the FLK-1 receptor and more specifically, the inhibition or activation of TK activity on the FLK-1 receptor. Specifically, the following assay was conducted to measure kinase activity of the FLK-1 receptor in cells genetically engineered to express Flk-1.

MATERIALS AND METHODS

Materials

The following reagents and supplies were used:
a. Corning 96-well ELISA plates (Corning Catalog No. 25805-96);
b. Cappel goat anti-rabbit IgG (catalog no. 55641);
c. PBS (Gibco Catalog No. 450-1300EB);
d. TBSW Buffer (50 mM Tris (pH 7.2), 150 mM NaCl and 0.1% Tween-20);
e. Ethanolamine stock (10% ethanolamine (pH 7.0), stored at 4° C.);
f. HNTG buffer (20 mM HEPES buffer (pH 7.5), 150 mM NaCl, 0.2% Triton X-100, and 10% glycerol);
g EDTA (0.5 M (pH 7.0) as a 100× stock);
h. Sodium orthovanadate (0.5 M as a 100× stock);
i. Sodium pyrophosphate (0.2 M as a 100× stock);
j. NUNC 96 well V bottom polypropylene plates (Applied Scientific Catalog No. AS-72092);
k. NIH3T3 C7#3 Cells (FLK-1 expressing cells);
l. DMEM with 1× high glucose L-Glutamine (catalog No. 11965-050);
m. FBS, Gibco (catalog no. 16000-028);
n. L-glutamine, Gibco (catalog no. 25030-016);
o. VEGF, PeproTech, Inc. (catalog no. 100-20)(kept as 1 µg/100 µL stock in Milli-Q dH$_2$O and stored at −20° C.;

p. Affinity purified anti-FLK-1 antiserum;

q. UB40 monoclonal antibody specific for phosphotyrosine (see, Fendley, et al., 1990, *Cancer Research* 50:1550–1558);

r. EIA grade Goat anti-mouse IgG-POD (BioRad catalog no. 172-1011);

s. 2,2-azino-bis(3-ethylbenz-thiazoline-6-sulfonic acid (ABTS) solution (100 mM citric acid (anhydrous), 250 mM $Na_2HPO_4$ (pH 4.0), 0.5 mg/mL ABTS (Sigma catalog no. A-1888)), solution should be stored in dark at 4° C. until ready for use;

t. $H_2O_2$ (30% solution) (Fisher catalog no. H325);

u. $ABTS/H_2O_2$ (15 mL ABTS solution, 2 μL $H_2O_2$) prepared 5 minutes before use and left at room temperature;

v. 0.2 M HCl stock in $H_2O$;

w. dimethylsulfoxide (100%) (Sigma Catalog No. D-8418); and y. Trypsin-EDTA (Gibco BRL Catalog No. 25200-049).

Protocol

The following protocol was used for conducting the assay:

1. Coat Corning 96-well ELISA plates with 1.0 μg per well Cappel Anti-rabbit IgG antibody in 0.1 M $Na_2CO_3$ pH 9.6. Bring final volume to 150 μL per well. Coat plates overnight at 4° C. Plates can be kept up to two weeks when stored at 4° C.

2. Grow cells in Growth media (DMEM, supplemented with 2.0 mM L-Glutamine, 10% FBS) in suitable culture dishes until confluent at 37° C., 5% $CO_2$.

3. Harvest cells by trypsinization and seed in Corning 25850 polystyrene 96-well round bottom cell plates, 25.000 cells/well in 200 μL of growth media.

4. Grow cells at least one day at 37° C., 5% $CO_2$.

5. Wash cells with D-PBS 1×.

6. Add 200 μL/well of starvation media (DMEM, 2.0 mM 1-Glutamine, 0.1% FBS). Incubate overnight at 37° C., 5% $CO_2$.

7. Dilute Compounds 1:20 in polypropylene 96 well plates using starvation media. Dilute dimethylsulfoxide 1:20 for use in control wells.

8. Remove starvation media from 96 well cell culture plates and add 162 μL of fresh starvation media to each well.

9. Add 18 μL of 1:20 diluted Compound dilution (from step 7) to each well plus the 1:20 dimethylsulfoxide dilution to the control wells (+/−VEGF), for a final dilution of 1:200 after cell stimulation. Final dimethylsulfoxide is 0.5%. Incubate the plate at 37° C., 5% $CO_2$ for two hours.

10. Remove unbound antibody from ELISA plates by inverting plate to remove liquid. Wash 3 times with TBSW+0.5% ethanolamine, pH 7.0. Pat the plate on a paper towel to remove excess liquid and bubbles.

11. Block plates with TBSW+0.5% Ethanolamine, pH 7.0, 150 μL per well. Incubate plate thirty minutes while shaking on a microtiter plate shaker.

12. Wash plate 3 times as described in step 10.

13. Add 0.5 μg/well affinity purified anti-FLU-1 polyclonal rabbit antiserum. Bring final volume to 150 μL/well with TBSW+0.5% ethanolamine pH 7.0. Incubate plate for thirty minutes while shaking.

14. Add 180 μL starvation medium to the cells and stimulate cells with 20 μL/well 10.0 mM sodium ortho vanadate and 500 ng/mL VEGF (resulting in a final concentration of 1.0 mM sodium ortho vanadate and 50 ng/mL VEGF per well) for eight minutes at 37° C., 5% $CO_2$. Negative control wells receive only starvation medium.

15. After eight minutes, media should be removed from the cells and washed one time with 200 μL/well PBS.

16. Lyse cells in 150 μL/well HNTG while shaking at room temperature for five minutes. HNTG formulation includes sodium ortho vanadate, sodium pyrophosphate and EDTA.

17. Wash ELISA plate three times as described in step 10.

18. Transfer cell lysates from the cell plate to ELISA plate and incubate while shaking for two hours. To transfer cell lysate pipette up and down while scrapping the wells.

19. Wash plate three times as described in step 10.

20. Incubate ELISA plate with 0.02 μg/well UB40 in TBSW+05% ethanolamine. Bring final volume to 150 μL/well. Incubate while shaking for 30 minutes.

21. Wash plate three times as described in step 10.

22. Incubate ELISA plate with 1:10,000 diluted EIA grade goat anti-mouse IgG conjugated horseradish peroxidase in TBSW+0.5% ethanolamine, pH 7.0. Bring final volume to 150 μL/well. Incubate while shaking for thirty minutes.

23. Wash plate as described in step 10.

24. Add 100 μL of $ABTS/H_2O_2$ solution to well. Incubate ten minutes while shaking.

25. Add 100 μL of 0.2 M HCl for 0.1 M HCl final to stop the color development reaction. Shake 1 minute at room temperature. Remove bubbles with slow stream of air and read the ELISA plate in an ELISA plate reader at 410 nm.

Example 3

HER-2 ELISA

Assay 1: EGF Receptor-HER2 Chimeric Receptor Assay In Whole Cells.

HER2 kinase activity in whole EGFR-NIH3T3 cells was measured as described below:

Materials and Reagents

The following materials and reagents were used to conduct the assay:

a. EGF: stock concentration: 16.5 ILM; EGF 201, TOYOBO, Co., Ltd. Japan.

b. 05-101 (UBI) (a monoclonal antibody recognizing an EGFR extracellular domain).

c. Anti-phosphotyrosine antibody (anti-Ptyr) (polyclonal) (see, Fendley, et al., supra).

d. Detection antibody: Goat anti-rabbit IgG horse radish peroxidase conjugate, TAGO, Inc., Burlingame, Calif.

e. TBST buffer:

|  |  |
|---|---|
| Tris-HCl, pH 7.2 | 50 mM |
| NaCl | 150 mM |
| Triton X-100 | 0.1 | f. HNTG 5× stock:

|  |  |
|---|---|
| HEPES | 0.1 M |
| NaCl | 0.75 M |
| Glycerol | 50% |
| Triton X-100 | 1.0% | g. ABTS stock:

|  |  |
|---|---|
| Citric Acid | 100 mM |
| $Na_2HPO_4$ | 250 mM |
| HCl, conc. | 0.5 pM |
| ABTS* | 0.5 mg/mL |

(2,2'-azinobis(3-ethylbenzthiazolinesulfonic acid)). Keep solution in dark at 4° C. until use.

h. Stock reagents of:
EDTA 100 mM pH 7.0
$Na_3VO_4$ 0.5 M
$Na_4(P_2O_7)$ 0.2 M

Procedure

The following protocol was used:
A. Pre-coat ELISA Plate
 1. Coat ELISA plates (Corning, 96 well, Cat. #25805-96) with 05-101 antibody at 0.5 g per well in PBS, 100 μL final volume/well, and store overnight at 4° C. Coated plates are good for up to 10 days when stored at 4° C.
 2. On day of use, remove coating buffer and replace with 100 μL blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.
B. Seeding Cells
 1. An NIH3T3 cell line overexpressing a chimeric receptor containing the EGFR extracellular domain and intracellular HER2 kinase domain can be used for this assay.
 2. Choose dishes having 80–90% confluence for the experiment. Trypsinize cells and stop reaction by adding 10% fetal bovine serum. Suspend cells in DMEM medium (10% CS DMEM medium) and centrifuge once at 1500 rpm, at room temperature for 5 minutes.
 3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 μL per well, in a 96 well microtiter plate. Incubate seeded cells in 5% $CO_2$ at 37° C. for about 40 hours.
C. Assay Procedures
 1. Check seeded cells for contamination using an inverted microscope. Dilute drug stock (10 mg/mL in DMSO) 1:10 in DMEM medium, then transfer 5 μL to a TBST well for a final drug dilution of 1:200 and a final DMSO concentration of 1%. Control wells receive DMSO alone. Incubate in 5% $CO_2$ at 37° C. for two hours.
 2. Prepare EGF ligand: dilute stock EGF in DMEM so that upon transfer of 10 μL dilute EGF (1:12 dilution), 100 nM final concentration is attained.
 3. Prepare fresh HNTG* sufficient for 100 μL per well; and place on ice.

| HNTG* (10 ml): | |
|---|---|
| HNTG stock | 2.0 mL |
| milli-Q $H_2O$ | 7.3 mL |
| EDTA, 100 mM, pH 7.0 | 0.5 mL |
| $Na_3VO_4$, 0.5 M | 0.1 mL |
| $Na_4(P_2O_7)$, 0.2 M | 0.1 mL |

4. After 120 minutes incubation with drug, add prepared SGF ligand to cells, 10 μL per well, to a final concentration of 100 nM. Control wells receive DMEM alone. Incubate, shaking, at room temperature, for 5 minutes.
 5. Remove drug, EGF, and DMEM. Wash cells twice with PBS. Transfer HNTG* to cells, 100 μL per well. Place on ice for 5 minutes. Meanwhile, remove blocking buffer from other ELISA plate and wash with TBST as described above.
 6. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.
 7. Remove lysate and wash 4 times with TBST. Transfer freshly diluted anti-Ptyr antibody to ELISA plate at 100 μL per well. Incubate shaking at room temperature for 30 minutes in the presence of the anti-Ptyr antiserum (1:3000 dilution in TBST).
 8. Remove the anti-Ptyr antibody and wash 4 times with TBST. Transfer the freshly diluted TAGO anti-rabbit IgG antibody to the ELISA plate at 100 μL per well. Incubate shaking at room temperature for 30 minutes (anti-rabbit IgG antibody: 1:3000 dilution in TBST).
 9. Remove TAGO detection antibody and wash 4 times with TBST. Transfer freshly prepared ABTS/$H_2O_2$ solution to ELISA plate, 100 μL per well. Incubate shaking at room temperature for 20 minutes. (ABTS/$H_2O_2$ solution: 1.0 μL 30% $H_2O_2$ in 10 mL ABTS stock).
 10. Stop reaction by adding 50 μL 5N $H_2SO_4$ (optional), and determine O.D. at 410 nm.
 11. The maximal phosphotyrosine signal is determined by subtracting the value of the negative controls from the positive controls. The percent inhibition of phosphotyrosine content for extract-containing wells is then calculated, after subtraction of the negative controls.

Example 4

PDGF-R ELISA

All cell culture media, glutamine, and fetal bovine serum were purchased from Gibco Life Technologies (Grand Island, N.Y.) unless otherwise specified. All cells were grown in a humid atmosphere of 90–95% air and 5–10% $CO_2$ at 37° C. All cell lines were routinely subcultured twice a week and were negative for mycoplasma as determined by the Mycotect method (Gibco).

For ELISA assays, cells (U1242, obtained from Joseph Schlessinger, NYU) were grown to 80–90% confluency in growth medium (MEM with 10% FBS, NEAA, 1 mM NaPyr and 2 mM GLN) and seeded in 96-well tissue culture plates in 0.5% serum at 25,000 to 30,000 cells per well. After overnight incubation in 0.5% serum-containing medium, cells were changed to serum-free medium and treated with test compound for 2 hr in a 5% $CO_2$, 37° C. incubator. Cells were then stimulated with ligand for 5–10 minute followed by lysis with HNTG (20 mM Hepes, 150 mM NaCl, 10% glycerol, 5 mM EDTA, 5 mM $Na_3VO_4$, 0.2% Triton X-100, and 2 mM NaPyr). Cell lysates (0.5 mg/well in PBS) were transferred to ELISA plates previously coated with receptor-specific antibody and which had been blocked with 5% milk in TBST (50 mM Tris-HCl pH 7.2, 150 mM NaCl and 0.1% Triton X-100) at room temperature for 30 min. Lysates were incubated with shaking for 1 hour at room temperature. The plates were washed with TBST four times and then incubated with polyclonal anti-phosphotyrosine antibody at room temperature for 30 minutes. Excess anti-phosphotyrosine antibody was removed by rinsing the plate with TBST four times. Goat anti-rabbit IgG antibody was added to the ELISA plate for 30 min at room temperature followed by rinsing with TBST four more times. ABTS (100 mM citric acid, 250 mM $Na_2HPO_4$ and 0.5 mg/mL 2,2'-azino-bis(3-ethylbenzthiazoline-6-sulfonic acid)) plus $H_2O_2$ (1.2 mL 30% $H_2O_2$ to 10 mL ABTS) was added to the ELISA plates to start color development. Absorbance at 410 nm with a reference wavelength of 630 nm was recorded about 15 to 30 min after ABTS addition.

Example 5

IGF-1 Receptor ELISA

The following protocol may be used to measure phosphotyrosine level on IGF-I receptor, which indicates IGF-I receptor tyrosine kinase activity.

Materials and Reagents

The following materials and reagents were used:

a. The cell line used in this assay is 3T3/IGF-1R, a cell line genetically engineered to overexpresses IGF-1 receptor.
b. NIH3T3/IGF-1R is grown in an incubator with 5% $CO_2$ at 37° C. The growth media is DMEM+10% FBS (heat inactivated)+2 mM L-glutamine.
c. Affinity purified anti-IGF-1R antibody 17-69.
d. D-PBS:

| | |
|---|---|
| $KH_2PO_4$ | 0.20 g/L |
| $K_2HPO_4$ | 2.16 g/L |
| KCl | 0.20 g/L |
| NaCl | 8.00 g/L (pH 7.2) | e. Blocking Buffer: TBST plus 5% Milk (Carnation Instant Non-Fat Dry Milk).
f. TBST buffer:

| | |
|---|---|
| Tris-HCl | 50 mM |
| NaCl | 150 mM (pH 7.2/HCl 10 N) |
| Triton X-100 | 0.1% |

Stock solution of TBS (10×) is prepared, and Triton X-100 is added to the buffer during dilution.
HNTG buffer:

| | |
|---|---|
| HEPES | 20 mM |
| NaCl | 150 mM (pH 7.2/HCl 1N) |
| Glycerol | 10% |
| Triton X-100 | 0.2% |

Stock solution (5×) is prepared and kept at 4° C.
h. EDTA/HCl: 0.5 M pH 7.0 (NaOH) as 100× stock.
i. $Na_3VO_4$: 0.5 M as 100× stock and aliquots are kept in −80° C.
j. $Na_4P_2O_7$: 0.2 M as 100× stock.
k. Insulin-like growth factor-1 from Promega (Cat# G5111).
l. Rabbit polyclonal anti-phosphotyrosine antiserum.
m. Goat anti-rabbit IgG, POD conjugate (detection antibody), Tago (Cat. No. 4520, Lot No. 1802): Tago, Inc., Burlingame, Calif.
n. ABTS (2,2'-azinobis(3-ethylbenzthiazolinesulfonic acid)) solution:

| | |
|---|---|
| Citric acid | 100 mM |
| $Na_2HPO_4$ | 250 mM (pH 4.0/1N HCl) |
| ABTS | 0.5 mg/mL |

ABTS solution should be kept in dark and 4° C. The solution should be discarded when turns green.
o. Hydrogen Peroxide: 30% solution is kept in the dark and at 4° C.

Procedure

All the following steps are conducted at room temperature unless it is specifically indicated. All ELISA plate washings are performed by rinsing the plate with tap water three times, followed by one TBST rinse. Pat plate dry with paper towels.
A. Cell Seeding:
  1. The cells, grown in tissue culture dish (Corning 25020-100) to 80–90% confluence, are harvested with Trypsin-EDTA (0.25%, 0.5 mL/D-100, GIBCO).
  2. Resuspend the cells in fresh DMEM+10% FBS+2 mM L-Glutamine, and transfer to 96-well tissue culture plate (Corning, 25806-96) at 20,000 cells/well (100 µL/well). Incubate for 1 day then replace medium to serum-free medium (90/µL) and incubate in 5% $CO_2$ and 37° C. overnight.
B. ELISA Plate Coating and Blocking:
  1. Coat the ELISA plate (Corning 25805-96) with Anti-IGF-1R Antibody at 0.5 µg/well in 100 µL PBS at least 2 hours.
  2. Remove the coating solution, and replace with 100 µL Blocking Buffer, and shake for 30 minutes. Remove the blocking buffer and wash the plate just before adding lysate.

C. Assay Procedures:

1. The drugs are tested in serum-free condition.
2. Dilute drug stock (in 100% DMSO) 1:10 with DMEM in 96-well poly-propylene plate, and transfer 10 µL/well of this solution to the cells to achieve final drug dilution 1:100, and final DMSO concentration of 1.0%. Incubate the cells in 5% $CO_2$ at 37° C. for 2 hours.
3. Prepare fresh cell lysis buffer (HNTG*)

|  |  |
|---|---|
| HNTG | 2 mL |
| EDTA | 0.1 mL |
| $Na_3VO_4$ | 0.1 mL |
| $Na_4(P_2O_7)$ | 0.1 mL |
| $H_2O$ | 7.3 mL |

4. After drug incubation for two hours, transfer 10 µL/well of 200 nM IGF-1 Ligand in PBS to the cells (Final Conc.=20 nM), and incubate at 5% $CO_2$ at 37° C. for 10 minutes.
5. Remove media and add 100 µL/well HNTG* and shake for 10 minutes. Look at cells under microscope to see if they are adequately lysed.
6. Use a 12-channel pipette to scrape the cells from the plate, and homogenize the lysate by repeated aspiration and dispensing. Transfer all the lysate to the antibody coated ELISA plate, and shake for 1 hour.
7. Remove the lysate, wash the plate, transfer anti-pTyr (1:3,000 with TBST) 100 µL/well, and shake for 30 minutes.
8. Remove anti-pTyr, wash the plate, transfer TAGO (1:3,000 with TBST) 100 µL/well, and shake for 30 minutes.
9. Remove detection antibody, wash the plate, and transfer fresh ABTS/$H_2O_2$ (1.2 µL $H_2O_2$ to 10 mL ABTS) 100 µL/well to the plate to start color development.
10. Measure OD at 410 nm with a reference wavelength of 630 nm in Dynatec MR5000.

Example 6

EGF Receptor ELISA

EGF Receptor kinase activity in cells genetically engineered to express human EGF-R was measured as described below:

Materials and Reagents

The following materials and reagents were used:

a. EGF Ligand: stock concentration=16.5 µM; EGF 201, TOYOBO, Co., Ltd. Japan.
b. 05-101 (UBI) (a monoclonal antibody recognizing an EGFR extracellular domain).
c. Anti-phosphotyosine antibody (anti-Ptyr) (polyclonal).
d. Detection antibody: Goat anti-rabbit IgG horse radish peroxidase conjugate, TAGO, Inc., Burlingame, Calif.
e. TBST buffer:

|  |  |
|---|---|
| Tris-HCl, pH 7 | 50 mM |
| NaCl | 150 mM |
| Triton X-100 | 0.1 | f. HNTG 5× stock:

|  |  |
|---|---|
| HEPES | 0.1 M |
| NaCl | 0.75 M |
| Glycerol | 50 |
| Triton X-100 | 1.0% | g. ABTS stock:

|  |  |
|---|---|
| Citric Acid | 100 mM |
| $Na_2HPO_4$ | 250 mM |
| HCl, conc. | 4.0 pH |
| ABTS* | 0.5 mg/mL |

Keep solution in dark at 4° C. until used.
h. Stock reagents of:
EDTA 100 mM pH 7.0
$Na_3VO_4$ 0.5 M
$Na_4(P_2O_7)$ 0.2 M Procedure The following protocol was used:
A. Pre-coat ELISA Plate
1. Coat ELISA plates (Corning, 96 well, Cat. #25805-96) with 05-101 antibody at 0.5 µg per well in PBS, 150 µL final volume/well, and store overnight at 4° C. Coated plates are good for up to 10 days when stored at 4° C.
2. On day of use, remove coating buffer and replace with blocking buffer (5% Carnation Instant NonFat Dry Milk in PBS). Incubate the plate, shaking, at room temperature (about 23° C. to 25° C.) for 30 minutes. Just prior to use, remove blocking buffer and wash plate 4 times with TBST buffer.
B. Seeding Cells
1. NIH 3T3/C7 cell line (Honegger, et al., Cell 51:199–209, 1987) can be use for this assay.
2. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm at room temperature for 5 minutes.
3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 µL per well, in a 96 well microtiter plate. Incubate seeded cells in 5% $CO_2$ at 37° C. for about 40 hours.
C. Assay Procedures.
1. Check seeded cells for contamination using an inverted microscope. Dilute drug stock (10 mg/mL in DMSO) 1:10 in DMEM medium, then transfer 5 µL to a test well for a final drug dilution of 1:200 and a final DMSO concentration of 1%. Control wells receive DMSO alone. Incubate in 5% $CO_2$ at 37° C. for one hour.
2. Prepare EGF ligand: dilute stock EGF in DMEM so that upon transfer of 10 µL dilute EGF (1:12 dilution), 25 nM final concentration is attained.

3. Prepare fresh 10 mL HNTG* sufficient for 100 μL per well wherein HNTG* comprises: HNTG stock (2.0 mL), milli-Q H$_2$O (7.3 mL), EDTA, 100 mM, pH 7.0 (0.5 mL), Na$_3$VO$_4$ 0.5 M (0.1 mL) and Na$_4$(P$_2$O$_7$), 0.2 M (0.1 mL).
4. Place on ice.
5. After two hours incubation with drug, add prepared EGF ligand to cells, 10 μL per well, to yield a final concentration of 25 nM. Control wells receive DMEM alone. Incubate, shaking, at room temperature, for 5 minutes.
6. Remove drug, EGF, and DMEM. Wash cells twice with PBS. Transfer HNTG* to cells, 100 μL per well. Place on ice for 5 minutes. Meanwhile, remove blocking buffer from other ELISA plate and wash with TBST as described above.
7. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.
8. Remove lysate and wash 4 times with TBST. Transfer freshly diluted anti-Ptyr antibody to ELISA plate at 100 μL per well. Incubate shaking at room temperature for 30 minutes in the presence of the anti-Ptyr antiserum (1:3000 dilution in TBST).
9. Remove the anti-Ptyr antibody and wash 4 times with TBST. Transfer the freshly diluted TAGO 30 anti-rabbit IgG antibody to the ELISA plate at 100 μL per well. Incubate shaking at room temperature for 30 minutes (anti-rabbit IgG antibody: 1:3000 dilution in TBST).
10. Remove detection antibody and wash 4 times with TBST. Transfer freshly prepared ABTS/H$_2$O$_2$ solution to ELISA plate, 100 μL per well. Incubate at room temperature for 20 minutes. ABTS/H$_2$O$_2$ solution: 1.2 μL 30% H$_2$O$_2$ in 10 mL ABTS stock.
11. Stop reaction by adding 50 μL 5N H$_2$SO$_4$ (optional), and determine O.D. at 410 nm.
12. The maximal phosphotyrosine signal is determined by subtracting the value of the negative controls from the positive controls. The percent inhibition of phosphotyrosine content for extract-containing wells is then calculated, after subtraction of the negative controls.

Example 7

Met Autophosphorylation Assay—ELISA

This assay determines Met tyrosine kinase activity by analyzing Met protein tyrosine kinase levels on the Met receptor.

Materials and Reagents

The following materials and reagents were used:
a. HNTG (5× stock solution): Dissolve 23.83 g HEPES and 43.83 g NaCl in about 350 mL dH$_2$O. Adjust pH to 7.2 with HCl or NaOH, add 500 mL glycerol and 10 mL Triton X-100, mix, add dH$_2$O to 1 L total volume. To make 1 L of 1× working solution add 200 mL 5× stock solution to 800 mL dH$_2$O, check and adjust pH as necessary, store at 4° C.
b. PBS (Dulbecco's Phosphate-Buffered Saline), Gibco Cat. #450-1300EB (1× solution).
c. Blocking Buffer: in 500 mL dH$_2$O place 100 g BSA, 12.1 g Tris-pH7.5, 58.44 g NaCl and 10 mL Tween-20, dilute to 1 L total volume.
d. Kinase Buffer: To 500 mL dH$_2$O add 12.1 g TRIS pH7.2, 58.4 g NaCl, 40.7 g MgCl$_2$ and 1.9 g EGTA; bring to 1 L total volume with dH$_2$O.
e. PMSF (Phenylmethylsulfonyl fluoride), Sigma Cat. #P-7626, to 435.5 mg, add 100% ethanol to 25 mL total volume, vortex.
f. ATP (Bacterial Source), Sigma Cat. #A-7699, store powder at −20° C.; to make up solution for use, dissolve 3.31 mg in 1 mL dH$_2$O.
g. RC-20H HRPO Conjugated Anti-Phosphotyrosine, Transduction Laboratories Cat. #E120H.
h. Pierce 1-Step (TM) Turbo TMB-ELISA (3,3',5,5'-tetramethylbenzidine, Pierce Cat. #34022.
i. H$_2$SO$_4$, add 1 mL conc. (18 N) to 35 mL dH$_2$O.
j. TRIS HCL, Fischer Cat. #BP152-5; to 121.14 g of material, add 600 mL MilliQ H$_2$O, adjust pH to 7.5 (or 7.2) with HCl, bring volume to 1 L with MilliQ H$_2$O.
k. NaCl, Fischer Cat. #S27-10, make up 5 M solution.
l. Tween-20, Fischer Cat. #S337-500.
m. Na$_3$VO$_4$, Fischer Cat. #S454-50, to 1.8 g material add 80 mL MilliQ H$_2$O, adjust pH to 10.0 with HCl or NaOH, boil in microwave, cool, check pH, repeat procedure until pH stable at 10.0, add MilliQ H$_2$O to 100 mL total volume, make 1 mL aliquots and store at −80° C.
n. MgCl$_2$, Fischer Cat. #M33-500, make up 1 M solution.
o. HEPES, Fischer Cat. #BP310-500, to 200 mL MilliQ H$_2$O, add 59.6 g material, adjust pH to 7.5, bring volume to 250 mL total, sterile filter.
p. Albumin, Bovine (BSA), Sigma Cat. #A-4503, to 30 grams material add sterile distilled water to make total volume of 300 mL, store at 4° C.
q. TBST Buffer: to approx. 900 mL dH$_2$O in a 1 L graduated cylinder add 6.057 g TRIS and 8.766 g NaCl, when dissolved, adjust pH to 7.2 with HCl, add 1.0 mL Triton X-100 and bring to 1 L total volume with dH$_2$O.
r. Goat Affinity purified antibody Rabbit IgG (whole molecule), Cappel Cat. #55641.
s. Anti h-Met (C-28) rabbit polyclonal IgG antibody, Santa Cruz Chemical Cat. #SC-161.
t. Transiently Transfected EGFR/Met chimeric cells (EMR) (Komada, et al., *Oncogene*, 8:2381–2390 (1993).
u. Sodium Carbonate Buffer, (Na$_2$CO$_4$, Fischer Cat. #S495): to 10.6 g material add 800 mL MilliQ H$_2$O, when dissolved adjust pH to 9.6 with NaOH, bring up to 1 L total volume with MilliQ H$_2$O, filter, store at 4° C.

Procedure

All of the following steps are conducted at room temperature unless it is specifically indicated otherwise. All ELISA plate washing is by rinsing 4× with TBST.

A. EMR Lysis

This procedure can be performed the night before or immediately prior to the start of receptor capture.
1. Quick thaw lysates in a 37° C. waterbath with a swirling motion until the last crystals disappear.
2. Lyse cell pellet with 1×HNTG containing 1 mM PMSF. Use 3 mL of HNTG per 15 cm dish of cells. Add ½ the calculated HNTG volume, vortex the tube for 1 min., add the remaining amount of HNTG, vortex for another min.

3. Balance tubes, centrifuge at 10,000×g for 10 min at 4° C.
4. Pool supernatants, remove an aliquot for protein determination.
5. Quick freeze pooled sample in dry ice/ethanol bath. This step is performed regardless of whether lysate will be stored overnight or used immediately following protein determination.
6. Perform protein determination using standard bicinchoninic acid (BCA) method (BCA Assay Reagent Kit from Pierce Chemical Cat. #23225).

B. ELISA Procedure

1. Coat Corning 96 well ELISA plates with 5 μg per well Goat anti-Rabbit antibody in Carbonate Buffer for a total well volume of 50 μL. Store overnight at 4° C.
2. Remove unbound Goat anti-rabbit antibody by inverting plate to remove liquid.
3. Add 150 μL of Blocking Buffer to each well. Incubate for 30 min. at room temperature with shaking.
4. Wash 4× with TBST. Pat plate on a paper towel to remove excess liquid and bubbles.
5. Add 1 μg per well of Rabbit anti-Met antibody diluted in TBST for a total well volume of 100 μL.
6. Dilute lysate in HNTG (90 μg lysate/100 μL)
7. Add 100 μL of diluted lysate to each well. Shake at room temperature for 60 min.
8. Wash 4× with TBST. Pat on paper towel to remove excess liquid and bubbles.
9. Add 50 μL of 1×lysate buffer per well.
10. Dilute compounds/extracts 1:10 in 1× Kinase Buffer in a polypropylene 96 well plate.
11. Transfer 5.5 μL of diluted drug to ELISA plate wells. Incubate at room temperature with shaking for 20 min.
12. Add 5.5 μL of 60 μM ATP solution per well. Negative controls do not receive any ATP. Incubate at room temperature for 90 min., with shaking.
13. Wash 4× with TBST. Pat plate on paper towel to remove excess liquid and bubbles.
14. Add 100 μL per well of RC20 (1:3000 dilution in Blocking Buffer). Incubate 30 min. at room temperature with shaking.
15. Wash 4× with TBST. Pat plate on paper towel to remove excess liquid and bubbles.
16. Add 100 μL per well of Turbo-TMB. Incubate with shaking for 30–60 min.
17. Add 100 μL per well of 1 M $H_2SO_4$ to stop reaction.
18. Read assay on Dynatech MR7000 ELISA reader. Test Filter=450 nm, reference filter=410 nm.

Example 8

Biochemical src Assay—ELISA

This assay is used to determine src protein kinase activity measuring phosphorylation of a biotinylated peptide as the readout.

Materials and Reagents

The following materials and reagents were used:
a. Yeast transformed with src.
b. Cell lysates: Yeast cells expressing src are pelleted, washed once with water, re-pelleted and stored at −80° C. until use.
c. N-terminus biotinylated EEEYEEYEEEYEEEYEEEY is prepared by standard procedures well known to those skilled in the art.
d. DMSO: Sigma, St. Louis, Mo.
e. 96 Well ELISA Plate: Corning 96 Well Easy Wash, Modified flat Bottom Plate, Corning Cat. #25805-96.
f. NUNC 96-well V-bottom polypropylene plates for dilution of compounds: Applied Scientific Cat. #A-72092.
g. Vecastain ELITE ABC reagent: Vector, Burlingame, Calif.
h. Anti-src (327) mab: Schizosaccharomyces Pombe was used to express recombinant Src (Superti-Furga, et al., *EMBO J.*, 12:2625–2634; Superti-Furga, et a., *Nature Biochem.*, 14:600–605). S. Pombe strain SP200 (h-s leu1.32 ura4 ade210) was grown as described and transformations were pRSP expression plasmids were done by the lithium acetate method (Superti-Furga, supra). Cells were grown in the presence of 1 μM thiamine to repress expression from the nmtl promoter or in the absence of thiamine to induce expression.
i. Monoclonal anti-phosphotyrosine, UBI 05-321 (UB40 may be used instead).
j. Turbo TMB-ELISA peroxidase substrate: Pierce Chemical.

Buffer Solutions a. PBS (Dulbecco's Phosphate-Buffered Saline): GIBCO PBS, GIBCO Cat. #450-1300EB.
b. Blocking Buffer: 5% Non-fat milk (Carnation) in PBS.
c. Carbonate Buffer: $Na_2CO_4$ from Fischer, Cat. #S495, make up 100 mM stock solution.
d. Kinase Buffer: 1.0 mL (from 1 M stock solution) $MgCl_2$; 0.2 mL (from a 1 M stock solution) $MnCl_2$; 0.2 mL (from a 1 M stock solution) DTT; 5.0 mL (from a 1 M stock solution) HEPES; 0.1 mL TX-100; bring to 10 mL total volume with MilliQ $H_2O$.
e. Lysis Buffer: 5.0 HEPES (from 1 M stock solution.); 2.74 mL NaCl (from 5 M stock solution); 10 mL glycerol; 1.0 mL TX-100; 0.4 mL EDTA (from a 100 mM stock solution); 1.0 mL PMSF (from a 100 mM stock solution); 0.1 mL $Na_3VO_4$ (from a 0.1 M stock solution); bring to 100 mL total volume with MilliQ $H_2O$.
f. ATP: Sigma Cat. #A-7699, make up 10 mM stock solution (5.51 mg/mL).
g. TRIS-HCl: Fischer Cat. #BP 152-5, to 600 mL MilliQ $H_2O$ add 121.14 g material, adjust pH to 7.5 with HCl, bring to 1 L total volume with MilliQ $H_2O$.
h. NaCl: Fischer Cat. #S271-10, Make up 5 M stock solution with MilliQ $H_2O$.
i. $Na_3VO_4$: Fischer Cat. #S454-50; to 80 mL MilliQ $H_2O$, add 1.8 g material; adjust pH to 10.0 with HCl or NaOH; boil in a microwave; cool; check pH, repeat pH adjustment until pH remains stable after heating/cooling cycle; bring to 100 mL total volume with MilliQ $H_2O$; make 1 mL aliquots and store at −80° C.
j. $MgCl_2$: Fischer Cat. #M33-500, make up 1 M stock solution with MilliQ $H_2O$.
k. HEPES: Fischer Cat. #BP 310-500; to 200 mL MilliQ $H_2O$, add 59.6 g material, adjust pH to 7.5, bring to 250 mL total volume with MilliQ $H_2O$, sterile filter (1 M stock solution).

l. TBST Buffer: TBST Buffer: To 900 mL dH$_2$O add 6.057 g TRIS and 8.766 g NaCl; adjust pH to 7.2 with HCl, add 1.0 mL Triton-X100; bring to 1 L total volume with dH$_2$O.

m. MnCl$_2$: Fischer Cat. #M87-100, make up 1 M stock solution with MilliQ H$_2$O.

n. DTT; Fischer Cat. #BP172-5.

o. TBS (TRIS Buffered Saline): to 900 mL MilliQ H$_2$O add 6.057 g TRIS and 8.777 g NaCl; bring to 1 L total volume with MilliQ H$_2$O.

p. Kinase Reaction Mixture: Amount per assay plate (100 wells): 1.0 mL Kinase Buffer, 200 μg GST-ζ, bring to final volume of 8.0 mL with MilliQ H$_2$O.

q. Biotin labeled EEEYEEYEEEYEEEYEEEY: Make peptide stock solution (1 mM, 2.98 mg/ml) in water fresh just before use.

r. Vectastain ELITE ABC reagent: To prepare 14 mL of working reagent, add 1 drop of reagent A to 15 mL TBST and invert tube several times to mix. Then add 1 drop of reagent B. Put tube on orbital shaker at room temperature and mix for 30 minutes.

Procedures a. Preparation of src coated ELISA plate.
  1. Coat ELISA plate with 0.5 μg/well anti-src mab in 100 μL of pH 9.6 sodium carbonate buffer at 4° C. overnight.
  2. Wash wells once with PBS.
  3. Block plate with 0.15 mL 5% milk in PBS for 30 min. at room temperature.
  4. Wash plate 5× with PBS.
  5. Add 10 μg/well of src transformed yeast lysates diluted in Lysis Buffer (0.1 mL total volume per well). (Amount of lysate may vary between batches.) Shake plate for 20 minutes at room temperature.

b. Preparation of Phosphotyrosine Antibody-coated ELISA Plate.
  1. 4G10 plate: coat 0.5 μg/well 4G10 in 100 μL PBS overnight at 4° C. and block with 150 μL of 5% milk in PBS for 30 minutes at room temperature.

c. Kinase Assay Procedure.
  1. Remove unbound proteins from step 1–7, above, and wash plates 5× with PBS.
  2. Add 0.08 mL Kinase Reaction Mixture per well (containing 10 μL of 10× Kinase Buffer and 10 μM (final concentration) biotin-EEEYEEYEEEYEEEYEEEY per well diluted in water.
  3. Add 10 μL of compound diluted in water containing 10% DMSO and pre-incubate for 15 minutes at room temperature.
  4. Start kinase reaction by adding 10 μL/well of 0.05 mM ATP in water (5 μM ATP final).
  5. Shake ELISA plate for 15 min. at room temperature.
  6. Stop kinase reaction by adding 10 μL of 0.5 M EDTA per well.
  7. Transfer 90 μL supernatant to a blocked 4G10 coated ELISA plate from section B, above.
  8. Incubate for 30 min. while shaking at room temperature.
  9. Wash plate 5× with TBST.
  10. Incubate with Vectastain ELITE ABC reagent (100 μL/well) for 30 min. at room temperature.
  11. Wash the wells 5× with TBST.
  12. Develop with Turbo TMB.

Example 9

Biochemical lck Assay—ELISA

This assay is used to determine lck protein kinase activities measuring phosphorylation of GST-ζ as the readout.

Materials and Reagents

The following materials and reagents were used:

a. Yeast transformed with lck. Schizosaccharomyces Pombe was used to express recombinant Lck (Superti-Furga, et al., *EMBO J*, 12:2625–2634; Superti-Furga, et al., *Nature Biotech.*, 14:600–605). S. Pombe strain SP200 (h-s leul.32 ura4 ade210) was grown as described and transformations with pRSP expression plasmids were done by the lithium acetate method (Superti-Furga, supra). Cells were grown in the presence of 1 μM thiamine to induce expression.

b. Cell lysates: Yeast cells expressing lck are pelleted, washed once in water, repelleted and stored frozen at −80° C. until use.

c. GST-ζ: DNA encoding for GST-ζ fusion protein for expression in bacteria obtained from Arthur Weiss of the Howard Hughes Medical Institute at the University of California, San Francisco. Transformed bacteria were grown overnight while shaking at 25° C. GST-ζ was purified by glutathione affinity chromatography, Pharmacia, Alameda, Calif.

d. DMSO: Sigma, St. Louis, Mo.

e. 96-Well ELISA plate: Corning 96 Well Easy Wash, Modified Flat Bottom Plate, Corning Cat. #25805-96.

f. NUNC 96-well V-bottom polypropylene plates for dilution of compounds: Applied Scientific Cat. #AS-72092.

g. Purified Rabbit anti-GST antiserum: Amrad Corporation (Australia) Cat. #90001605.

h. Goat anti-Rabbit-IgG-HRP: Amersham Cat. #V0103011. Sheep ant-mouse IgG (H+L): Jackson Labs Cat. #5215-005-003.

j. Anti-Lck (3A5) mab: Santa Cruz Biotechnology Cat #sc-433.

k. Monoclonal anti-phosphotyrosine UBI 05–321 (UB40 may be used instead).

Buffer Solutions a. PBS (Dulbecco's Phosphate-Buffered Saline) 1× solution: GIBCO PBS, GIBCO Cat. #450-1300EB.

b. Blocking Buffer: 100 g. BSA, 12.1 g. TRIS-pH7.5, 58.44 g NaCl, 10 mL Tween-20, bring up to 1 L total volume with MilliQ H$_2$O.

c. Carbonate Buffer: Na$_2$CO$_4$ from Fischer, Cat. #S495; make up 100 mM solution with MilliQ H$_2$O.

d. Kinase Buffer: 1.0 mL (from 1 M stock solution) MgCl$_2$; 0.2 mL (from a 1 M stock solution) MnCl$_2$; 0.2 mL (from a 1 M stock solution) DTT; 5.0 mL (from a 1 M stock solution) HEPES; 0.1 mL TX-100; bring to 10 mL total volume with MilliQ H$_2$O.

e. Lysis Buffer: 5.0 HEPES (from 1 M stock solution.); 2.74 mL NaCl (from 5 M stock solution); 10 mL glycerol; 1.0 mL TX-100; 0.4 mL EDTA (from a 100 mM stock solution); 1.0 mL PMSF (from a 100 mM stock solution); 0.1 mL Na$_3$VO$_4$ (from a 0.1 M stock solution); bring to 100 mL total volume with MilliQ H$_2$O.
f. ATP: Sigma Cat. #A-7699, make up 10 mM stock solution (5.51 mg/mL).
g TRIS-HCl: Fischer Cat. #BP 152-5, to 600 mL MilliQ H$_2$O add 121.14 g material, adjust pH to 7.5 with HCl, bring to 1 L total volume with MilliQ H$_2$O.
h. NaCl: Fischer Cat. #S271-10, Make up 5 M stock solution with MilliQ H$_2$O.
i. Na$_3$VO$_4$: Fischer Cat. #S454-50; to 80 mL MilliQ H$_2$O, add 1.8 g material; adjust pH to 10.0 with HCl or NaOH; boil in a microwave; cool; check pH, repeat pH adjustment until pH remains stable after heating/cooling cycle; bring to 100 mL total volume with MilliQ H$_2$O; make 1 mL aliquots and store at −80° C.
j. MgCl$_2$: Fischer Cat. #M33-500, make up 1 M stock solution with MilliQ H$_2$O.
k. HEPES: Fischer Cat. #BP 310-500; to 200 mL MilliQ H$_2$O, add 59.6 g material, adjust pH to 7.5, bring to 250 mL total volume with MilliQ H$_2$O, sterile filter (1 M stock solution).
l. Albumin, Bovine (BSA), Sigma Cat. #A4503; to 150 mL MilliQ H$_2$O add 30 g material, bring 300 mL total volume with MilliQ H$_2$O, filter through 0.22 μm filter, store at 4° C.
m. TBST Buffer: To 900 mL dH$_2$O add 6.057 g TRIS and 8.766 g NaCl; adjust pH to 7.2 with HCl, add 1.0 mL Triton-X100; bring to 1 L total volume with dH$_2$O.
n. MnCl$_2$: Fischer Cat. #M87-100, make up 1 M stock solution with MilliQ H$_2$O.
o. DTT; Fischer Cat. #BP172-5.
p. TBS (TRIS Buffered Saline): to 900 mL MilliQ H$_2$O add 6.057 g TRIS and 8.777 g NaCl; bring to 1 L total volume with MilliQ H$_2$O.
q Kinase Reaction Mixture: Amount per assay plate (100 wells): 1.0 mL Kinase Buffer, 200 μg GST-ζ, bring to final volume of 8.0 mL with MilliQ H$_2$O.

Procedures a. Preparation of Lck coated ELISA plate.
  1. Coat 2.0 μg/well Sheep anti-mouse IgG in 100 μL of pH 9.6 sodium carbonate buffer at 4° C. overnight.
  2. Wash well once with PBS.
  3. Block plate with 0.15 mL of blocking Buffer for 30 min. at room temp.
  4. Wash plate 5× with PBS.
  5. Add 0.5 μg/well of anti-lck (mab 3A5) in 0.1 mL PBS at room temperature for 1–2 hours.
  6. Wash plate 5× with PBS.
  7. Add 20 μg/well of lck transformed yeast lysates diluted in Lysis Buffer (0.1 mL total volume per well). (Amount of lysate may vary between batches) Shake plate at 4° C. overnight to prevent loss of activity.
b. Preparation of Phosphotyrosine Antibody-coated ELISA Plate.
  1. UB40 plate: 1.0 μg/well UB40 in 100 L of PBS overnight at 4° C. and block with 150 μL of Blocking Buffer for at least 1 hour.
c. Kinase Assay Procedure.
  1. Remove unbound proteins from step 1–7, above, and wash plates 5× with PBS.
  2. Add 0.08 mL Kinase Reaction Mixture per well (containing 10 μL of 10× Kinase Buffer and 2 μg GST-ζ per well diluted with water).
  3. Add 10 μL of compound diluted in water containing 10% DMSO and pre-incubate for 15 minutes at room temperature.
  4. Start kinase reaction by adding 10 μL/well of 0.1 mM ATP in water (10 μM ATP final).
  5. Shake ELISA plate for 60 min. at room temperature.
  6. Stop kinase reaction by adding 10 μL of 0.5 M EDTA per well.
  7. Transfer 90 μL supernatant to a blocked 4G10 coated ELISA plate from section B, above.
  8. Incubate while shaking for 30 min. at room temperature.
  9. Wash plate 5× with TBST.
  10. Incubate with Rabbit anti-GST antibody at 1:5000 dilution in 100 μL TBST for 30 min. at room temperature.
  11. Wash the wells 5× with TBST.
  12. Incubate with Goat anti-Rabbit-IgG-HRP at 1:20,000 dilution in 100 μL of TBST for 30 min. at room temperature.
  13. Wash the wells 5× with TBST.
  14. Develop with Turbo TMB.

Example 10

Assay Measuring Phosphorylating Function of RAF

The following assay reports the amount of RAF-catalyzed phosphorylation of its target protein MEK as well as MEK's target MAPK. The RAF gene sequence is described in Bonner et al., 1985, *Molec. Cell. Biol.* 5: 1400–1407, and is readily accessible in multiple gene sequence data banks. Construction of the nucleic acid vector and cell lines utilized for this portion of the invention are fully described in Morrison et al., 1988, *Proc. Natl. Acad. Sci.* USA 85: 8855–8859.

Materials and Reagents

1. Sf9 (*Spodoptera frugiperda*) cells; GIBCO-BRL, Gaithersburg, Md.
2. RIPA buffer: 20 mM Tris/HCl pH 7.4, 137 mM NaCl, 10% glycerol, 1 mM PMSF, 5 mg/L Aprotenin, 0.5% Triton X-100;
3. Thioredoxin-MEK fusion protein (T-MEK): T-MEK expression and purification by affinity chromatography were performed according to the manufacturer's procedures.
Catalog#K 350-01 and R 350-40, Invitrogen Corp., San Diego, Calif.
4. His-MAPK (ERK 2); His-tagged MAPK was expressed in XL1 Blue cells transformed with pUC18 vector encoding His-MAPK. His-MAPK was purified by Ni-affinity chromatography. Cat#27-4949-01, Pharmacia, Alameda, Calif., as described herein.
5. Sheep anti mouse IgG: Jackson laboratories, West Grove, Pa. Catalog, #515-006-008, Lot#28563
6. RAF-1 protein kinase specific antibody: URP2653 from UBI.
7. Coating buffer: PBS; phosphate buffered saline, GIBCO-BRL, Gaithersburg, Md.
8. Wash buffer: TBST-50 mM Tris/HCL pH 7.2, 150 mM NaCl, 0.1% Triton X-100
9. Block buffer: TBST, 0.1% ethanolamine pH 7.4

10. DMSO, Sigma, St. Louis, Mo.
11. Kinase buffer (KB): 20 mM HEPES/HCl pH 7.2, 150 mM NaCl, 0.1% Triton X-100, 1 mM PMSF, 5 mg/L Aprotenin, 75 mM sodium ortho vanadate, 0.5 MM DTT and 10 mM $MgCl_2$.
12. ATP mix: 100 mM $MgCl_2$, 300 mM ATP, 10 mCi $^{33}P$ ATP (Dupont-NEN)/mL.
13. Stop solution: 1% phosphoric acid; Fisher, Pittsburgh, Pa.
14. Wallac Cellulose Phosphate Filter mats; Wallac, Turku, Finnland.
15. Filter wash solution: 1% phosphoric acid, Fisher, Pittsburgh, Pa.
16. Tomtec plate harvester, Wallac, Turku, Finnland.
17. Wallac beta plate reader #1205, Wallac, Turku, Finnland.
18. NUNC 96-well V bottom polypropylene plates for compounds Applied Scientific Catalog #AS-72092.

Procedure

All of the following steps were conducted at room temperature unless specifically indicated.

1. ELISA plate coating: ELISA wells are coated with 100 mL of Sheep anti mouse affinity purified antiserum (1 mg/100 mL coating buffer) over night at 4° C. ELISA plates can be used for two weeks when stored at 4° C.
2. Invert the plate and remove liquid. Add 100 mL of blocking solution and incubate for 30 min.
3. Remove blocking solution and wash four times with wash buffer. Pat the plate on a paper towel to remove excess liquid.
4. Add 1 mg of antibody specific for RAF-1 to each well and incubate for 1 hour. Wash as described in step 3.
5. Thaw lysates from RAS/RAF infected Sf9 cells and dilute with TBST to 10 mg/100 mL. Add 10 mg of diluted lysate to the wells and incubate for 1 hour. Shake the plate during incubation. Negative controls receive no lysate. Lysates from RAS/RAF infected Sf9 insect cells are prepared after cells are infected with recombinant baculoviruses at a MOI of 5 for each virus, and harvested 48 hours later. The cells are washed once with PBS and lysed in RIPA buffer. Insoluble material is removed by centrifugation (5 min at 10 000×g). Aliquots of lysates are frozen in dry ice/ethanol and stored at −80° C. until use.
6. Remove non-bound material and wash as outlined above (step 3).
7. Add 2 mg of T-MEK and 2 mg of His-MAEPK per well and adjust the volume to 40 mL with kinase buffer. Methods for purifying T-MEK and MAPK from cell extracts are provided herein by example.
8. Pre-dilute compounds (stock solution 10 mg/mL DMSO) or extracts 20 fold in TBST plus 1% DMSO. Add 5 mL of the pre-diluted compounds/extracts to the wells described in step 6. Incubate for 20 min. Controls receive no drug.
9. Start the kinase reaction by addition of 5 mL ATPmix; Shake the plates on an ELISA plate shaker during incubation.
10. Stop the kinase reaction after 60 min by addition of 30 mL stop solution to each well.
11. Place the phosphocellulose mat and the ELISA plate in the Tomtec plate harvester. Harvest and wash the filter with the filter wash solution according to the manufacturers recommendation. Dry the filter mats. Seal the filter mats and place them in the holder. Insert the holder into radioactive detection apparatus and quantify the radioactive phosphorous on the filter mats.

Alternatively, 40 mL aliquots from individual wells of the assay plate can be transferred to the corresponding positions on the phosphocellulose filter mat. After air drying the filters, put the filters in a tray. Gently rock the tray, changing the wash solution at 15 min intervals for 1 hour. Air-dry the filter mats. Seal the filter mats and place them in a holder suitable for measuring the radioactive phosphorous in the samples. Insert the holder into a detection device and quantify the radioactive phosphorous on the filter mats.

Example 11

CDK2/Cyclin A—Inhibition Assay

This assay analyzes the protein kinase activity of CDK2 in exogenous substrate.

Materials and Reagents

A. Buffer A (80 mM Tris (pH 7.2), 40 mM $MgCl_2$): 4.84 G. Tris (F.W.=121.1 g/mol), 4.07 g. $MgCl_2$ (F.W.=203.31 g/mol) dissolved in 500 mL $H_2O$. Adjust pH to 7.2 with HCl.
B. Histone H1 solution (0.45 mg/mL Histone H1 and 20 mM HEPES pH 7.2 (pH 7.4 is OK): 5 mg Histone H1 (Boehinger Mannheim) in 11.111 mL 20 mM HEPES pH 7.2 (477 mg HEPES (F.W.=238.3 g/mol) dissolved in 100 mL $ddH_2O$, stored in 1 mL aliquots at −80° C.
C. ATP solution (60 μM ATP, 300 g/mL BSA, 3 mM DTT): 120 μL 10 mM ATP, 600 μL 10 mg/mL BSA to 20 mL, stored in 1 mL aliquots at −80° C.
D. CDK2 solution: cdk2/cyclin A in 10 mM HEPES pH 7.2, 25 mM NaCl, 0.5 mM DTT, 10% glycerol, stored in 9 μL aliquots at −80° C.

Description of Assay

1. Prepare solutions of inhibitors at three times the desired final assay concentration in $ddH_2O$/15% DMSO by volume.
2. Dispense 20 μL of inhibitors to wells of polypropylene 96-well plates (or 20 μL 15% DMSO for positive and negative controls).
3. Thaw Histone H1 solution (1 mL/plate), ATP solution (1 mL/plate plus 1 aliquot for negative control), and CDK2 solution (9 μL/plate). Keep CDK2 on ice until use. Aliquot CDK2 solution appropriately to avoid repeated freeze-thaw cycles.
4. Dilute 9 μL CDK2 solution into 2.1 mL Buffer A (per plate). Mix. Dispense 20 μL into each well.
5. Mix 1 mL Histone H1 solution with 1 mL ATP solution (per plate) into a 10 mL screw cap tube. Add $\gamma^{33}P$ ATP to a concentration of 0.15 μCi/20 μL (0.15 μCi/well in assay). Mix carefully to avoid BSA frothing. Add 20 μL to appropriate wells. Mix plates on plate shaker. For negative control, mix ATP solution with an equal amount of 20 mM HEPES pH 7.2 and add $\gamma^{33}P$ ATP to a concentration of 0.15 μCi/20 μL solution. Add 20 μL to appropriate wells.
6. Let reactions proceed for 60 minutes.
7. Add 35 μL 10% TCA to each well. Mix plates on plate shaker.

8. Spot 40 μL of each sample onto P30 filter mat squares. Allow mats to dry (approx. 10–20 minutes).
9. Wash filter mats 4×10 minutes with 250 mL 1% phosphoric acid (10 mL phosphoric acid per liter ddH$_2$O).
10. Count filter mats with beta plate reader.

Cellular/Biologic Assays

Example 12

PDGF-Induced BrdU Incorporation Assay

Materials and Reagents (1) PDGF: human PDGF B/B; 1276-956, Boehringer Mannheim, Germany
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution: 1× PBS, pH 7.4.
(7) Albumin, Bovine (BSA): fraction V powder; A-8551, Sigma Chemical Co., USA.
(8) 3T3 cell line genetically engineered to express human PDGF-R.

Protocol (1) Cells are seeded at 8000 cells/well in DMEM, 10% CS, 2 mM Gln in a 96 well plate. Cells are incubated overnight at 37° C. in 5% CO$_2$.
(2) After 24 hours, the cells are washed with PBS, and then are serum starved in serum free medium (0% CS DMEM with 0.1% BSA) for 24 hours.
(3) On day 3, ligand (PDGF, 3.8 nM, prepared in DMEM with 0.1% BSA) and test compounds are added to the cells simultaneously. The negative control wells receive serum free DMEM with 0.1% BSA only; the positive control cells receive the ligand (PDGF) but no test compound. Test compounds are prepared in serum free DMEM with ligand in a 96 well plate, and serially diluted for 7 test concentrations.
(4) After 20 hours of ligand activation, diluted BrdU labeling reagent (1: 100 in DMEM, 0.1% BSA) is added and the cells are incubated with BrdU (final concentration=10 μM) for 1.5 hours.
(5) After incubation with labeling reagent, the medium is removed by decanting and tapping the inverted plate on a paper towel. FixDenat solution is added (50 μL/well) and the plates are incubated at room temperature for 45 minutes on a plate shaker.
(6) The FixDenat solution is thoroughly removed by decanting and tapping the inverted plate on a paper towel. Milk is added (5% dehydrated milk in PBS, 200 μL/well) as a blocking solution and the plate is incubated for 30 minutes at room temperature on a plate shaker.
(7) The blocking solution is removed by decanting and the wells are washed once with PBS. Anti-BrdU-POD solution (1:100 dilution in PBS, 1% BSA) is added (100 μL/well) and the plate is incubated for 90 minutes at room temperature on a plate shaker.
(8) The antibody conjugate is thoroughly removed by decanting and rinsing the wells 5 times with PBS, and the plate is dried by inverting and tapping on a paper towel.
(9) TMB substrate solution is added (100 μL/well) and incubated for 20 minutes at room temperature on a plate shaker until color development is sufficient for photometric detection.
(10) The absorbance of the samples are measured at 410 nm (in "dual wavelength" mode with a filter reading at 490 nm, as a reference wavelength) on a Dynatech ELISA plate reader.

Example 13

EGF-Induced BrdU Incorporation Assay

Materials and Reagents (1) EGF: mouse EGF, 201; Toyobo, Co., Ltd. Japan
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse,monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution: 1× PBS, pH 7.4.
(7) Albumin, Bovine (BSA): fraction V powder; A-8551, Sigma Chemical Co., USA.
(8) 3T3 cell line genetically engineered to express human EGF-R.

Protocol (1) Cells are seeded at 8000 cells/well in 10% CS, 2 mM Gin in DMEM, in a 96 well plate. Cells are incubated overnight at 37° C. in 5% CO$_2$.
(2) After 24 hours, the cells are washed with PBS, and then are serum starved in serum free medium (0% CS DMEM with 0.1% BSA) for 24 hours.
(3) On day 3, ligand (EGF, 2 nM, prepared in DMEM with 0.1%/BSA) and test compounds are added to the cells simultaneously. The negative control wells receive serum free DMEM with 0.1% BSA only; the positive control cells receive the ligand (EGF) but no test compound. Test compounds are prepared in serum free DMEM with ligand in a 96 well plate, and serially diluted for 7 test concentrations.
(4) After 20 hours of ligand activation, diluted BrdU labeling reagent (1: 100 in DMEM, 0.1% BSA) is added and the cells are incubated with BrdU (final concentration=10 μM) for 1.5 hours.
(5) After incubation with labeling reagent, the medium is removed by decanting and tapping the inverted plate on a paper towel. FixDenat solution is added (50 μL/well) and the plates are incubated at room temperature for 45 minutes on a plate shaker.

119

(6) The FixDenat solution is thoroughly removed by decanting and tapping the inverted plate on a paper towel. Milk is added (5% dehydrated milk in PBS, 200 μL/well) as a blocking solution and the plate is incubated for 30 minutes at room temperature on a plate shaker.
(7) The blocking solution is removed by decanting and the wells are washed once with PBS. Anti-BrdU-POD solution (1:100 dilution in PBS, 1% BSA) is added (100 μL/well) and the plate is incubated for 90 minutes at room temperature on a plate shaker.
(8) The antibody conjugate is thoroughly removed by decanting and rinsing the wells 5 times with PBS, and the plate is dried by inverting and tapping on a paper towel.
(9) TMB substrate solution is added (100 μL/well) and incubated for 20 minutes at room temperature on a plate shaker until color development is sufficient for photometric detection.
(10) The absorbance of the samples are measured at 410 nm (in "dual wavelength" mode with a filter reading at 490 nm, as a reference wavelength) on a Dynatech ELISA plate reader.

Example 14

EGF-Induced Her2-Driven BrdU Incorporation

Materials and Reagents (1) EGF: mouse EGF, 201; Toyobo,Co., Ltd. Japan
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution: 1× PBS, pH 7.4, made in house.
(7) Albumin, Bovine (BSA): fraction V powder; A-8551, Sigma Chemical Co., USA.
(8) 3T3 cell line engineered to express a chimeric receptor having the extra-cellular domain of EGF-R and the intra-cellular domain of Her2.

Protocol (1) Cells are seeded at 8000 cells/well in DMEM, 10% CS, 2 mM Gln in a 96-well plate. Cells are incubated overnight at 37° C. in 5% $CO_2$.
(2) After 24 hours, the cells are washed with PBS, and then are serum starved in serum free medium (0% CS DMEM with 0.1% BSA) for 24 hours.
(3) On day 3, ligand (EGF=2 nM, prepared in DMEM with 0.1% BSA) and test compounds are added to the cells simultaneously. The negative control wells receive serum free DMEM with 0.1% BSA only; the positive control cells receive the ligand (EGF) but no test compound. Test compounds are prepared in serum free DMEM with ligand in a 96 well plate, and serially diluted for 7 test concentrations.

120

(4) After 20 hours of ligand activation, diluted BrdU labeling reagent (1:100 in DMEM, 0.1% BSA) is added and the cells are incubated with BrdU (final concentration=10 M) for 1.5 hours.
(5) After incubation with labeling reagent, the medium is removed by decanting and tapping the inverted plate on a paper towel. FixDenat solution is added (50 μL/well) and the plates are incubated at room temperature for 45 minutes on a plate shaker.
(6) The FixDenat solution is thoroughly removed by decanting and tapping the inverted plate on a paper towel. Milk is added (5% dehydrated milk in PBS, 200 μL/well) as a blocking solution and the plate is incubated for 30 minutes at room temperature on a plate shaker.
(7) The blocking solution is removed by decanting and the wells are washed once with PBS. Anti-BrdU-POD solution (1:100 dilution in PBS, 1% BSA) is added (100 μL/well) and the plate is incubated for 90 minutes at room temperature on a plate shaker.
(8) The antibody conjugate is thoroughly removed by decanting and rinsing the wells 5 times with PBS, and the plate is dried by inverting and tapping on a paper towel.
(9) TMB substrate solution is added (100 μL/well) and incubated for 20 minutes at room temperature on a plate shaker until color development is sufficient for photometric detection.
(10) The absorbance of the samples are measured at 410 nm (in "dual wavelength" mode with a filter reading at 490 nm, as a reference wavelength) on a Dynatech ELISA plate reader.

Example 15

IGF1-Induced BrdU Incorporation Assay

Materials and Reagents (1) IGF1 Ligand: human, recombinant; G511, Promega Corp, USA.
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution: 1× PBS, pH 7.4.
(7) Albumin, Bovine (BSA): fraction V powder; A-8551, Sigma Chemical Co., USA.
(8) 3T3 cell line genetically engineered to express human IGF-1 receptor.

Protocol (1) Cells are seeded at 8000 cells/well in DMEM, 10% CS, 2 mM Gln in a 96-well plate. Cells are incubated overnight at 37° C. in 5% $CO_2$.
(2) After 24 hours, the cells are washed with PBS, and then are serum starved in serum free medium (0%CS DMEM with 0.1% BSA) for 24 hours.

(3) On day 3, ligand (IGF1=3.3 nM, prepared in DMEM with 0.1% BSA) and test compounds are added to the cells simultaneously. The negative control wells receive serum free DMEM with 0.1% BSA only; the positive control cells receive the ligand (IGF1) but no test compound. Test compounds are prepared in serum free DMEM with ligand in a 96 well plate, and serially diluted for 7 test concentrations.

(4) After 16 hours of ligand activation, diluted BrdU labeling reagent (1:100 in DMEM, 0.1% BSA) is added and the cells are incubated with BrdU (final concentration=10 μM) for 1.5 hours.

(5) After incubation with labeling reagent, the medium is removed by decanting and tapping the inverted plate on a paper towel. FixDenat solution is added (50 μL/well) and the plates are incubated at room temperature for 45 minutes on a plate shaker.

(6) The FixDenat solution is thoroughly removed by decanting and tapping the inverted plate on a paper towel. Milk is added (5% dehydrated milk in PBS, 200 μL/well) as a blocking solution and the plate is incubated for 30 minutes at room temperature on a plate shaker.

(7) The blocking solution is removed by decanting and the wells are washed once with PBS. Anti-BrdU-POD solution (1:100 dilution in PBS, 1% BSA) is added (100 μL/well) and the plate is incubated for 90 minutes at room temperature on a plate shaker.

(8) The antibody conjugate is thoroughly removed by decanting and rinsing the wells 5 times with PBS, and the plate is dried by inverting and tapping on a paper towel.

(9) TMB substrate solution is added (100 μL/well) and incubated for 20 minutes at room temperature on a plate shaker until color development is sufficient for photometric detection.

(10) The absorbance of the samples are measured at 410 nm (in "dual wavelength" mode with a filter reading at 490 nm, as a reference wavelength) on a Dynatech ELISA plate reader.

Example 16

HUV-EC-C Assay

The following protocol may also be used to measure a compound's activity against PDGF-R, FGF-R, VEGF, aFGF or Flk-1/KDR, all of which are naturally expressed by HUV-EC cells.

Day 0

1. Wash and trypsinize HUV-EC-C cells (human umbilical vein endothelial cells, (American Type Culture Collection; catalogue no. 1730 CRL). Wash with Dulbecco's phosphate-buffered saline (D-PBS; obtained from Gibco BRL; catalogue no. 14190-029) 2 times at about 1 mL/10 cm$^2$ of tissue culture flask. Trypsinize with 0.05% trypsin-EDTA in non-enzymatic cell dissociation solution (Sigma Chemical Company; catalogue no. C-1544). The 0.05% trypsin was made by diluting 0.25% trypsin/1 mM EDTA (Gibco; catalogue no. 25200-049) in the cell dissociation solution. Trypsinize with about 1 mL/25–30 cm$^2$ of tissue culture flask for about 5 minutes at 37° C. After cells have detached from the flask, add an equal volume of assay medium and transfer to a 50 mL sterile centrifuge tube (Fisher Scientific; catalogue no. 05-539-6).

2. Wash the cells with about 35 mL assay medium in the 50 mL sterile centrifuge tube by adding the assay medium, centrifuge for 10 minutes at approximately 200 g, aspirate the supernatant, and resuspend with 35 mL D-PBS. Repeat the wash two more times with D-PBS, resuspend the cells in about 1 mL assay medium/15 cm$^2$ of tissue culture flask. Assay medium consists of F12K medium (Gibco BRL; catalogue no. 21127-014)+0.5% heat-inactivated fetal bovine serum. Count the cells with a Coulter Counter (Coulter Electronics, Inc.) and add assay medium to the cells to obtain a concentration of 0.8–1.0×10$^5$ cells/mL.

3. Add cells to 96-well flat-bottom plates at 100 μL/well or 0.8–1.0×10$^4$ cells/well; incubate ~24h at 37° C., 5% $CO_2$.

Day 1

1. Make up two-fold drug titrations in separate 96-well plates, generally 50 μM on down to 0 μM. Use the same assay medium as mentioned in day 0, step 2 above. Titrations are made by adding 90 μL/well of drug at 200 μM (4× the final well concentration) to the top well of a particular plate column. Since the stock drug concentration is usually 20 mM in DMSO, the 200 μM drug concentration contains 2% DMSO.

Therefore, diluent made up to 2% DMSO in assay medium (F12K+0.5% fetal bovine serum) is used as diluent for the drug titrations in order to dilute the drug but keep the DMSO concentration constant. Add this diluent to the remaining wells in the column at 60 μL/well. Take 60 μL from the 120 μL of 200 μM drug dilution in the top well of the column and mix with the 60 μL in the second well of the column. Take 60 μL from this well and mix with the 60 μL in the third well of the column, and so on until two-fold titrations are completed. When the next-to-the-last well is mixed, take 60 μL of the 120 μL in this well and discard it. Leave the last well with 60 μL of DMSO/media diluent as a non-drug-containing control. Make 9 columns of titrated drug, enough for triplicate wells each for 1) VEGF (obtained from Pepro Tech Inc., catalogue no. 100–200, 2) endothelial cell growth factor (ECGF) (also known as acidic fibroblast growth factor, or aFGF) (obtained from Boehringer Mannheim Biochemica, catalogue no. 1439 600); or, 3) human PDGF B/B (1276-956, Boehringer Mannheim, Germany) and assay media control. ECGF comes as a preparation with sodium heparin.

2. Transfer 50 μL/well of the drug dilutions to the 96-well assay plates containing the 0.8–1.0×10$^4$ cells/100 μL/well of the HUV-EC-C cells from day 0 and incubate ~2 h at 37° C., 5% $CO_2$.

3. In triplicate, add 50 μL/well of 80 μg/mL VEGF, 20 ng/mL ECGF, or media control to each drug condition. As with the drugs, the growth factor concentrations are 4× the desired final concentration. Use the assay media from day 0 step 2 to make the concentrations of growth factors. Incubate approximately 24 hours at 37° C., 5% $CO_2$. Each well will have 50 μL drug dilution, 50 μL growth factor or media, and 100 μL cells,=200 μL/well total. Thus the 4× concentrations of drugs and growth factors become 1× once everything has been added to the wells.

Day 2

1. Add $^3$H-thymidine (Amersham; catalogue no. TRK-686) at 1 Ci/well (10 l/well of 100 Ci/mL solution made up in RPMI media+10% heat-inactivated fetal bovine serum) and incubate ~24 h at 37° C., 5% $CO_2$. Note: $^3$H-thymidine is made up in RPMI media because all of the other applications for which we use the $^3$H-thymidine involve experiments done in RPMI. The media difference at this step is probably not significant. RPMI was obtained from Gibco BRL, catalogue no. 11875-051.

Day 3

1. Freeze plates overnight at −20° C.

Day 4

1. Thaw plates and harvest with a 96-well plate harvester (Tomtec Harvester 96(R)) onto filter mats (Wallac; catalogue no. 1205-401); read counts on a Wallac Betaplate(TM) liquid scintillation counter.

Example 17

FGF-Induced BrdU Incorporation Assay

This assay measures FGF-induced DNA synthesis in 3Tc7/EGFr cells that express endogenous FGF receptors.

Materials and Reagents

1. FGF: human FGF2/bFGF (Gibco BRL, No. 13256-029).
2. BrdU Labeling reagent, (10 mM PBS (pH 7.4), Boehringer Mannheim Cat No. 1 647 229).
3. FIXDENAT fixation solution (Boehringer Mannheim Cat No. 1 647 229).
4. Anti-BrdU-POD (mouse monoclonal antibody conjugated with peroxidase, Boehringer Mannheim Cat. No. 1 647 229).
5. TMB (tetramethylbenzidine, Boehringer Mannheim Cat. No. 1 647 229).
6. PBS washing solution, pH 7.4.
7. Albumin, bovine (BSA), fraction V powder (Sigma Chemical Co., Cat. No. A-8551)

Procedure 1. 3T3 engineered cell line: 3T3c7/EGFr.
2. Cells are seeded at 8,000 cells/well in DMEM, 10% CS and 2 mM Gln in a 96-well plate. Incubate 24 hours at 37° C. in 5% $CO_2$.
3. After 24 hours, wash cells with PBS then serum starve in serum free medium (0% DMEM, 0.1% BSA) for 24 hours.
4. Add ligand (FGF2 (1.5 nM in DMEM with 0.1% BSA) and test compound simultaneously. Negative control wells receive serum free DMEM with 0.1% BSA only; positive control wells receive FGF2 ligand but no test compound. Test compounds are prepared in serum-free DMEM with ligand in a 96-well plate and serially diluted to make seven (7) test concentrations.
5. After 20 hours, add diluted BrdU labeling reagent (1:100 BrdU:DMEM, 0.1% BSA, final concentration is 10 μM) to the cells and incubate for 1.5 hours.
6. Decant medium. Remove traces of material with paper towel. Add FIXDENAT (50 μl/well) and incubate at room temperature for 45 minutes on a plate shaker.
7. Remove FIXDENAT solution. Add blocking solution (5% dehydrated milk in PBS (200 μl/well)) and incubate for 30 minutes at room temperature on a plate shaker.
8. Decant blocking solution; wash wells once with PBS. Add anti-BrdU-POD solution (1:100 dilution in PBS, 0.1% BSA); incubate for 90 minutes at room temperature on a plate shaker.
9. Decant antibody conjugate; rinse wells 5 times with PBS. Dry plate by inverting on paper towel and tapping.
10. Add TMB solution (100 μL/well); incubate 20 minutes at room temperature on a plate shaker until color development is sufficient for photometric detection.
11. Measure absorbance at 410 nM on a Dynatech ELISA plate reader using "Dual wavelength" mode with a filter at 490 nM.

Example 18

Biochemical EGFR Assay

This assay measures the in vitro kinase activity of EGFR using ELISA.

Materials And Reagents

1. Corning 96-well ELISA plates (Corning Catalog No. 25805-96).
2. SUMO1 monoclonal anti-EGFR antibody.
3. PBS (Dulbecco's Phosphate-Buffered Saline, Gibco Catalog No. 450-1300EB).
4. TBST Buffer

| Reagent | M.W. | Working Concentration | Amount per L |
|---|---|---|---|
| Tris | 121.14 | 50 mM | 6.057 g |
| NaCl | 58.44 | 150 mM | 8.766 g |
| Triton X-100 | NA | 0.1% | 1.0 mL |

5. Blocking Buffer:

| Reagent | M.W. | Working Concentration | Amount per 100 mL |
|---|---|---|---|
| Carnation Instant Non-Fat Milk | NA | 5% | 5.0 g |
| PBS | NA | NA | 100 mL |

6. A431 cell lysate
7. TBS Buffer:

| Reagent | M.W. | Working Concentration | Amount per L |
|---|---|---|---|
| Tris | 121.14 | 50 mM | 6.057 g |
| NaCl | 58.44 | 150 mM | 8.766 g |

8. TBS+10% DMSO

| Reagent | M.W. | Working Concentration | Amount per L |
|---|---|---|---|
| Tris | 121.14 | 50 mM | 1.514 g |
| NaCl | 58.44 | 150 mM | 2.192 g |
| DMSO | NA | 10% | 25 mL |

9. Adenosine-5'-triphosphate (ATP, from Equine muscle, Sigma Cat. No. A-5394).

Prepare a 1.0 mM solution in dH$_2$O. This reagent should be made up immediately prior to use and kept on ice.

10. MnCl$_2$. Prepare a 1.0 M stock solution in dH$_2$O.

a11. ATP/MnCl$_2$ phosphorylation mix

| Reagent | M.W. | Amount per 10 mL | Working Concentration |
|---|---|---|---|
| ATP | 1.0 mM | 300 μL | 30 μM |
| MnCl$_2$ | 1.0 M | 500 μL | 50 mM |
| dH$_2$O | | 9.2 mL | |

This reagent should be prepared immediately before use and kept on ice

12. NUNC 96-well V bottom polypropylene plates (Applied Scientific Cat. No. AS-72092).

13. Ethylenediaminetetraacetic acid (EDTA)

Prepare 200 mM working solution in dH$_2$O. Adjust to pH 8.0 with 10 N NaOH.

14. Rabbit polyclonal anti-phosphotyrosine serum.

15. Goat anti-rabbit IgG peroxidase conjugate (Biosource Cat. No. ALI0404)

16. ABTS (2,2'-azino-bis(3-ethylbenzthiazoline-6-sulfonic acid), Sigma Cat. No. A-1888).

| Reagent | M.W. | Working Concentration | Amount per L |
|---|---|---|---|
| Citric Acid | 192.12 | 100 mM | 19.21 g |
| Na$_2$HPO$_4$ | 141.96 | 250 mM | 35.49 g |
| ABTS | NA | 0.5 mg/mL | 500 mg |

Mix first two ingredients in about 900 mL dH$_2$O, adjust pH to 4.0 with phosphoric acid. Add ABTS, cover, let sit about 0.5 hr., filter. The solution should be kept in the dark at 4° C. until ready to use.

17. Hydrogen peroxide 30% solution (Fisher Cat. No. H325)

18. ABTS/H$_2$O$_2$ Mix 15 mL ABTS solution and 2.0 μL H$_2$O$_2$. Prepare 5 minutes before use.

19. 0.2 M HCl

Procedure

1. Coat Corning 96 well ELISA plates with 0.5 μg SUMO1 in 100 μL PBS per well, store overnight at 4° C.
2. Remove unbound SUMO1 from wells by inverting plate to remove liquid. Wash 1× with dH$_2$O. Pat the plate on a paper towel to remove excess liquid.
3. Add 150 μL of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in PBS (7 μg lysate/100 μL PBS).
6. Add 100 μL of diluted lysate to each well. Shake at room temperature for 60 min.
7. Wash plates as described in 4, above.
8. Add 120 μL TBS to ELISA plate containing captured EGFR.
9. Dilute test compound 1:10 in TBS in 96-well polypropylene plates (ie. 10 μL compound+90 μL TBS).
10. Add 13.5 μL diluted test compound to ELISA plate. To control wells (wells which do not receive any test compound), add 13.5 μL TBS+10% DMSO.
11. Incubate for 30 minutes while shaking at room temperature.
12. Add 15 μL phosphorylation mix directly to all wells except negative control well which does not receive ATP/MnCl$_2$ (final well volume should be approximately 150 μL with 3 μM ATP/5 mM MnCl$_2$ final concentration in each well.) Incubate 5 minutes while shaking.
13. After 5 minutes, stop reaction by adding 16.5 μL of 200 mM EDTA (pH 8.0) to each well, shaking continuously. After the EDTA has been added, shake for 1 mm.
14. Wash 4× with deionized water, twice with TBST.
15. Add 100 μL anti-phosphotyrosine (1:3000 dilution in TBST) per well. Incubate 30–45 min. at room temperature, with shaking.
16. Wash as described in 4, above.
17. Add 100 μL Biosource Goat anti-rabbit IgG peroxidase conjugate (1:2000 dilution in TBST) to each well. Incubate 30 min. at room temperature, with shaking.
18. Wash as described in 4, above.
19. Add 100 μL of ABTS/H$_2$O$_2$ solution to each well.
20. Incubate 5 to 10 minutes with shaking. Remove any bubbles.
21. If necessary stop reaction with the addition of 100 μL 0.2 M HCl per well.
22. Read assay on Dynatech MR7000 ELISA reader. Test Filter: 410 nM Reference Filter: 630 Nm.

Example 19

Biochemical PDGFR Assay

This assay measures the in vitro kinase activity of PDGFR using ELISA.

Materials And Reagents

Unless otherwise noted, the preparation of working solution of the following reagents is the same as that for the Biochemical EGFR assay, above.

1. Corning 96-well Elisa plates (Corning Catalog No. 25805-96).
2. 28D4C10 monoclonal anti-PDGFR antibody.
3. PBS (Dulbecco's Phosphate-Buffered Saline, Gibco Catalog No. 450-1300EB)
4. TBST Buffer.
5. Blocking Buffer.
6. PDGFR-β expressing NIH 3T3 cell lysate.
7. TBS Buffer.
8. TBS+10% DMSO.
9. Adenosine-5'-triphosphate (ATP, from Equine muscle, Sigma Cat. No. A-5394).
10. MnCl$_2$.

11. Kinase buffer phosphorylation mix.

| Reagent | Stock solution | Amount per 10 mL | Working Concentration |
|---------|----------------|------------------|----------------------|
| Tris    | 1 M            | 250 μL           | 25 mM                |
| NaCl    | 5 M            | 200 μL           | 100 mM               |
| MnCl₂   | 1 M            | 100 μL           | 10 mM                |
| TX-100  | 100 mM         | 50 μL            | 0.5 mM               |

12. NUNC 96-well V bottom polypropylene plates (Applied Scientific Cat. No. AS-72092).
13. Ethylenediaminetetraacetic acid (EDTA).
14. Rabbit polyclonal anti-phosphotyrosine serum.
15. Goat anti-rabbit IgG peroxidase conjugate (Biosource Cat. No. ALI0404).
16. 2,2'-azino-bis(3-ethylbenzthiazoline-6-sulfonic acid) (ABTS, Sigma Cat. No. A-1888).
17. Hydrogen peroxide 30% solution (Fisher Cat. No. H325). 18. ABTS/H$_2$O$_2$.
19. 0.2 M HCl.

Procedure

1. Coat Corning 96 well ELISA plates with 0.5 μg 28D4C10 in 100 μL PBS per well, store overnight at 4° C.
2. Remove unbound 28D4C10 from wells by inverting plate to remove liquid. Wash 1× with dH$_2$O. Pat the plate on a paper towel to remove excess liquid.
3. Add 150 μL of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in HNTG (10 μg lysate/100 μL HNTG)
6. Add 100 μL of diluted lysate to each well. Shake at room temperature for 60 min.
7. Wash plates as described in 4, above.
8. Add 80 μL working kinase buffer mix to ELISA plate containing captured PDGFR.
9. Dilute test compound 1:10 in TBS in 96-well polypropylene plates (i.e., 10 μL compound+90 μL TBS).
10. Add 10 μL diluted test compound to ELISA plate. To control wells (wells which do not receive any test compound), add 10 μL TBS+10% DMSO.
11. Incubate for 30 minutes while shaking at room temperature.
12. Add 10 μL ATP directly to all wells except negative control well (final well volume should be approximately 100 μL with 20 μM ATP in each well.) Incubate 30 minutes while shaking.
13. After 30 minutes, stop reaction by adding 10 μL of 200 mM EDTA (pH 8.0) to each well.
14. Wash 4× with deionized water, twice with TBST.
15. Add 100 μL anti-phosphotyrosine (1:3000 dilution in TBST) per well. Incubate 30–45 min. at room temperature, with shaking.
16. Wash as described in 4, above.
17. Add 100 μL Biosource Goat anti-rabbit IgG peroxidase conjugate (1:2000 dilution in TBST) to each well. Incubate 30 min. at room temperature, with shaking.
18. Wash as described in 4, above.
19. Add 100 μL of ABTS/H$_2$O$_2$ solution to each well.
20. Incubate 10 to 30 minutes with shaking. Remove any bubbles.
21. If necessary stop reaction with the addition of 100 μL 0.2 M HCl per well.
22. Read assay on Dynatech MR7000 ELISA reader: test filter: 410 nM, reference filter: 630 nM.

Example 20

Biochemical FGFR Assay

This assay measures in vitro kinase activity of the Myc-GyrB-FGFR fusion protein using ELISA.

Materials And Reagents

1. HNTG

| Reagent      | M.W.   | 5x Stock Concentration | Amount per L | 1x Working Concentration |
|--------------|--------|------------------------|--------------|--------------------------|
| HEPES        | 238.3  | 100 mM                 | 23.83 g      | 20 mM                    |
| NaCl         | 58.44  | 750 mM                 | 43.83 g      | 150 mM                   |
| Glycerol     | NA     | 50%                    | 500 mL       | 10%                      |
| Triton X-100 | NA     | 5%                     | 10 mL        | 1.0%                     |

To make a liter of 5× stock solution, dissolve HEPES and NaCl in about 350 mLl dH$_2$O, adjust pH to 7.2 with HCl or NaOH (depending on the HEPES that is used), add glycerol, Triton X-100 and then dH$_2$O to volume.

2. PBS (Dulbecco's Phosphate-Buffered Saline, Gibco Catalog #450-1300EB).
3. Blocking Buffer.
4. Kinase Buffer.

| Reagent        | M.W.   | 10x Stock Concentration | 1x Working Concentration |
|----------------|--------|-------------------------|--------------------------|
| HEPES (pH 7.2) | 238.3  | 500 mM                  | 50 mM                    |
| MnCl₂          |        | 20 mM                   | 2 mM                     |
| MgCl₂          | 203.32 | 200 mM                  | 10 mM                    |
| Triton-X-100   |        | 1%                      | 0.1%                     |
| DTT            | 380.35 | 5 mM                    | 0.5 mM                   |

5. Phenylmethylsulfonyl fluoride (PMSF, Sigma, Cat. No. P-7626): Working solution: 100 mM in ethanol.
6. ATP (Bacterial source, Sigma Cat. No. A-7699) Use 3.31 mg per mL MilliQ H$_2$O for a stock concentration of 6 mM.
7. Biotin conjugated anti-phosphotyrosine mab (clone 4G10, Upstate Biotechnology Inc. Cat. No. 16-103, Ser. No. 14495).
8. VECTASTAIN ELITE ABC reagent (Avidin peroxidase conjugate, Vector Laboratories Cat. No. PK-6 100).
9. ABTS Solution.
10. Hydrogen peroxide 30% solution (Fisher Catalog #H325).
11. ABTS/H$_2$O$_2$.
12. 0.2 M HCl.
13. TRIS HCl (Fischer Cat. No. BP 152-5). Prepare 1.0 mM solution in MilliQ H$_2$O, adjust pH to 7.2 with HCl.

14. NaCl (Fisher Cat. No. S271-10). Prepare 5 M solution in MilliQ H$_2$O.
15. MgCl$_2$ (Fisher Cat. No. M33-500). Prepare 1 M solution in MilliQ H$_2$O.
16. HEPES (Fisher Cat. No. BP310-500). Prepare 1 M solution in MilliQ H$_2$O, adjust pH to 7.5, sterile filter.
17. TBST Buffer.
18. Sodium Carbonate Buffer (Fisher Cat. No. S495). Prepare 0.1 M solution in MilliQ H$_2$O, adjust pH to 9.6 with NaOH, filter.
19. Dithiothreitol (DTT, Fisher Cat. No. BP172-25). Prepare 0.5 mM working solution in MilliQ H$_2$O just prior to use. Store at −20° C until used, discard any leftover.
20. MnCl$_2$.
21. Triton X-100.
22. Goat α-Rabbit IgG (Cappel).
23. Affinity purified Rabbit α GST GyrB.

Procedure

All of the following steps are conducted at room temperature unless otherwise indicated.
1. Coat Corning 96-well ELISA plates with 2 µg Goat a-Rabbit antibody per well in Carbonate Buffer such that total well volume is 100 µl. Store overnight at 4° C.
2. Remove unbound Goat a-Rabbit antibody by inverting plate to remove liquid. Pat plate on a paper towel to remove excess liquid and bubbles
3. Add 150 µL Blocking Buffer (5% Low Fat Milk in PBS) to each well. Incubate while shaking on a micro-titer plate shaker for 30 min.
4. Wash 4× with TBST. Pat plate on a paper towel to remove excess liquid and bubbles.
5. Add 0.5 µg Rabbit a-GyrB antibody per well. Dilute antibody in DPBS to a final volume of 100 µL per well. Incubate with shaking on a micro-titer plate shaker at room temperature for 1 hour.
6. Wash 4× with TBST as described in step 4.
7. Add 2 µg COS/FGFR cell lysate (Myc-GyrB-FGFR source) in HNTG to each well to give a final volume of 100 µL per well. Incubate with shaking on a micro-titer plate shaker for 1 hour.
8. Wash 4× with TBST as described in step 4.
9. Add 80 µL of 1× kinase buffer per well.
10. Dilute test compound 1:10 in 1× kinase buffer+1% DMSO in a polypropylene 96-well plate.
11. Transfer 10 µL of diluted test compound solution and control wells from polypropylene plate wells to the corresponding ELISA plate wells, incubate with shaking on a micro-titer plate shaker for 20 minutes.
12. Add 10 µL of 70 µM ATP diluted in kinase buffer to positive control and test wells (final ATP concentration is 7 µM/well). Add 10 µL 1× kinase buffer to negative control wells. Incubate with shaking on a micro-titer plate shaker for 15 min.
13. Stop kinase reaction by adding 5 µL 0.5 M EDTA to all wells. 14. Wash 4× with TBST as described in step 4.
15. Add 100 µL biotin conjugated α-phosphotyrosine mab (b4G10) diluted in TBST to each well. Incubate with shaking on a micro-titer plate shaker for 30 minutes.
16. Prepare VECTASTAIN ABC reagent. Add 1 drop reagent A to 15 mL TBST. Mix by inverting tube several times. Add 1 drop reagent B and mix again.
17. Wash 4× with TBST as described in step 4.
18. Add 100 µL ABC HRP reagent to each well. Incubate with shaking on a micro-titer plate shaker for 30 minutes.
19. Wash 4× with TBST as described in step 4.
20. Add 100 µL of ABTS/H$_2$O$_2$ solution to each well.
22. Incubate 5 to 15 minutes with shaking. Remove any bubbles.
23. If necessary stop reaction by adding 100 µL of 0.2 M HCl/well.
24. Read assay on Dynatech MR7000 ELISA Plate Reader; test filter: 410 nM, reference filter: 630 nM.

Example 21

Biochemical FLK-1 Assay

This assay evaluates flk-1 autophosphorylation activity in vitro using ELISA.

Materials And Reagents 1. 15 cm tissue culture dishes
2. Flk-1/NIH cells: NIH fibroblast line over-expressing human flk-1 clone 3.
3. Growth medium: DMEM plus heat inactivated 10% FBS and 2 mM Glutamine (Gibco-BRL).
4. Starvation medium: DMEM plus 0.5% heat-inactivated FBS, 2 mM Glutamine (Gibco-BRL).
5. Corning 96-well ELISA plates (Corning Cat. No. 25805-96).
6. L4 or E38 monoclonal antibody specific for flk-1; Purified by Protein-A agarose affinity chromatography.
7. PBS (Dulbecco's Phosphate-Buffered Saline) Gibco Cat. No. 450-1 300EB).
8. HNTG (see BIOCHEMICAL FGFR for preparation).
9. Pierce BCA protein determination kit.
10. Blocking buffer
11. TBST (pH 7.0)
12. Kinase Buffer
13. Kinase Stop Solution: 200 mM EDTA.
14. Biotinylated 4G10, specific for phosphotyrosine (UBI, Cat. No. No. 16-103).
15. AB kit (Vector Laboratories Cat. No. PK 4000).
16. DMSO
17. NUNC 96-well V bottom polypropylene plates (Applied Scientific Cat. No. AS-72092).
18. TURBO-TMB (Pierce).
19. TURBO-TMB stop solution: 1 M H$_2$SO$_4$.
20. ATP (Sigma Cat. No. A-7699).
21. 20% DMSO in TBS (pH 7.0).

Procedure

Cell Growth and Lysate Preparation.

1. Seed cell into growth medium and grow for 2–3 days to 90–100% confluency at 37° C. and 5% CO$_2$. Do not exceed passage #20.
2. Remove the medium and wash the cells twice with PBS. Lyse with HNTG lysis buffer. Collect all lysates and vortex mix them for 20–30 seconds.
3. Remove insoluble material by centrifugation (5–10 min at about 10,000 xg).

4. Determine the protein concentration using BCA kit.
5. Partition lysate into 1 mg aliquots, store at −80° C.

Assay Procedure

1. Coat Corning 96-well ELISA plates with 2 μg/well purified L4 (or E 38) in 100 μL of PBS. Store overnight at 4° C.
2. Remove unbound proteins from wells by inverting the plate to remove the liquid. Wash one time with $dH_2O$, pat plate on paper towel to remove excess liquid.
3. Block plates with 150 μL blocking buffer per well. Incubate for 45–60 minutes with shaking at 4° C.
4. Remove the blocking buffer and wash the ELISA plate three times with $dH_2O$ and one time with TBST. Pat plate on paper towel to remove excess liquid.
5. Dilute lysate in PBS to give final concentration of 50 μg/100 μl. Add 100 μL of diluted lysate to each well. Incubate with shaking at 4° C. overnight.
6. Remove unbound proteins from wells by inverting the plate. Wash as in step 4.
7. Add 80 μL of kinase buffer to wells (90 μL to negative control wells).
8. Dilute test compounds (normally 10-fold) into wells of a polypropylene plate containing 20% DMSO in TBS.
9. Add 10 μL of the diluted compounds to the ELISA wells containing immobilized flk-1 and shake. Control wells receive no compounds.
10. From stock 1 mM ATP, prepare 0.3 mM ATP solution in $dH_2O$ (alternatively, kinase buffer may be used).
11. Add 10 μL of 0.3 mM ATP to all wells except the negative controls. Incubate for 60 min. at room temperature with shaking.
12. After 1 hr stop the kinase reaction by adding 11 μL 200 mM EDTA. Shake for 1–2 min.
13. Wash the ELISA plate 4 times with $dH_2O$ and twice with TBST.
14. Add 100 μL of 1:5000 biotinylated 4G10:TBST to all wells. Incubate 45 min with shaking at room temperature.
15. While the above is incubating, add 50 μL of solutions A & B from the ABC kit to 10 mL of TBST. These solutions must be combined approximately 30 min prior to use.
16. Wash plates as in step 4.
17. Add 100 μL of the preformed A & B complex to all wells. Incubate 30 min with shaking at room temperature.
18. Wash plates as in step 4.
19. Add 100 μL TURBO-TMB. Shake at room temperature for 10–15 min.
20. When the color in the positive control wells reaches an absorbance of about 0.35–0.4, stop the reaction with 100 μL of TURBO-TMB stop solution.
21. Read plates on Dynatech MR7000 ELISA reader; test filter: 450 nM, reference filter: 410 nM.

In Vivo Animal Models

Example 22

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, *Acta Pathol. Microbial. Scand.* 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC #CCL 107), A375 cells (melanoma, ATCC #CRL 1619), A431 cells (epidermoid carcinoma, ATCC #CRL 1555), Calu 6 cells (lung, ATCC #HTB 56), PC3 cells (prostate, ATCC #CRL 1435) and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, 2–10×10⁶ cells/animal). Tumor growth is measured over 3 to 6 weeks using venier calipers. Tumor volumes are calculated as a product of length×width×height unless otherwise indicated. P values are calculated using the Students t-test. Test compounds in 50–100 μL excipient (DMSO, or VPD:D5W) was delivered by IP injection at different concentrations generally starting at day one after implantation.

Example 23

Tumor Invasion Model

The following tumor invasion model has been developed and maybe used for the evaluation of therapeutic value and efficacy of the compounds identified to selectively inhibit KDR/FLK-1 receptor.

Procedure 8 week old nude mice (female) (Simonsen Inc.) were used as experimental animals. Implantation of tumor cells was performed in a laminar flow hood. For anesthesia, Xylazine/

Ketamine Cocktail (100 mg/kg ketamine and 5 mg/kg Xylazine) are administered intraperitoneally. A midline incision is done to expose the abdominal cavity (approximately 1.5 cm in length) to inject $10^7$ tumor cells in a volume of 100 µL medium. The cells are injected either into the duodenal lobe of the pancreas or under the serosa of the colon. The peritoneum and muscles are closed with a 6-0 silk continuous suture and the skin was closed by using wound clips. Animals were observed daily.

Analysis

After 2–6 weeks, depending on gross observations of the animals, the mice are sacrificed, and the local tumor metastases, to various organs (lung, liver, brain, stomach, spleen, heart, muscle) are excised and analyzed (measurements of tumor size, grade of invasion, immunochemistry, and in situ hybridization).

Example 24

Measurement of Cell Toxicity

Therapeutic compounds should be more potent in inhibiting protein kinase activity than in exerting a cytotoxic effect. A measure of the effectiveness and cell toxicity of a compound can be obtained by determining the therapeutic index: $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques (Mossman, 1983, *J. Immunol. Methods*, 65:55–63), by measuring the amount of LDH released (Korzeniewski and Callewaert, 1983, *J. Immunol. Methods*, 64:313; Decker and Lohmann-Matthes, 1988, *J. Immunol. Methods*, 115:61), or by measuring the lethal dose in animal models. Compounds with a large therapeutic index are preferred. The therapeutic index should be greater than 2, preferably at least 10, more preferably at least 50.

Example 25

The Activity of the Compounds of the Invention

The biological or biochemical activity of some of the compounds of the invention were tested using the assays described above. The $IC_{50}$ values were measured for several of the compounds of the invention. The results are shown in the tables below.

TABLE 4

| Compound Number | Her-2 kinase $IC_{50}$ (µM) | bio PDGFr $IC_{50}$ (µM) | bio EGFr $IC_{50}$ (µM) |
| --- | --- | --- | --- |
| AHI-1 | >100 | >100 | >100 |
| AHI-2 | 31.51 | 49.88 | >100 |
| AHI-3 | >100 | >100 | >100 |
| AHI-4 | >100 | >100 | >100 |
| AHI-5 | >100 | >100 | >100 |
| AHI-6 | 57.31 | 76.56 | >100 |
| AHI-7 | 16.76 | 0.02 | 12.08 |
| AHI-8 | 70.97 | 0.52 | >100 |

TABLE 5

| Compound | HER2 kinase $IC_{50}$ (µM) | PDGFr biochem $IC_{50}$ (µM) | EGFr biochem $IC_{50}$ (µM) | SKOV3 growth $IC_{50}$ (µM) | A431 growth $IC_{50}$ (µM) | BrdU DNA syn. HER2 $IC_{50}$ (µM) | BrdU DNA syn. EGFr $IC_{50}$ (µM) | BrdU DNA syn. PDFGr $IC_{50}$ (µM) |
| --- | --- | --- | --- | --- | --- | --- | --- | --- |
| AAI-1 | >100 | >100 | >100 | | | | | |
| AAI-2 | 50.5 | >100 | >100 | | | | | |
| AAI-3 | >100 | >100 | >100 | | | | | |
| AAI-4 | >100 | >100 | >100 | | | | | |
| AAI-5 | 16.4 | >100 | >100 | 17.86 | 5.26 | 32.67 | 29.95 | 32.7 |
| AAI-6 | >100 | >100 | >100 | | | 27.3 | >50 | >50 |
| AAI-7 | >100 | >100 | >100 | | | 6.8 | 28.11 | 31.1 |
| AAI-8 | >100 | >100 | >100 | | | 11.5 | >50 | >50 |
| AAI-9 | >100 | >100 | >100 | 5.2 | 5.25 | | | |
| AAI-10 | 22.2 | >100 | >100 | 17.27 | 17.7 | 34.06 | >50 | >50 |
| AAI-11 | >100 | >100 | >100 | 21.78 | 29.64 | >50 | >50 | >50 |
| AAI-12 | >100 | >100 | >100 | >50 | >50 | | | |
| AAI-13 | >100 | >100 | >100 | >50 | >50 | >50 | >50 | >50 |
| AAI-14 | >100 | >100 | >100 | | | | | |
| AAI-15 | >100 | >100 | >100 | | | | | |
| AAI-16 | >100 | >100 | >100 | | | >50 | >50 | >50 |
| AAI-17 | >100 | >100 | >100 | | | >50 | >50 | >50 |
| AAI-18 | 28.47 | 0.56 | >100 | 42.97 | >50 | >50 | >50 | 3.87 |
| AAI-19 | >100 | 0.25 | >100 | | | | | |
| AAI-20 | 20.95 | 2.13 | >100 | 8.81 | 11.06 | 29.24 | 38.5 | 8.81 |
| AAI-21 | 52.92 | 3.42 | 48.66 | | | >50 | 27.77 | 1.2 |
| AAI-22 | 21.45 | 80.03 | >100 | >50 | 32.94 | >50 | 27.56 | 1.15 |
| AAI-23 | 54.09 | 0.81 | >100 | | | >50 | 32.21 | 0.35 |
| AAI-24 | 26.12 | >100 | >100 | | | 30.94 | >50 | >50 |
| AAI-25 | >100 | >100 | >100 | | | >50 | >50 | >50 |
| AAI-26 | 67.62 | >100 | >100 | | | | | |
| AAI-27 | >100 | >100 | >100 | | | >50 | >50 | >50 |
| AAI-28 | 48 | >100 | >100 | | | | | |

TABLE 6

| Compound No. | Her2-Driven BrdU Incorp. $IC_{50}$ (µM) | EGF-Driven BrdU Incorp. $IC_{50}$ (µM) | PDGF-Driven BrdU Incorp. $IC_{50}$ (µM) |
| --- | --- | --- | --- |
| DAI-I | 46.9 | >50 | 0.77 |
| DAI-II | 30.2 | 38.3 | 0.26 |

TABLE 7

| Comp'd No. | HER2 Kinase IC$_{50}$ ($\mu$M) | PDGFr biochem IC$_{50}$ ($\mu$M) | EGFr biochem IC$_{50}$ ($\mu$M) | SKOV3 growth IC$_{50}$ ($\mu$M) | A431 growth IC$_{50}$ ($\mu$M) | BrdU DNA syn. HER2 IC$_{50}$ ($\mu$M) | BrdU DNA syn. EGFr IC$_{50}$ ($\mu$M) | BrdU DNA syn. PDGFr IC$_{50}$ ($\mu$M) |
|---|---|---|---|---|---|---|---|---|
| IN-001 | 16.6 | >100 | >100 | 27.8 | 12.3 | 28.9 | 32.5 | 35.2 |
| IN-002 | 18 | >100 | >100 | 24.5 | 8.2 | 30 | 41.5 | 37.1 |
| IN-003 | 15.5 | 20.2 | >100 | 17.8 | 8.7 | 12.1 | 29 | 22 |
| IN-004 | 10.6 | >100 | >100 | 2.9 | 1.1 | 3.6 | 4.7 | 3.3 |
| IN-005 | 12.9 | >100 | >100 | N/A* | N/A* | 1.6 | 3 | 1.7 |
| IN-006 | 10.6 | >100 | >100 | 5 | 6 | 6.6 | 11.1 | 4.6 |
| IN-007 | 22.7 | >100 | >100 | 9.7 | 4.2 | N/A* | N/A* | N/A* |
| IN-008 | 8.5 | >100 | >100 | 1.5 | 2.5 | 2.3 | 31.3 | 5.5 |
| IN-009 | >100 | 0.43 | >100 | 25.2 | 13.6 | 4.2 | 25.3 | 0.56 |
| IN-010 | >100 | N/A* | >100 | >25 | >25 | N/A* | N/A* | N/A* |
| IN-011 | >100 | N/A* | >100 | >50 | >50 | N/A* | N/A* | N/A* |
| IN-012 | >100 | N/A* | >100 | >50 | >50 | N/A* | N/A* | N/A* |
| IN-013 | >100 | N/A* | >100 | >50 | >50 | N/A* | N/A* | N/A* |
| IN-014 | >100 | N/A* | >100 | >50 | >50 | N/A* | N/A* | N/A* |
| IN-015 | >100 | N/A* | >100 | 20.5 | 21 | N/A* | N/A* | N/A* |
| IN-016 | >100 | N/A* | >100 | >50 | >50 | N/A* | N/A* | N/A* |
| IN-017 | >100 | N/A* | >100 | >50 | N/A* | N/A* | N/A* | N/A* |
| IN-018 | >100 | N/A* | >100 | N/A* | N/A* | N/A* | N/A* | N/A* |
| IN-019 | >100 | N/A* | >100 | N/A* | N/A* | N/A* | N/A* | N/A* |
| IN-020 | >100 | N/A* | >100 | >50 | 15.2 | N/A* | N/A* | N/A* |
| IN-021 | >100 | N/A* | >100 | N/A* | N/A* | N/A* | N/A* | N/A* |
| IN-022 | >100 | >100 | >100 | N/A* | N/A* | >50 | >50 | >50 |
| IN-023 | >100 | 49.1 | >100 | N/A* | N/A* | 33.8 | 28.7 | 23.6 |
| IN-024 | >100 | 97.5 | >100 | N/A* | N/A* | >50 | >50 | 49.6 |
| IN-025 | 3.9 | 70.8 | >100 | N/A* | N/A* | N/A* | N/A* | N/A* |

*Designation "N/A" indicates that no data is available for this compound.

CONCLUSION

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein.suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the. art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims.

What is claimed is:

1. A compound of formula II:

(II)

[chemical structure showing indolin-2-one with substituents $R_{16}$, $R_{17}$, $R_{18}$, $R_{19}$, $R_{20}$, $R_{21}$, $R_{22}$, $R_{23}$, $R_{24}$ and ring atoms M, Q, T, U, V]

or a pharmaceutically acceptable salt thereof wherein,

P is 0;

M, Q, U, and V are independently selected from the group consisting of carbon, nitrogen, oxygen and sulfur, it being understood that, when M, Q, U, or V is oxygen or sulfur or nitrogen (wherein said nitrogen is participating in a double bond), $R_{20}$, $R_{21}$, $R_{23}$, or $R_{24}$, respectively, do not exist;

$R_{16}$, $R_{17}$, $R_{18}$, $R_{19}$, and $R_{20}$ are independently selected from the group consisting of hydrogen, alkyl, trihaloalkyl, cycloalkyl, alkenyl, alkynyl, aryl, heteroaryl, heteroalicyclic, hydroxy, alkoxy, mercapto, alkylthio, aryloxy, sulfinyl, sulfonyl, S-sulfonamido, N-sulfonamido, carbonyl, C-carboxy, O-carboxy, carboxyalkyl, cyano, nitro, halo, O-carbamyl, N-carbamyl, C-amido, N-amido and —$NR_{25}R_{26}$;

$R_{21}$, $R_{23}$, and $R_{24}$ are independently selected from the group consisting of halo, hydroxy, —$NR_{25}R_{26}$, lower alkyl optionally substituted with one or more groups selected from the group consisting of hydroxy, one or more halo groups, C-carboxy, C-amido, heteroalicyclic and —$NR_{25}R_{26}$, cycloalkyl, lower alkoxy optionally substituted with one or more halo groups, aryl, —$NR_{25}R_{26}$ and heteroaryl, aryl optionally substituted with one or more groups selected from the group consisting of halo, hydroxy, lower alkoxy, —$NR_{25}R_{26}$ and C-carboxy; and, $R_{25}$ and $R_{26}$ are independently selected from the group consisting of hydrogen, alkyl, cycloalkyl, alkenyl, alkynyl, aryl, heteroaryl, carbonyl, sulfonyl, and, when combined may form a five-member or a six-member heteroalicyclic ring.

2. The compound of claim 1 wherein, $R_{16}$, $R_{17}$, $R_{18}$, $R_{19}$, $R_{20}$, $R_{21}$, $R_{23}$, or $R_{24}$ are independently selected from the group consisting of:

hydrogen, lower alkyl, optionally substituted with one or more groups selected from the group consisting of cycloalkyl, aryl, heteroaryl, heteroalicyclic, halo, hydroxy, C-carboxy and

—$NR_{25}R_{26}$, cycloalkyl, hydroxy, lower alkoxy, optionally substituted with one or more groups selected from the group consisting of one or more halo groups, aryl, heteroaryl and heteroalicyclic, trihalomethyl, trihalomethoxy, halo, carboxyalkyl, aryl, optionally substituted with one or more groups selected from the group consisting of lower alkyl, lower alkyl substituted with one or more halo groups, trihalomethyl, trihalomethoxy, halo, hydroxy, lower alkoxy, aryloxy and —$NR_{25}R_{26}$, aryloxy, heteroaryl, optionally substituted with one or more groups selected from the group consisting of lower alkyl trihalomethyl, halo, hydroxy, (lower alkyl)alkoxy, amino and

—$NR_{25}R_{26}$, heteroalicyclic, (lower alkyl)carboxy, (lower alkyl)carbonyl, aryl carbonyl, (lower alkyl)-S-sulfonamido, aryl-S-sulfonamido, (lower alkyl)-N-sulfonamido, aryl-N-sulfonamido, (lower alkyl)-N-carbamoyl, (lower alkyl)-C-amido, (lower alkyl)-N-amido, (cycloalkyl)-N-amido, and

—$NR_{25}R_{26}$.

3. The compound of claim 1 wherein, one of M or Q is —NH, oxygen or sulfur; and, the other of M or Q, along with U and V are each carbon.

4. The compound of claim 3 wherein, $R_{16}$, $R_{17}$, $R_{18}$, and $R_{19}$ are independently selected from the group consisting of:

hydrogen, halo, hydroxy,

—$NR_{25}R_{26}$,

S-sulfonamido optionally substituted with one or more groups selected from the group consisting of hydrogen, lower alkyl and aryl, lower alkyl optionally substituted with a group selected from the group consisting of:

hydroxy, one or more halo groups,

C-carboxy,

C-amido, heteroalicyclic and,

—$NR_{25}R_{26}$, lower alkoxy optionally substituted with one or more halo groups, aryl optionally substituted with one or more groups selected from the group consisting of lower alkyl, lower alkoxy, halo, hydroxy and —$NR_{25}R_{26}$, N-amido optionally substituted with one or more groups selected from hydrogen, lower alkyl, cycloalkyl and aryl; and, $R_{20}$, $R_{21}$, $R_{23}$, and $R_{24}$ are independently selected from the group consisting of:

hydrogen, halo, hydroxy,

—$NR_{25}R_{26}$, lower alkyl optionally substituted with one or more groups selected from the group consisting of:

hydroxy,
one or more halo groups,
C-carboxy,
C-amido,
heteroalicyclic and,
—$NR_{25}R_{26}$,
cycloalkyl,
lower alkoxy optionally substituted with one or more groups selected from the group consisting of:
one or more halo groups,
aryl,
—$NR_{25}R_{26}$ and,
heteroaryl.

5. The compound of claim 1 wherein,
$R_{16}$, $R_{17}$, $R_{18}$, and $R_{19}$ are independently selected from the group consisting of:
hydrogen,
halo,
hydroxy,
—$NR_{25}R_{26}$,
S-sulfonamido optionally substituted with one or more groups selected from the group consisting of hydrogen, lower alkyl and aryl,
lower alkyl optionally substituted with a group selected from the group consisting of:
hydroxy,
one or more halo groups,
C-carboxy,
C-amido,
heteroalicyclic and,
$NR_{25}R_{26}$,
lower alkoxy optionally substituted with one or more halo groups,
aryl optionally substituted with one or more groups selected from the group consisting of lower alkyl, lower alkoxy, halo, hydroxy and —$NR_{25}R_{26}$,
N-amido optionally substituted with one or more groups selected from hydrogen, lower alkyl, cycloalkyl and aryl; and,
$R_{20}$, $R_{23}$, and $R_{24}$ are independently selected from the group consisting of:
hydrogen,
halo,
hydroxy,
—$NR_{25}R_{26}$,
lower alkyl optionally substituted with one or more groups selected from the group consisting of:
hydroxy,
one or more halo groups,
C-carboxy,
C-amido,
heteroalicyclic and,
—$NR_{25}R_{26}$,
cycloalkyl,
lower alkoxy optionally substituted with one or more groups selected from the group consisting of:
one or more halo groups,
aryl,
—$NR_{25}R_{26}$ and,
heteroaryl,
aryl optionally substituted with one or more groups selected from the group consisting of:
halo,
hydroxy,
lower alkoxy,
—$NR_{25}R_{26}$ and,
C-carboxy.

6. A method for the modulation of the catalytic activity of a protein kinase comprising contacting said protein kinase with said compound of claim 1.

7. A method of modulating signal transduction pathways in cells with a compound according to claim 1, comprising the step of contacting said cells with said compound.

8. The method of claim 7, wherein said cells express a protein kinase and wherein said compound modulates the function of said protein kinase.

9. A method of identifying indolinone compounds that modulate the function of protein kinase, comprising the following steps:
(a) contacting cells expressing said protein kinase with a compound of claim 1; and
(b) monitoring an effect upon said cells.

10. The method of claim 9, wherein said effect is selected from the group consisting of a change in cell phenotype, a change in cell proliferation, a change in the catalytic activity of said protein kinase, and a change in the interaction between said protein kinase and a binding partner.

11. A method of regulating an unregulated protein kinase signal transduction comprising administering to a subject a therapeutically effective amount of a compound according to claim 1.

12. The method of claim 11, wherein unregulated protein kinase signal transduction leads to a cell proliferation disorder or an inflammatory disorder in an organism and said method leads to the treatment of cell proliferation disorder or inflammatory disorder;
wherein said cell proliferation disorder or inflammatory disorder is associated with an aberration in a signal transduction pathway characterized by an interaction between a protein kinase and a binding partner, and wherein said method further comprises the steps of promoting or disrupting said abnormal interaction.

13. The method of claim 10, wherein said cell proliferation disorder is a cancer.

14. The method of claim 11, wherein said unregulated protein kinase signal transduction leads to a disease that is selected from the group consisting of an immunological disorder, a hyperproliferation disorder, a cardiovascular disorder, an inflammatory disorder, restenosis, fibrosis, psoriasis, osteoarthritis, rheumatoid arthritis, aetherosclerosis, diabetes, and angiogenesis.

15. The method of claim 6 wherein said protein kinase is selected from the group consisting of receptor protein tyrosine kinase, cellular tyrosine kinase and serine-threonine kinase.

16. A pharmaceutical composition comprising
(i) a physiologically acceptable carrier, diluent, or excipient or a combination thereof; and
(ii) a compound according to claims 1.

17. The method of claim 8 wherein said protein kinase is selected from the group consisting of receptor protein tyrosine kinase, cellular tyrosine kinase and serine-threonine kinase.

18. The method of claim 10 wherein said protein kinase is selected from the group consisting of receptor protein tyrosine kinase, cellular tyrosine kinase and serine-threonine kinase.

19. The method of claim 11 wherein said protein kinase is selected from the group consisting of receptor protein tyrosine kinase, cellular tyrosine kinase and serine-threonine kinase.

* * * * *